United States Patent
Law et al.

(10) Patent No.: US 12,276,803 B2
(45) Date of Patent: Apr. 15, 2025

(54) POSITIONING, STABILISING AND INTERFACING STRUCTURES AND SYSTEM INCORPORATING SAME

(71) Applicant: RESMED PTY LTD, Bella Vista (AU)

(72) Inventors: Ian Andrew Law, Sydney (AU); Aaron Samuel Davidson, Sydney (AU); Stewart Joseph Wagner, Hawkesbury (AU); David James Braund, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 18/262,817

(22) PCT Filed: Jan. 28, 2022

(86) PCT No.: PCT/AU2022/050043
§ 371 (c)(1),
(2) Date: Jul. 25, 2023

(87) PCT Pub. No.: WO2022/160012
PCT Pub. Date: Aug. 4, 2022

(65) Prior Publication Data
US 2024/0111163 A1   Apr. 4, 2024

(30) Foreign Application Priority Data

Jan. 29, 2021 (AU) .............................. 2021900199
Feb. 3, 2021 (AU) .............................. 2021900242

(Continued)

(51) Int. Cl.
*G02B 27/01* (2006.01)

(52) U.S. Cl.
CPC .... *G02B 27/0176* (2013.01); *G02B 2027/015* (2013.01); *G02B 2027/0152* (2013.01);
(Continued)

(58) Field of Classification Search
CPC .......... A61M 16/0066; A61M 16/0683; A61M 16/161; A61M 2021/0022;
(Continued)

(56) References Cited

U.S. PATENT DOCUMENTS

| | | |
|---|---|---|
| 4,782,832 A | 11/1988 | Trimble et al. |
| 4,944,310 A | 7/1990 | Sullivan |

(Continued)

FOREIGN PATENT DOCUMENTS

| | | |
|---|---|---|
| CN | 105404004 A | 3/2016 |
| CN | 205992090 U | 3/2017 |

(Continued)

OTHER PUBLICATIONS

Notice of Grant dated Mar. 16, 2024 issued in Chinese Application No. 202321228955.3 (2 pages).

(Continued)

*Primary Examiner* — Kenneth Bukowski
(74) *Attorney, Agent, or Firm* — Nixon & Vanderhye P.C.

(57) ABSTRACT

A head-mounted display system includes a head-mounted display unit a display that, in use, is held in an operational position over a user's face. The head-mounted display system further comprises a flow generator configured to generate a flow of air, and an air guide arrangement coupled to the flow generator to enable the flow generator to direct air to, or draw air from, one or more selected areas in proximity of the head-mounted display system.

28 Claims, 56 Drawing Sheets

(30) Foreign Application Priority Data

| Feb. 3, 2021 | (AU) | 2021900243 |
|---|---|---|
| Feb. 3, 2021 | (AU) | 2021900244 |
| Feb. 3, 2021 | (SG) | 10202101162X |
| Feb. 5, 2021 | (AU) | 2021900272 |
| Mar. 24, 2021 | (AU) | 2021900871 |
| Mar. 29, 2021 | (WO) | PCT/AU2021/050277 |
| Jun. 30, 2021 | (AU) | 2021901994 |
| Jul. 16, 2021 | (AU) | 2021902184 |
| Aug. 31, 2021 | (AU) | 2021902827 |

(52) U.S. Cl.
CPC .............. *G02B 2027/0169* (2013.01); *G02B 2027/0178* (2013.01); *G02B 2027/0192* (2013.01)

(58) Field of Classification Search
CPC .... A61M 2021/0027; A61M 2021/005; A61M 2021/0066; A61M 21/00; A61M 2205/07; A61M 2205/3306; A61M 2205/332; A61M 2205/3331; A61M 2205/3334; A61M 2205/3365; A61M 2205/3368; A61M 2205/3584; A61M 2205/3592; A61M 2205/3606; A61M 2205/362; A61M 2205/505; A61M 2205/507; A61M 2205/581; A61M 2205/582; A61M 2205/8206; A61M 2209/088; A61M 2230/005; A61M 2230/50; A61M 2230/62; A61M 2230/63; G02B 2027/015; G02B 2027/0152; G02B 2027/0169; G02B 2027/0178; G02B 2027/0192; G02B 27/0176; G06F 1/163; G06F 3/011; G06F 3/012

See application file for complete search history.

(56) References Cited

U.S. PATENT DOCUMENTS

| 5,687,715 | A | 11/1997 | Landis |
| 5,796,374 | A | 8/1998 | Cone et al. |
| 6,529,331 | B2 | 3/2003 | Massof et al. |
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 9,134,548 | B1 * | 9/2015 | Olsson .............. G02C 9/00 |
| 9,980,416 | B2 | 5/2018 | Reynolds et al. |
| 10,078,349 | B1 | 9/2018 | Morris et al. |
| 10,379,366 | B1 | 8/2019 | Bristol et al. |
| 10,502,363 | B2 * | 12/2019 | Edwards ............... F16M 13/04 |
| 10,571,691 | B1 | 2/2020 | Yee et al. |
| 10,754,175 | B2 | 8/2020 | Lee |
| 10,898,798 | B2 | 1/2021 | Chapman et al. |
| 2009/0044808 | A1 | 2/2009 | Guney et al. |
| 2009/0050156 | A1 | 2/2009 | Ng et al. |
| 2010/0000534 | A1 | 1/2010 | Kooij et al. |
| 2013/0188080 | A1 * | 7/2013 | Olsson .............. G06F 1/163 381/151 |
| 2015/0235426 | A1 * | 8/2015 | Lyons ............... A63F 13/26 345/8 |
| 2016/0019423 | A1 * | 1/2016 | Ortiz ............... G06V 40/10 345/633 |
| 2017/0153672 | A1 * | 6/2017 | Shin ............... H04M 1/724097 |
| 2017/0337737 | A1 * | 11/2017 | Edwards ............... F16M 13/04 |
| 2018/0239151 | A1 * | 8/2018 | Chang ............... G02B 27/0176 |
| 2019/0000556 | A1 | 1/2019 | Sela et al. |
| 2019/0075689 | A1 | 3/2019 | Selvakumar et al. |
| 2019/0192965 | A1 * | 6/2019 | Chapman ............... A63F 13/50 |
| 2019/0243145 | A1 | 8/2019 | Ellis et al. |
| 2020/0110449 | A1 | 4/2020 | Chang et al. |

FOREIGN PATENT DOCUMENTS

| CN | 106802484 | A | | 6/2017 |
| CN | 206657145 | U | | 11/2017 |
| CN | 109445100 | A | | 3/2019 |
| CN | 208607439 | U | | 3/2019 |
| CN | 110471184 | A | | 11/2019 |
| CN | 117289469 | A | * | 12/2023 |
| FR | 2944416 | A1 | | 10/2010 |
| JP | 6-175066 | A | | 6/1994 |
| JP | H0934376 | A | * | 2/1997 |
| JP | 2011-209472 | A | | 10/2011 |
| KR | 10-2014-0025121 | A | | 3/2014 |
| WO | WO 98/004310 | A1 | | 2/1998 |
| WO | WO 98/034665 | A1 | | 8/1998 |
| WO | WO 2000/078381 | A1 | | 12/2000 |
| WO | WO 2004/073778 | A1 | | 9/2004 |
| WO | WO 2005/063328 | A1 | | 7/2005 |
| WO | WO 2006/074513 | A1 | | 7/2006 |
| WO | WO 2006/130903 | A1 | | 12/2006 |
| WO | WO 2009/052560 | A1 | | 4/2009 |
| WO | WO 2010/135785 | A1 | | 12/2010 |
| WO | WO 2012/171072 | A1 | | 12/2012 |
| WO | 2013/0005615 | A1 | | 1/2013 |
| WO | WO 2013/020167 | A1 | | 2/2013 |
| WO | 2019/000556 | A1 | | 1/2019 |
| WO | 2020/0017627 | A1 | | 1/2020 |

OTHER PUBLICATIONS

Office Action dated Mar. 25, 2024 issued in U.S. Appl. No. 18/263,303 (15 pages).
Office Action dated Feb. 26, 2024 issued in Japanese Application No. 2022-558254 with English translation (15 pages).
International Preliminary Report on Patentability dated Aug. 10, 2023 issued in International Application No. PCT/AU2022/050043 (13 pages).
Decision of Refusal dated Jul. 31, 2023 issued in Taiwanese Application No. 110131601 with English translation (11 pages).
Decision of Refusal dated Aug. 8, 2023 issued in Taiwanese Application No. 110131604 with English translation (11 pages).
Office Action dated Aug. 16, 2023 issued in Chinese Application No. 202320571641.7 with English translation (6 pages).
"*Respiratory Physiology*", by John B. West, Lippincott Williams & Wilkins, 9th edition published 2012 (8 pages).
International Search Report dated Apr. 26, 2022 issued in International Application No. PCT/AU2022/050043 (7 pages).
Written Opinion dated Apr. 26, 2022 issued in International Application No. PCT/AU2022/050043 (11 pages).
Extended European Search Report mailed Oct. 28, 2024 in European Application No. 22744939.4, 8 pages.

* cited by examiner

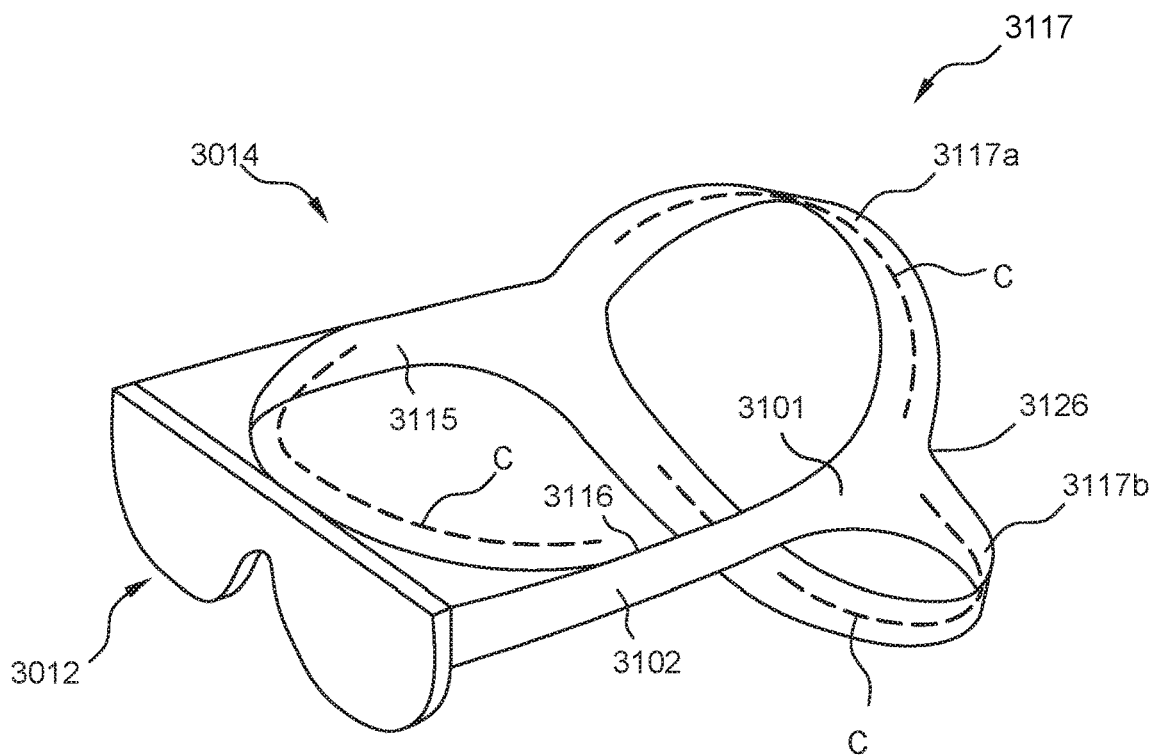
FIG. 26A
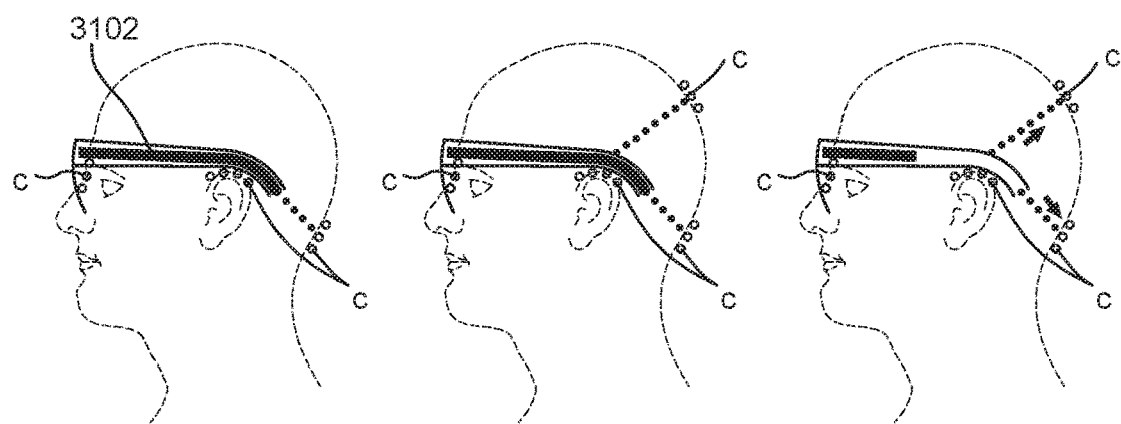
FIG. 26B     FIG. 26C     FIG. 26D

POSITIONING, STABILISING AND INTERFACING STRUCTURES AND SYSTEM INCORPORATING SAME

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

CROSS-REFERENCE TO RELATED APPLICATIONS

This application claims the benefit of Australian Provisional Application No. 2021900244, filed Feb. 3, 2021, Australian Provisional Application No. 2021900199, filed Jan. 29, 2021, Australian Provisional Application No. 2021901994, filed Jun. 30, 2021, Australian Provisional Application No. 2021900243, filed Feb. 3, 2021, Australian Provisional Application No. 2021900272, filed Feb. 5, 2021, Singapore Provisional Application No. 10202101162X, filed Feb. 3, 2021, Australian Provisional Application No. 2021900242, filed Feb. 3, 2021, Australian Provisional Application No. 2021900871, filed Mar. 24, 2021, Australian Provisional Application No. 2021902827, filed Aug. 31, 2021, Australian Provisional Application No. 2021902184, filed Jul. 16, 2021, and International Application PCT/AU2021/050277, filed Mar. 29, 2021, each of which is incorporated herein by reference in its entirety.

FIELD OF THE TECHNOLOGY

The present technology relates to a positioning and stabilising structure to hold a head-mounted display unit and an associated head-mounted display assembly including a display unit and positioning and stabilising structure. The present technology finds particular application in the use of augmented reality head-mounted displays and is herein described in that context. However, it is to be appreciated that the present technology may have broader application and may be used in other head-mounted display arrangements including virtual reality displays.

BACKGROUND OF THE TECHNOLOGY

It is to be understood that, if any prior art is referred to herein, such reference does not constitute an admission that the prior art forms a part of the common general knowledge in the art, in Australia or any other country.

Augmented reality head-mounted displays enable a user to add digital elements to a live view to create an interactive experience of a real-world environment where the objects that reside in the real world may be enhanced by computer-generated perceptual information. This information can sometimes cross multiple sensory modalities, including visual, auditory, haptic, somatosensory and olfactory. Augmented reality head-mounted displays can have broad application in fields such as communications, training, medical and surgical practice, engineering and video gaming.

Augmented reality systems can combine the real world with a virtual world in real-time and in an interactive manner. The overlaid augmented reality sensory information can sometimes be additive to the real world (i.e. constructive), or in some forms can be used to mask or remove elements of the real world (i.e. destructive). By seamlessly interweaving the augmented reality experience with the real-world environment, augmented reality may in some forms also be perceived by a user as an immersive experience. Where virtual reality completely replaces the user's real-world environment with a simulated one, augmented reality instead alters the user's real-time perception of their real-world environment.

Augmented reality head-mounted displays typically are provided as a system or assembly that includes a display unit which is arranged to be held in an operational position in front of a user's face. The display unit typically includes a housing containing a display and a user interface structure constructed and arranged to be in opposing relation with the user's face. The user interface structure may extend about the display and define a viewing opening to the display. The user interface structure may engage with the user's face and in some forms may include a cushion for user comfort.

To hold the display unit in its correct operational position, the head-mounted display system further comprises a positioning and stabilising structure that is disposed on the user's head. In the past, these positioning and stabilising structures have been formed from straps or expandable rigid structures that are typically applied to the user's head under tension to maintain the display unit in its operational position. Such systems have been prone to exert a clamping pressure on the user's face which can result in user discomfort at localised stress points. Also, previous systems may be difficult to adjust to allow wide application head sizes. Further, the display unit and associated positioning and stabilising structure are often heavy and difficult to clean, which further limit the comfort and usability of the system.

Thus, there is a need for an improved system that does not suffer from the above-mentioned drawbacks.

BRIEF SUMMARY OF THE TECHNOLOGY

An aspect of the present technology relates to a head-mounted display system including a positioning and stabilising structure that includes at least one electrical component configured to operate while the system is in use.

An aspect of the present technology relates to a head-mounted display system comprising a display and a flow generator, both configured to be supported on a user's head.

An aspect of the present technology relates to a head-mounted display system that comprises a flow generator configured to generator a flow of air. The flow generator configured to be supported on the user's head and counter-balance a display unit.

An aspect of the present technology relates to a positioning and stabilising structure that is configured to support a head-mounted display unit on a user's face. The positioning and stabilising structure includes at least one strap housing an air guide arrangement configured to connect between the head-mounted display unit and a flow generator supported by the at least one strap. The air guide arrangement configured to direct airflow between the flow generator and the head-mounted display unit.

An aspect of the present technology relates to a positioning and stabilising structure including at least one energy storage device configured to power to a display unit.

An aspect of the present technology relates to a head-mounted display system comprising a head-mounted display unit comprising a display that, in use, is held in an operational position over a user's face. The head-mounted display system further comprises a flow generator, i.e. an air moving device (or blower), configured to generate a flow of air and an air guide arrangement coupled to the flow generator to enable the flow generator to direct air to, or draw air from, one or more selected areas in proximity of the head-mounted display system.

In some forms, the head-mounted display system may be an augmented reality display system, a virtual reality display system, or other type of head-mounted display system.

The flow generator, i.e. the air moving device, may be disposed on the head-mounted display system and arranged to create a flow of air, i.e. an air draft, in the vicinity of the head mounted display system.

In some forms the head-mounted display system may further comprise a positioning and stabilising structure structured and arranged to hold the head-mounted display unit over the user's face, wherein the flow generator is mounted on the positioning and stabilising structure.

In some forms the head-mounted display system may further comprise an isolating member between the flow generator and the positioning and stabilising structure to dampen vibration from the flow generator. In some forms, the isolating member is elastically deformable.

In some forms of the head-mounted display system, the guide arrangement may comprise at least one port in pneumatic communication with the flow generator and through which air may be directed from, or drawn into, under the generated air flow.

In some forms, the flow generator may comprise a housing. The at least one port may be integrated within the housing.

In some forms, the air guide arrangement may comprise at least one conduit through which the generated air flow can flow. The at least one port may be disposed in the conduit remote from the flow generator.

In some forms, the at least one conduit may be formed within, or disposed along, a portion of the positioning and stabilising structure.

The head-mounted display system may further comprise a positioning and stabilising structure structured and arranged to hold the head-mounted display unit over the user's face. The positioning and stabilising structure may comprise componentry of the head-mounted display system. The flow generator may be able to direct air to, or draw air from, the vicinity of the componentry. In some forms, the flow generator may be able to direct air to, or draw air from, the vicinity of the head-mounted display unit.

In some forms, the head mounted display unit may define a closed-in space around a portion of the user's face, for example, a space defined between the display and the user's eyes. The flow generator may be able to direct air to, or draw air from, that closed-in space. In some forms, the flow generator may be able to direct air to, or draw air across, the user. For example, across the user's skin. In some forms, the air may be directed onto, or drawn air across, the user to promote a sensory response.

The head-mounted display system may further comprise a control system having a processor to control the operation of the flow generator. At least one sensor in communication with the processor may be provided to the head-mounted display system, wherein the at least one sensor is configured to measure a parameter, e.g. temperature, and communicate a measured value (e.g. of the temperature) to the processor. The processor may be configured to control the flow generator (e.g. rate of output/input airflow) based on the measured value.

In some forms, the sensor may be one of a group (of sensors) consisting of (but not limited to) a pressure sensor, a flow rate sensor, a temperature sensor, and a humidity sensor.

In some forms of the head-mounted display system, the control system may be operative to control the flow generator in coordination with information displayed in the head mounted display unit to provide sensory feedback to the user. For example, a measurement of the user's body temperature measured by temperature sensors may be displayed to the user (via the display) during use.

In some forms of the head-mounted display system, the flow generator may comprise a blower. The blower may comprise at least one impellor to move air through the blower. In some forms, the blower may be adapted to provide bidirectional air flows.

The head-mounted display system may further comprise a power supply configured to provide electrical power to the flow generator. In some forms, the power supply is in the form of one or more battery packs.

In some forms, the head-mounted display system may further comprise a positioning and stabilising structure structured and arranged to hold the head-mounted display unit over the user's face. The positioning and stabilising structure may comprise a rear support adapted to contact posterior regions of a user's head. In some forms, the flow generator may be mounted on the rear support.

In some forms, the rear support may comprise an occipital portion configured to overlie or lie below an occipital bone of the user's head. In some forms, the flow generator may be mounted on the occipital portion.

In one example, the rear support (i.e. rear support structure) comprises an occipital portion configured and arranged to engage the user's head along a portion of the occipital bone adjacent a junction where the neck muscles attach to the occipital bone in use. The flow generator may be mounted on the occipital portion.

In some forms of the head-mounted display system, the flow generator may create a counterbalance to the head-mounted display unit. In some forms, the flow generator may be configured to be located in a sagittal plane of the user's head.

In some forms, the rear support may further comprise a parietal portion adapted to engage the user's head proximate the parietal bone. Componentry for the head-mounted display system may be mounted the parietal portion.

In some forms of the head-mounted display system, the positioning and stabilising structure may further comprise at least one connector to interconnect the rear support to the head-mounted display unit. The at least one connector may comprise opposing temporal connectors structured and arranged to interconnect the rear support to the head-mounted display unit. The opposing temporal connectors may be adapted to be disposed on opposing sides of the user's head and extend along the temporal regions of the user's head.

Each of the temporal connectors may be rigid along at least a portion of its length.

In some forms, each of the temporal connectors may comprise a temporal arm having an anterior end connected to the head-mounted display unit and a posterior end connected to the rear support. In some forms, the temporal arm may be rigid.

In some forms, the head mounted-display may comprise a plurality of flow generators. The flow generators may be controllable such that two or more flow generators can operate together to direct air to, or draw air from, an area in the vicinity of the head-mounted display system. Additionally, or alternatively, the two or more flow generators may operate to direct air to, or draw air from, different areas in the vicinity of the head-mounted display system.

The present technology may be directed toward providing positioning and stabilising structures used in the supporting, stabilising, mounting, utilising, and/or securing of a head-mounted display having one or more of improved comfort, cost, efficacy, ease of use and manufacturability.

An aspect of the present technology relates to apparatuses used in the supporting, stabilising, mounting, utilising, and/or securing of a head-mounted display.

Another aspect of the present technology relates to methods used in the supporting, stabilising, mounting, utilising, and/or securing of a head-mounted display.

Another aspect is a positioning and stabilising structure for a head-mounted display that comprising a rear (or posterior) support structure (or portion) arranged, in use, to contact a posterior region of the user's head.

In some forms, the posterior support portion or at least a portion thereof may be disposed posterior of the otobasion superior of the user.

In some forms, the posterior support portion may be biased into contact with the occipital region of the user.

In some forms, the positioning and stabilising structure further comprises opposing connectors that are disposed on opposing sides of, and extending along the temporal regions of, the user's head to interconnect the posterior support portion to the head-mounted display unit.

In some forms the positioning and stabilising structure comprises an anterior support portion connecting the posterior support portion to the head-mounted display unit.

The present technology may also be directed toward providing interfacing structures used in the supporting, cushioning, stabilising, positioning, and/or sealing a head-mounted display in opposing relation with the user's face.

Another aspect relates to apparatuses used in the supporting, cushioning, stabilising, positioning, and/or sealing a head-mounted display in opposing relation with the user's face.

Another aspect relates to methods used in supporting, cushioning, stabilising, positioning, and/or sealing a head-mounted display in opposing relation with the user's face.

Another aspect of the present technology relates to a positioning and stabilising structure that comprises: a posterior support portion configured to engage a posterior portion of a user's head; an anterior support portion configured to connect the posterior support portion and a head-mounted display unit in use; and a pair of superior support pads each located on a respective lateral side of the user's head and configured to lie against an at least partially superior-facing portion of the user's head in use to support at least some weight of the head-mounted display system.

Another aspect of the present technology relates to a positioning and stabilising structure that comprises: a posterior support portion configured to engage a posterior portion of a user's head; an anterior support portion configured to connect the posterior support portion and an interface in use; and a pair of superior support pads each located on a respective lateral side of the user's head and configured to lie against an at least partially superior-facing portion of the user's head in use to support at least some weight of the head-mounted display system.

Another aspect of the present technology relates to a head-mounted display system comprising a head-mounted display unit and a positioning and stabilising structure, which includes a pair of superior support pads that are separate and spaced apart from one another. The pair of superior support pads are configured to distribute the weight of the display unit.

Another aspect of the present technology relates to a user interface comprising a head-mounted display unit and a positioning and stabilising structure, which includes a pair of superior support pads that are separate and spaced apart from one another. The pair of superior support pads are configured to distribute the weight of plenum chamber and/or seal-forming structure.

Another aspect of the present technology relates to a pair of superior support pads configured to be included in a positioning and stabilising structure. Each support pad includes a curvature configured to correspond to a shape of the user's head. In some forms, each support pad is configured to be biased into the user's head in order to provide weight distribution from a head-mounted display unit.

Another aspect of the present technology relates to a pair of superior support pads configured to be included in a positioning and stabilising structure. Each support pad includes a curvature configured to correspond to a shape of the user's head. In some forms, each support pad is configured to be biased into the user's head in order to provide weight distribution from a plenum chamber and/or seal-forming structure.

Another aspect of the present technology relates to a user interface that comprises: a cushion comprising a plenum chamber and a seal-forming structure; a positioning and stabilising structure configured to hold the seal-forming structure in an sealing position on the user's head in use, the positioning and stabilising structure comprising: a posterior support portion configured to engage a posterior portion of a user's head: an anterior support portion connecting the posterior support portion and the cushion in use; a pair of superior support pads each located between the posterior support portion and the anterior support portion and configured to lie against an at least partially superior-facing portion of the user's head in use, wherein the pair of superior support pads spaced apart from one another; wherein the pair of superior support pads configured to support at least some weight of the cushion by distributing the weight across pair of superior support pads.

Another aspect of the present technology relates to a head-mounted display system that comprises: a head-mounted display unit comprising a display; a positioning and stabilising structure configured to hold the head-mounted display unit in an operable position on the user's head in use, the positioning and stabilising structure comprising: a posterior support portion configured to engage a posterior portion of a user's head: an anterior support portion connecting the posterior support portion and the head-mounted display unit in use; a pair of superior support pads each located between the posterior support portion and the anterior support portion and configured to lie against an at least partially superior-facing portion of the user's head in use, wherein the pair of superior support pads spaced apart from one another; wherein the pair of superior support pads configured to support at least some weight of the head-mounted display system by distributing the weight across pair of superior support pads.

Another aspect of the present technology relates to a head-mounted display system comprising a head-mounted display unit comprising a display and a positioning and stabilising structure configured to hold the head-mounted display unit in an operable position on the user's head in use. The positioning and stabilising structure comprises: a posterior support portion configured to engage a posterior portion of a user's head; an anterior support portion configured to connect the posterior support portion and the head-mounted display unit in use; and a pair of superior support pads each located on a respective lateral side of the user's head and configured to lie against an at least partially superior-facing portion of the user's head in use to support at least some weight of the head-mounted display system.

In some forms the posterior support portion comprises an occipital strap portion configured to overlie or lie below an occipital bone of the user's head.

In some forms the anterior support portion comprises a frontal support portion configured to engage the user's head at a region overlying a frontal bone of the user's head.

In some forms the positioning and stabilising structure comprises a band portion configured to fit around the user's head, the band portion comprising the occipital strap portion and the frontal support portion.

In some forms each of the superior support pads extends superiorly and medially from the band portion on a respective side of the user's head.

In some forms each of the superior support pads curves medially.

In some forms each of the superior support pads may be located at or proximate a mid-coronal plane of the user's head in use.

In some forms the superior support pads are not connected to each other across a superior surface of the user's head;

In some forms the positioning and stabilising structure comprises a frontal connector connected between the frontal support portion and the head-mounted display unit.

In some forms the frontal connector may be located substantially in the sagittal plane of the user's head.

In some forms the frontal connector may be configured to pivot with respect to the frontal support portion;

In some forms the head-mounted display unit may be configured to pivot with respect to the frontal connector.

In some forms the occipital strap portion may be adjustable in length.

In some forms the occipital strap portion of the positioning and stabilising structure comprises a pair of lateral occipital strap portions, each located on a respective side of the user's head, and a medial occipital strap portion connecting medial ends of the lateral occipital strap portions.

In some forms the medial occipital strap portion may be adjustable in length.

In some forms the medial occipital strap portion may be elastically extendable.

In some forms the lateral occipital strap portions are adjustable in length;

In some forms the lateral occipital strap portions are configured to be releasably connected to the medial occipital strap portion;

In some forms the lateral occipital strap portions comprise magnetic clips configured to magnetically connect to corresponding connection points on the medial occipital strap portion.

In some forms the head-mounted display system further comprises a battery pack for powering the head-mounted display system, the battery pack connected to the occipital strap portion.

In some forms the battery pack may be configured to be located in a sagittal plane of the user's head in use.

Another aspect of the present technology relates to a positioning and stabilising structure that comprises a dial adjustment mechanism comprising a rotatable dial. The adjustment mechanism is configured to cause a change in length of at least one of the strap portions when the dial is rotated.

The positioning and stabilising structure may be usable with a virtual reality system, an augmented reality system, or any similar system.

Another aspect of the present technology relates to a positioning and stabilising structure that comprises a rear strap that extends along the sagittal plane of the user.

In one form, a dial adjustment mechanism comprising a rotatable dial is connected to the rear strap. The dial adjustment mechanism being configured to cause a change in length of at least one of the strap portions (e.g., the rear strap and/or another strap) when the dial is rotate.

Another aspect of the present technology comprises a positioning and stabilising structure structure that comprises a dial adjustment mechanism comprising a rotatable dial. The dial adjustment mechanism is configured to hold at least one of the strap portions in a taut state regardless of whether the positioning and stabilising structure is worn by a user.

In one form, the dial adjustment mechanism is configured to simultaneously adjust at least two different straps. Both straps are held in tension regardless of whether the positioning and stabilising structure is worn by a user.

In certain forms, strap(s) not adjustable by the dial adjustment mechanism are configured to remain loose while the positioning and stabilising structure is not worn by the user.

Another aspect of the present technology relates to a head-mounted display system comprising a positioning and stabilising structure further that comprises a dial adjustment mechanism comprising a rotatable dial. The rotatable dial is configured to overlay the user's occipital bone in use.

Another aspect of the present technology relates to a head-mounted display system comprising a head-mounted display unit comprising a display and a positioning and stabilising structure configured to hold the head-mounted display unit in an operable position on the user's head in use. The positioning and stabilising structure comprises: a plurality of strap portions; and wherein the positioning and stabilising structure further comprises a dial adjustment mechanism comprising a rotatable dial, the dial adjustment mechanism being configured to overlay the user's occipital bone.

Another aspect of the present technology relates to a head-mounted display system comprising a head-mounted display unit comprising a display and a positioning and stabilising structure configured to hold the head-mounted display unit in an operable position on the user's head in use. The positioning and stabilising structure comprises: a plurality of strap portions; and wherein the positioning and stabilising structure further comprises a dial adjustment mechanism comprising a rotatable dial, the dial adjustment mechanism being configured to cause a change in length of at least one of the strap portions when the dial is rotated.

In some forms, the dial may change the length of multiple straps simultaneously.

Another aspect of the present technology relates to a head-mounted display system comprising a head-mounted display unit comprising a display and a positioning and stabilising structure configured to hold the head-mounted display unit in an operable position on the user's head in use. The positioning and stabilising structure comprises: a plurality of strap portions; and wherein the positioning and stabilising structure further comprises a dial adjustment mechanism comprising a rotatable dial, the dial adjustment mechanism being configured to overlay the user's occipital bone. Movement of the dial adjustment structure is configured to cause a change in length of multiple strap portions simultaneously when the dial is rotated.

Another aspect of the present technology relates to a head-mounted display system comprising a head-mounted display unit comprising a display and a positioning and stabilising structure configured to hold the head-mounted display unit in an operable position on the user's head in use. The positioning and stabilising structure comprises: a posterior support portion configured to engage a posterior portion of a user's head; and an anterior support portion configured to connect the posterior support portion and the head-mounted display unit in use; wherein the posterior support portion and the anterior support portion are together formed by a plurality of strap portions; and wherein the positioning and stabilising structure further comprises a dial adjustment mechanism comprising a rotatable dial, the dial adjustment mechanism being configured to cause a change in length of at least one of the strap portions when the dial is rotated.

In some forms the posterior support portion comprises an occipital strap portion configured to overlie or lie inferior to the occipital bone of the user's head.

In some forms the dial adjustment mechanism may be configured to cause a change in length of the occipital strap portion when the dial is rotated.

In some forms the posterior support portion comprises a parietal strap portion configured to overlie the parietal bones of the user's head.

In some forms the dial adjustment mechanism may be configured to cause a change in length of the parietal strap portion when the dial is rotated.

In some forms the anterior support portion comprises a pair of lateral strap portions configured to connect between the posterior support portion and the head-mounted display unit, each configured to be located on a respective lateral side of the user's head in use.

In some forms the dial adjustment mechanism may be configured to cause a change in length of the lateral strap portions.

In some forms the dial adjustment mechanism comprises a pair of extending portions connected to and extending away from the dial, each extending portion being fixedly connected to a portion of the positioning and stabilising structure or to the head-mounted display unit, wherein rotation of the dial causes a change in an amount of extension away from the dial of each extending portion.

In some forms, each extending portion is connected to two different straps of the positioning and stabilising structure.

In some forms, rotation of the dial is configured to simultaneously adjust the at least two different straps.

In some forms the dial may be provided to the occipital strap portion.

In some forms each extending portion may be located within a hollow interior of the occipital strap portion.

In some further forms, the dial adjustment mechanism comprises: a pair of extending portions connected to and extending away from the dial, each extending portion being fixedly connected to a portion of the positioning and stabilising structure or to the head-mounted display unit, wherein rotation of the dial causes a change in an amount of extension away from the dial of each extending portion.

In some forms each extending portion comprises a non-elastic portion.

In some forms each extending portion comprises an elastic portion.

In some forms the posterior support portion comprises an occipital strap portion configured to overlie or lie inferior to the occipital bone of the user's head.

In some further forms again, the dial may be provided to the occipital strap portion and each extending portion of the dial adjustment mechanism may be fixedly connected to the occipital strap portion at a respective location spaced from the dial.

In some forms, rotation of the dial of the dial adjustment mechanism causes a change in length of the occipital strap portion.

In some forms the occipital strap portion may be elastically extendable.

In some forms each extending portion of the dial adjustment mechanism may be fixedly connected to a respective end of the occipital strap portion.

In some forms each extending portion may be located within a hollow interior of the occipital strap portion.

In some forms the posterior support portion comprises a parietal strap portion configured to overlie the parietal bones of the user's head.

In some forms the anterior support portion comprises a pair of lateral strap portions configured to connect between the posterior support portion and the head-mounted display unit, each lateral strap portion configured to be located on a respective lateral side of the user's head in use.

In some forms the positioning and stabilising structure further comprises a sagittal strap portion connecting between the parietal strap portion and the occipital strap portion and configured to lie against the user's head along a path in the sagittal plane of the user's head in use.

In some forms the sagittal strap portion connects to the head-mounted display unit.

In some forms the sagittal strap portion may be substantially inextensible.

In some forms the posterior support portion comprises a parietal strap portion configured to overlie the parietal bones of the user's head.

In some forms the dial may be provided to the occipital strap portion and each extending portion of the dial adjustment mechanism may be fixedly connected to the parietal strap portion.

In some forms rotation of the dial of the dial adjustment mechanism causes a change in length of both the occipital strap portion and parietal strap portion.

In some forms each extending portion may be connected to the parietal strap portion at or proximate the sagittal plane of the user's head in use.

In some forms the occipital strap portion may be elastically extendable.

In some forms the parietal strap portion may be elastically extendable.

In some forms the change in length of the occipital strap portion may be substantially equal to the change in length of the parietal strap portion.

In some forms each extending portion may be located within a hollow interior of the occipital strap portion.

In some forms each extending portion may be located within a hollow interior of the parietal strap portion.

In some forms the positioning and stabilising structure comprises a pair of guides, each guide configured to guide a respective extending portion of the dial adjustment mechanism to change direction.

In some forms each guide comprises a curved portion configured to allow a respective extending portion to travel over the curved portion.

In some forms each curved portion faces anteriorly such that the extending portion slides over an anterior side of the guide in use.

In some forms each guide comprises a semicylindrical structure comprising the curved portion, the curved portion defining a circumferential surface over which a respective extending portion may be able to slide.

In some forms each guide comprises a sheath portion through which the respective extending portion passes, the sheath portion comprising the curved portion.

In some forms the occipital strap portion and parietal strap portion each comprise a pair of ends, each end of the occipital strap portion being connected to a respective end of the parietal strap portion.

In some forms each guide may be fixedly located at a respective junction between the occipital strap portion and the parietal strap portion.

In some forms each guide may be internal to the parietal strap portion and/or occipital strap portion.

In some forms each guide may be external to the parietal strap portion and/or occipital strap portion.

In some forms the anterior support portion comprises a pair of lateral strap portions configured to connect between the posterior support portion and the head-mounted display unit, wherein each lateral strap portion may be configured to be located on a respective lateral side of the user's head in use.

In some forms the anterior support portion further comprises.

In some forms a pair of elastically extendable connector strap portions each configured to be located on a respective lateral side of the user's head in use and each configured to connect between the posterior support portion and the head-mounted display unit to allow a predetermined amount of separation of the posterior support portion from the head-mounted display unit.

In some forms the lateral strap portions are substantially inextensible and are each configured to releasably attach the posterior support portion to the head-mounted display unit to prevent separation of the posterior support portion from the head-mounted display unit.

In some forms each elastically extendable connector strap portion and each lateral strap portion connects a junction of the parietal strap portion and occipital strap portion to the head-mounted display unit.

In some forms each lateral strap portion comprises a magnetic clip configured to magnetically attach to a connection point to releasably attach the posterior support portion to the head-mounted display unit.

In some forms each connection point may be located at or proximate a respect one of the junctions of the parietal strap portion and occipital strap portion.

In some forms each connection point may be located at or proximate the head-mounted display unit.

In some forms the positioning and stabilising structure further comprises a sagittal strap portion connecting between the parietal strap portion and the occipital strap portion and configured to lie against the user's head along a path in the sagittal plane of the user's head in use.

In some forms the sagittal strap portion connects to the head-mounted display unit.

In some forms the sagittal strap portion may be substantially inextensible.

In some further forms, the anterior support portion comprises a pair of lateral strap portions configured to connect between the posterior support portion and the head-mounted display unit, wherein each lateral strap portion may be configured to be located on a respective lateral side of the user's head in use.

In some forms the dial may be provided to the occipital strap portion and each extending portion of the dial adjustment mechanism may be fixedly connected to a respective one of the lateral strap portions or to a respective side of the head-mounted display unit, wherein rotation of the dial of the dial adjustment mechanism causes a change in length of the lateral strap portions.

In some forms each extending portion may be located within a hollow interior of the occipital strap portion.

In some forms each extending portion may be located exterior to a respective one of the lateral strap portions.

In some forms each lateral strap portion may be elastically extendable.

In some forms the occipital strap portion may be substantially inextensible.

In some forms the positioning and stabilising structure comprises a pair of guides, each guide configured to guide a respective extending portion of the dial adjustment mechanism to change direction.

In some forms each guide comprises a curved portion configured to allow a respective extending portion to travel over the curved portion.

In some forms each curved portion faces superiorly and/or posteriorly such that the extending portion travels over a superior and/or posterior side of the guide in use.

In some forms each guide comprises a semicylindrical structure comprising the curved portion, the curved portion defining a circumferential surface over which a respective extending portion may be able to slide.

In some forms each guide comprises a sheath portion through which the respective extending portion passes, the sheath portion comprising the curved portion.

In some forms each guide may be fixedly located at a respective junction between the occipital strap portion and a respective one of the lateral strap portions.

In some forms each guide may be internal to the occipital strap portion and respective lateral strap portion.

In some forms each guide may be external to the occipital strap portion and respective lateral strap portion.

In some forms the posterior support portion comprises a parietal strap portion configured to overlie the parietal bones of the user's head.

In some forms the parietal strap portion connects to the occipital strap portion and the lateral strap portions at the junctions between the occipital strap portion and the lateral strap portions.

In some forms the parietal strap portion may be substantially inextensible.

In some forms the positioning and stabilising structure further comprises a sagittal strap portion connecting between the parietal strap portion and the occipital strap portion and configured to lie against the user's head along a path in the sagittal plane of the user's head in use.

In some forms the sagittal strap portion may connect to the head-mounted display unit.

In some forms the sagittal strap portion may be substantially inextensible.

In some forms, the dial adjustment mechanism includes an extending portion that retains some straps of the positioning and stabilising structure in tension at any rotational position of the dial.

Another form of the present technology comprises a head mounted display system for a person comprising:
  a head-mounted display unit comprising a display;
  a control system for operation of the head-mounted display system; and a positioning and stabilising structure configured to configured to hold the head-mounted display unit anterior to a user's eyes such that the display may be viewable by the user in use.

The head-mounted display system may be helmet mounted, may be configured for virtual reality display, may be configured for augmented reality display, may be configured for mixed reality display.

Another form of the present technology comprises a head-mounted display system for a person comprising a head-mounted display unit comprising a display; a control system for operation of the head-mounted display system; and a positioning and stabilising structure comprising an anterior support portion and a posterior support portion. The posterior portion may be configured to engage in use a posterior region of the person's head. The anterior support portion comprises: a left lateral portion configured to interconnect the posterior support portion and the head-mounted display system; and a right lateral portion configured to interconnect the posterior portion and the head-mounted display system.

In some examples: a) the head mounted display apparatus further comprises a light shield; b) the light shield may be constructed and arranged to substantially obstruct in use the receipt of ambient light upon an eye region of the person; c) the light shield may be configured for use in virtual reality display; d) the head-mounted display system comprises an interfacing structure constructed and arranged to contact in use an eye region of the person's face; e) the interfacing structure may be constructed from foam, silicone, and/or gel; f) the interfacing structure may be constructed from a light absorbing material; and/or g) the interfacing structure may be configured to function as a light shield.

In some examples: a) the head mounted display apparatus further comprises a sound system; b) a left ear transducer; and/or c) a right ear transducer.

In some examples: a) the head-mounted display unit comprises a binocular display unit; and/or b) the positioning and stabilising structure may be configured to maintain the binocular display unit in an operation position in use.

In some examples: a) the control system comprises a visual display controller and at least one battery; b) the at least one battery includes a first battery and a second battery; c) the first battery may be a lower power system battery configured to power an RT clock; d) the second battery may be a main battery; e) a battery support configured to retain the battery; f) the battery support may be connected to the positioning and stabilising structure using a tether; g) an orientation sensor configured to sense the orientation of the person's head in use; and/or h) a control support system.

In some examples: a) the positioning and stabilising structure comprises a frontal support portion configured to contact a region overlying a frontal bone of the person's head; and/or (b) the positioning and stabilising structure comprises a length adjustment mechanism for adjusting a length of a portion of the positioning and stabilising structure.

Another form of the present technology comprises a head mounted display apparatus for a person comprising: a display unit; a light shield; a control system comprising a visual display controller, at least one battery, a battery support, an orientation sensor, and a control support system; a sound system; and a positioning and stabilising structure comprising an anterior portion, a frontal portion, a left lateral portion, a right lateral portion, a posterior portion, and a length adjustment mechanism, wherein: the anterior portion comprises an eye cushion constructed and arranged to contact in use an eye region of the user; the posterior portion may be configured to engage in use a region of the person's head adjacent to a junction between the occipital bone and the trapezius muscle; the left lateral portion may be configured to interconnect the anterior portion and the posterior portion; the right lateral portion may be configured to interconnect the anterior portion and the posterior portion; the frontal portion configured to interconnect the anterior portion and the posterior portion; and the length adjustment mechanism adjustable to a first position and to a second position; wherein: the display unit comprises a binocular display unit; the light shield may be constructed and arranged to substantially obstruct in use the receipt of ambient light upon an eye region of the person; the orientation sensor configured to sense the orientation of the person's head in use the sound system comprises a left ear transducer and a right ear transducer; and the positioning and stabilising structure may be configured to maintain the binocular display unit in an operational position in use. The head-mounted display apparatus may comprise a positioning and stabilising structure and/or an interfacing structure substantially as described in any example disclosed herein.

Another form of the present technology comprises a head mounted display interface comprising an electronic display screen configured to output multiple images to a user; a display housing configured to at least partially house the electronic display screen; and a positioning and stabilising structure coupled to the display housing and supporting the display housing and the electronic display screen in an operating position, the positioning and stabilising structure being configured to provide a force against a user's head in order to counteract a moment produced by a combined weight of the electronic display screen and the display housing, and maintain a position of the electronic display screen anterior to the user's eyes while in the operating position. The positioning and stabilising structure may be substantially as described in any example disclosed herein.

Another form of the present technology comprises a positioning and stabilising structure for supporting an electronic display screen of a head-mounted display interface, the positioning and stabilising structure being configured to provide a force against a user's head in order to counteract a moment produced by a weight of the electronic display screen, and maintain a position of the electronic display screen anterior to the user's eyes while in use, the positioning and stabilising structure comprising a rear strap configured to contact a region of the user's head posterior to the coronal plane of the user's head. The rear strap configured to anchor the head-mounted display interface to the user's head.

Another form of the present technology comprises a positioning and stabilising structure for supporting an electronic display unit, the positioning and stabilising structure being configured to provide a force against a user's head in order to counteract a moment produced by a weight of the electronic display unit, and maintain a position of the electronic display unit anterior to the user's eyes while in use, the positioning and stabilising structure comprising headgear configured to be coupled to a housing of the electronic display unit and engage the user's head in order to support the housing.

Another aspect of the present technology comprises a display interface comprising: a display screen configured to output a computer generated image observable by a user; a display housing at least partially supporting the display screen; an interfacing structure coupled to the display screen and/or the display housing, the interfacing structure configured to be positioned and/or arranged to conform to at least a portion of the user's face; a positioning and stabilising structure configured to maintain a position of the display screen and/or the display housing relative to the user's eyes, the positioning and stabilising structure configured to provide a force against a user's head in order to counteract a moment produced by a weight of the display screen and/or the display housing; and a control system configured to assist in controlling the computer generated image observable by the user, the control system including at least one sensor.

Another aspect of the present technology comprises a virtual reality display interface comprising: a display screen configured to output a computer generated image observable by a user; a display housing at least partially supporting the display screen; an interface structure coupled to the display housing, the interfacing structure configured to be positioned and/or arranged to conform to at least a portion of a user's face, the interface structure including a light shield configured to at least partially block ambient light from reaching the user's eyes; a positioning and stabilising structure coupled to the display housing and configured to provide a force against a user's head in order to counteract a moment produced by a weight of the display screen and/or the display housing. The positioning and stabilising structure comprises; a pair of temporal connectors, each temporal connector of the pair of temporal connectors being directly coupled to the display housing, each temporal connector configured to overlay a respective temporal bone when in contact the user's head; and a rear support coupled to each of the temporal connectors, the rear support configured to contact a posterior portion of the user's head. The virtual reality display interface further comprises a control system configured to assist in controlling the computer generated image observable by the user, the control system including at least one sensor configured to measure movement of the user.

In some forms, the light shield may be configured to seal against the user's face and prevent ambient light from reaching the user's eyes.

In some forms, the display screen may be completely enclosed within the display housing.

In some forms, the light shield may be constructed from an opaque material.

In some forms, the interfacing structure may be constructed from a resilient material.

In some forms, the positioning and stabilising structure includes a rotational control configured to allow the display housing and/or the display interface to pivot relative to the rear support.

For example, the temporal arms may rotate with the display housing and/or the display interface. In other examples, the rotational control may couple the display housing to each of the temporal connectors, so that the display housing and/or the display interface pivots relative to the temporal connectors.

In some forms, the temporal connectors may include an adjustable length.

Another aspect of the present technology comprises an augmented reality display interface comprising; a display screen configured to output a computer generated image observable by a user, the display screen including at least one optical lens constructed from a transparent and/or translucent material configured to allow a user to observe their physical environment while observing the computer generated image; a display housing at least partially supporting the display screen; an interface structure coupled to the display housing and/or the display interface, the interfacing structure configured to be positioned and/or arranged to conform to at least a portion of a user's face; a positioning and stabilising structure coupled to the display housing and configured to provide a force against a user's head in order to counteract a moment produced by a weight of the display screen and/or the display housing. The positioning and stabilising structure comprises; a pair of temporal connectors, each temporal connector of the pair of temporal connectors being directly coupled to the display housing, each temporal connector configured to overlay a respective temporal bone when in contact the user's head; and a control system configured to assist in controlling the computer generated image observable by the user, the control system including at least one sensor configured to measure movement of the user.

In some forms, the positioning and stabilising structure further includes a rear support configured to overlay the user's occiput, each temporal connector coupled to the rear support.

In some forms, the augmented reality display interface further comprises a power source coupled to the display interface and/or to the positioning and stabilising structure.

For example, the power source may be a rechargeable battery.

In some forms, the display screen configured to selectively output a computer generated image observable by a user.

For example, the computer generated image may be displayed on the transparent and/or translucent material. The user may be able to see observe their physical environment regardless of whether the computer generated image is displayed on the transparent and/or translucent material.

Another aspect of the present technology comprises a virtual reality display interface comprising examples of the aspects of the head-mounted display system described above.

In examples of the aspects of the head-mounted display system described above, the display unit comprises a display configured to selectively output computer generated images that are visible to the user in an operational position.

In examples of the aspects of the head-mounted display system described above, the display unit comprises a housing.

In some forms, the housing supports a display.

In examples of the aspects of the head-mounted display system described above, the display unit comprises an interfacing structure coupled to the housing and arranged to be in opposing relation with the user's face in the operational position.

In some forms, the interfacing structure at least partially forms a viewing opening configured to at least partially receive the user's face in the operational position.

In some forms, the interfacing structure being constructed at least partially from an opaque material configured to at least partially block ambient light from reaching the viewing opening in the operational position.

In examples of the aspects of the head-mounted display system described above, the display unit comprises at least one lens coupled to the housing and disposed within the viewing opening and aligned with the display so that in the operational position.

In some forms, the user can view the display through the at least one lens.

In examples of the aspects of the head-mounted display system described above, a control system having at least one sensor in communication with a processor.

In some forms, the at least one sensor configured to measure a parameter and communicate a measured value to the processor.

In some forms, the processor configured to change the computer generated images output by the display based on the measured value.

Another aspect of the present technology comprises an augmented reality display interface comprising examples of the aspects of the head-mounted display system described above.

In examples of the aspects of the head-mounted display system described above, the display unit comprises a display constructed from a transparent or translucent material and configured to selectively provide computer generated images viewable by the user.

In examples of the aspects of the head-mounted display system described above, the display unit comprises a housing.

In some forms, the housing that supports a display.

In examples of the aspects of the head-mounted display system described above, the display unit comprises an interfacing structure coupled to the housing and arranged to be in opposing relation with the user's face in the operational position.

In examples of the aspects of the head-mounted display system described above, in an operational position, the positioning and stabilising structure configured to support the display unit.

In examples of the aspects of the head-mounted display system described above, the display configured to be aligned with the user's eyes in an operation position such that the user may at least partially view a physical environment through the display regardless of the computer generated images output by the display.

In examples of the aspects of the head-mounted display system described above, the head-mounted display system further comprising a control system having at least one sensor in communication with a processor.

In some forms, the at least one sensor may be configured to measure a parameter and communicate a measured value to the processor.

In some forms, the processor may be configured to change the computer generated images output by the display based on the measured value.

In some forms, the at least one lens includes a first lens configured to be aligned with the user's left eye in the operational position and a second lens configured to be aligned with the user's right eye in the operational position In some forms, the first lens and the second lens are Fresnel lenses.

In some forms, the display comprises a binocular display partitioned into a first second and a second section, the first section aligned with the first lens and the second section aligned with the second lens.

In some forms, a controller having at least one button selectively engageable by a user's finger, the controller being in communication with the processor and configured to send a signal to the processor when the at least one button is engaged, the processor configured to change the computer generated images output by the display based on the signal.

In some forms, the at least one lens includes a first lens configured to be aligned with the user's left eye in the operational position and a second lens configured to be aligned with the user's right eye in the operational position.

Another aspect of one form of the present technology is a positioning and stabilising structure that is constructed with a shape which is complementary to that of an intended wearer.

Another aspect of one form of the present technology is an interfacing structure that is constructed with a shape which is complementary to that of an intended wearer.

An aspect of one form of the present technology is a method of manufacturing apparatus.

An aspect of certain forms of the present technology is a positioning and stabilising structure that is easy to use, e.g. by a person who has limited dexterity, vision or by a person with limited experience in using a head-mounted display.

An aspect of certain forms of the present technology is an interfacing structure that is easy to use, e.g. by a person who has limited dexterity, vision or by a person with limited experience in using a head-mounted display.

An aspect of the present technology relates to a positioning and stabilising structure for an augmented reality display unit including a rear support structure arranged, in use, to contact regions of the user's head, and opposing temporal connectors that are disposed on opposing sides of the user's head in use, and extending along the temporal regions of the user's head in use, to interconnect the rear support structure to the display unit.

In some forms, the rear support structure includes a hoop having an occipital portion and a parietal portion. In some forms, the hoop or at least one of the occipital and parietal portions may be resiliently extensible along at least a portion of its length. In some forms, the hoop is flexible along at least a portion of its length. In some forms, where the rear support structure is a hoop, the occipital portion may extend low on the user's head such that it resists upward movement (as a result of its location in contact with the occipital region of the head) and as such provides an anchor for the system. In some forms, the hoop is orientated in a generally upright plane (such upright plane including, as an example, the coronal plane).

In some forms, the rear support structure is disposed posterior to the otobasion superior of the user.

In some forms, the temporal connectors are rigid along at least a portion of their length. In some forms, the temporal connectors each comprise a temporal arm having an anterior end connected to the display unit and a posterior end connected to the rear support structure. In some forms, the temporal arm is rigid. In some forms, the posterior end of the temporal arm is disposed posterior to the otobasion superior of the user.

In some forms, at least one of the temporal connectors further comprises an adjustment mechanism for adjustment of the positioning and stabilising structure to fit different size heads. In some forms, the adjustment mechanism is disposed at the connection between the posterior end of the temporal arm and the rear support structure.

In some forms, the rear support structure comprises a connection tab that connects to the temporal arm, and the adjustment mechanism allows for adjustment of the effective length of the connection tab. In some forms, a posterior end of the temporal arm incorporates an eyelet that is arranged to receive the connection tab, the adjustment mechanism comprising a releasable fastening arrangement to fasten the connection tab to the temporal arm. In some forms, the releasable fastening arrangement may be arranged to secure a free end of the connection tab back onto a proximal portion of the connection tab. The releasable fastening arrangement may take other forms, such as clips or retainers that allow a friction, interference, snap or other mechanical fixing arrangement.

In some forms, the positioning and stabilising structure may further include a forehead support connector that extends generally in the direction of the sagittal plane and connects the rear support structure to a superior edge region of the display unit. In some forms, the forehead support connector may comprise a strap. In some forms, the strap of the forehead support connector may be resiliently extensible along at least a portion of its length. In some forms, the strap of the forehead support connector may be flexible along at least a portion of its length.

In some forms, the forehead support connector may further include an adjustment mechanism for adjustment of the positioning and stabilising structure to fit different size heads. In some forms, the adjustment mechanism may adjust the effective length of the strap of the forehead support connector when the forehead support connector is in that form.

In some forms, the forehead support connector further comprises a forehead support rigidiser that provides rigidification to a portion of the forehead support connector. In some forms, the forehead support rigidiser provides rigidification to a portion of the forehead support connector located along the frontal region of the user's head. The extent and positioning of the forehead support rigidiser may assist in correct positioning of the display unit and relieve pressure being applied to the zygomatic bone of the user. In some forms, the forehead support rigidiser may be adjustable (angularly or translational) on other components of the forehead support connector, such as the strap of the forehead support connector, to allow fine positioning of the head-mounted display unit and assist in improving user comfort and fit.

In some forms, the positioning and stabilising structure further includes additional rigidisers which may bridge the rear support structure and the temporal connectors. In some forms, these additional rigidisers may assist in controlling the movement of the display unit about the rear support structure to further stabilise and support the system. In some forms, these additional rigidisers may limit hinging movement at the connection of the temporal connectors to the rear support structure. In some forms, these additional rigidisers may also extend through along the occipital region of the rear support structure to further anchor the display unit in its correct operational position. In some forms, these additional rigidisers may be adjustable (angularly or translational) on other components of the forehead support connector to further assist in comfort, adjustability, and fit.

In some forms, the positioning and stabilising structure may allow for upward, e.g., superior, pivoting movement of the display unit to allow for movement of the display unit to a non-operational position without removal of the positional and stabilising structure (e.g., flip-up version). In some forms, this pivoting arrangement may provide a release mechanism at the forehead support connector and/or provide limited hinging regions at the temporal connectors.

The positioning and stabilising structure in any form described above may be incorporated in a hood or other head wear either integrated therein or releasably connected thereto. The positional and stabilising structure may also include other components integrated therein such as audio, tactile (haptic) stimulation or feedback.

An aspect of the present technology relates to an augmented reality display system including an augmented reality display unit and a positioning and stabilising structure structured and arranged to hold the augmented reality display unit in an operational position over a user's face in use. The positioning and stabilising structure includes a rear support structure adapted to contact posterior regions of a user's head and at least one connector structured and arranged to interconnect the rear support structure to the augmented reality display unit. The rear support structure is in the form of a hoop comprising an occipital portion configured and arranged engage the user's head along the occipital bone (e.g., along a portion of the occipital bone adjacent a junction where the neck muscles attach to the occipital bone) in use.

An aspect of the present technology relates to a positioning and stabilising structure to hold an augmented reality display unit in an operational position over a user's face. The positioning and stabilising structure includes a rear support structure adapted to contact posterior regions of a user's head and at least one connector structured and arranged to interconnect the rear support structure to the augmented reality display unit. The rear support structure is in the form of a hoop comprising an occipital portion configured and arranged engage the user's head along the occipital bone (e.g., along a portion of the occipital bone adjacent a junction where the neck muscles attach to the occipital bone) in use.

An aspect of the present technology relates to a positioning and stabilising structure to hold an augmented reality display unit in an operational position over a user's face. The positioning and stabilising structure includes a rear support structure adapted to contact posterior regions of a user's head and opposing temporal connectors structured and arranged to interconnect the rear support structure to the augmented reality display unit. The opposing temporal connectors are adapted to be disposed on opposing sides of the user's head and extend along the temporal regions of the user's head. The rear support structure is in the form of a hoop comprising an occipital portion configured and arranged engage the user's head along the occipital bone (e.g., along a portion of the occipital bone adjacent a junction where the neck muscles attach to the occipital bone) in use.

An aspect of the present technology relates to an augmented reality display system including an augmented reality display unit and a positioning and stabilising structure structured and arranged to hold the augmented reality display unit in an operational position over a user's face in use. The positioning and stabilising structure includes a rear support structure adapted to contact posterior regions of a user's head and at least one connector structured and arranged to interconnect the rear support structure to the augmented reality display unit. At least the rear support structure comprises a textile material configured to conform to the posterior regions of the user's head.

An aspect of the present technology relates to a positioning and stabilising structure to hold an augmented reality display unit in an operational position over a user's face. The positioning and stabilising structure includes a rear support structure adapted to contact posterior regions of a user's head and at least one connector structured and arranged to interconnect the rear support structure to the augmented reality display unit. At least the rear support structure comprises a textile material configured to conform to the posterior regions of a user's head.

An aspect of the present technology relates to an augmented reality display system including an augmented reality display unit and a positioning and stabilising structure structured and arranged to hold the augmented reality display unit in an operational position over a user's face in use. The positioning and stabilising structure includes a rear support structure adapted to contact posterior regions of a user's head and opposing temporal connectors structured and arranged to interconnect the rear support structure to the augmented reality display unit, the opposing temporal connectors adapted to be disposed on opposing sides of the user's head and extend along the temporal regions of the user's head. At least the rear support structure comprises a textile material configured to conform to the posterior regions of the user's head.

An aspect of the present technology relates to a positioning and stabilising structure to hold an augmented reality display unit in an operational position over a user's face. The positioning and stabilising structure includes a rear support structure adapted to contact posterior regions of a user's head and opposing temporal connectors structured and arranged to interconnect the rear support structure to the augmented reality display unit, the opposing temporal connectors adapted to be disposed on opposing sides of the user's head and extend along the temporal regions of the user's head. At least the rear support structure comprises a textile material configured to conform to the posterior regions of the user's head.

An aspect of the present technology relates to a positioning and stabilising structure to hold an augmented reality display unit in an operational position over a user's face. The positioning and stabilising structure includes a rear support structure adapted to contact regions of a user's head and at least one connector or strap structured and arranged to interconnect the rear support structure to the augmented reality display unit.

The positioning and stabilising structure and/or the augmented reality display unit may be configured to help distribute contact forces from more sensitive regions of the user's face (forehead, nose) to regions that are better suited to oppose a force applied. For example, the rear support structure may be sufficiently flexible to evenly and snugly engage the rear of the user's head, e.g., anchor on the occipital bone but above the neck muscles, and/or have increased rigidity in one or more portions to better support the load of the augmented reality display unit in a comfortable and sustainable manner. For example, the rear support structure may be made of a strap material (e.g., textile) that is breathable and flexible to allow it to adjust to the shape and/or size of the user's head, where certain parts of the strap material may be rigidised and/or a rigid portion added (e.g., sewn, laminated, clipped, inserted into a pocket, overmolded, and/or ultrasonically welded into place) to help maintain stability and offset a portion of the force applied to a portion of the user's face via the augmented reality display unit.

In an example, the positioning and stabilising structure and/or the augmented reality display unit may be configured to cooperatively work together to reduce the force applied to the user's forehead and/or nasal bridge, by effectively transferring those forces to the rear support and/or to the at least one connector or strap(s), and/or by simply distributing the forces from the augmented reality display unit more evenly along the augmented reality display unit and/or the rear support structure and/or the at least one connector or strap(s). This is done in a way that adds comfort and/or stability, e.g., to prevent the augmented reality unit from sliding down the user's face/forehead.

An aspect of the present technology relates to an augmented reality display system comprising an augmented reality display unit and a positioning and stabilising structure structured and arranged to hold the augmented reality display unit in an operational position over a user's face in use. The positioning and stabilising structure comprises a rear support structure adapted to contact posterior regions of a user's head and at least one connector structured and arranged to interconnect the rear support structure to the augmented reality display unit. The rear support structure comprises an occipital portion configured and arranged engage the user's head along a portion of the occipital bone adjacent a junction where the neck muscles attach to the occipital bone in use.

In some forms, the rear support structure is in the form of a hoop. The hoop may comprise the occipital portion and a parietal portion adapted to engage the user's head proximate the parietal bone in use.

In some forms, the rear support structure may be resiliently extensible along at least a portion of its length.

In some forms the rear support structure may be flexible along at least a portion of its length.

In some forms, the at least one connector comprises opposing temporal connectors structured and may be arranged to interconnect the rear support structure to the augmented reality display unit. The opposing temporal connectors may be adapted to be disposed on opposing sides of the user's head and extend along the temporal regions of the user's head.

In some forms, each of the temporal connectors may be rigid along at least a portion of its length.

In some forms, each of the temporal connectors may comprise a temporal arm having an anterior end connected to the display unit and a posterior end connected to the rear support structure.

In some forms, the temporal arm may be rigid.

In some forms, the posterior end of the temporal arm may be disposed at or posterior to the otobasion superior of the user.

In some forms, at least one of the temporal connectors may further comprise an adjustment mechanism for adjustment of the positioning and stabilising structure to fit different size heads.

In some forms, the adjustment mechanism may be disposed at a connection between the posterior end of the temporal arm and the rear support structure.

In some forms, the rear support structure may comprise a connection tab that connects to the temporal arm and the adjustment mechanism to allow for adjustment of an effective length of the tab.

In some forms, the posterior end of the temporal arm may include an eyelet that is arranged to receive the connection tab. The adjustment mechanism may comprise a releasable fastening arrangement to fasten the connection tab to the temporal arm.

In some forms, the releasable fastening arrangement may be arranged to secure a free end of the connection tab back onto a proximal portion of the connection tab.

In some forms, the at least one connector may further comprise a forehead support connector that extends generally in the direction of the sagittal plane and connects the rear support structure to a superior edge region of the display unit.

In some forms, the forehead support connector may comprise a strap.

In some forms, the strap of the forehead support connector may be resiliently extensible along at least a portion of its length.

In some forms, the strap of the forehead support connector may be flexible along at least a portion of its length.

In some forms, the forehead support connector further may comprise an adjustment mechanism for adjustment of the positioning and stabilising structure to fit different size heads.

In some forms, the adjustment mechanism may adjust an effective length of the strap of the forehead support connector.

In some forms, the forehead support connector may further comprise a forehead support rigidiser that provides rigidification to a portion of the forehead support connector.

In some forms, the forehead support rigidiser may provide rigidification to a portion of the forehead support connector located at a frontal portion of the user's head.

In some forms, the augmented reality display unit may comprise a housing containing a display that is visible to the user when the augmented reality display unit is in the operational position. The augmented reality display unit may also comprise a user interface structure constructed arranged to be in opposing relation with the user's face, the user interface structure extending at least partially about the display.

In some forms, the augmented reality display system may further comprise at least one battery pack supported on the positioning and stabilising structure.

In some forms, the at least one battery pack may be disposed on the occipital portion of the rear support portion.

In some forms, the augmented reality display system may comprise two battery packs disposed on a respective lateral side of the sagittal plane of the user's head in use.

In some forms, the occipital portion may be formed in two portions and battery packs are spaced apart in use to allow the two portions of the occipital portion to connect to each other at or proximate the sagittal plane of the user's head in use.

In some forms, the two portions of the occipital portion are releasably attachable to each other at a pair of connection portions. Each connection point may be provided to a respective one of the two portions of the occipital portion.

In some forms, the occipital strap portion may be formed in two portions each located on a respective lateral side of the sagittal plane of the user's head in use. The two portions of the occipital strap portion are not connected to each other in use. The medial ends of the two portions of the occipital strap portion are spaced apart from each other and are each spaced laterally from the sagittal plane in use.

In some forms, the augmented reality display system may further comprise a power cable connecting the battery pack to the augmented reality display unit to provide power from the battery to the augmented reality display unit in use.

In some forms, a portion of the power cable is located within the battery pack and is able to be extended from and retracted into the battery pack.

An aspect of the present technology relates to an augmented reality display system, comprising an augmented reality display unit and a positioning and stabilising structure structured and arranged to hold the augmented reality display unit in an operational position over a user's face in use. The positioning and stabilising structure comprises a rear support structure adapted to contact posterior regions of a user's head and opposing temporal connectors structured and arranged to interconnect the rear support structure to the augmented reality display unit. The opposing temporal connectors are adapted to be disposed on opposing sides of the user's head and extend along the temporal regions of the user's head. At least the rear support structure comprises a textile material configured to conform to the posterior regions of the user's head.

In some forms the textile material may be resiliently extensible along at least a portion of its length.

In some forms, the textile material may be flexible along at least a portion of its length.

In some forms, the rear support structure may further comprise a rigidiser along at least a portion of the textile material.

In some forms, each of the opposing temporal connectors may comprise a textile material.

In some forms, each of the opposing temporal connectors may further comprise a rigidiser along at least a portion of the textile material.

In some forms, the augmented reality display system may further comprise a forehead support connector that extends generally in the direction of the sagittal plane and may connect the rear support structure to a superior edge region of the augmented reality display unit.

In some forms, the augmented reality display unit may comprise a housing containing a display that is visible to the user when the augmented reality display unit is in the operational position. The augmented reality display unit may also comprise a user interface structure constructed and arranged to be in opposing relation with the user's face. The user interface structure may extend at least partially about the display.

An aspect of the present technology relates to an augmented reality display system comprising an augmented reality display unit and a positioning and stabilising structure structured and arranged to hold the augmented reality display unit in an operational position over a user's face in use. The positioning and stabilising structure is configured to support the display unit away from the user's nose.

In some forms, the positioning and stabilising structure may comprise an over-extension portion that is adapted to contact the parietal region of the user's head to support the display unit. The positioning and stabilising structure may also comprise at least one connector structured and arranged to interconnect the over-extension portion to the augmented reality display unit.

In some forms, the over-extension portion may be shaped to compliment the shape of the user's head so as to hold against the user's head. In some forms, the over-extension portion may be generally S-shaped when viewed in profile.

In some forms, the over-extension portion may comprise a lower arm that extends in the temporal region posterior to the otobasion superior of the user, an upper arm that extends forward of the coronial plane, and a spine that extends in the direction of the sagittal plane towards the occipital region of the user's head.

In some forms, the augmented reality display system may further comprise at least one battery pack supported on the positioning and stabilising structure. In some forms, the at least one battery pack may be mounted on the spine.

In some forms, the spine may include a movable counterweight to assist in supporting the display system on the user's head. In some forms, the at least one counterweight may comprise the battery pack.

In some forms, the lower arm may support componentry of the display system.

In some forms, the positioning and stabilising structure may comprise a rear support structure that comprises lateral hook portions that locate below the user's occipital bone. The positioning and stabilising structure may also comprise a forehead support connector that extends generally in the direction of the sagittal plane and connects the rear support structure to a superior edge region of the display unit.

In some forms, the forehead support connector may comprise an adjustment mechanism for adjustment of the positioning and stabilising structure to fit different size heads.

In some forms, the lateral hook portions may support componentry of the display system.

An aspect of the present technology relates to a positioning and stabilising structure to hold an augmented reality display unit in an operational position over a user's face in use. The positioning and stabilising structure comprises at least one strap and at least one rigidiser arm. The positioning and stabilising structure is arranged to position the at least one strap around the at least one rigidiser arm.

An aspect of the present technology relates to a positioning and stabilising structure including at least one strap in the form of a sleeve configured to removably connect to a rigidiser arm.

An aspect of the present technology relates to a display system comprising a display unit, a pair of rigidiser arms, and a headgear connector having a spacer forming a gap between the display unit and each rigidiser arm. In some forms, a strap includes a cavity configured to receive the pair of rigidiser arms. In some forms, the strap includes an opening configured to connected to the headgear connector via the spacer.

An aspect of the present technology relates to a positioning and stabilising structure configured to connect to a rigidised arm in order to maintain the shape of the rigidised arm. In some forms, the positioning and stabilising structure is removable from the rigidised arm. In some forms, the positioning and stabilising structure includes at least one electronic component configured to electrically connect to a display unit when connected to the positioning and stabilising structure is connected to the rigidised arm.

An aspect of the present technology relates to an augmented reality display system comprising an augmented reality display unit having a display and a positioning and stabilising structure to hold the augmented reality display unit in an operational position over a user's face in use. The positioning and stabilising structure comprises at least one strap and at least one rigidiser arm. The positioning and stabilising structure is arranged to position the at least one strap and the at least one rigidiser arm with regard to one another such that the at least one rigidiser arm imparts a predetermined shape to the at least one strap at a rigidised portion of the at least one strap.

In some forms, the positioning and stabilising structure may be arranged to position the at least one strap and the at least one rigidiser arm with regard to one another to allow at least the rigidised portion of the at least one strap to move relative to the at least one rigidiser arm.

In some forms, the at least one rigidiser arm may be affixed to the at least one strap at one localised point or area only.

In some forms, the at least one rigidiser arm may be affixed to the at least one strap in a limited area of the at least one strap. In some forms, the limited area may be adjacent a pocket or a sleeve opening of the at least one strap.

In some forms, the at least one rigidiser arm may be multi-axially deformable to conform to a user's facial profile.

In some forms, the at least one strap may be made of an elastic textile material and the positioning and stabilising structure may be arranged such that the at least one strap is substantially free to move by elastically expanding and/or contracting, relative to the at least one rigidiser arm, and along a longitudinal axis of the at least one strap and/or rigidiser arm.

In some forms, the at least one strap has a stretchable length that remains substantially unaltered relative to the at least one strap without the at least one rigidiser arm.

In some forms, the elastic textile material may be any one from the group consisting of: elastane, TPE, nylon and silicone.

In some forms, the positioning and stabilising structure may be able to stretch along its substantially entire length.

In some forms, the at least one strap may be stretchable and is in the form of a sleeve arranged to slip over the at least one rigidiser arm. The arrangement may be such that the at least one strap maintains its substantially entire stretchable length and is able to substantially freely stretch over the at least one rigidiser arm.

In some forms, the at least one strap may comprise a hollow sleeve for receiving the at least one rigidiser arm in place and at least one opening, for receiving the at least one rigidiser arm into the sleeve. In some forms, the sleeve and the at least one rigidiser arm may be arranged to allow the at least one rigidiser arm to move substantially axially inside the sleeve.

In some forms, an end portion of the at least one rigidiser arm may be affixed to the at least one strap.

In some forms, the at least one rigidiser arm may be affixed to the at least one strap by sewing, welding, gluing, heat staking, clamping, buttoning, snapping a cover over an end, and/or snapping on an external part.

In some forms, the imparted predetermined shape may direct pressure of the positioning and stabilising structure to predetermined portions of the user's face.

In some forms, a plurality of attachment points for attachment may be provided such that at least one fixation location may be chosen and varied to allow adjustment of an elastic length of the at least one strap.

In some forms, the at least one rigidiser arm may be incapable of stretching and is relatively more rigid than the at least one strap.

In some forms, the augmented reality display system may further comprise two or more rigidiser arms symmetrically disposed on opposite sides of a user's face.

In some forms, the two or more rigidiser arms may form opposing temporal connectors adapted to be disposed on opposing sides of the user's head and extend along the temporal regions of the user's head.

In some forms, the at least one rigidiser arm may be completely removable from the at least one strap.

In some forms, the positioning and stabilising structure may maintain its entire operational length and may be able to freely stretch along the at least one rigidiser arm.

In some forms, the at least one strap may include two side strap portions arranged to extend from a user interface along the sides of a user's head, and two back strap portions arranged to extend along the back of the user's head.

In some forms, the two back strap portions may not be adjustable, except through the elasticity of the back strap portions or through increasing the back strap portions in tightness equally by shortening the total length of the positioning and stabilising structure.

In some forms, the augmented reality display system may further comprise three, four or more separate straps connected by two or more joints.

In some forms, the at least one strap may comprise two pockets, each receiving a rigidiser arm to releasably secure the at least one strap to the rigidiser arms.

In some forms, the at least one strap may comprise a back portion that is split into at least two back straps. In some forms, the at least two back straps may comprise a first back strap adapted to engage a user proximal to the crown of the head and a second back strap adapted to engage the user proximal to the rear of the head. In some forms, each of the at least two back straps may be adapted to retain the augmented reality display unit on the nose of a user with substantially equal tension forces on each of the at least two back straps. In some forms, when the augmented reality display system is donned by a user each of the at least two back straps may be in tension with a substantially equal force.

While in form set forth above, the augmented reality display unit is described as being supported on the nose of a user, the augmented reality display unit may additionally, or alternatively, be supported against portions of the user's face. For example, the augmented reality display unit may be supported on a user's nose bridge and cheeks (i.e. cheek bones), or in other forms, supported by the user's forehead and cheeks (i.e. excluding the nose bridge).

In some forms, each of the at least two back straps may be non-independently adjustable such that the at least two back straps naturally center on respective sides of the crown of the head of a user.

In some forms, the at least two back straps are symmetrical.

In some forms, the at least one electrical component is a battery configured to provide electrical charge to the augmented reality display unit. In some forms, the at least one electrical component is a flow generator that provides airflow to a space proximate to the augmented reality display unit and/or draws air from the space proximate to the augmented reality display unit. In some forms, the flow generator includes a bidirectional blower. In some forms, the at least one strap includes a conduit that is configured to convey airflow to or from the flow generator.

In some forms, the at least one rigidiser arm includes a headgear connector having an electrical connector and configured to engage a complementary connector of the at least one strap. In some forms, a spacing element spaces the at least one rigidiser arm away from the augmented reality display unit. In some forms, the at least one strap engages the spacing element.

An aspect of the present technology relates to a method for donning an augmented reality display system on the head of a user. The augmented reality display system includes an augmented reality display unit and a positioning and stabilising structure. The method comprises: stretching the positioning and stabilising structure away from the augmented reality display unit; placing the augmented reality display unit over the face of the user; releasing a portion of tension of the positioning and stabilising structure by locating a rear portion of the positioning and stabilising structure against a rear portion of the user's head; and adjusting tension of the positioning and stabilising structure by pulling apart back straps of the rear portion of the positioning and stabilising structure.

A further aspect of the present technology relates to a method for repeatedly engaging a positioning and stabilising structure to an augmented reality display system. The method comprises: inserting a rigidiser arm via an opening of a hollow stretchable fabric strap into a portion of the strap; and releasably securing an end portion of the strap to the rigidiser arm. The positioning and stabilising structure is arranged to position the strap and the rigidiser arm with regard to one another such that the rigidiser arm imparts a predetermined shape to the strap at a rigidised portion while allowing the rigidised portion of the strap to freely elongate relative to the rigidiser arm in a direction parallel to a longitudinal axis of the rigidiser arm.

In some forms of the method, the rigidiser arm may be inextensible.

In some forms of the method, the rigidiser arm may be permanently connected to an augmented reality display unit of the augmented reality display system.

In some forms of the method, the end portion of the strap may be a pocketed end that is secured to a corresponding catching member of the rigidiser arm. In some forms of the method, the pocketed end may be wrapped over the corresponding catching member of the rigidiser arm. In some forms of the method, the catching member may be an edge of the rigidiser arm.

An aspect of the present technology relates to a head-mounted display system, comprising: a head-mounted display unit having a display housing, and a user interface structure constructed and arranged to be in opposing relation with the user's face, the user interface structure extends about a display contained by the display unit housing.

In some forms, the user interface structure is spaced from the display unit housing along at least a portion of the structure to form one or more gaps therebetween.

In some forms, the user interface structure is in the form of at least one stabilising flange.

In some forms, the stabilising flange is positioned in-use to engage with the user's face generally around a periphery of a user's eyes.

In some forms, the flange, in-use, overlays one or more of a portion of the frontal bone region and each of the left and right infraorbital margin regions of the face.

In some forms, the head-mounted display system further comprises a positioning and stabilising structure structured and arranged to hold the head-mounted display unit in an operational position over a user's face in use.

Another aspect of the present technology relates to a head mounted-display system or assembly including a positional and stabilising structure in any form described above, and a display unit connected thereto.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE DRAWINGS

The present technology is illustrated by way of example, and not by way of limitation, in the figures of the accompanying drawings, in which like reference numerals refer to similar elements including.

Exemplary bones shown include frontal, sphenoid, nasal, zygomatic, maxilla, mandible, parietal, temporal and occipital.

Figure 1A:
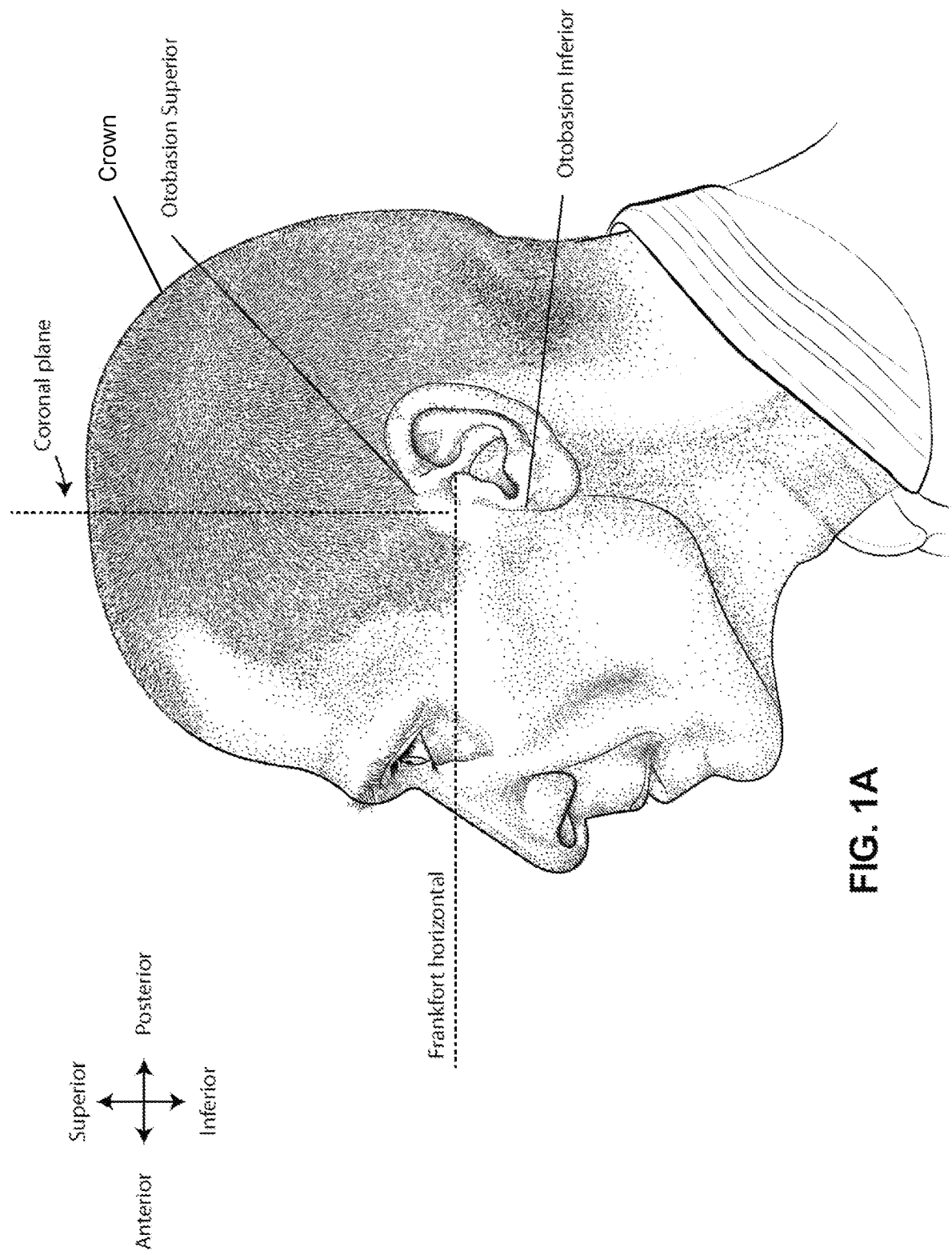
FIG. 1A is a side view of a head with several features of surface anatomy identified including otobasion superior and otobasion inferior. The approximate location of the Frankfort horizontal is indicated. The coronal plane is also indicated. Also indicated are the directions superior & inferior, and anterior & posterior.
Figures 1B, 1C:
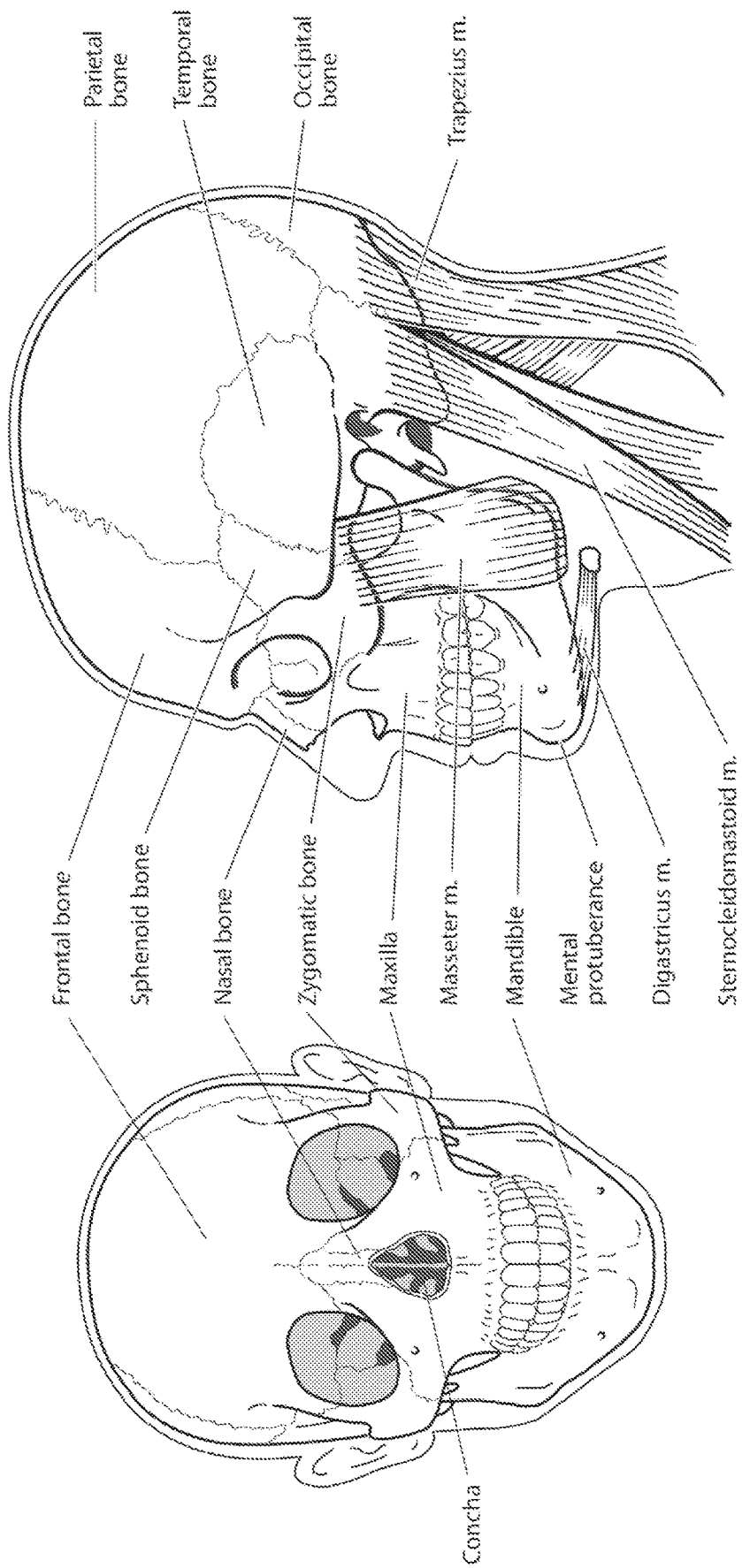
FIG. 1B shows a front view of the bones of a skull including the frontal, nasal and zygomatic bones.
FIG. 1C shows a lateral view of a skull with the outline of the surface of a head, as well as several muscles.
Figure 2A:
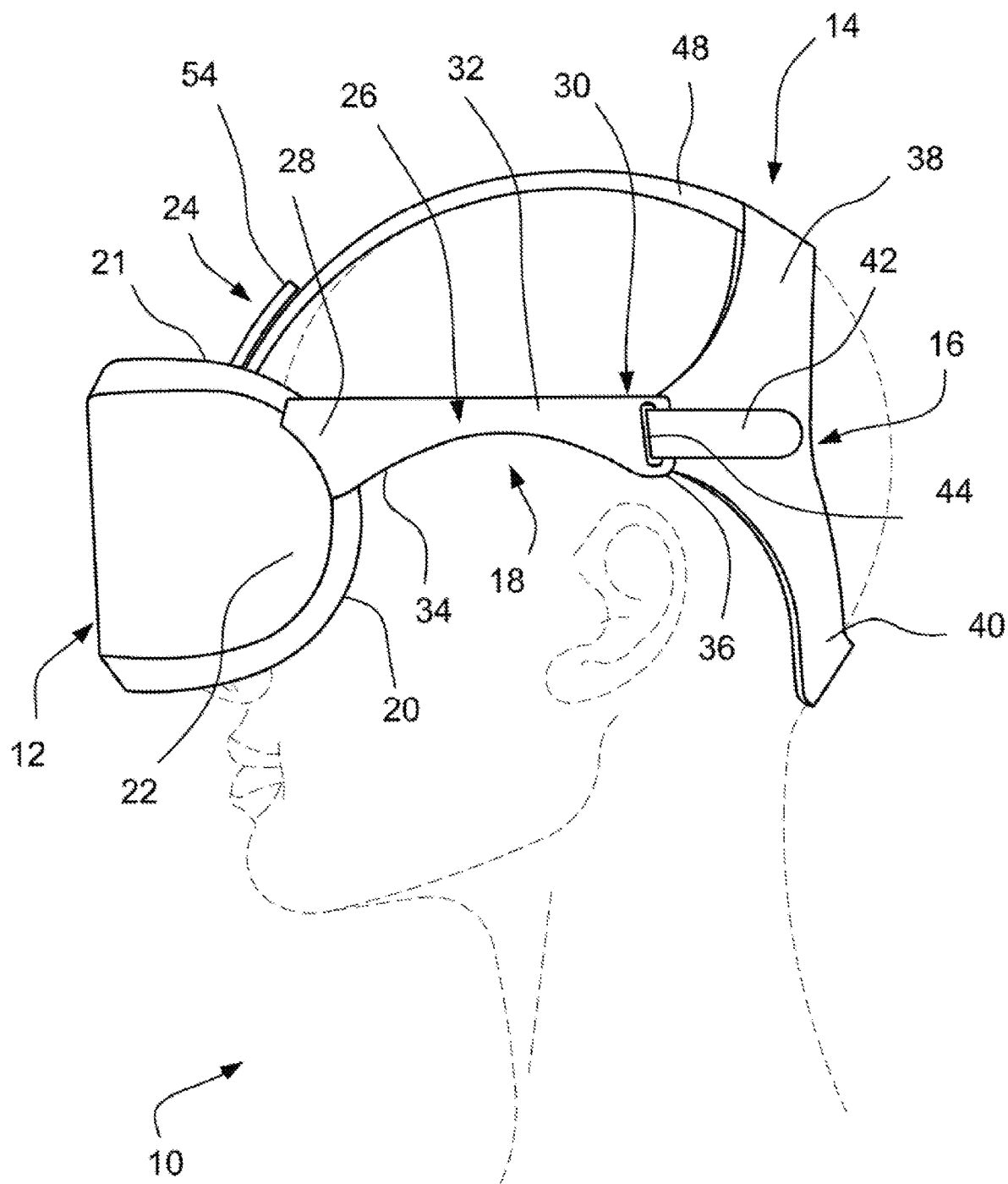
Figure 2B:
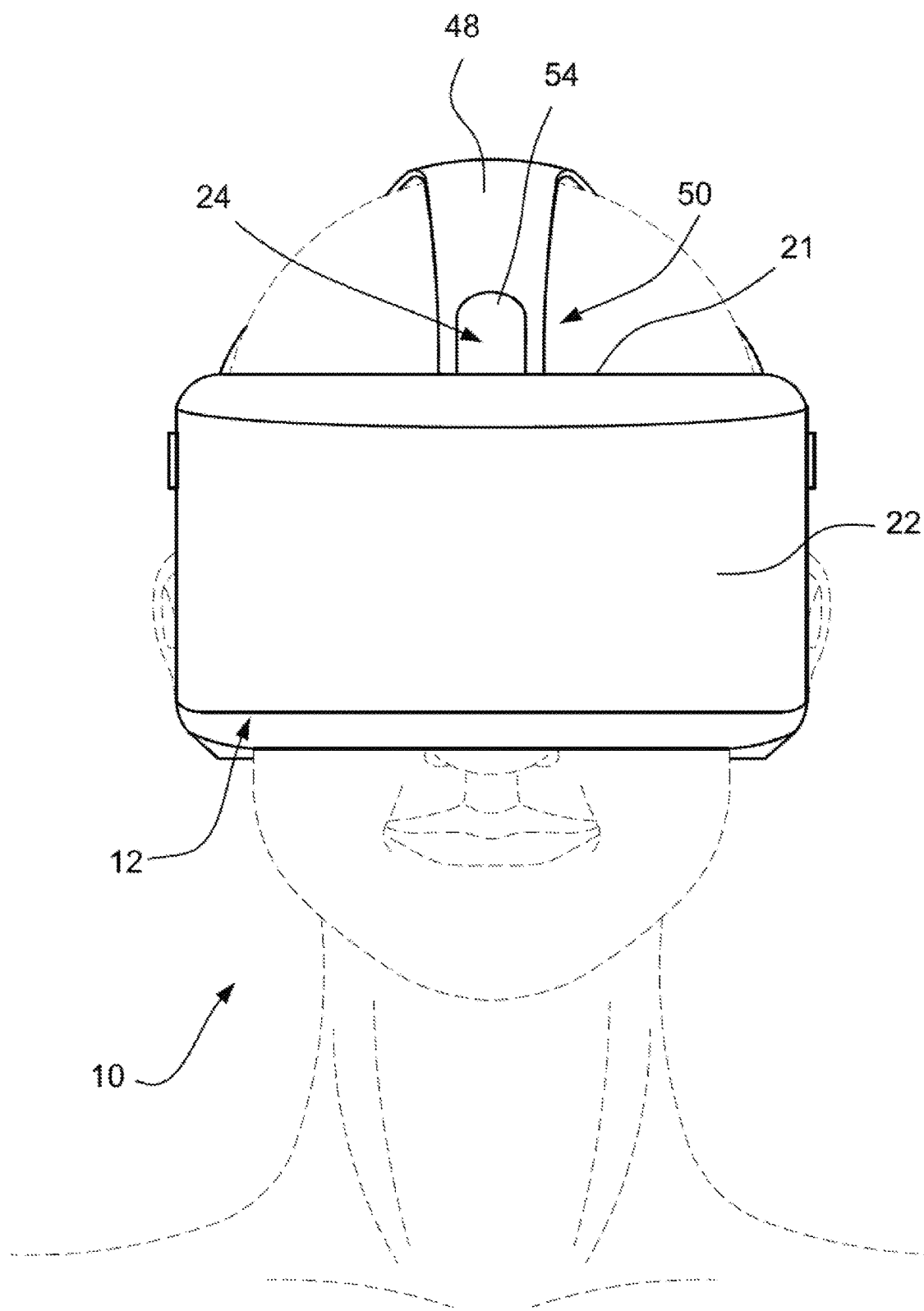
Figure 2C:
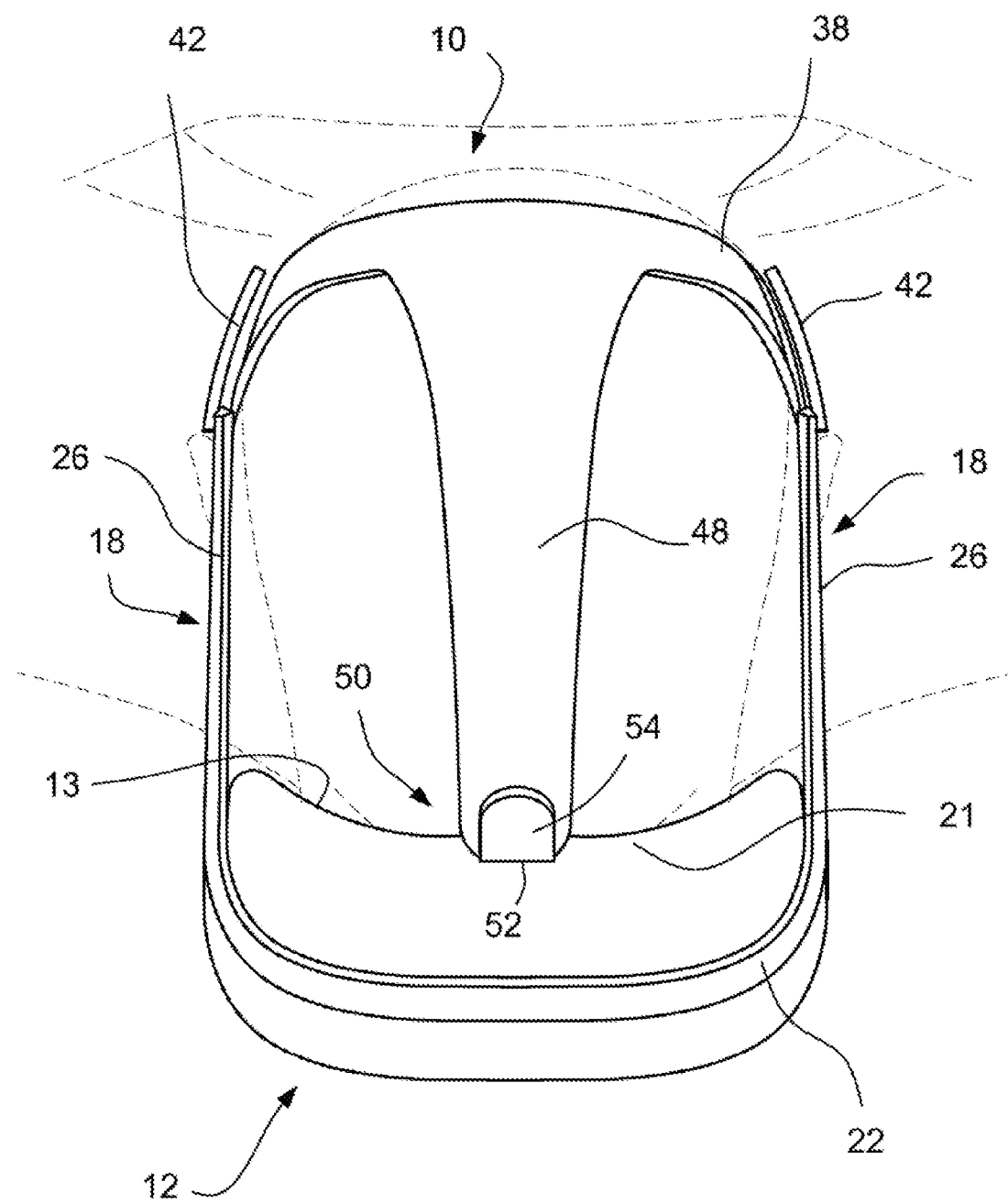

FIGS. 2A to 2C are respective side, front and top views of a head-mounted display assembly in-use according to a first example of the present technology.

Figure 2D:
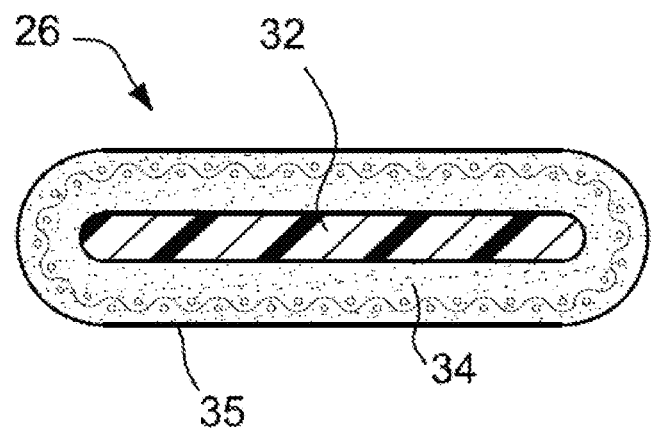

FIG. 2D is a cross-sectional view of a temporal arm of the head-mounted display assembly of FIGS. 2A to 2C according to an example of the present technology.

Figure 2E:
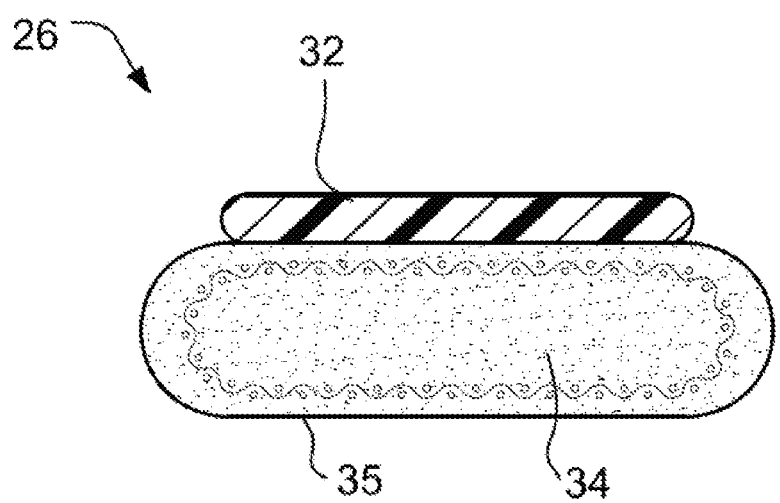

FIG. 2E is a cross-sectional view of a temporal arm of the head-mounted display assembly of FIGS. 2A to 2C according to another example of the present technology.

Figure 3A:
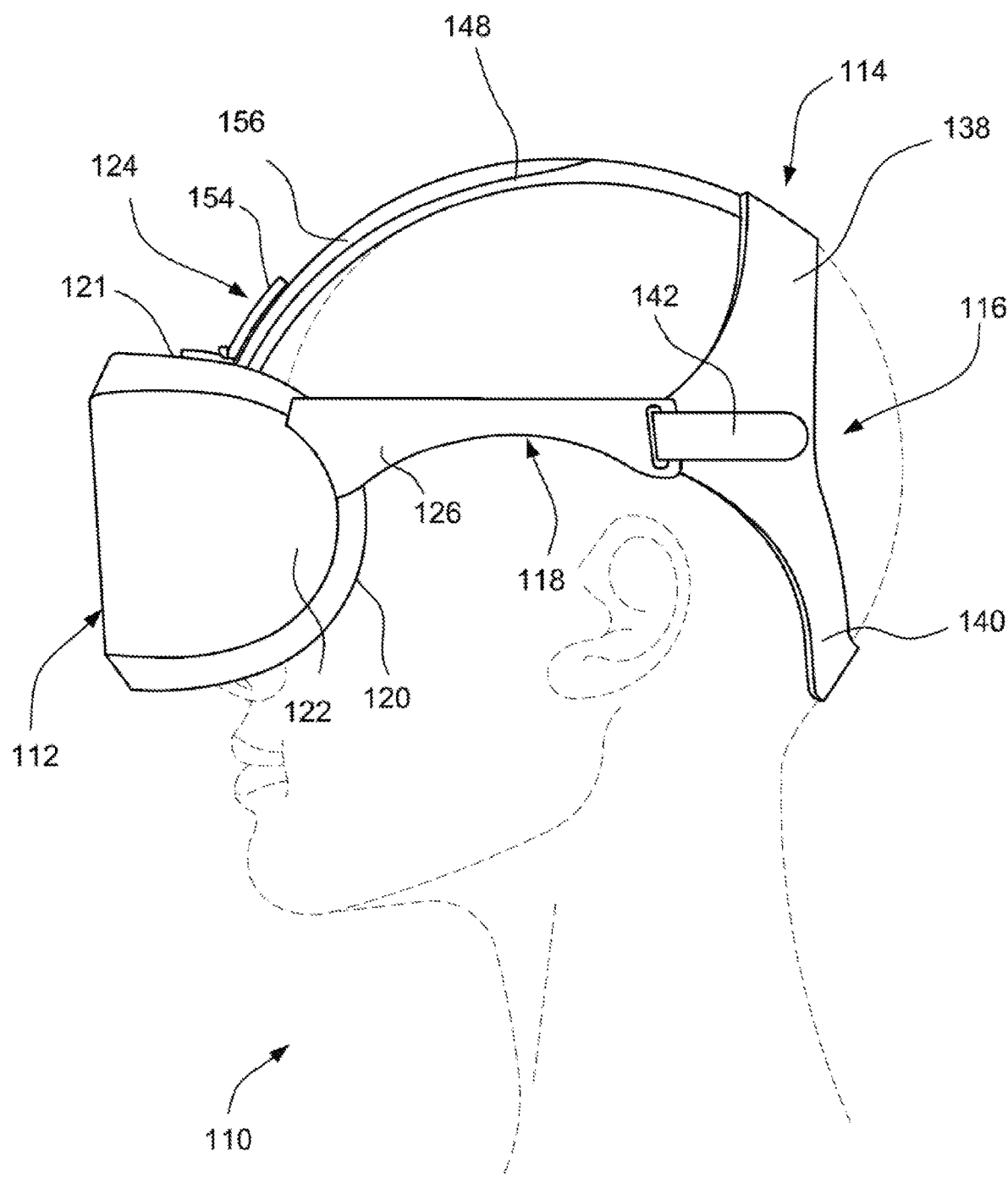
Figure 3B:
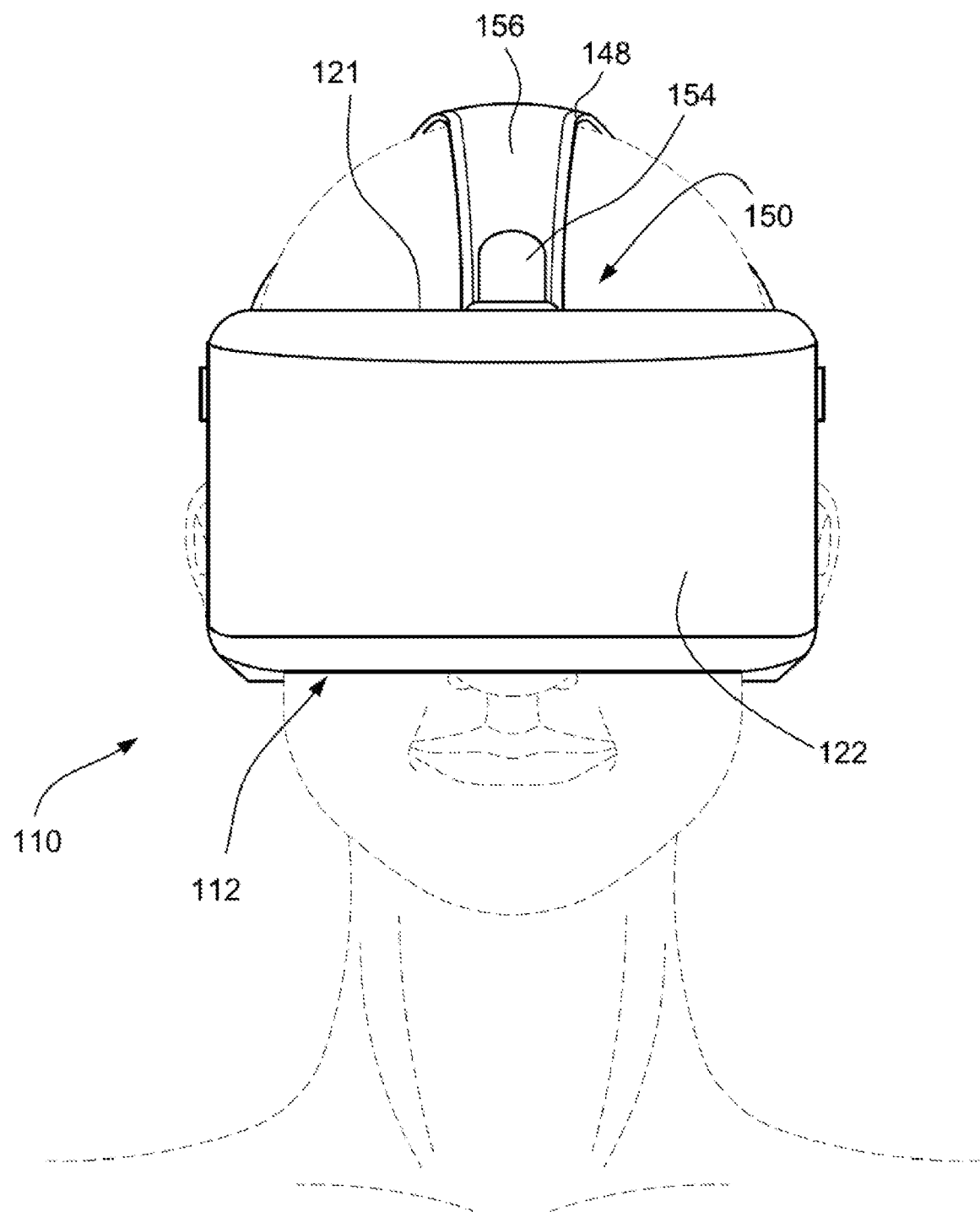
Figure 3C:
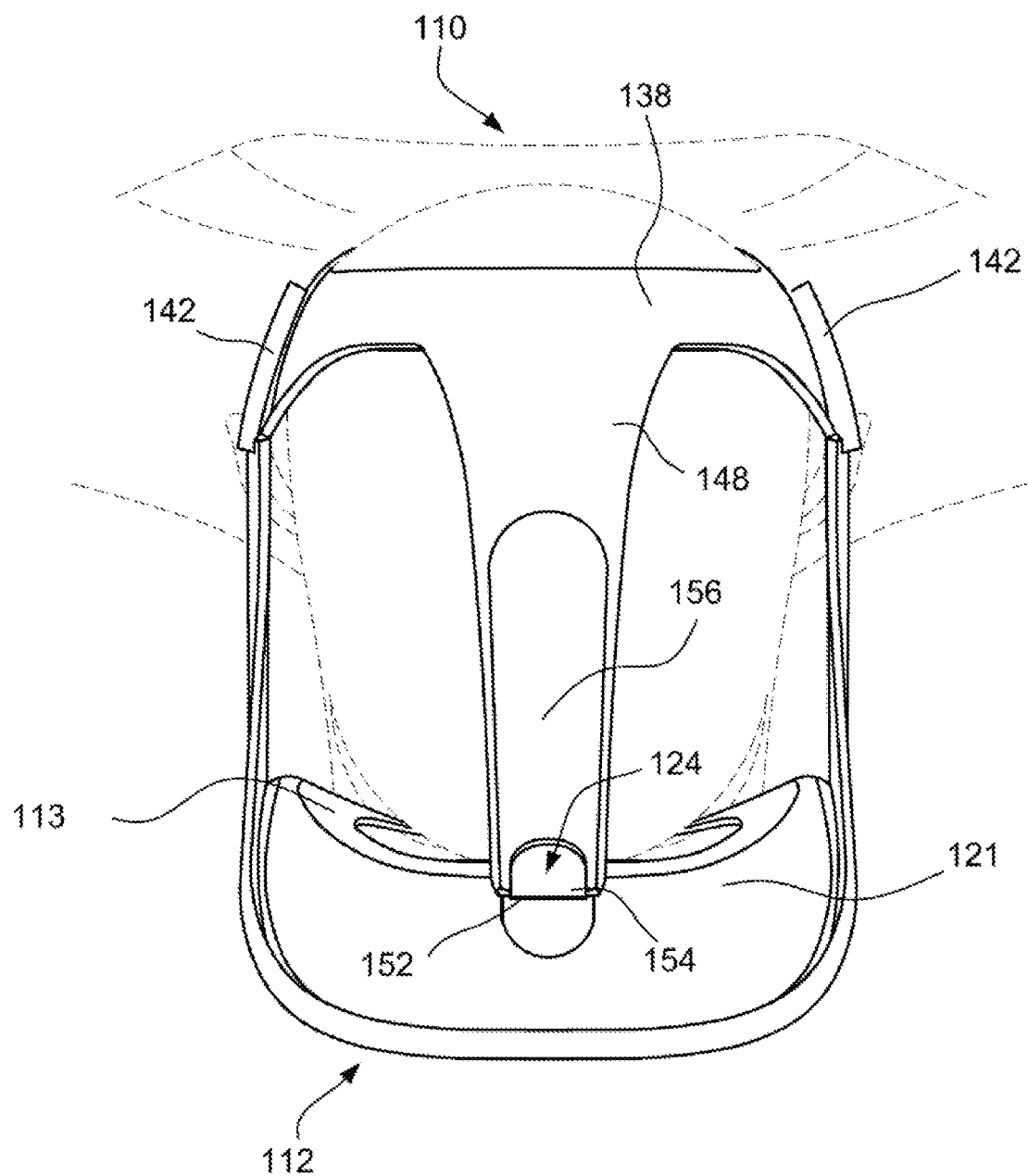

FIGS. 3A to 3C are respective side, front and top views of a head-mounted display assembly in-use according to a second example of the present technology.

Figure 4A:
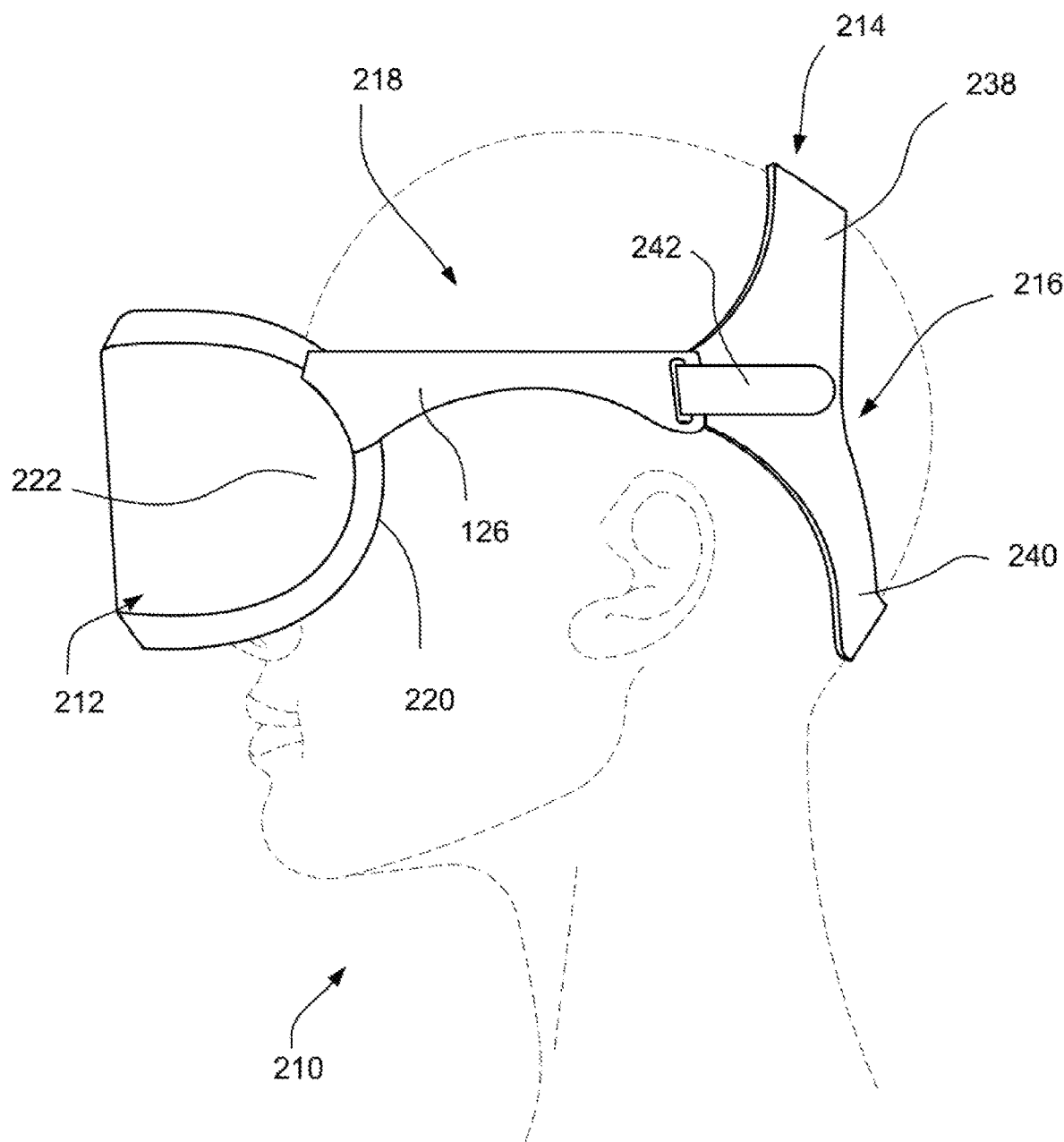
Figure 4B:
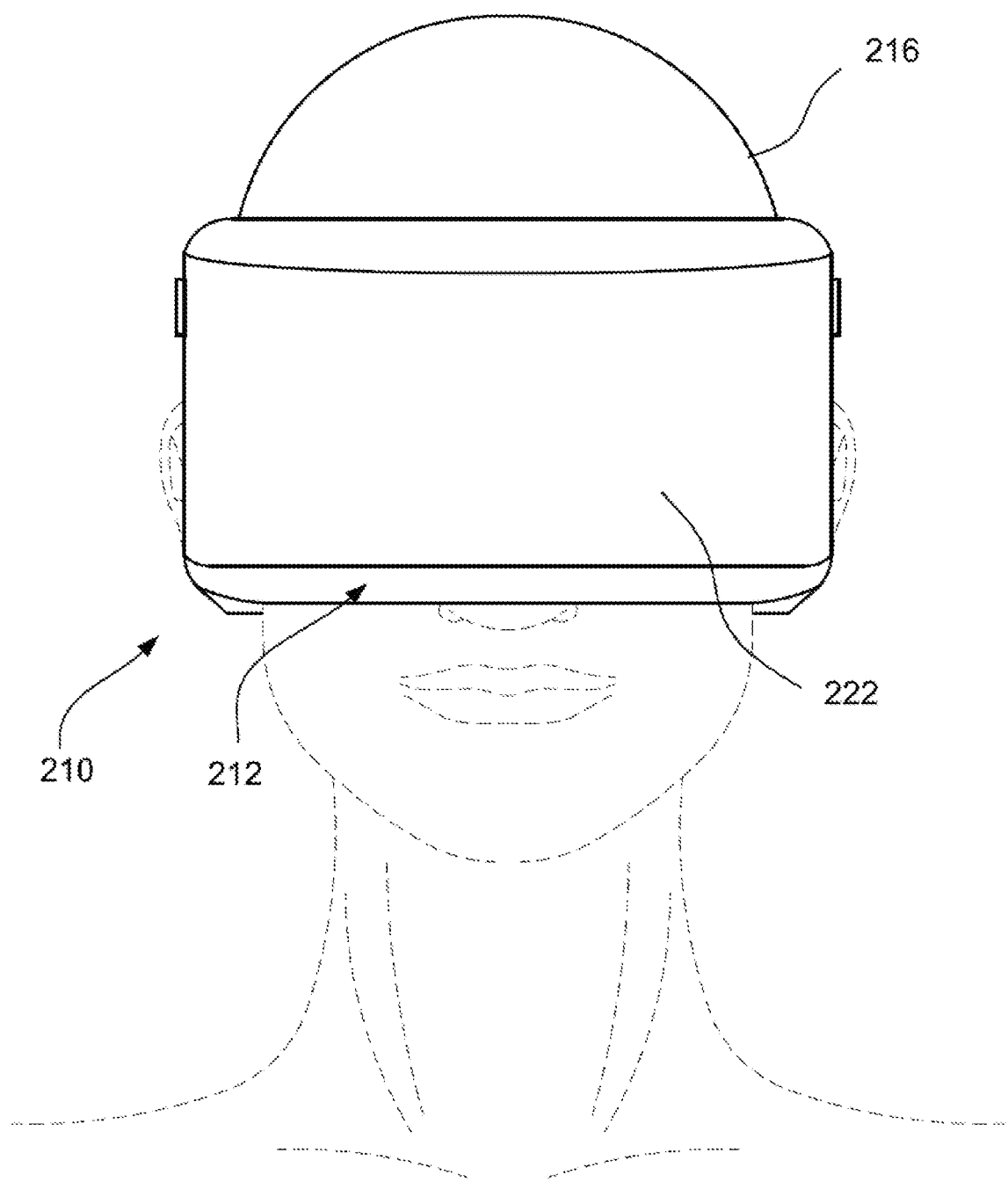
Figure 4C:
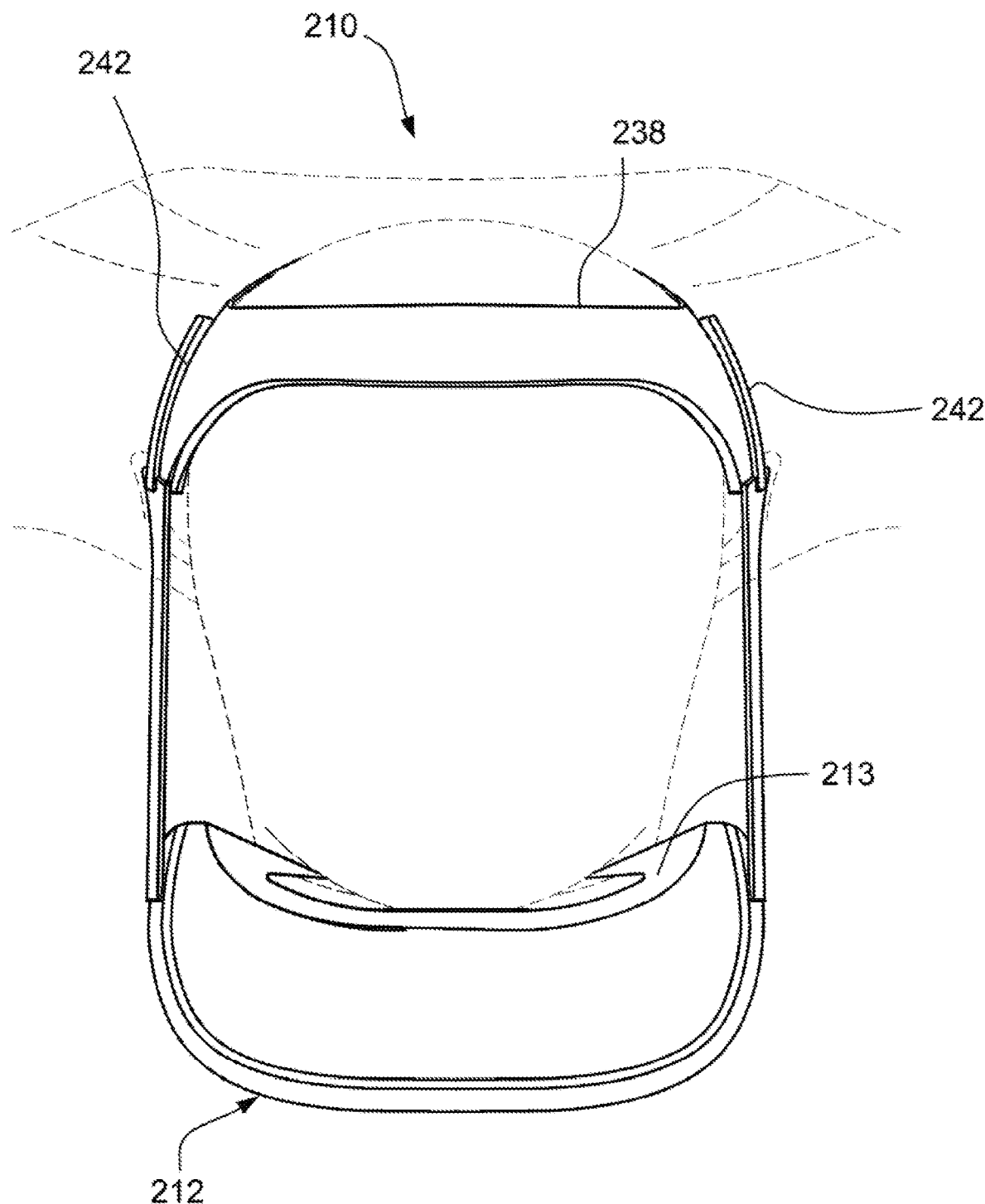

FIGS. 4A to 4C are respective side, front and top views of a head-mounted display assembly in-use according to a third example of the present technology.

Figure 5:
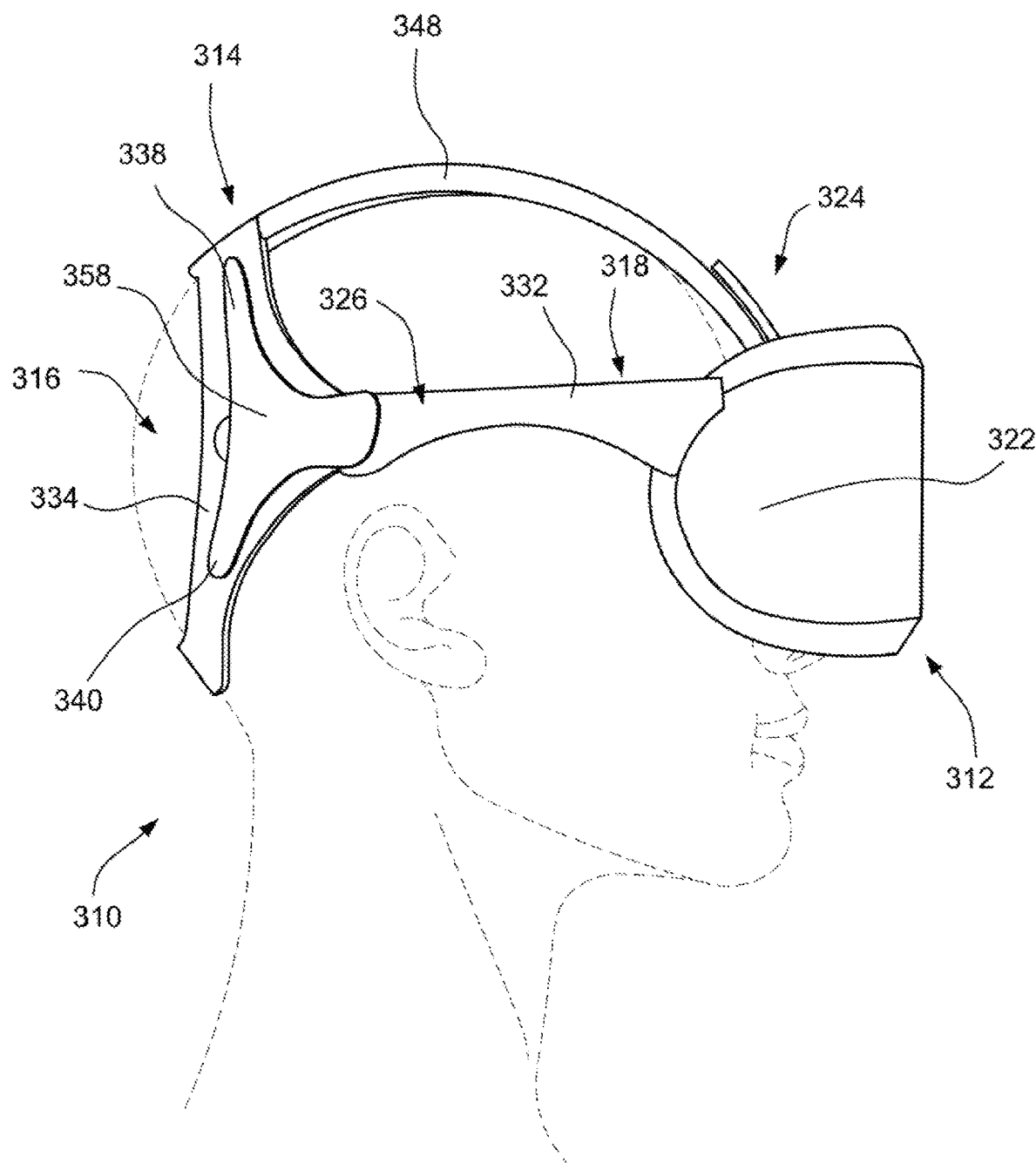

FIG. 5 is a side view of a head-mounted display assembly in-use according to a fourth example of the present technology.

Figure 6A:
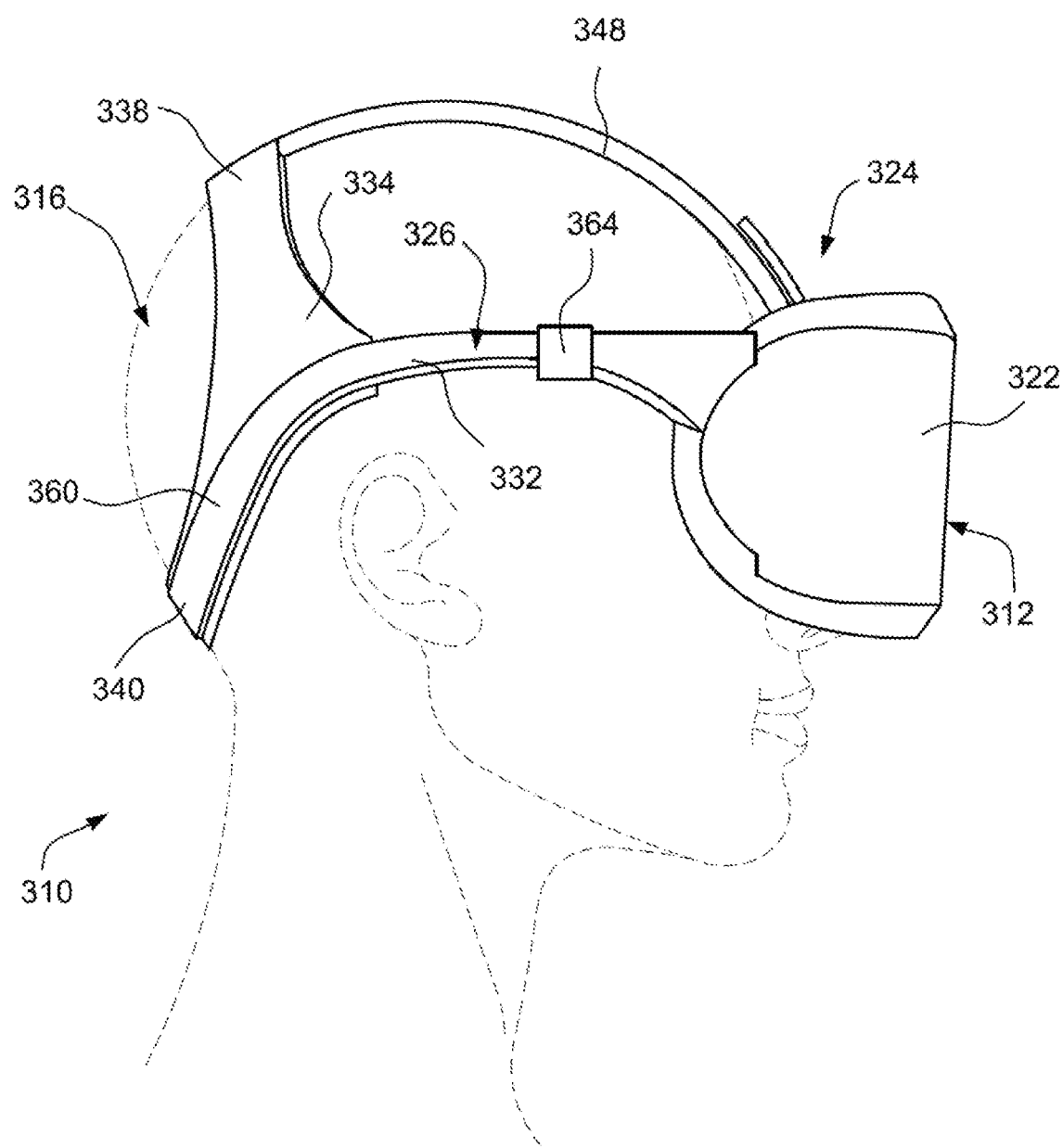
Figure 6B:
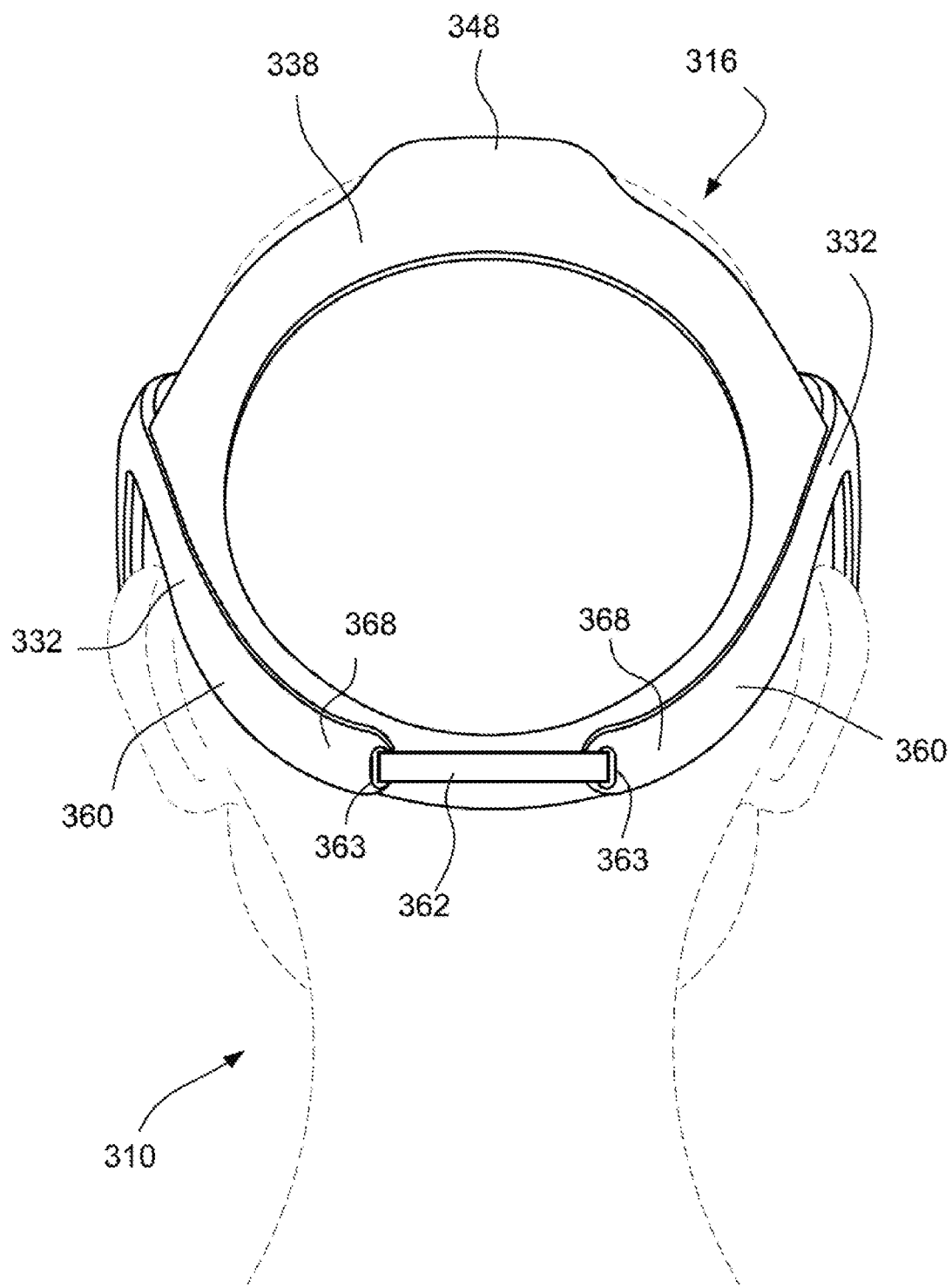
Figure 6C:
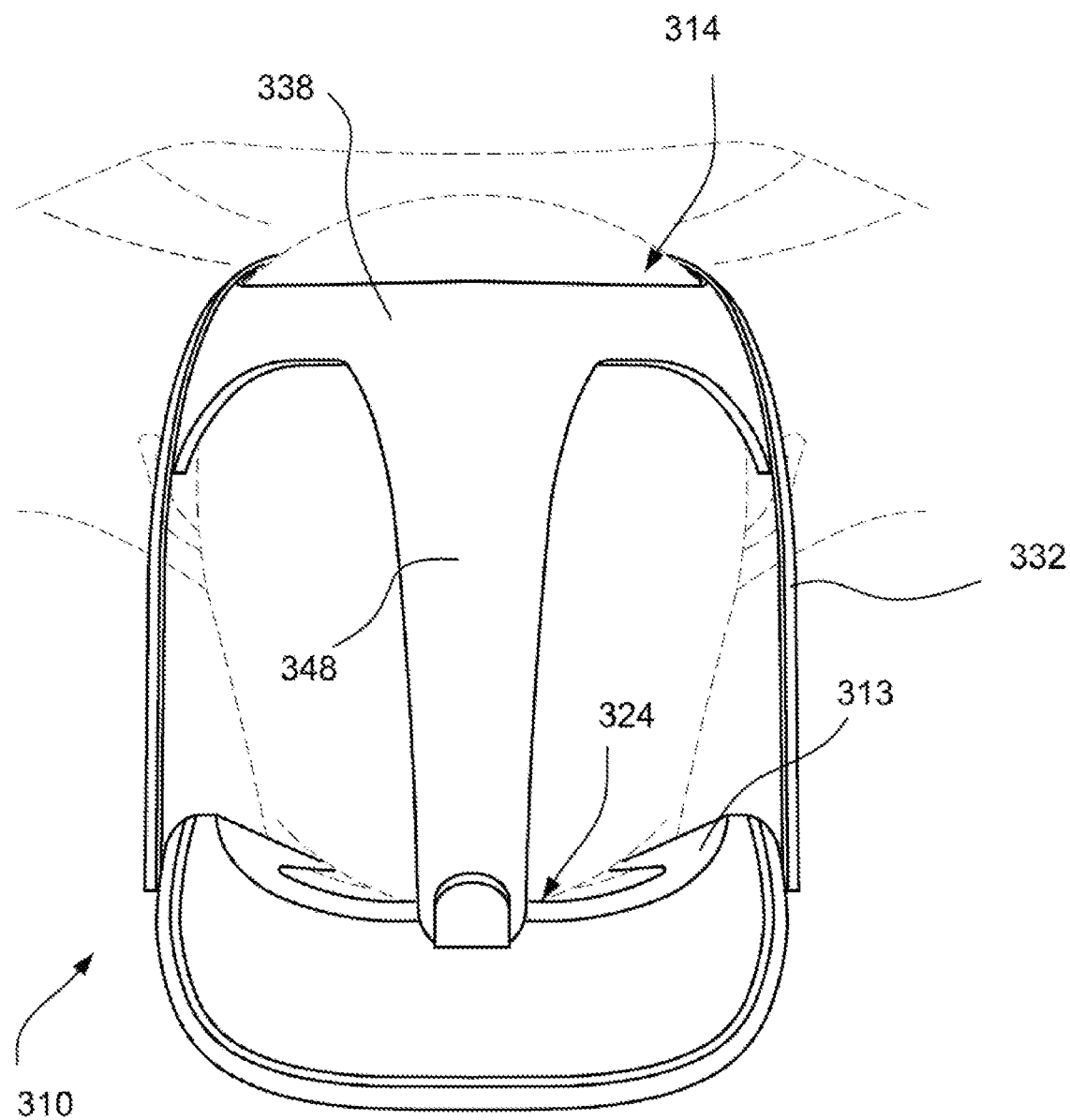

FIGS. 6A to 6C are respective side, rear and top views of a head-mounted display assembly in-use according to a variation of the fourth example of the present technology.

Figure 7:
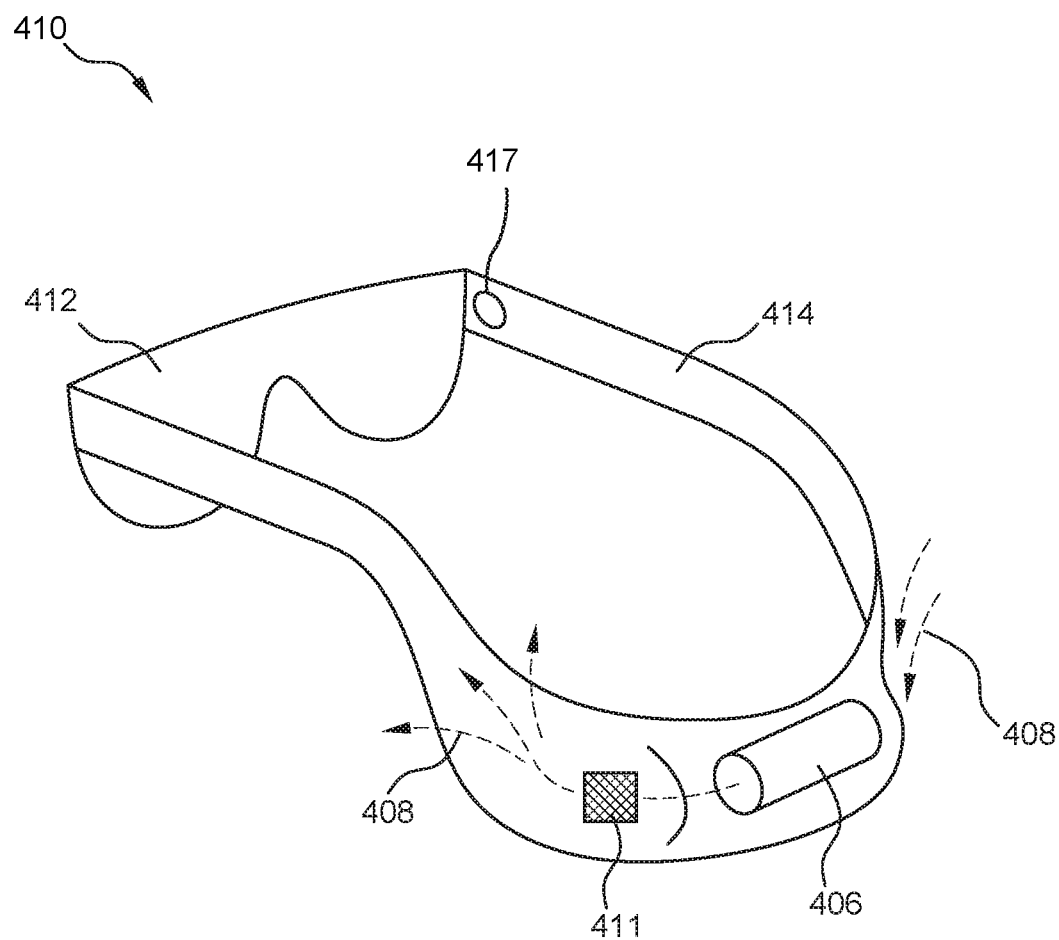

FIG. 7 is a perspective view of a head-mounted display assembly according to a fifth example of the present technology.

Figure 8:
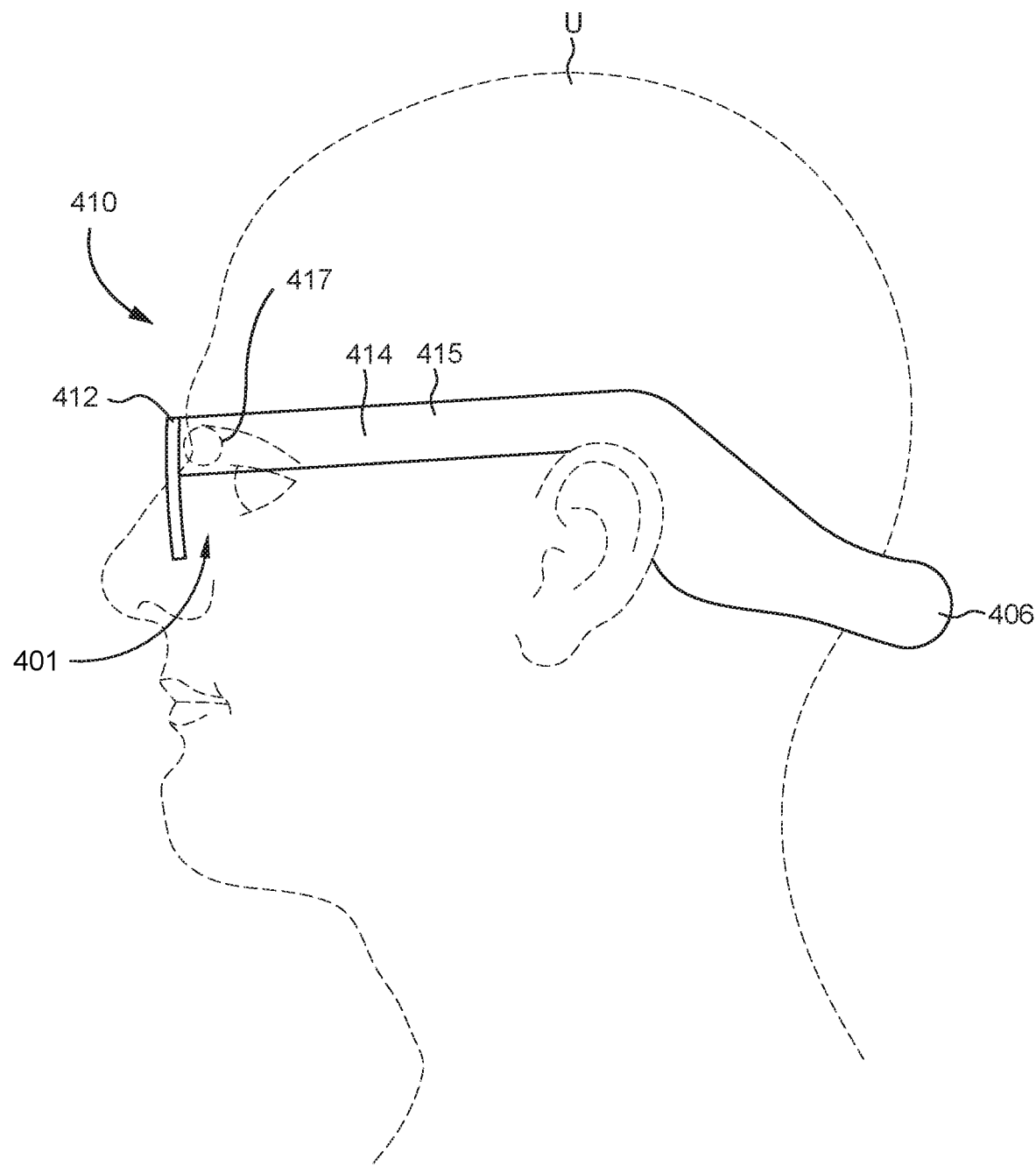

FIG. 8 is a side view of a head-mounted display assembly in use, according to a fifth example of the present technology.

Figure 9:
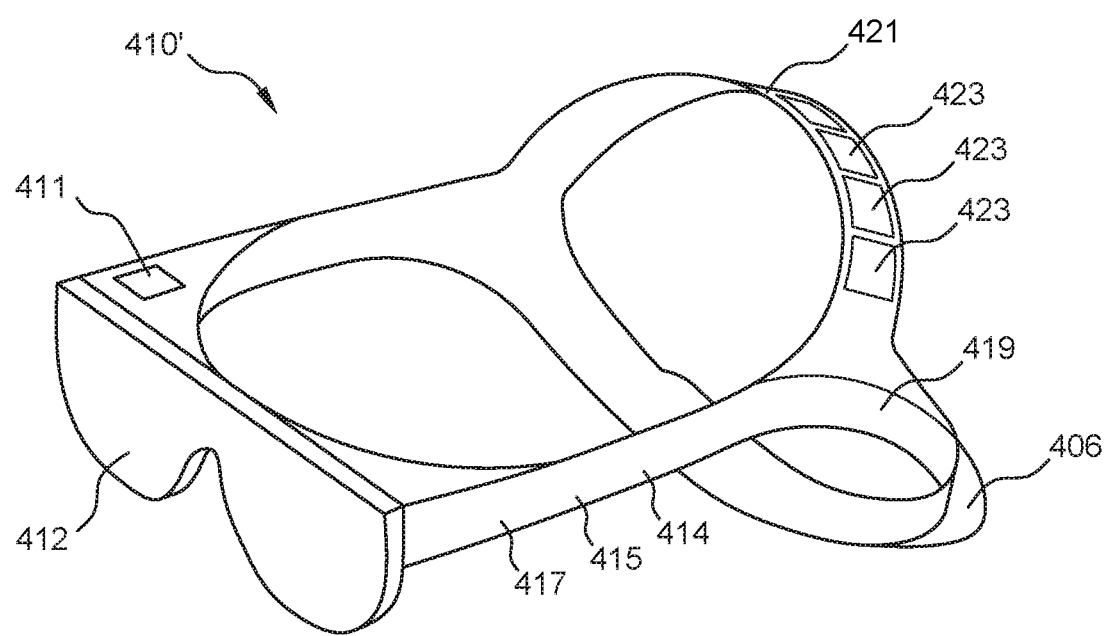

FIG. 9 is a perspective view of a head-mounted display assembly, according to an alternate version of the fifth example of the present technology.

Figure 10:
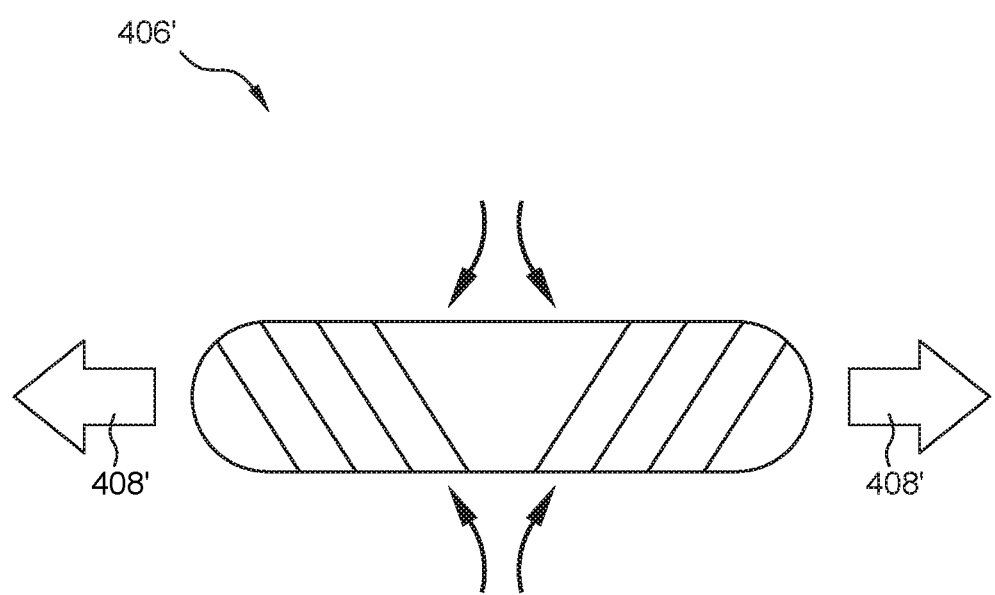

FIG. 10 is an illustration of a flow generator, according to a fifth example of the present technology.

Figure 11:
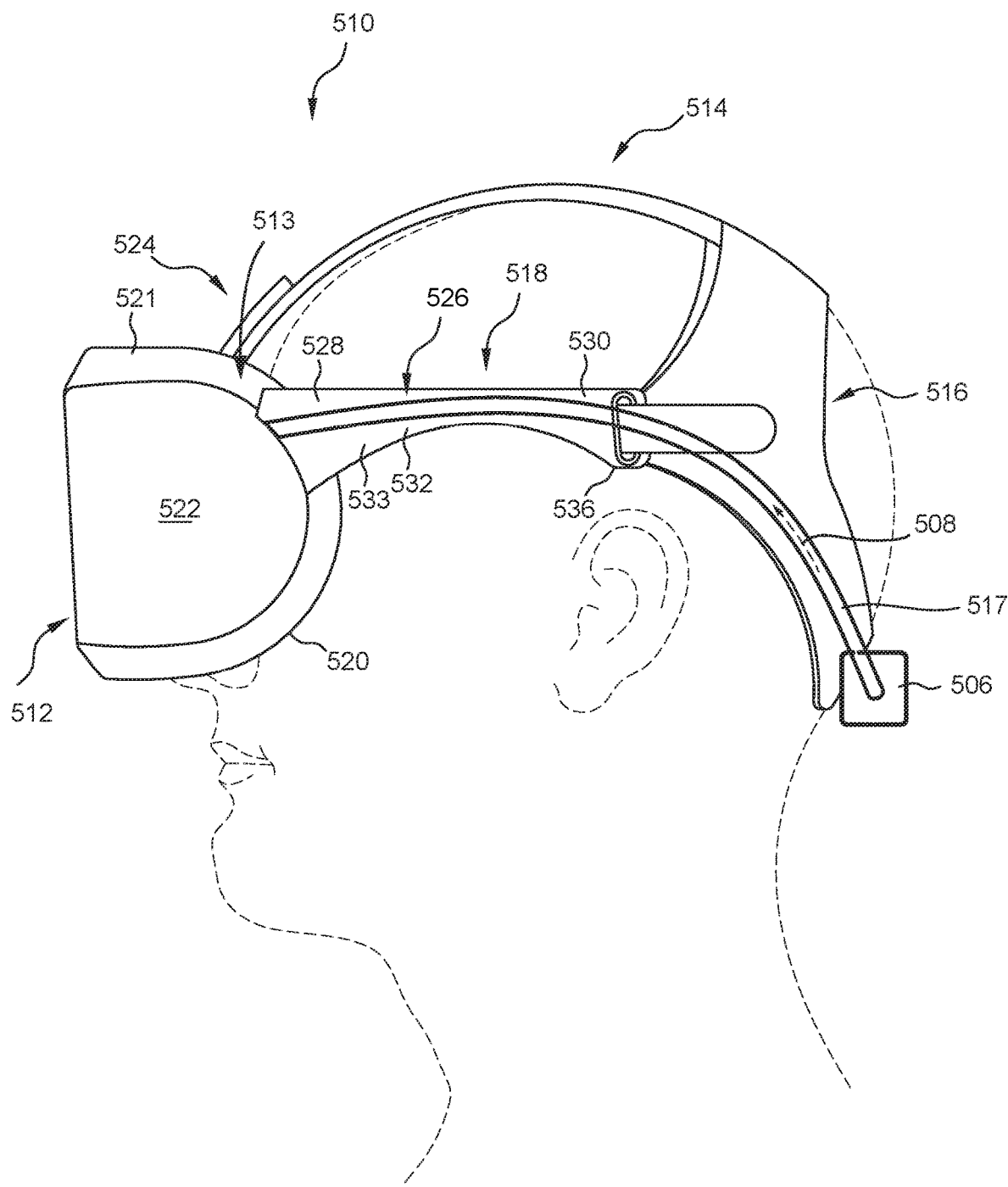

FIG. 11 is a side view of a head-mounted display assembly in-use according to a further alternate version of the fifth example of the present technology.

Figures 1, 11:
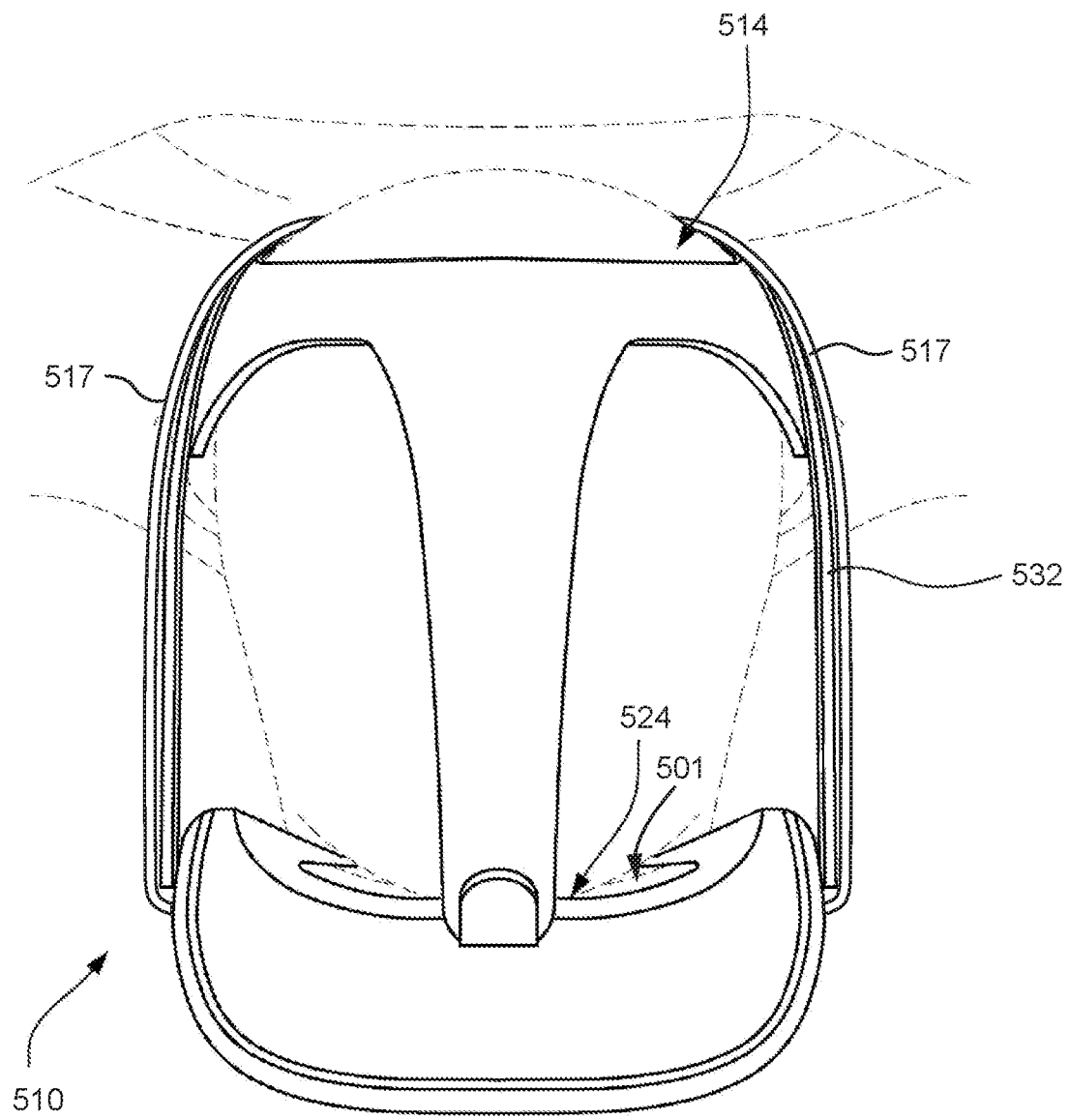

FIG. 11-1 is a top view of the head-mounted display assembly of FIG. 11, in-use.

Figure 12:
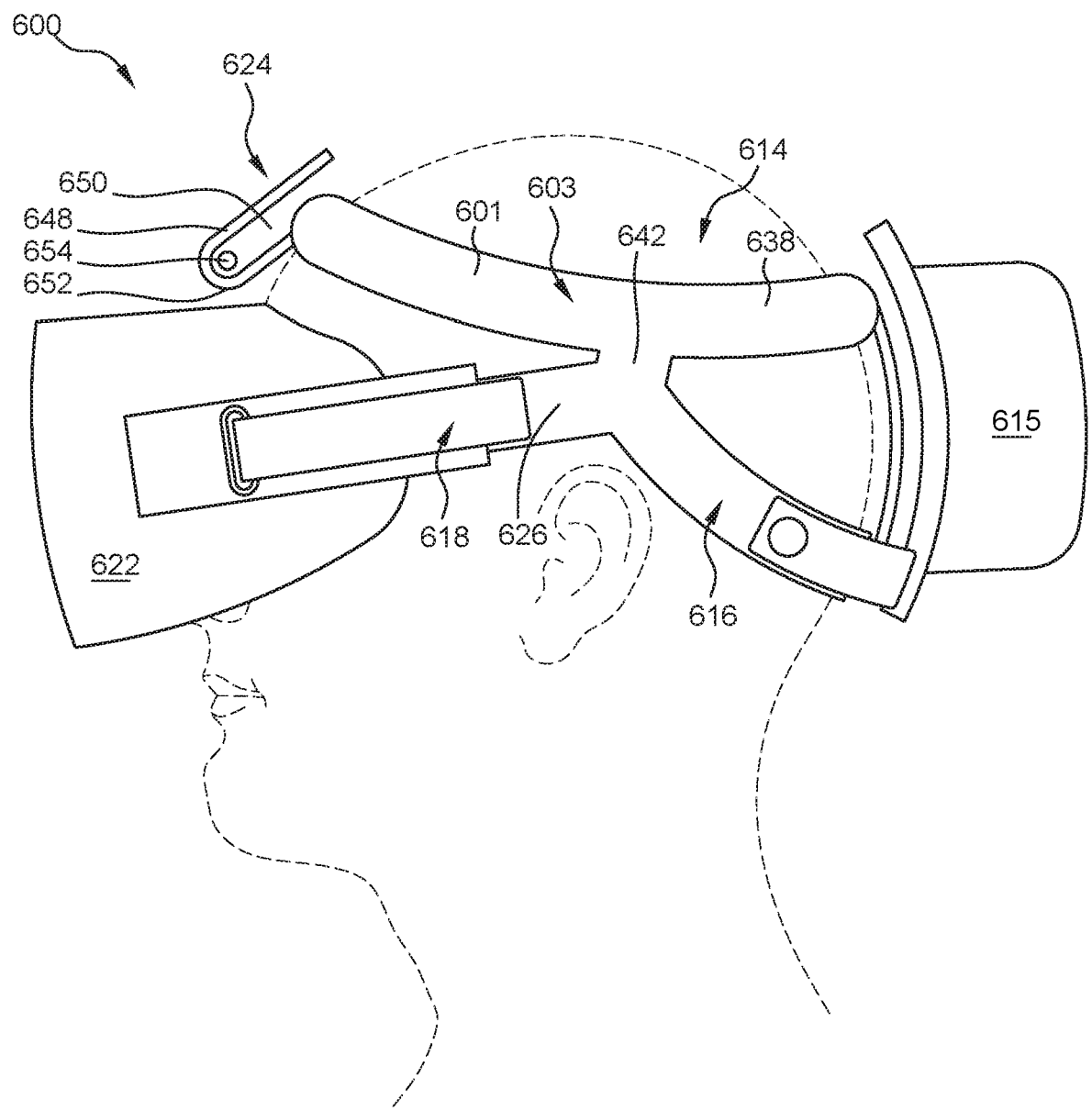

FIG. 12 shows a side view of a positioning and stabilising structure according to a sixth example of the present technology.

Figure 13:
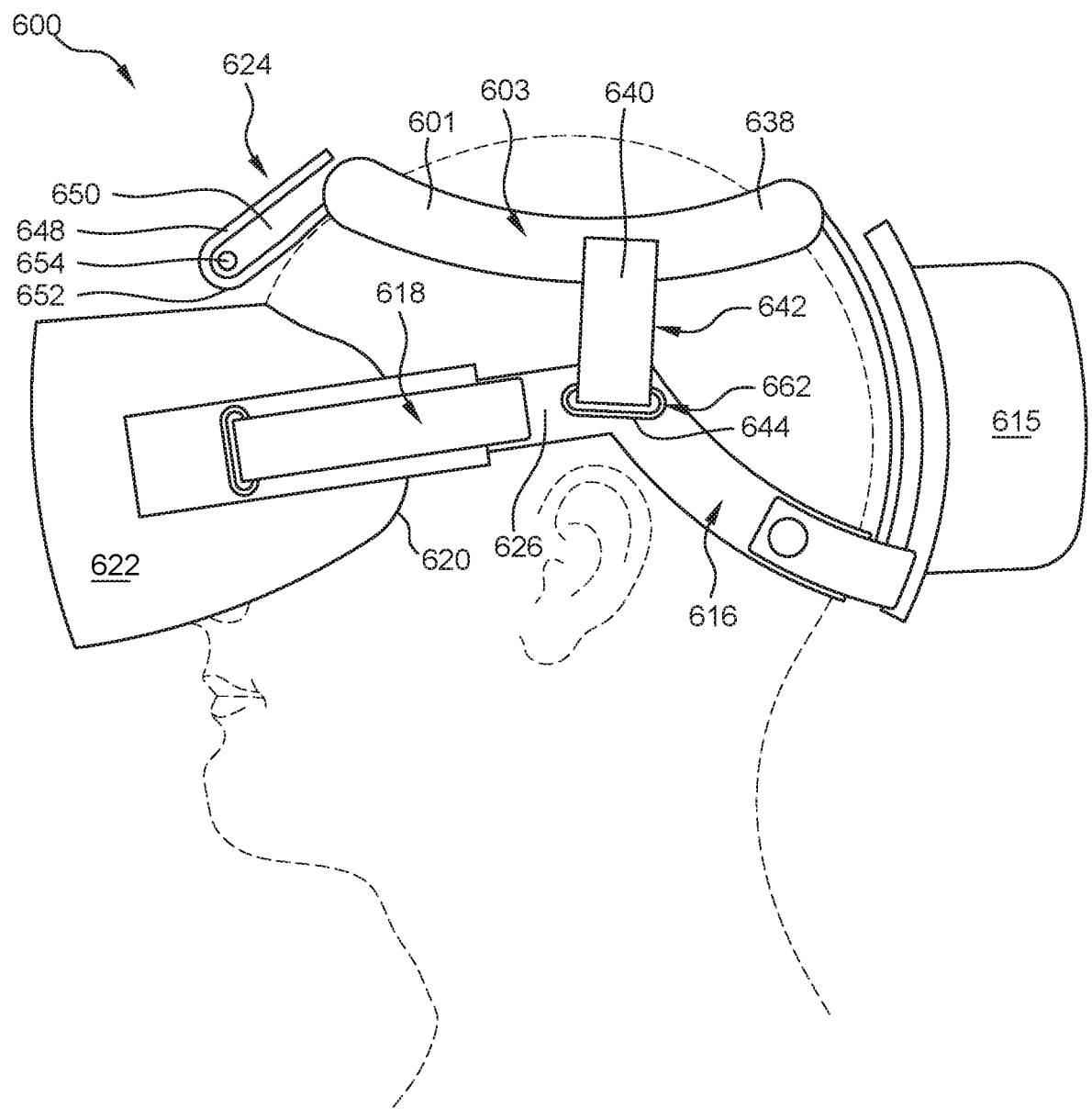

FIG. 13 shows a side view of a variation of the positioning and stabilising structure shown in FIG. 12.

Figure 14:
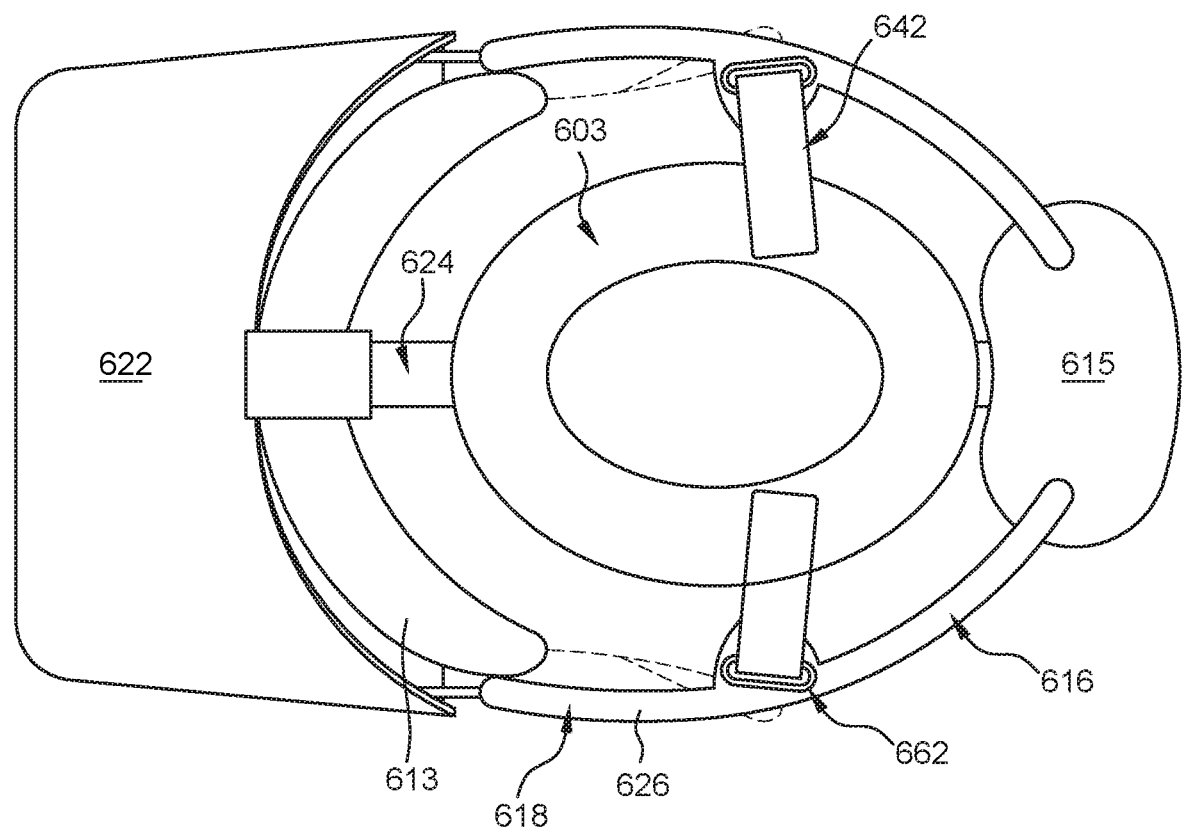

FIG. 14 shows a top view of the variation of the positioning and stabilising structure shown in FIG. 13.

Figure 15A:
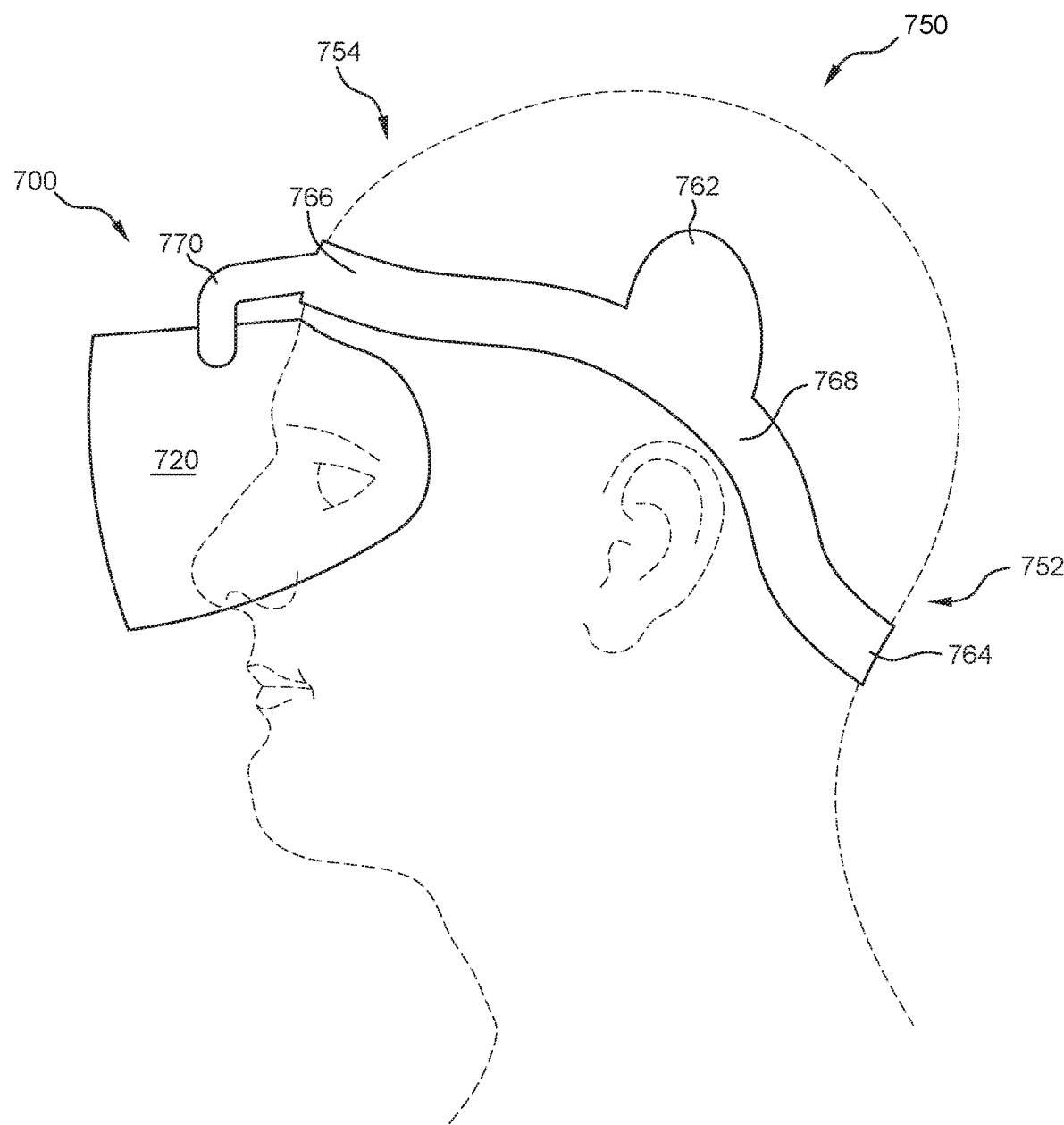

FIG. 15A is a side view of a head-mounted display system according to a seventh example of the present technology, in use.

Figure 15B:
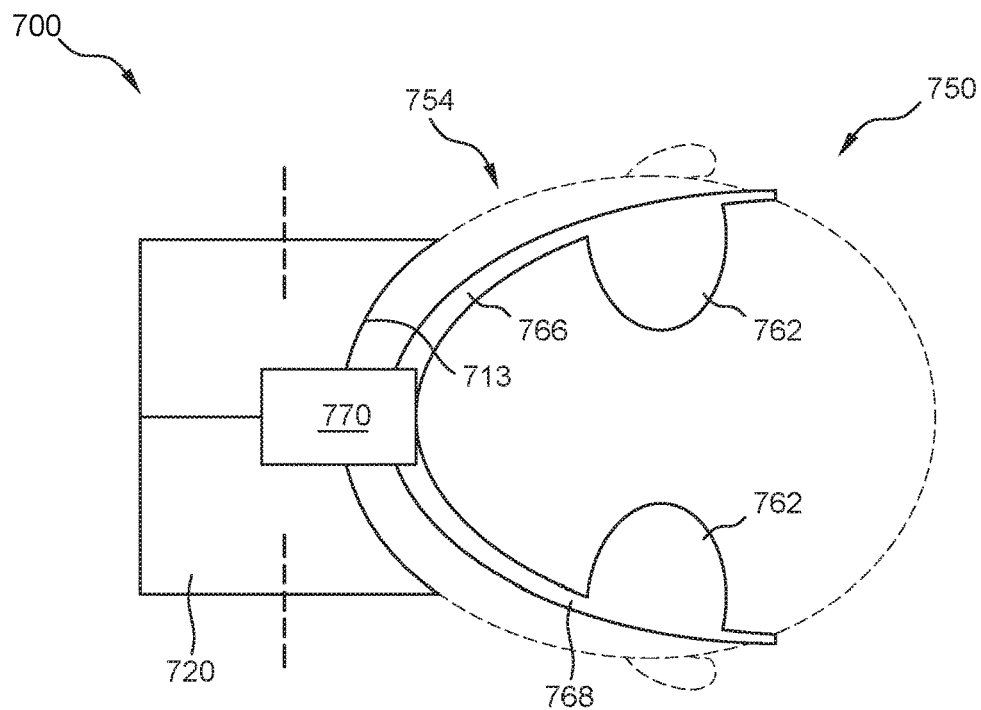

FIG. 15B is a superior view of the head-mounted display system shown in FIG. 15A, in use.

Figure 15C:
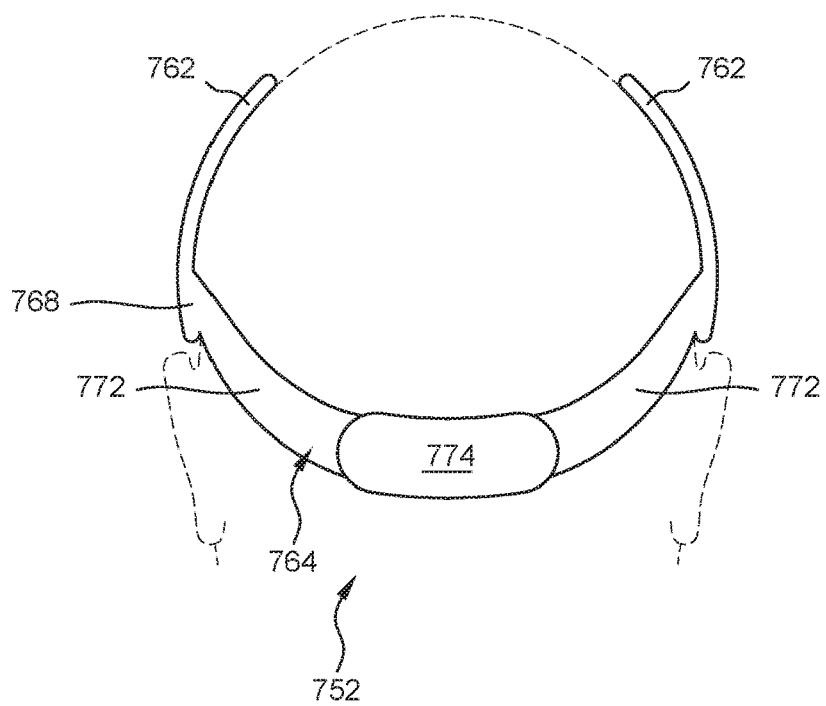

FIG. 15C is a rear view of the head-mounted display system shown in FIG. 15A, in use.

Figure 15D:
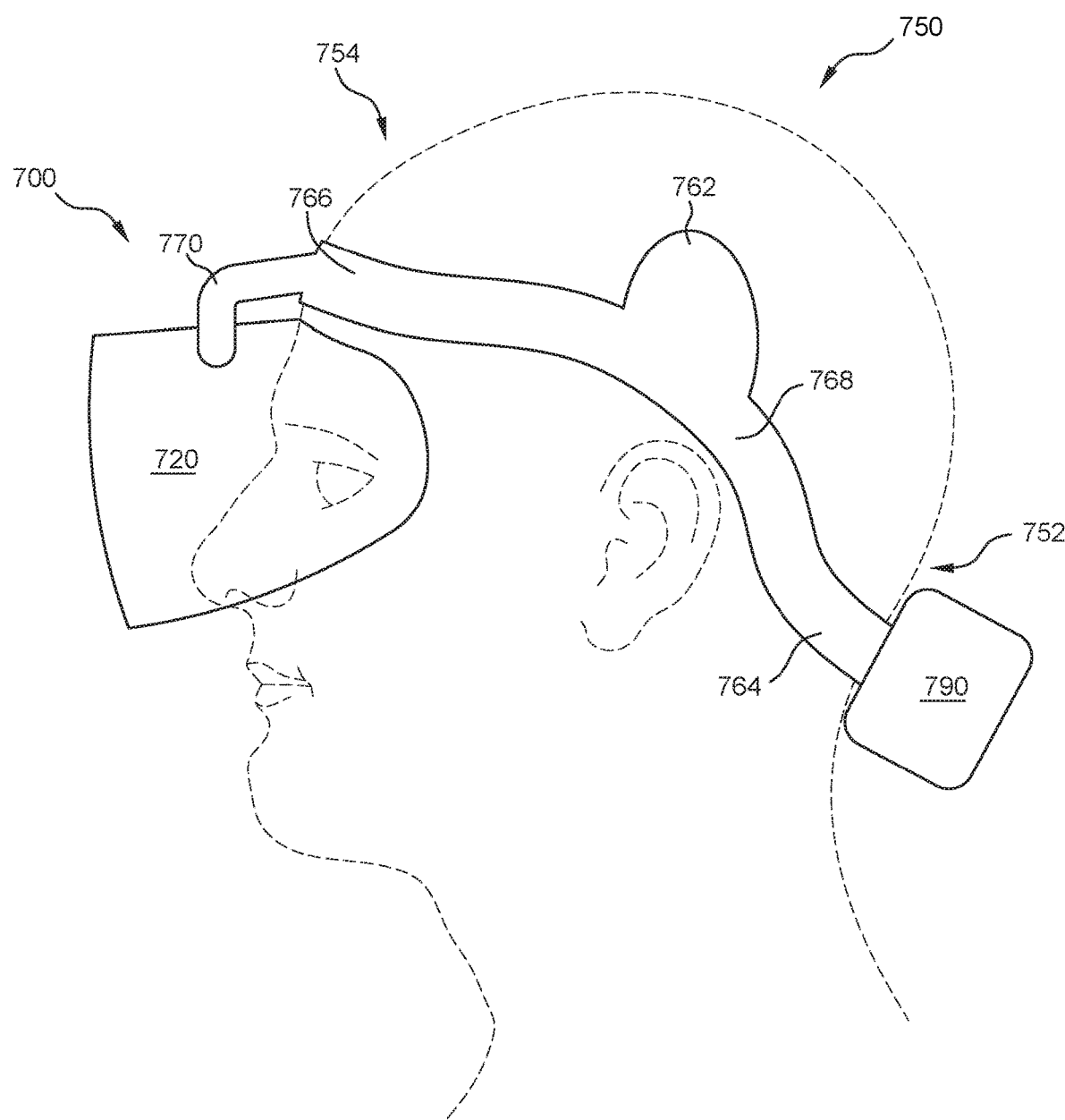

FIG. 15D is a side view of a head-mounted display system according to an alternate version of the seventh example of the present technology, in use.

Figure 15E:
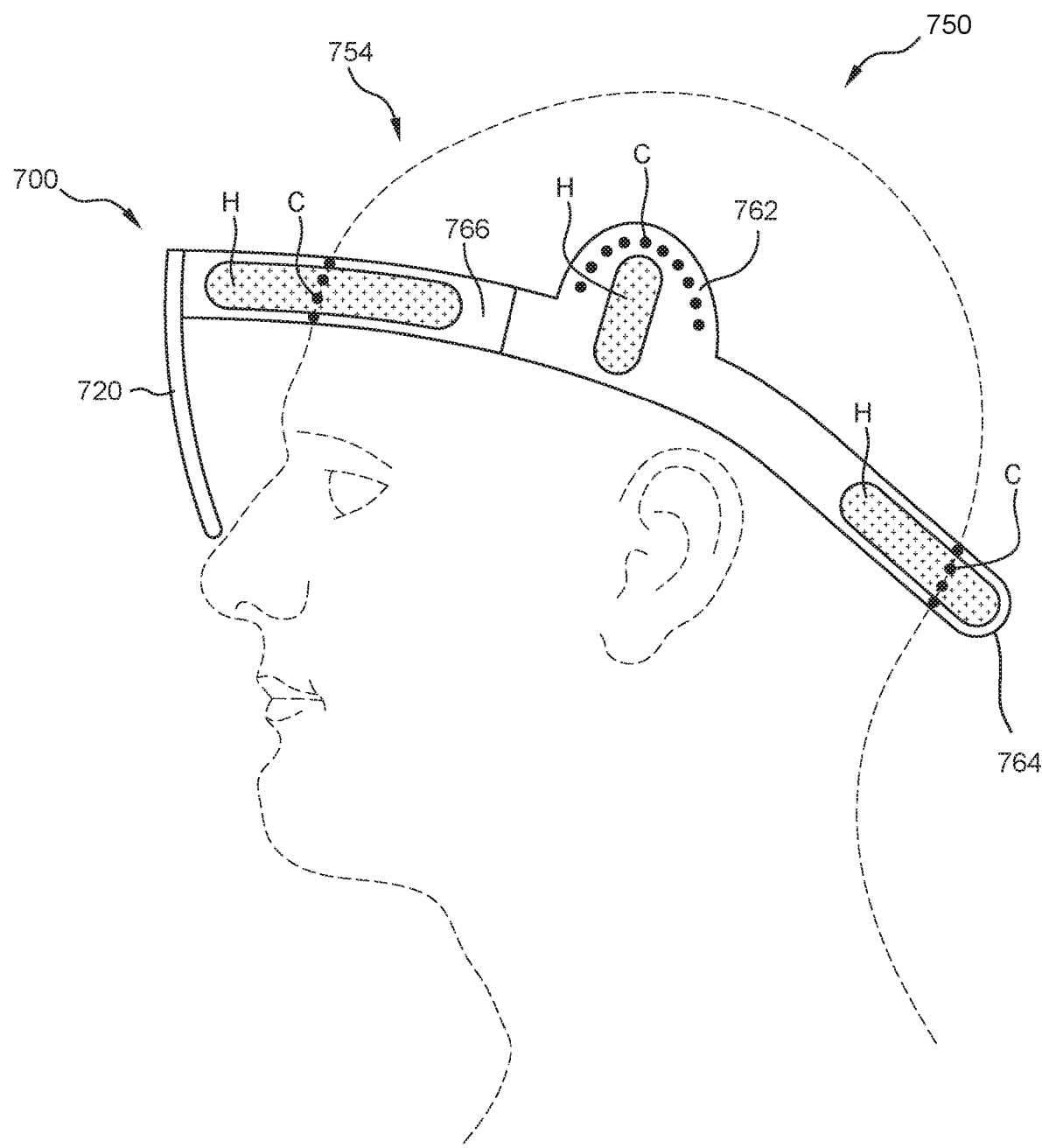

FIG. 15E is a side view of a head-mounted display system according to a further alternate version of the seventh example of the present technology, in use.

Figure 16A:
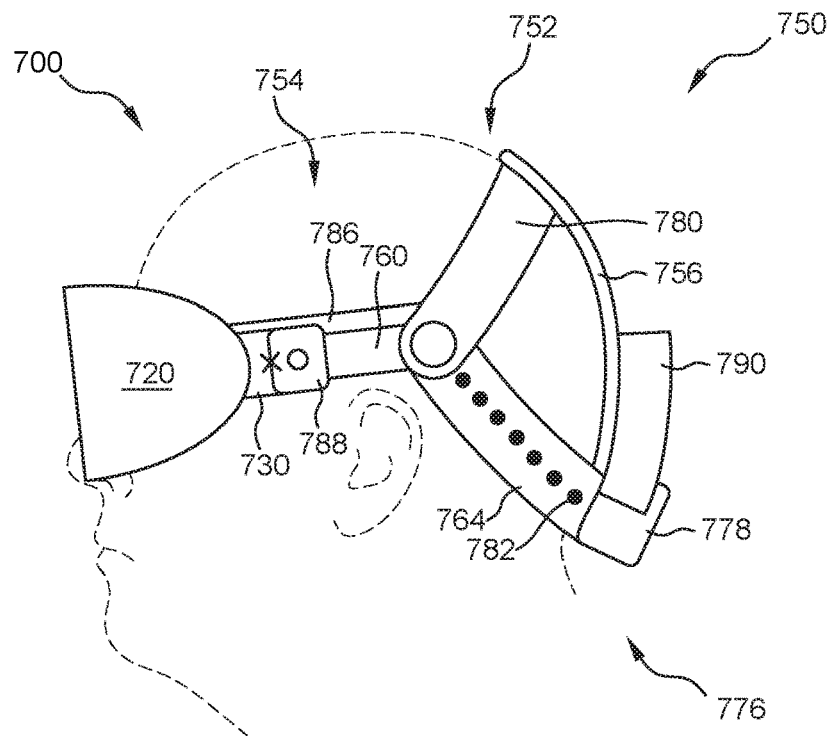
Figure 16B:
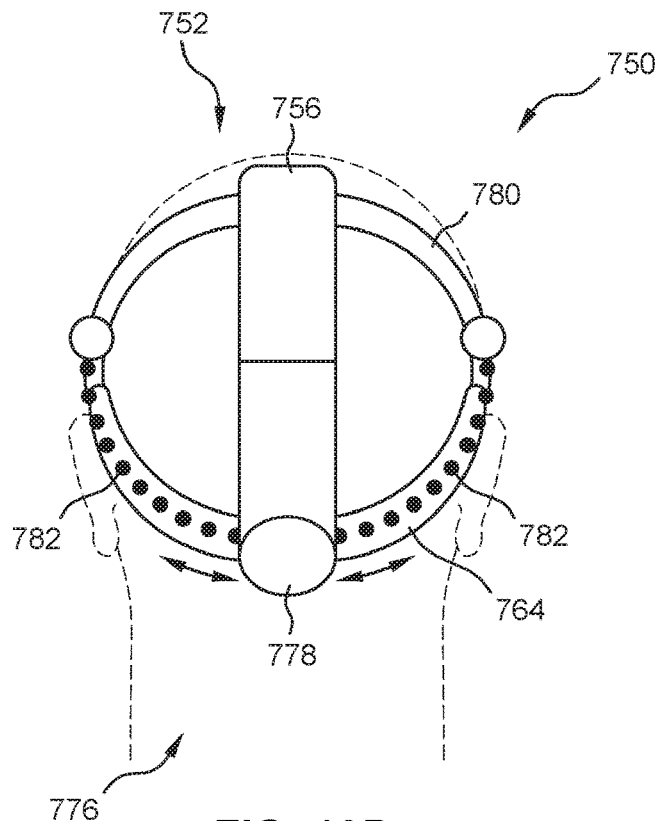

FIGS. 16A and 16B are side and rear views, respectively, of a head-mounted display system according to a further alternate version of the seventh example of the present technology, in use.

Figure 16C:
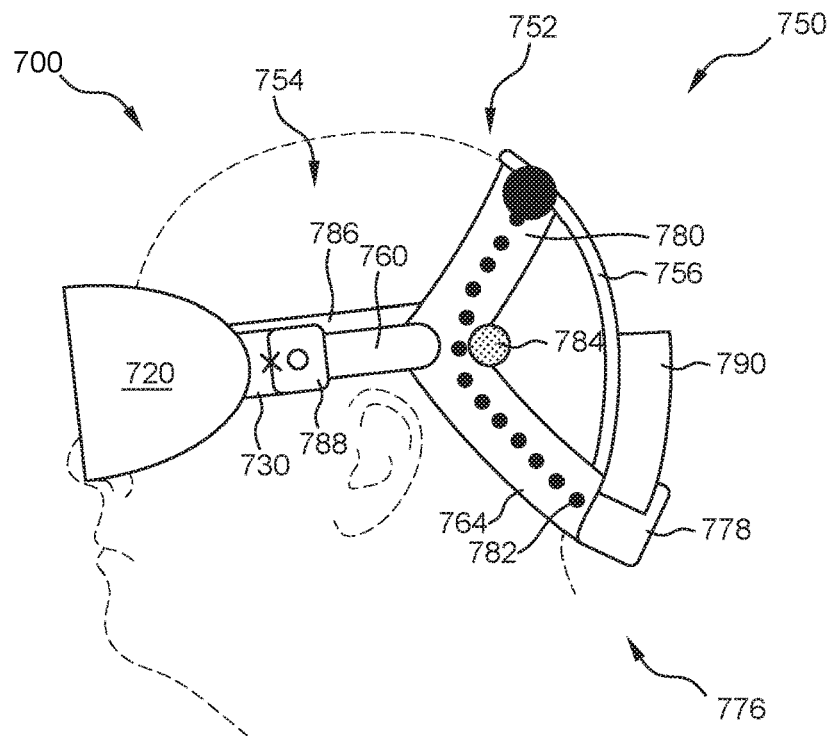
Figure 16D:
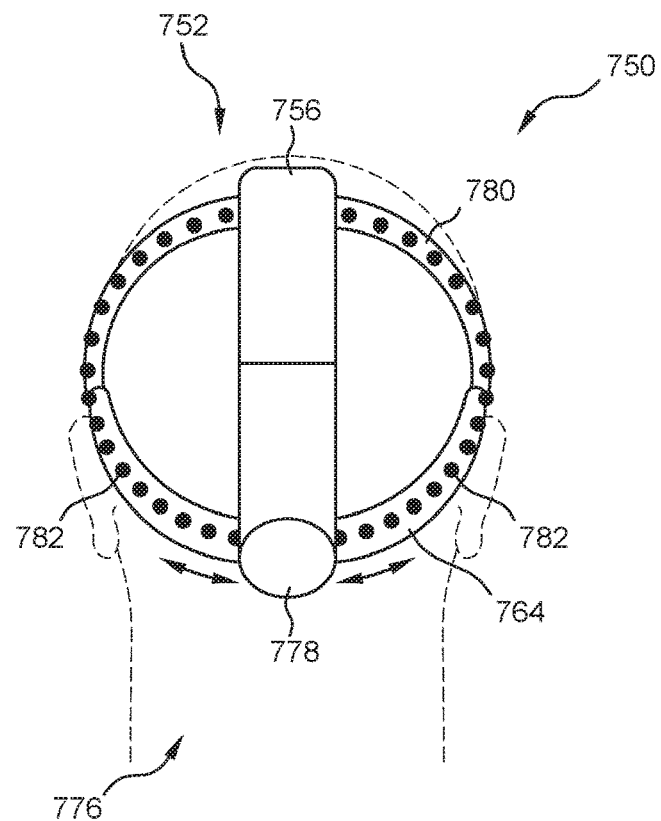

FIGS. 16C and 16D are side and rear views, respectively, of a head-mounted display system according to a further alternate version of the seventh example of the present technology, in use.

Figure 16E:
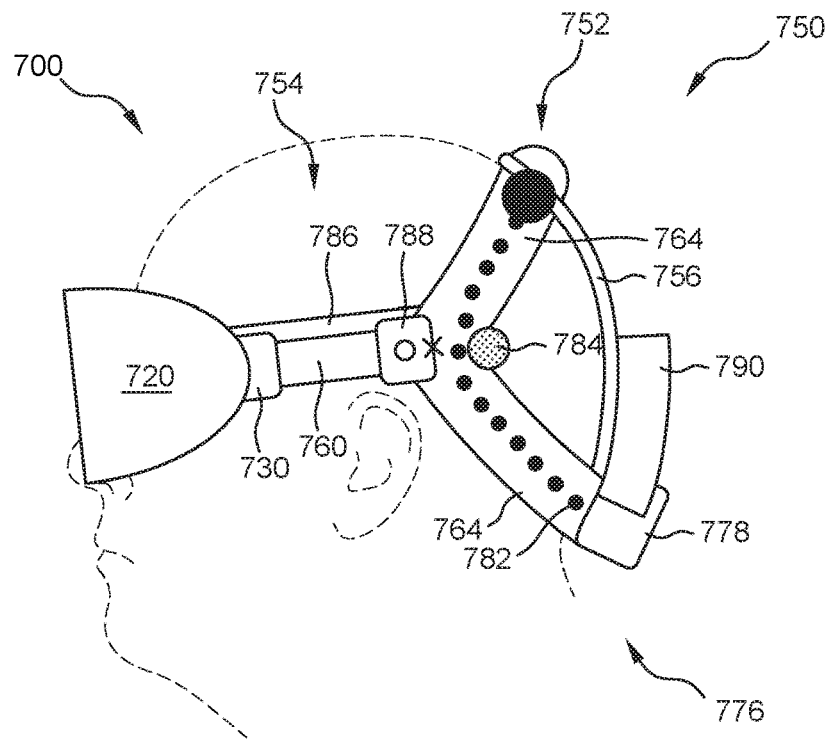
Figure 16F:
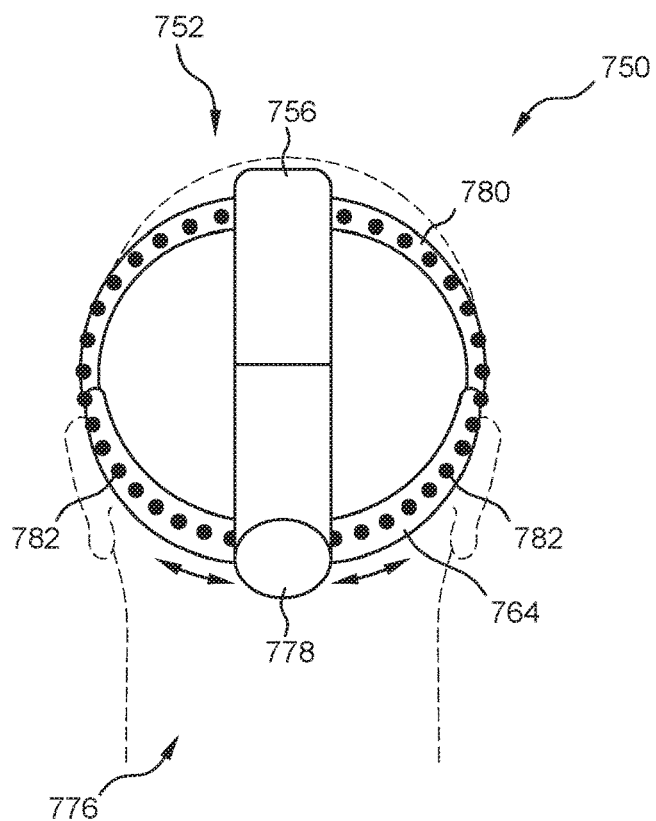

FIGS. 16E and 16F are side and rear views, respectively, of a head-mounted display system according to a further alternate version of the seventh example of the present technology, in use.

Figure 16G:
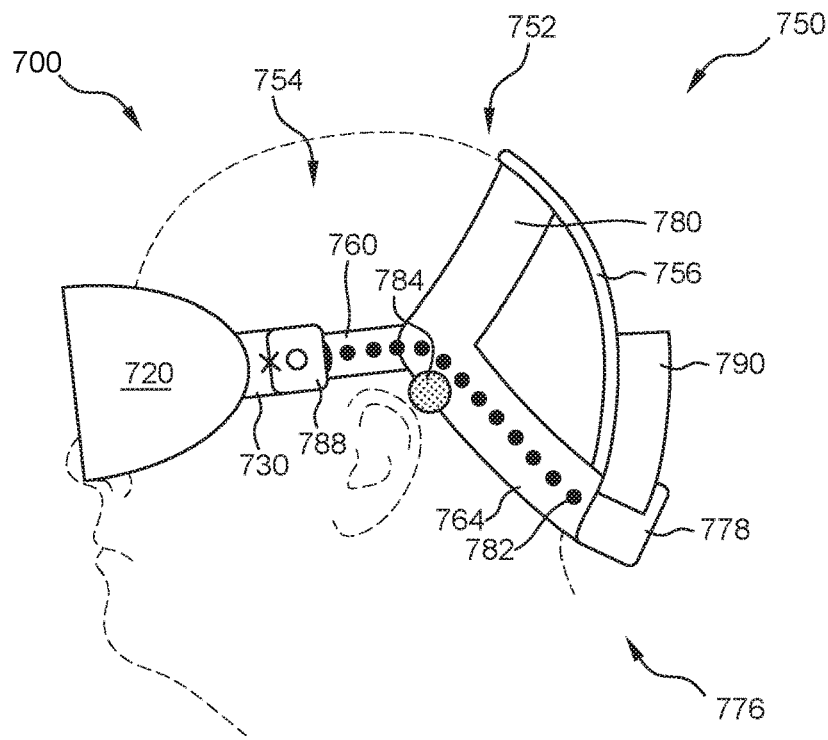
Figure 16H:
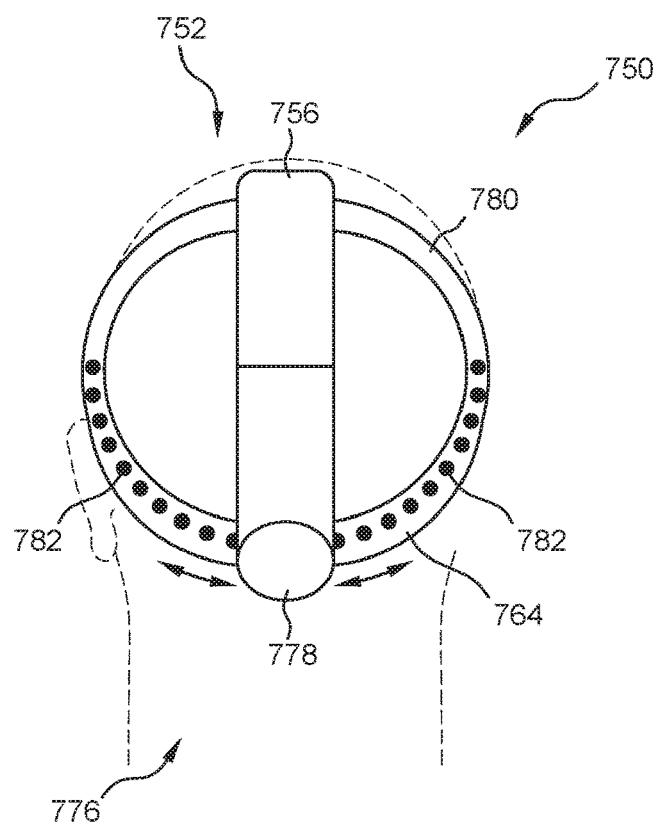

FIGS. 16G and 16H are side and rear views, respectively, of a head-mounted display system according to a further alternate version of the seventh example of the present technology, in use.

Figure 17A:
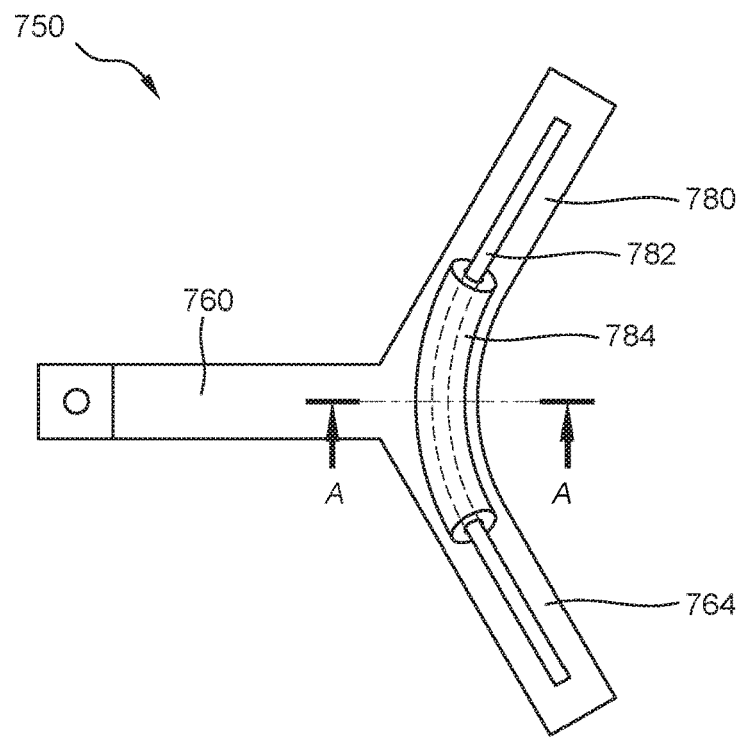

FIG. 17A shows a side view of a portion of a positioning and stabilising for use with a head-mounted display system according to a seventh example of the present technology.

Figure 17B:
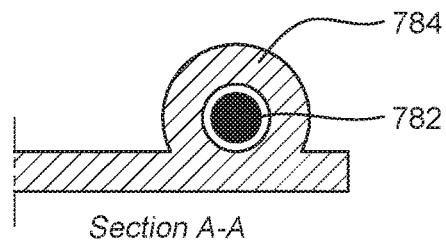

FIG. 17B shows a cross sectional view of a guide of the positioning and stabilising structure of FIG. 17A, viewed along line A-A.

Figure 17C:
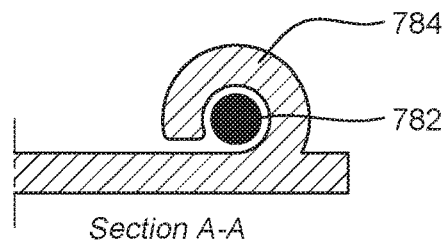

FIG. 17C shows a cross sectional view of an alternate guide of the positioning and stabilising structure of FIG. 17A, viewed along line A-A.

Figure 18A:
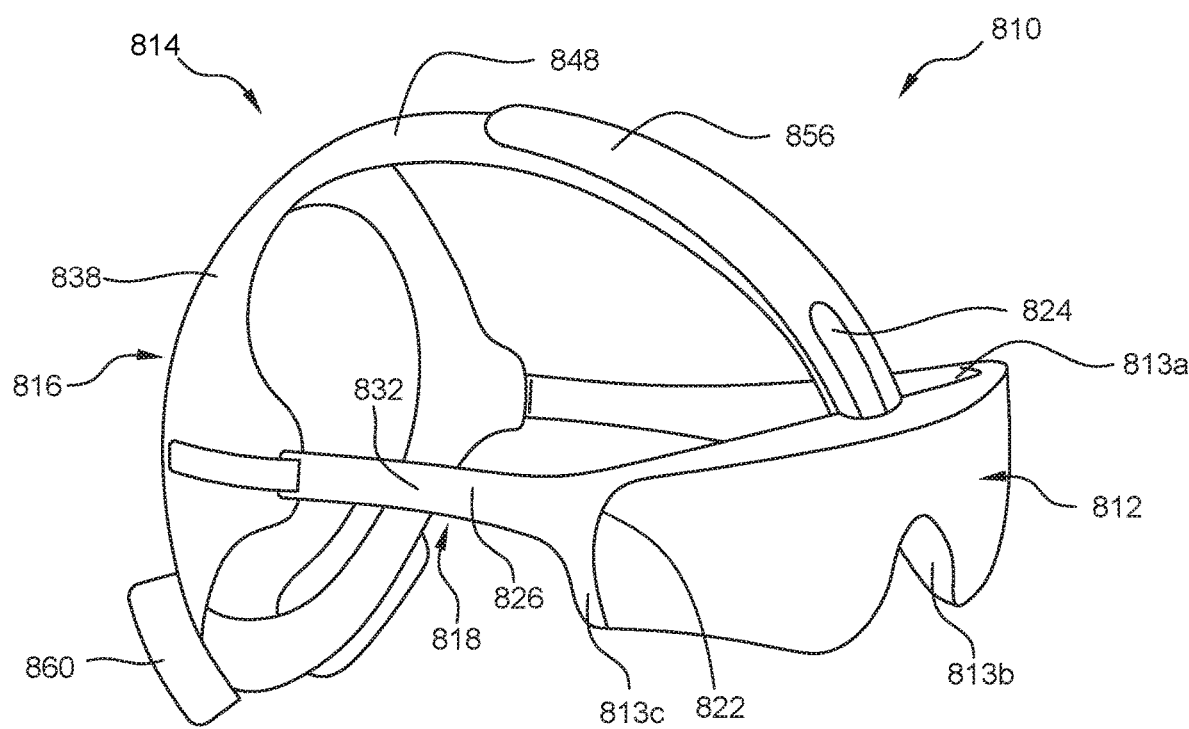
Figure 18B:
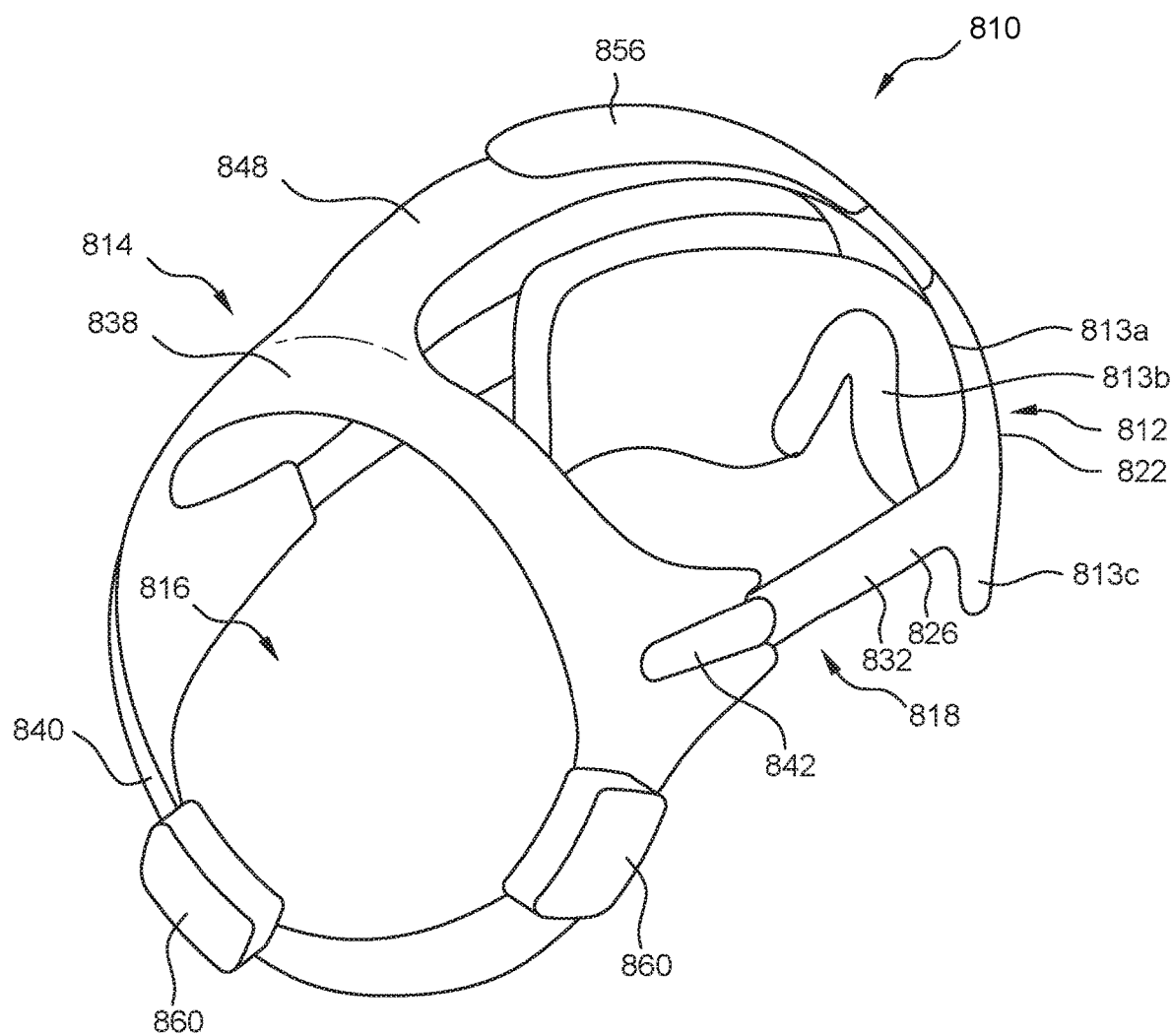

FIGS. 18A and 18B are respective side and posterior projection views of an augmented reality display assembly according to an eighth example of the present technology.

Figure 19A:
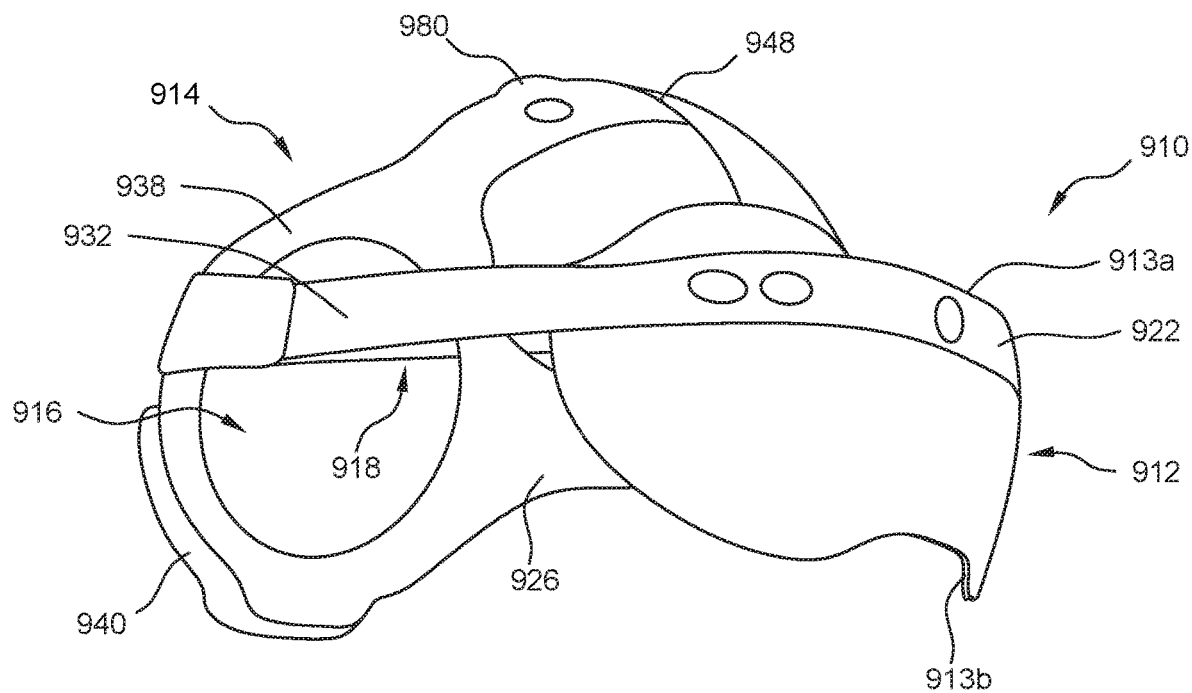
Figure 19B:
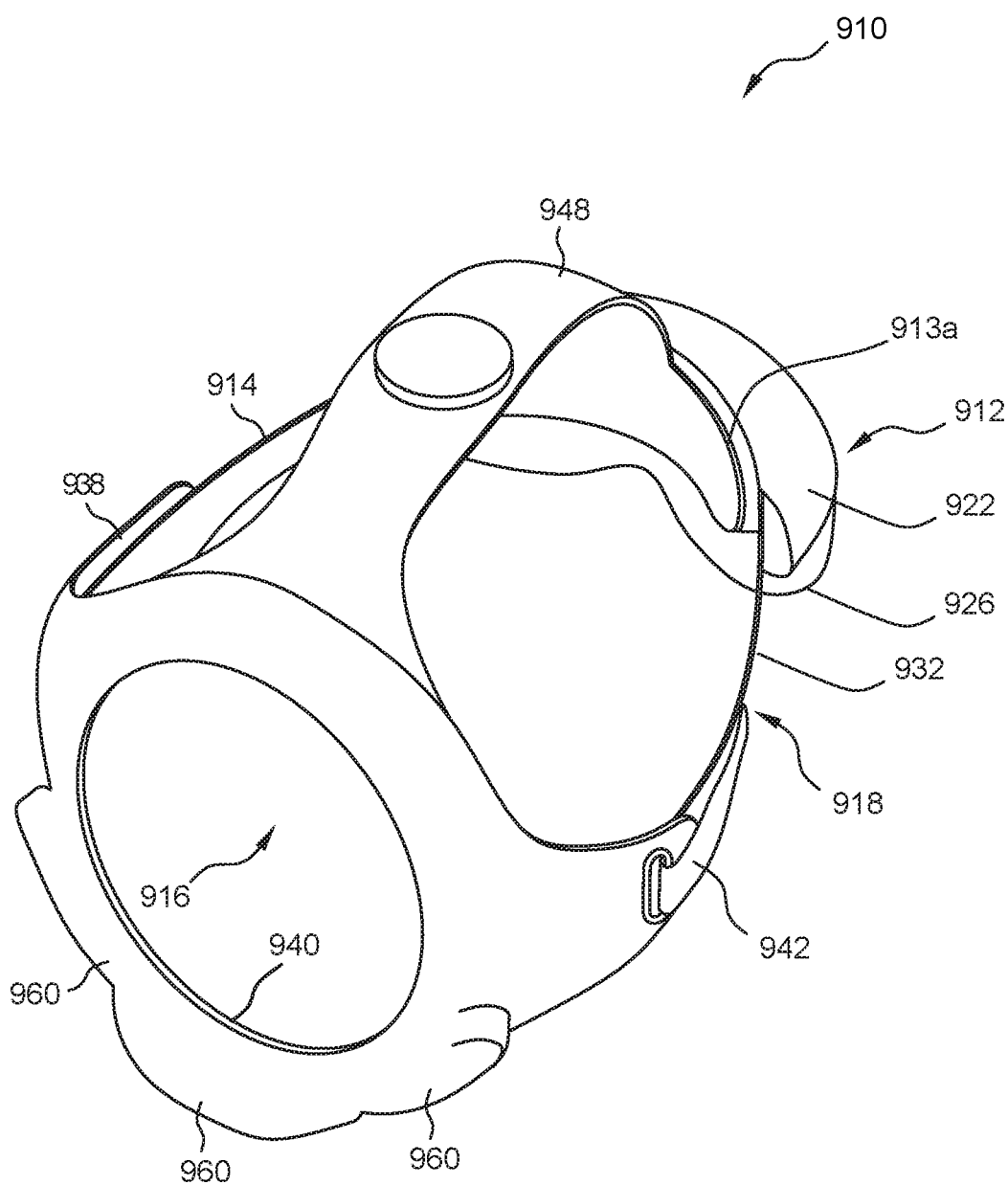
Figure 19C:
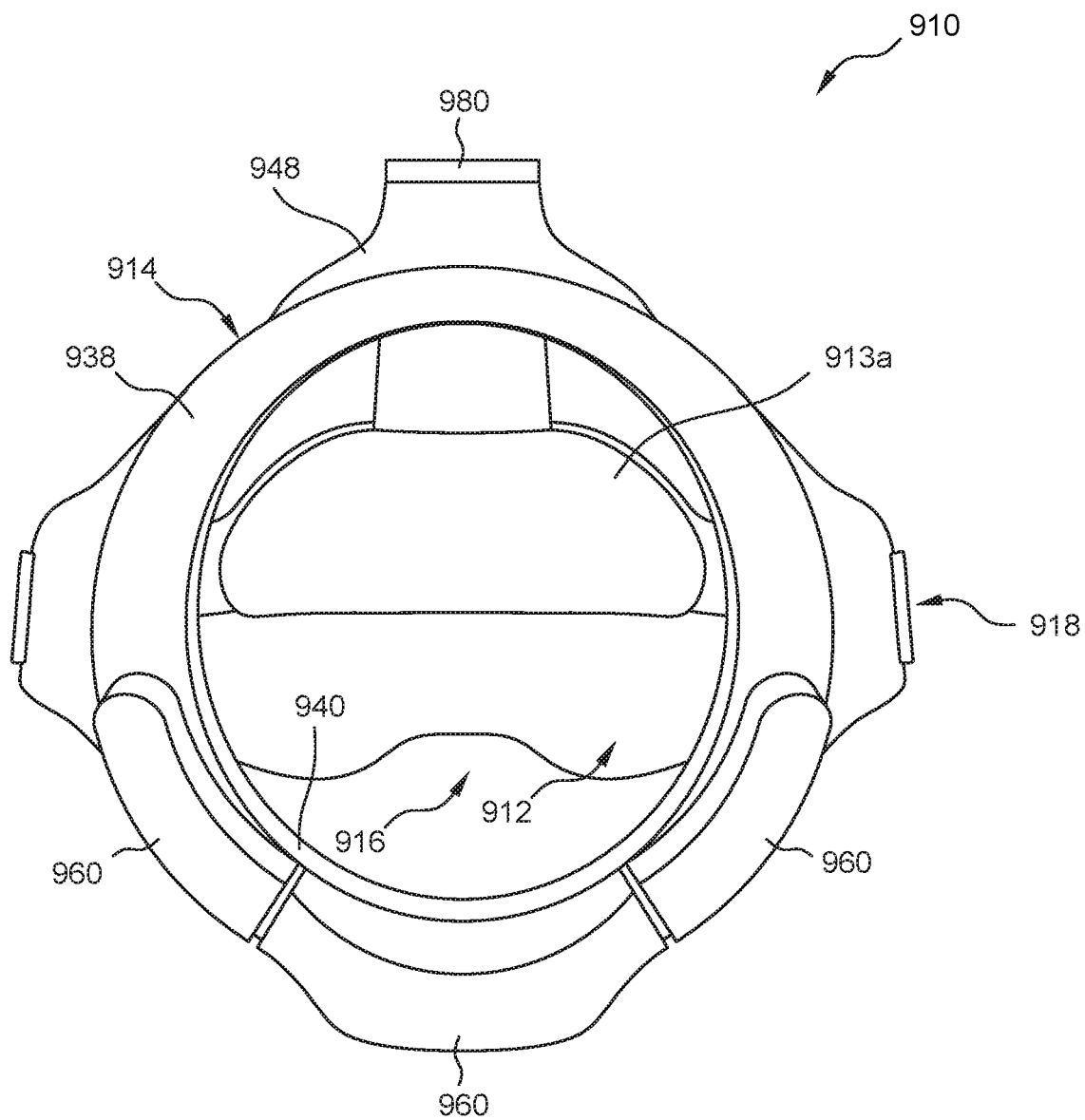

FIGS. 19A to 19C are respective anterior projection, posterior projection and rear views of an augmented reality display assembly according to a ninth example of the present technology.

Figure 20:
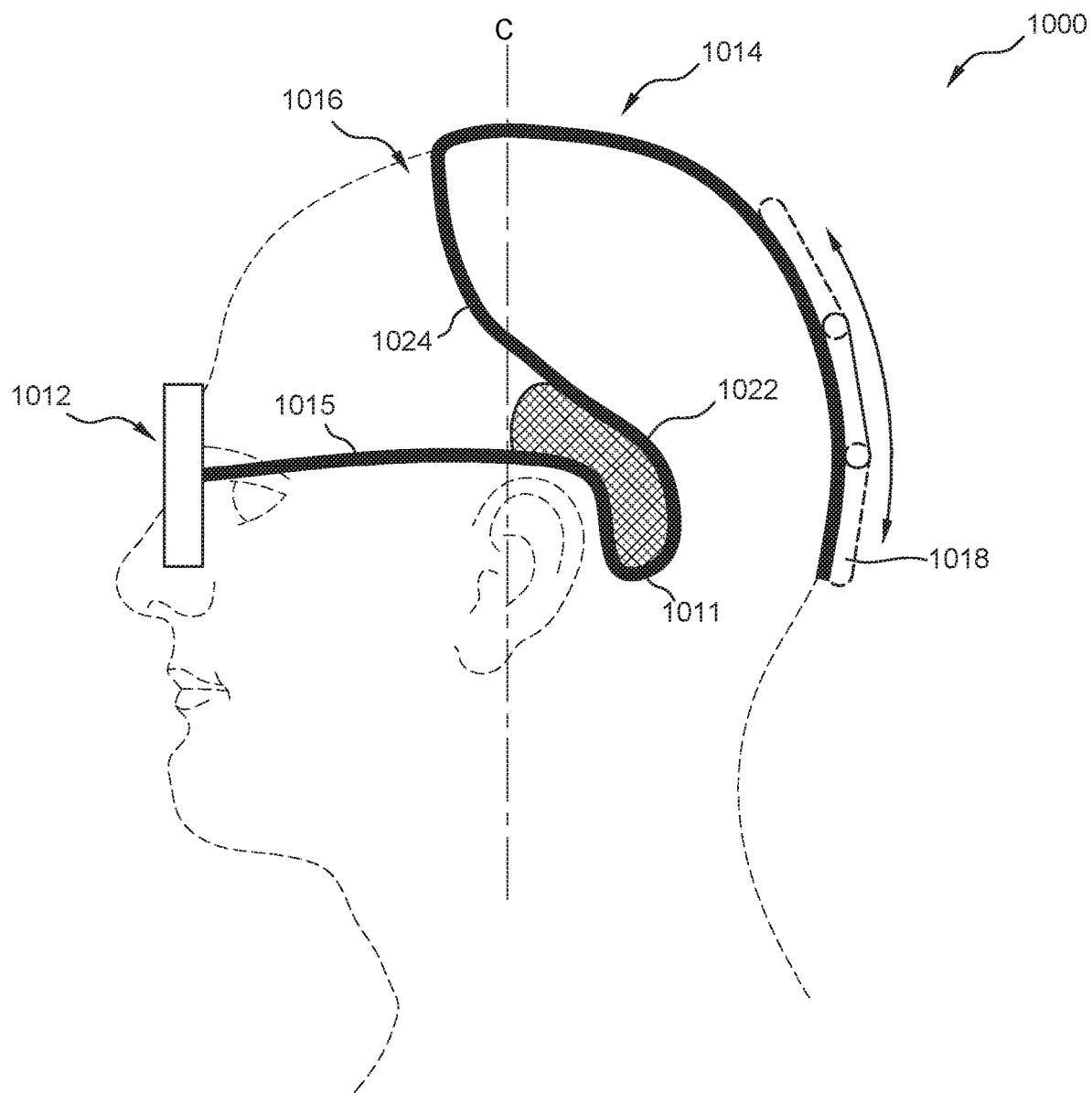

FIG. 20 shows a side view of an augmented reality display system or assembly according to a tenth example of the present technology.

Figure 21:
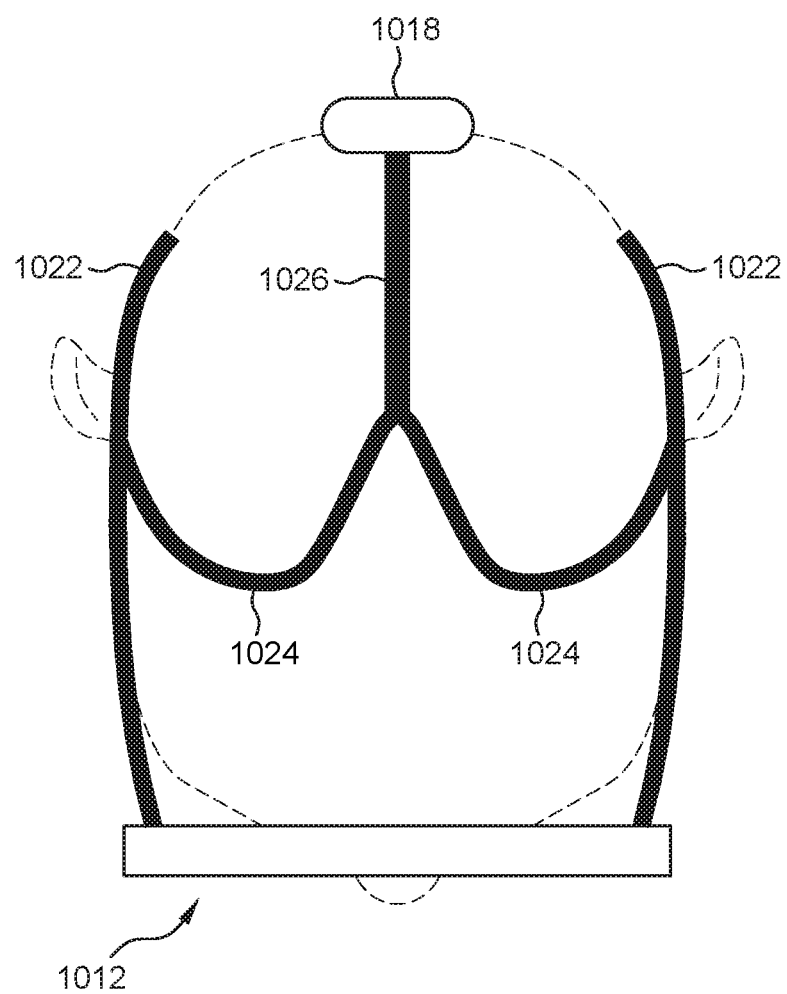

FIG. 21 shows a top view of the augmented reality display system or assembly of FIG. 20.

Figure 22:
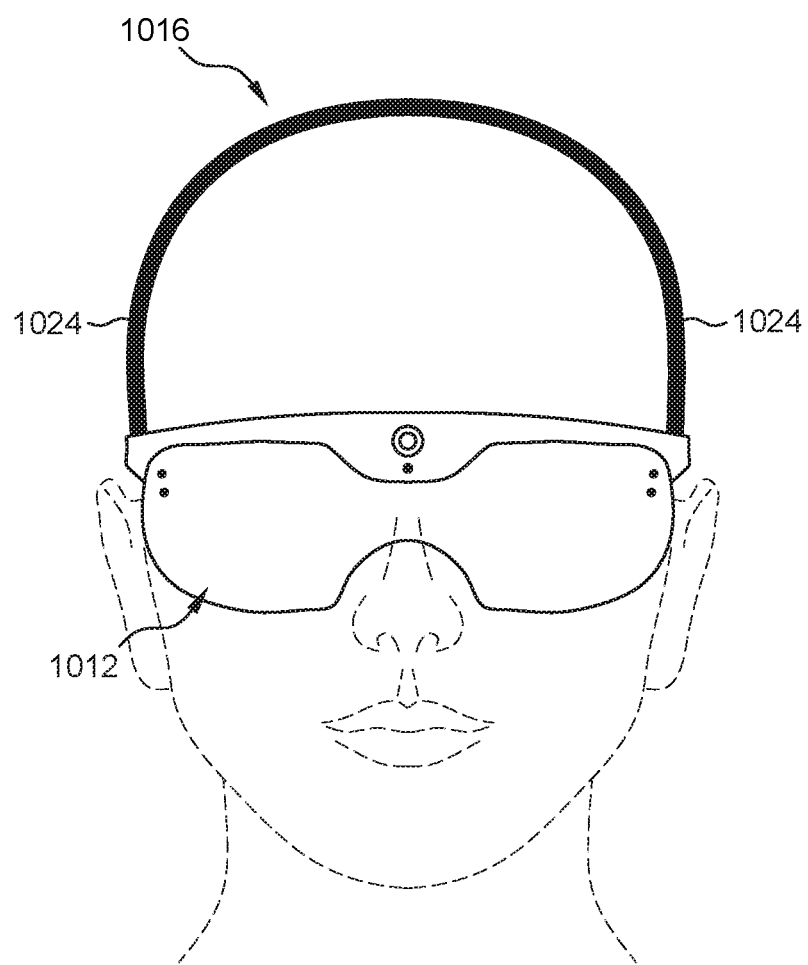

FIG. 22 shows a front view of the augmented reality display system or assembly of FIG. 20.

Figure 23A:
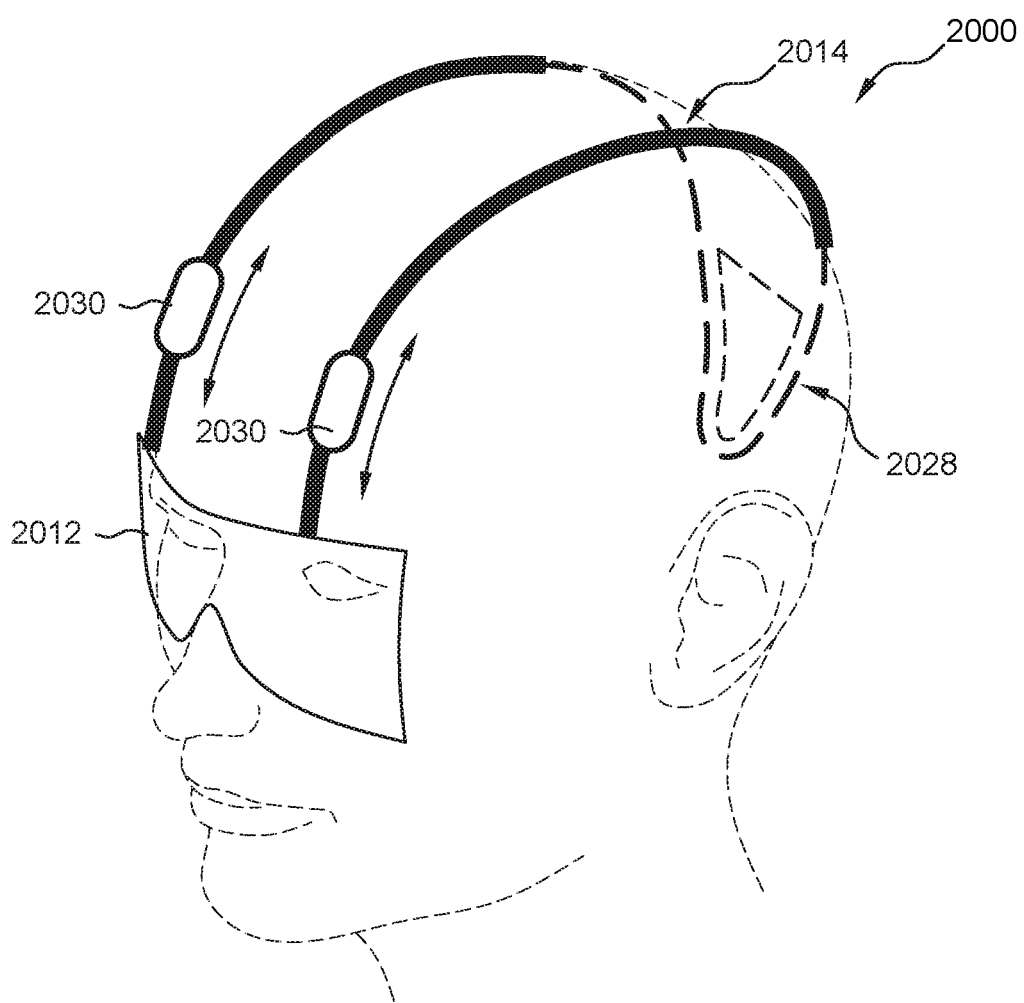

FIG. 23A shows a front perspective view of an augmented reality display system or assembly according to an eleventh example of the present technology.

Figure 23B:
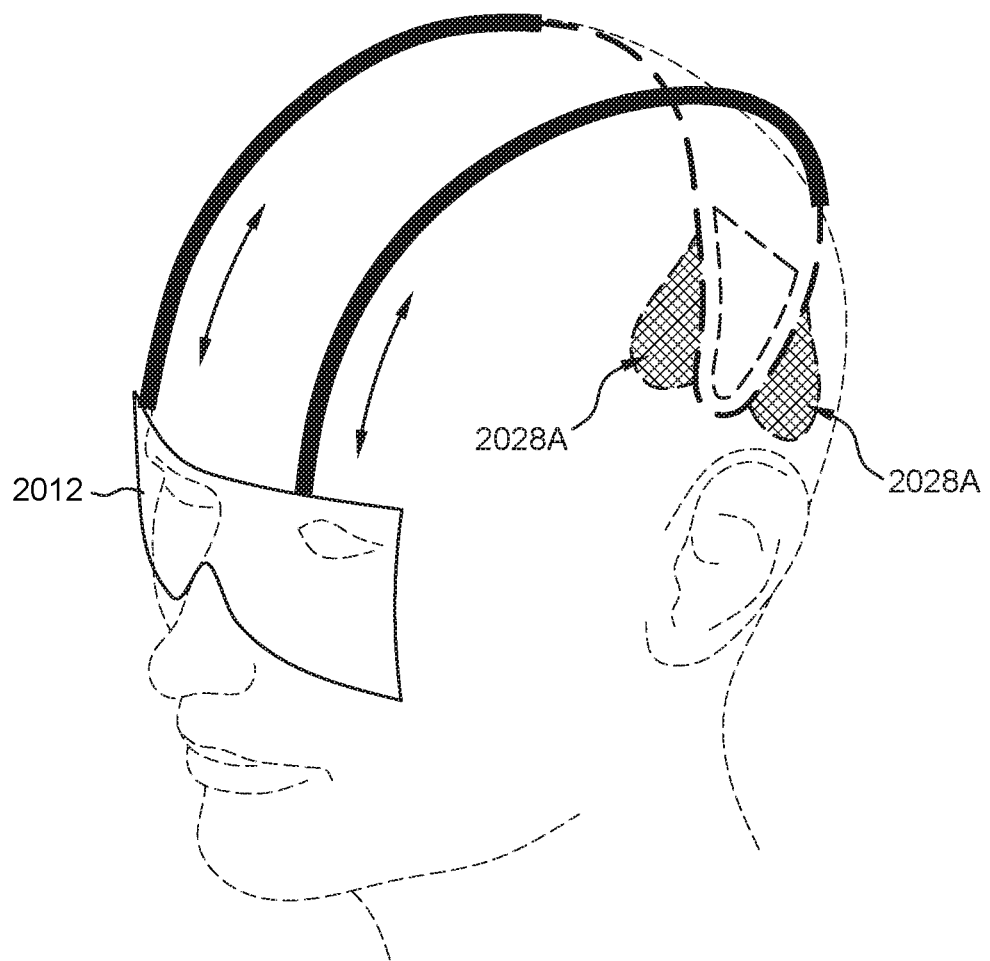

FIG. 23B shows a front perspective view of an augmented reality display system or assembly according to an alternate version of the eleventh example of the present technology.

Figure 24A:
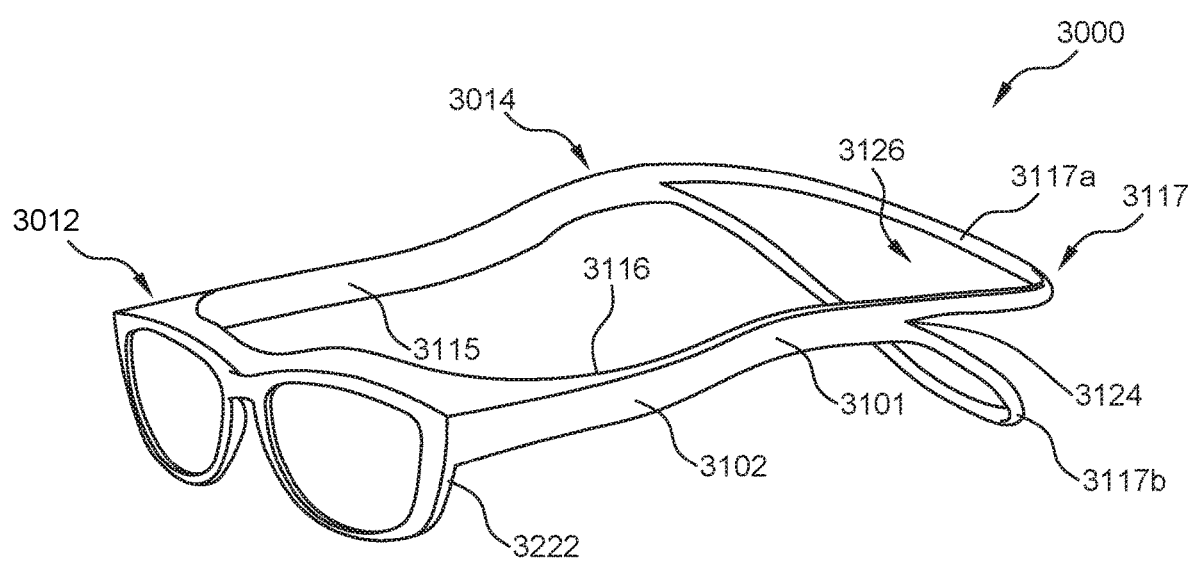

FIG. 24A shows a front perspective view of a head-mounted display system or assembly according to a twelfth example of the present technology.

Figure 24B:
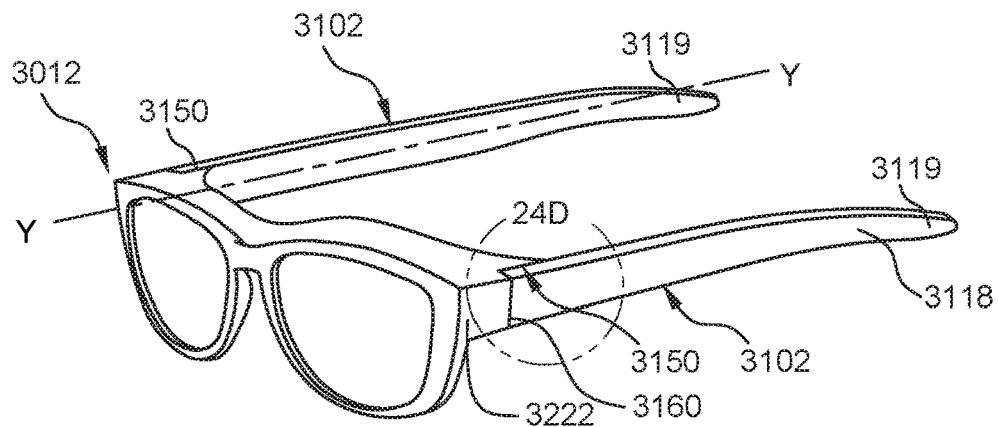

FIG. 24B shows a front perspective view of a display unit and a rigidiser arm formed as part of the head-mounted display system or assembly of FIG. 24A.

Figure 24C:
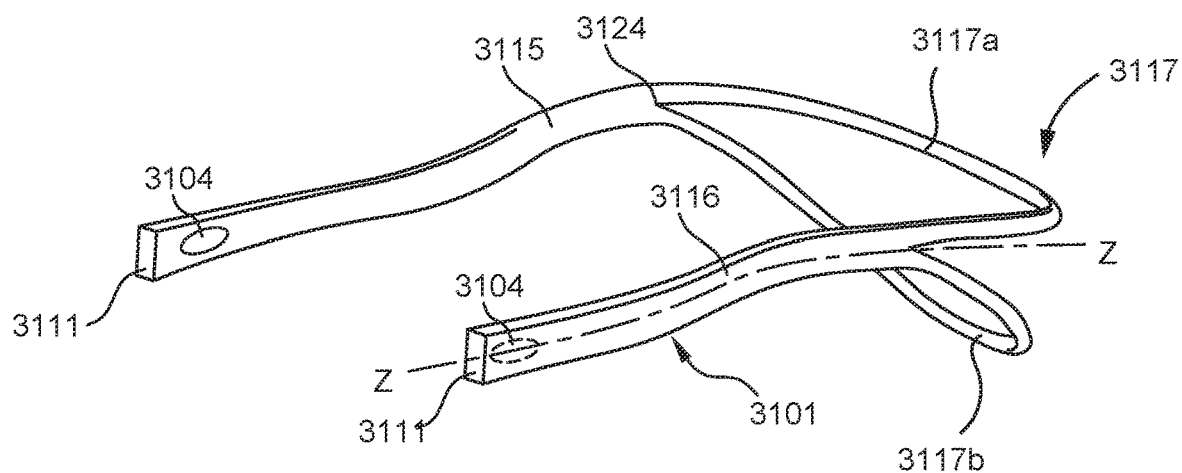

FIG. 24C shows a front perspective view of a strap removable from the rigidiser arm of FIG. 24B.

Figure 24D:
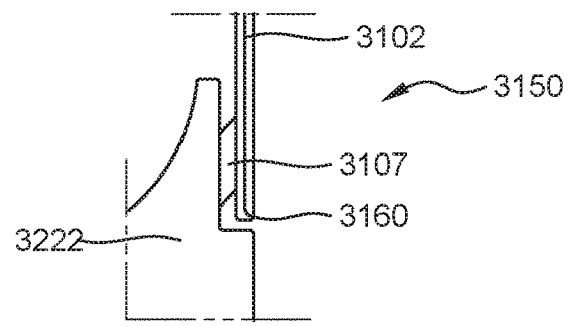

FIG. 24D shows detailed view of FIG. 24B illustrating a headgear connector.

Figure 25A:
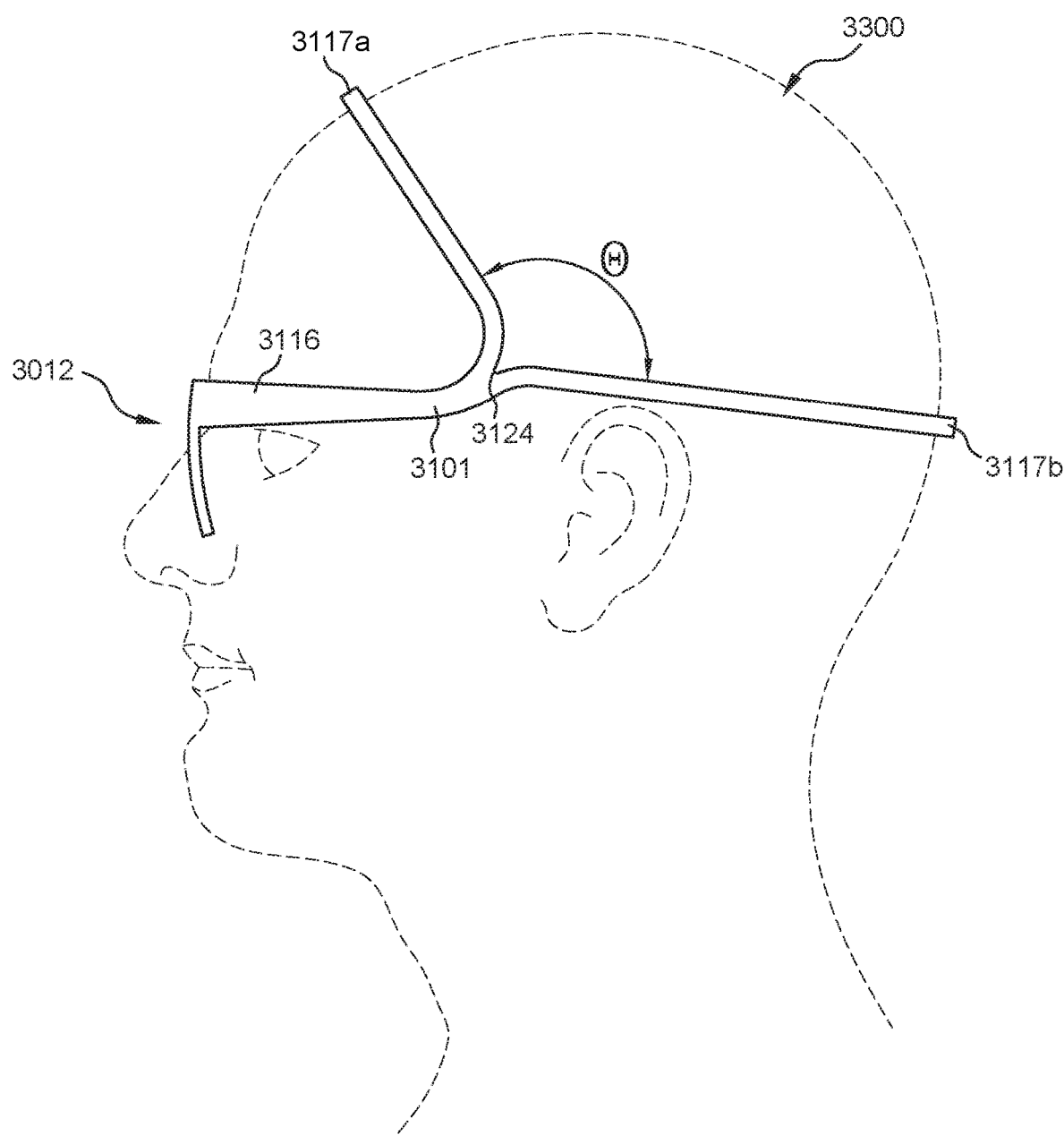

FIG. 25A shows a side view of the head-mounted display system or assembly of FIG. 24A in-use.

Figure 25B:
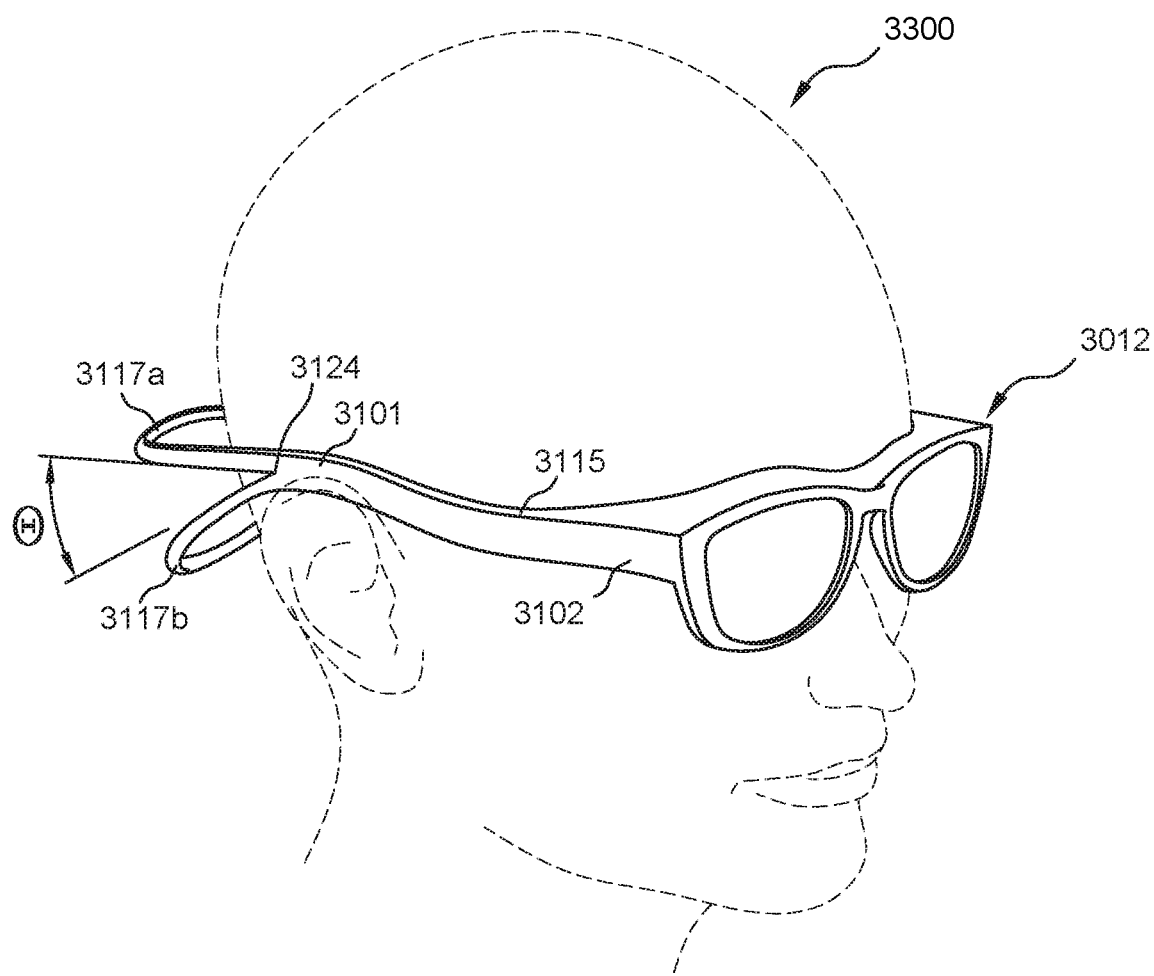

FIG. 25B shows a perspective view of a user donning the head-mounted display system or assembly of FIG. 24A.

FIG. 26A shows perspective view of a head-mounted display system or assembly according to an alternate version of a twelfth example of the present technology.

FIGS. 26B to 26D show variations of the positioning and stabilising of the head-mounted display system according to an alternate version of the twelfth example of the present technology.

Figure 27A:
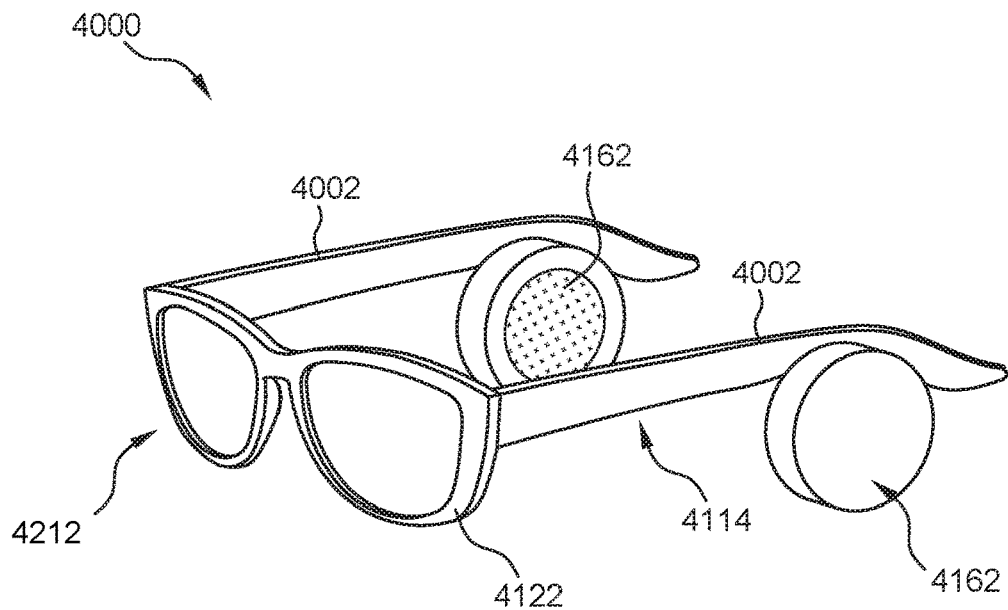

FIG. 27A shows a perspective view of a head-mounted display system or assembly according to a thirteenth example of the present technology.

Figure 27B:
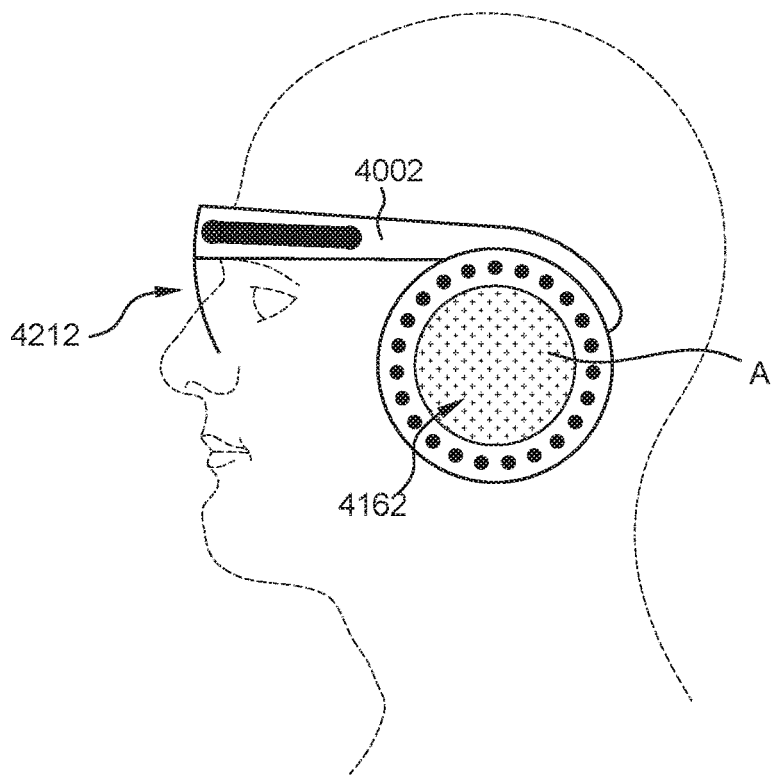

FIG. 27B shows a side view of the head-mounted display system or assembly of FIG. 27A in-use.

Figure 27C:
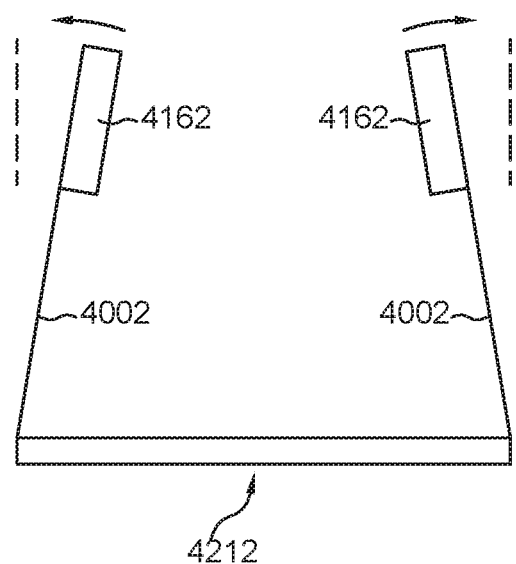

FIG. 27C shows a top view of the head-mounted display system or assembly according to a thirteenth example of the present technology.

Figure 27D:
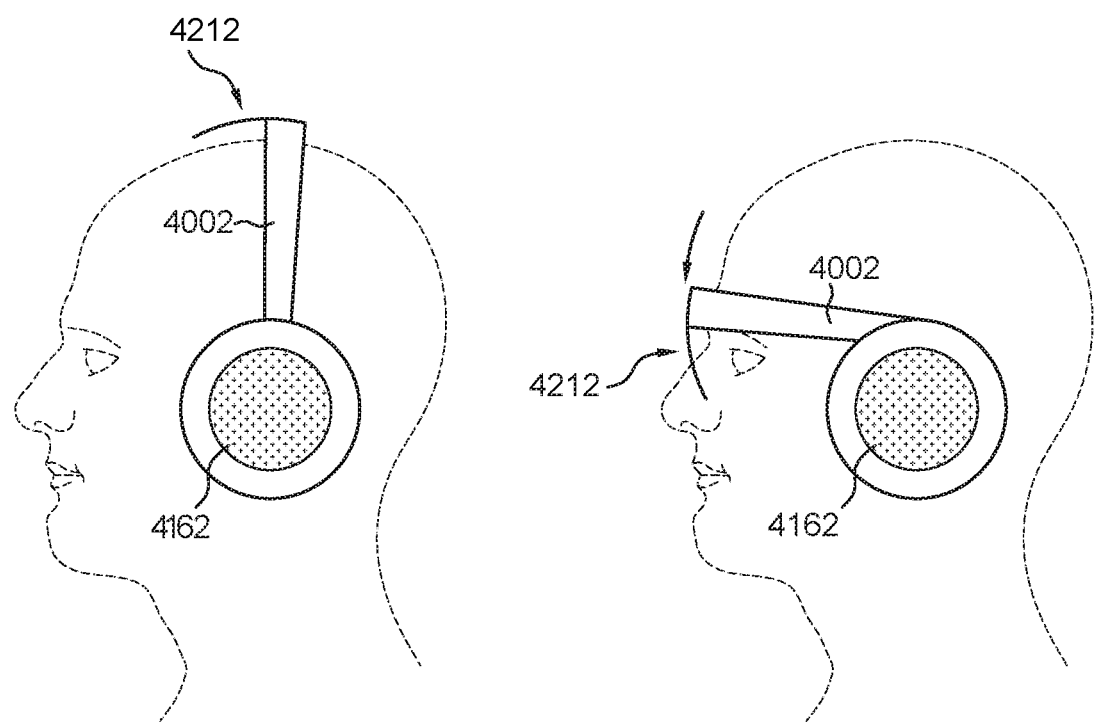

FIG. 27D shows the head-mounted display system or assembly of FIG. 27C in-use, movable between a first position and a second position.

Figures 1, 28A:
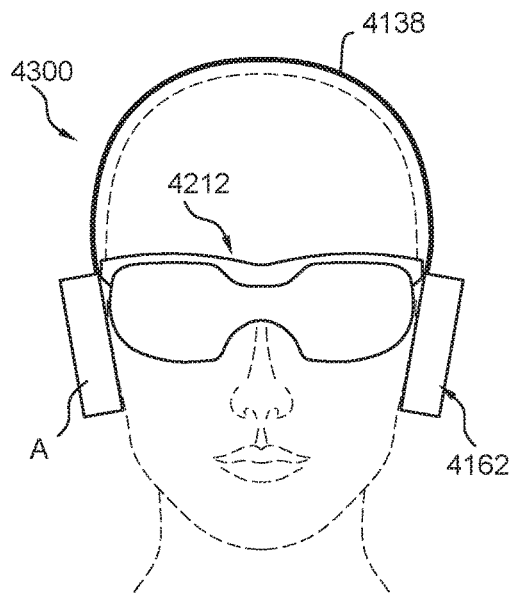

FIG. 28A-1 is a front view of a head-mounted display system or assembly worn by a user according to an alternate version of the thirteenth example of the present technology.

Figures 2, 28A:
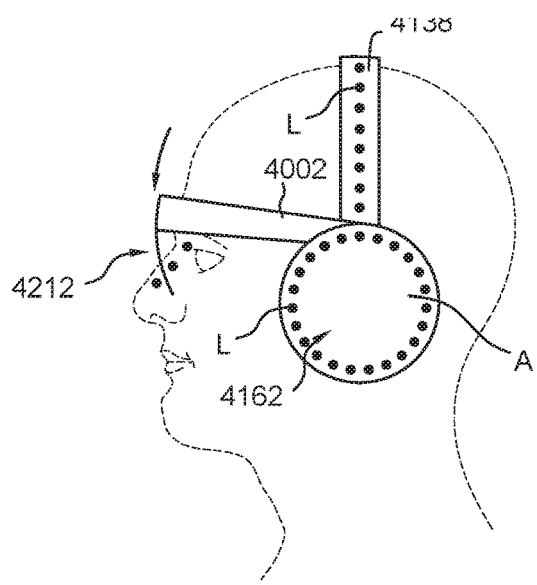

FIG. 28A-2 is a side view of the head-mounted display system or assembly of FIG. 28A-1.

Figures 1, 28B:
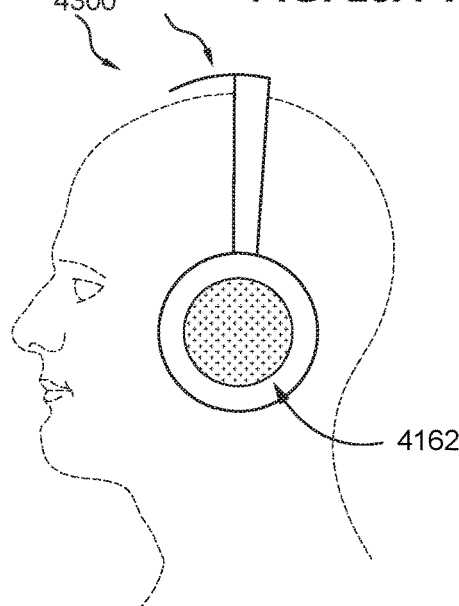
Figures 2, 28B:
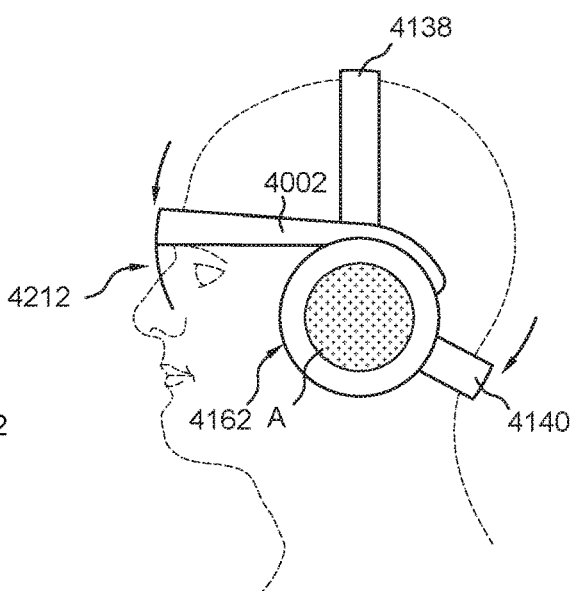

FIG. 28B-1 is a side view of a head-mounted display or assembly worn by a user in a non-use position according to another alternate version of the thirteenth example of the present technology.

FIG. 28B-2 is a side view of a head-mounted display or assembly worn by a user in an in use position according to another alternate version of the thirteenth example of the present technology.

Figures 1, 28C:
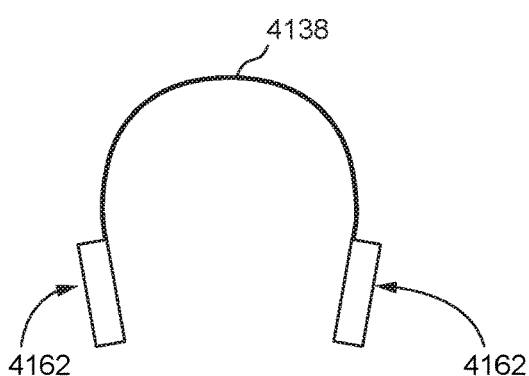
Figures 2, 28C:
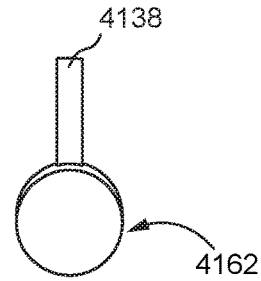

FIG. 28C-1 shows a front view of a coronal portion for use with a head-mounted display system or assembly of the thirteenth example of the present technology.

28C-2 show a side view of the coronal portion of FIG. 28C-1.

Figure 29:
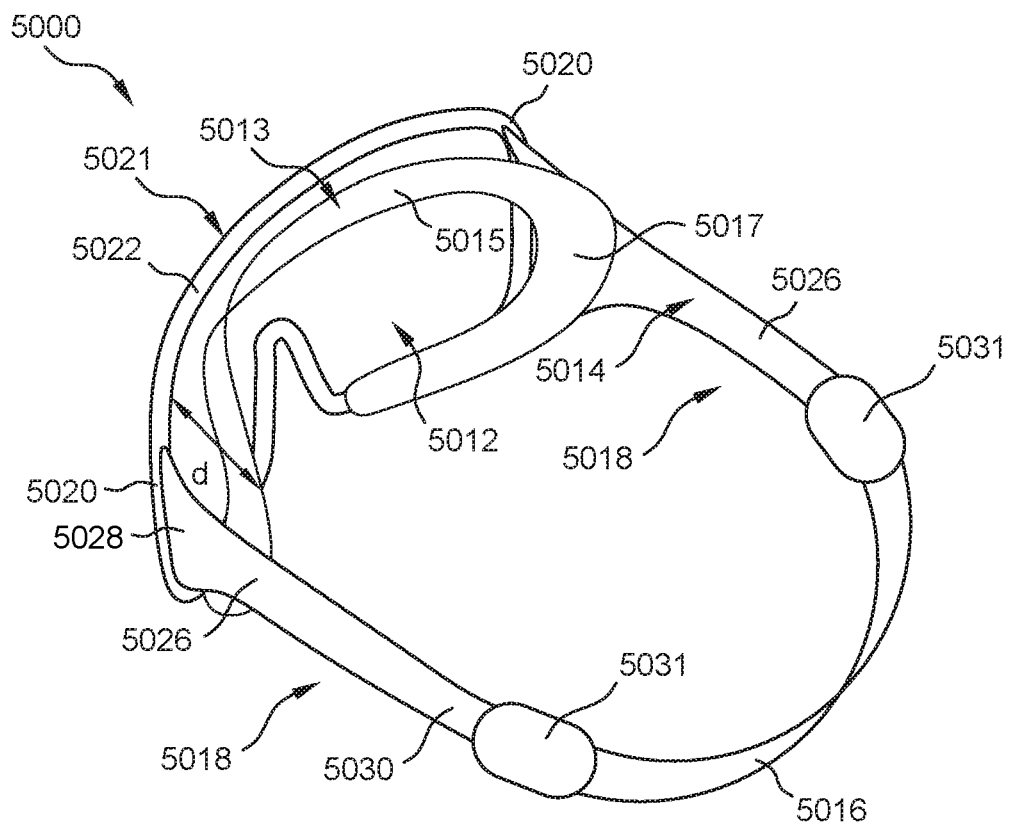

FIG. 29 is a rear perspective view of a head-mounted display according to a fourteenth example of the present technology.

Figure 30:
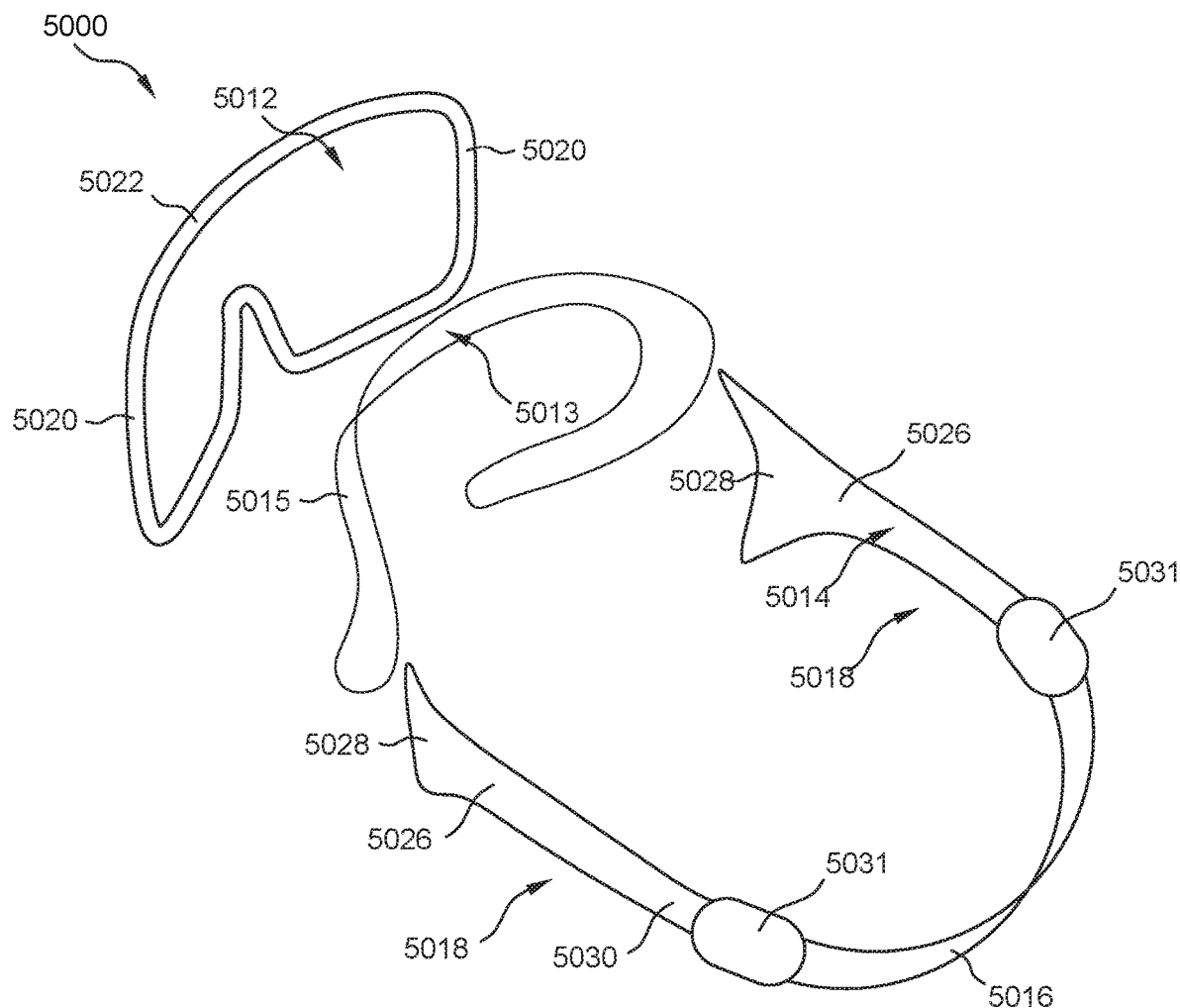

FIG. 30 is a perspective view showing components of a head-mounted display, in-line for assembly, according to the fourteenth example shown in FIG. 29.

Figure 31:
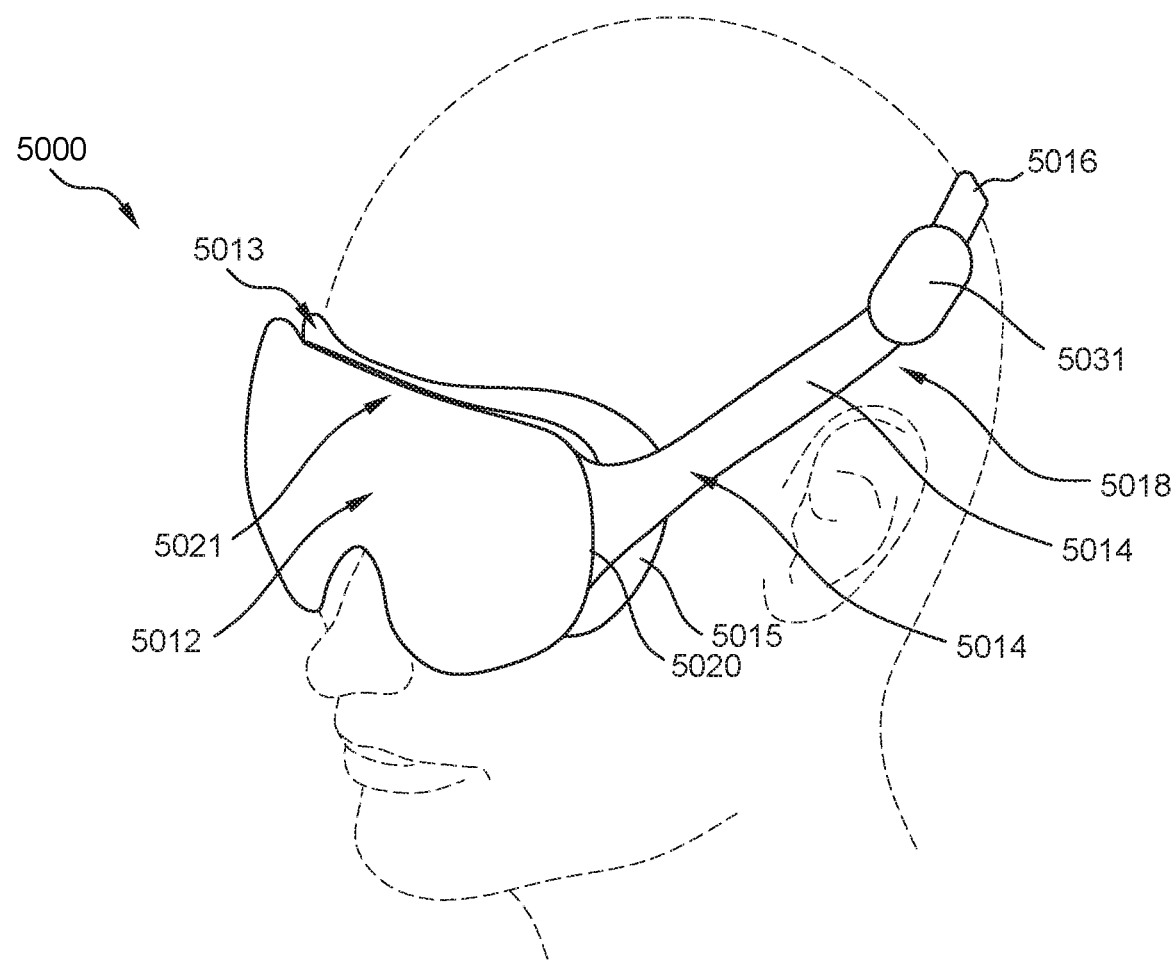

FIG. 31 is a perspective view of the fourteenth example of head-mounted display of FIG. 29, in-use.

Figure 32:
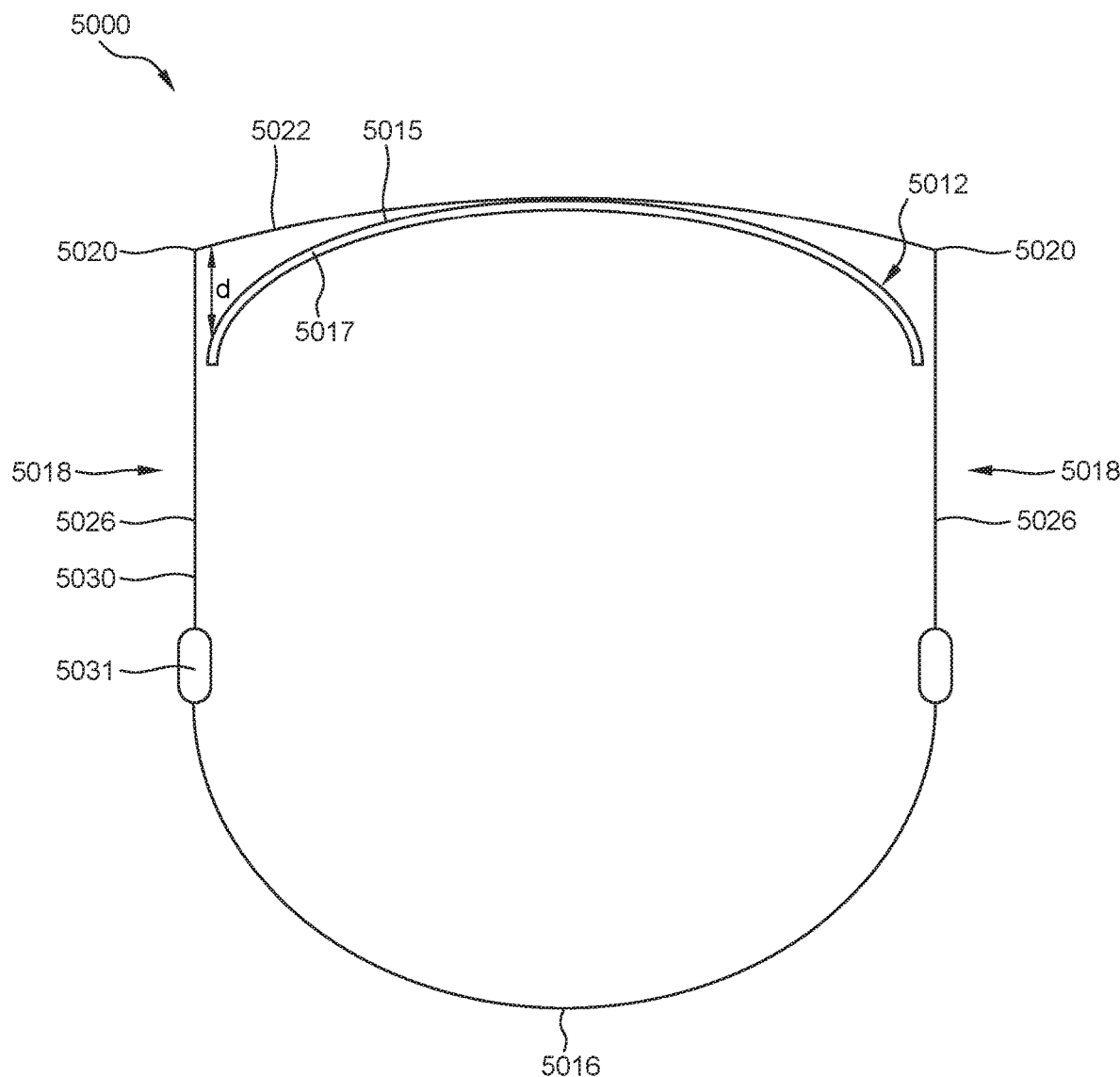

FIG. 32 is a schematic representation of a top view of the head-mounted display of FIG. 29.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

FIGS. 2A to 2C show a support for a head-mounted display system or assembly 10 according to a first example of the present technology. The head-mounted display system 10 comprises a head-mounted display unit 12 (also referred to as a display), and a positioning and stabilising structure 14 (also referred to as a support and stabilising structure, or a support structure) to maintain or hold the display unit 12 in an operational position over a user's face in use.

The display unit 12 includes a user interface structure 13 constructed and arranged to be in opposing relation with the user's face. The user interface structure 13 extends about a display (i.e. a display screen) contained by the display unit housing 22. The user interface structure 13 may extend about the display and define a viewing opening to the display. The user interface structure 13 extends around the user's eyes, and may engage with the user's face, e.g., along the user's nose, cheeks and/or forehead.

In an example, the display screen or display may be configured to selectively output computer generated images that are visible to the user in an operational position. In some forms, the display screen is an electronic display. The display screen may be a liquid crystal display (LCD), or a light emitting diode (LED) screen.

In some forms, the interfacing structure 13 may extend at least partially around the display housing 22 and may form a viewing opening. The viewing opening may at least partially receive the user's face in use. Specifically, the user's eyes may be received within the viewing opening formed by the interfacing structure 13.

The display unit may optionally comprise a light shield that may be constructed from an opaque material and can block ambient light from reaching the user's eyes. The light shield may be configured to extend around the entire perimeter of the display so as to prevent, i.e. shield, light from entering the user's eyes at most entry angles. Alternatively, the light shield may be arranged in specific locations around the perimeter to prevent light entering the user's eyes at known regions of the display unit. For example, the shield may be positioned at opposing sides of the display housing, proximal to the user's temples. In this position, the light shields may limit the amount of light entering the sides of the head-mounted display system.

The light shield may be part of the interfacing structure 13, or may be a separate, detachable or releasable, element.

In some forms, the display screen may include an optical lens (not shown) constructed from a transparent or translucent material configured to allow a user to observe their physical environment while observing the computer generated image.

For example, the display screen may be glass, so the user can see through the display screen. This may be particularly beneficial in augmented reality applications, so that the user can continue to see the physical environment.

In an example, at least one lens may be disposed between the user's eyes and the display screen. The user may view an image provided by the display screen through the lens. The at least one lens may assist in spacing the display screen away from the user's face to limit eye strain. The at least one lens may also assist in better observing the image being displayed by the display screen.

The at least one lens may include a first lens configured to be aligned with the user's left eye in the operational position and a second lens configured to be aligned with the user's right eye in the operational position. In some forms, the lenses may be Fresnel lenses.

The display may comprise a binocular display partitioned into a first section and a second section, whereby the first section may be aligned with the first lens and the second section may be aligned with the second lens.

The head-mounted display system 10 may include a control system that assists in controlling the output received by the user, i.e. the display observed by the user. In other words, the control system can control visual output from the display screen.

The head-mounted display system of the present technology can comprise various configurations (e.g. types) and arrangements of control systems. One example of the control system is set forth below, however, further examples are set forth later in the specification in relation to further examples of the present technology.

The control system may include sensors that monitor different parameters or values (e.g., in the physical environment), and communicates measured parameters to a processor. The output received by the user may be affected by the measured parameters. For example, the processor is configured to change the computer generated images output by the display based on the measured value.

The sensors may include an orientation sensor that can sense the orientation of the user's body, at least one camera that can be positioned to view the physical environment of the user (e.g., in order to determine orientation), and/or an eye sensor that can track movement of the user's eyes to determine which direction at least one of the user's eyes are looking.

In some forms, the processor may comprise a computer or smart phone. Alternatively, the control system can be integrated into the display unit 12, or housed in a control system support that is separate from, but connected to (e.g., electrically connected to) the display unit.

The display unit 12, may also include a controller that can be engagable by the user in order to provide user input to the augmented reality/display and/or to control the operation of the system. The controller can be connected to the display unit 3100, and provide the user the ability to interact with objects output to the user from the display unit 12 (i.e. augmented realities). For example, the controller may have at least one button selectively engageable by a user's finger, that when e.g. depressed/engaged, communicates with the processor (by sending a signal to the processor) to change the computer generated images output (e.g. overlaid) by the display based on the signal.

As described below, the head-mounted display system according to examples of the present technology is structured and arranged to provide a balanced system, i.e., system that is not overly tight at any singular point along the user's head and/or face. That is, the head-mounted display system according to examples of the present technology provides a more even fit that is structured and arranged to distribute pressure over more of the user's head to lessen hot spots or localised stress points.

Also, the head-mounted display system according to examples of the present technology comprises soft and flexible (e.g., elastic) materials (e.g., breathable material, e.g., textile-foam composite) structured and arranged to allow more conformity to the user's head and cushioning for comfort. In addition, the head-mounted display system according to examples of the present technology comprises simple adjustment mechanisms to facilitate adjustment while on the user's head and allow a wide fit range.

In the illustrated example of FIGS. 2A to 2C, the positioning and stabilising structure 14 comprises a rear support structure 16 (also referred to as a rear support hoop) adapted to contact regions of a user's head (e.g., positionable at a crown of the user's head) and at least one connector structured and arranged to interconnect the rear support structure 16 to the head-mounted display unit 12. The crown may be a rear portion of the user's head including the parietal and/or occipital bone. Specifically, the crown may extend approximately between the coronal plane and the Frankfort horizontal. In the illustrated example, the at least one connector comprises opposing temporal connectors 18 disposed on respective sides of the user's head that interconnect the rear support hoop 16 to respective posterior edge regions 20 of the display unit housing 22 of the display unit 12, and a forehead support connector 24 that extends across the frontal bone of the user to interconnect the rear support hoop 16 with a superior edge region 21 of the display unit housing 22. However, it should be appreciated that more or less connectors may be provided to interconnect the rear support structure 16 to the head-mounted display unit 12. The rear support hoop 16 may not cover the entire crown but may be positionable along a portion of the user's crown.

Each of the opposing temporal connectors 18 comprises a temporal arm 26. Each temporal arm 26 includes an anterior end 28 mounted to the respective posterior edge region 20 of the display unit housing 22 and a posterior end 30 that forms part of a releasable coupling to connect the temporal arm 26 to the rear support hoop 16.

Each temporal arm 26 comprises a rigidiser 32, a textile component 34 and a tab 36 arranged at the posterior end 30 for connecting to the rear support hoop 16. In an example, a portion of each of the temporal arms 26, in-use, is in contact with a region of the user's head proximal to the otobasion superior, i.e., above the user's ear. In an example, the temporal arms 26 are arranged in-use to run generally along or parallel to the Frankfort Horizontal plane of the head and superior to the zygomatic bone, i.e., above the user's cheek bone.

In one form, the rigidiser 32 may be encapsulated within the textile component 34 of each temporal arm 26. For example, FIG. 2D shows an example of the textile component 34 in the form of a cover configured to encapsulate the rigidiser 32. In this example, the textile component 34 includes a face contacting side arranged on one side of the rigidiser 32 that can provide a soft, face contacting surface 35 adapted to contact the user's face in use. In some alternative forms, the rigidiser 32 may be stitched or otherwise attached (e.g., overmolded) to the textile component 34, or the textile component can be made of materials that can be selectively rigidised by heat treatment (e.g., heat treatment). For example, FIG. 2E shows an example of the textile component 34 attached to a face contacting side of the rigidiser 32 that can provide a soft, face contacting surface 35 adapted to contact the user's face in use. In an example, the textile component 34 may comprise a textile material or a textile-foam composite (e.g., breathable material, e.g., multi-layered construction including an outer textile layer and an inner foam layer) to provide a soft support for the rigidiser 32 to cushion against the user's head for optimised comfort. The rigidiser 32 can allow each temporal arm 26 to retain an in-use shape and configuration when not worn by a user. Advantageously, maintaining the temporal arms 26 in the in-use state prior to use may prevent or limit distortion whilst the user is donning the positioning and stabilising structure 14 and allow a user to quickly fit or wear the display system 10.

In an example, the rigidiser 32 can be made from a rigid material, e.g., hytrel (thermoplastic polyester elastomer). As such, the rigidiser 32 (or the temporal connector 18 or the temporal arm 26) is rigid along at least a portion of its length. The rigid nature, i.e., inextensibility, of the rigidiser 32 of each temporal arm 26 limits the magnitude of elongation or deformation of the temporal arm 26 while in-use. Advantageously, this configuration enables a more effective, i.e., direct, translation of tension through the temporal arm 26. In an example, the rigidiser 32 may be more rigid than the rear support hoop 16 and/or connection straps 42 (e.g., formed from an elastic and/or textile material). Consequently, the temporal arm 26 of each opposing temporal connector 18 may be more rigid than the other parts of the positioning and stabilising structure 14, such as more rigid than the rear support hoop 16 and/or connection straps 42. The temporal arm 26 (or temporal connector 18) may be more rigid along at least a portion of its length than the other parts of the positioning and stabilising structure 14, such as more rigid than the rear support hoop 16 and/or connection straps 42. For example, in contrast to the rigidiser 32 (or the temporal connector 18 or the temporal arm 26), the rear support hoop 16 and/or connection straps 42 may be stretchable to a desired length, i.e., resiliently extensible along at least a portion of its length.

In an example, the rigidiser 32 may be structurally rigid or stiff to resist bending deformation vertically up and down alongside the user's face, but may allow bending deformation towards and away from the user's face (e.g., to adjust for varying facial width). In an example, the rigidiser 32 may be structurally rigid or stiff to resist deformation under twisting. In an example, the rigidiser 32 may be structurally rigid or stiff to maintain a preformed shape.

In an example, the rigidiser 32 forms a lever-arm, i.e., a means to pivot, about the rear support hoop 16. Advantageously, the rear support hoop 16 can provide an anchor point for the positioning and stabilising structure 14. The rigidiser 32 may articulate about the anchor point of the rear support hoop 16 to enable the forehead support connector 24 to raise or lower the position of the display unit 12 relative to the user's nose. Advantageously, this configuration can minimise the magnitude of clamping pressure to stabilise the display unit 12 on the user's head.

In an example, the thickness and/or width of the temporal arm 26 may vary along at least a portion of its length, e.g., temporal arm 26 may include wider and thinner sections along its length to facilitate connection and to distribute load.

In the illustrated example, the rear support structure or hoop 16 is in the form of a hoop having a ring-like form (similar to the ring-like form of rear support hoop 316 shown in the FIG. 6B example) and is arranged to have a three-dimensional contour curve to fit or conform to the shape of the rear of the user's head, e.g., a user's crown. The rear support hoop 16 comprises a parietal portion or parietal strap portion 38, adapted to be in proximity to the parietal bone of the user's head in use, and an occipital portion or occipital strap portion 40, adapted to be in proximity to the occipital bone of the user's head in use. In an example, the occipital portion 40 is preferably arranged along a portion of the occipital bone in use, e.g., along a portion of the occipital bone adjacent or near a junction where the neck muscles attach, and the parietal portion 38 is preferably arranged rearward of the coronal plane in use. In an example, the occipital portion 40 is adapted to be positioned along a portion of the occipital bone just above a junction where the neck muscles attach to the occipital bone. The junction may also be referred to as the external occipital protuberance (EOP). However, the exact location of the occipital portion 40 on the user's head may vary depending on the size and shape of the user's head with which it is being used, e.g., the occipital portion 40 may be positioned adjacent to, just above, or just below a portion of the occipital bone where the neck muscles attach. In an example, the occipital portion 40 may be arranged beneath or underneath the occipital bone near the junction where the neck muscles attach. This hoop-like arrangement (e.g., circular or ovular or part circular/oval or C-shaped) of the rear support hoop 16 anchors the positioning and stabilising structure 14 around the rear or rear bump of the user's head, which provides an effective support structure to hold weight (i.e. the display unit) at the front of the user's head. The rear support hoop 16 may be formed from an elastic material, which elasticity may be used to stretch the hoop and securely hold the rear support hoop 16 in position.

The rear support hoop 16 further comprises opposing connection straps or tabs 42. The straps 42 are adjustable and operate to change the distance between the rear support hoop 16 and the display unit housing 22 of the display unit 12. Each of the straps 42, in use, is threaded through an eyelet 44 in the tab 36 of a respective temporal arm 26. The length of each strap 42 through the tab 36 of a respective temporal connector 18 may be adjusted by pulling more or less of the strap 42 through a respective eyelet 44. The strap 42 may be secured to itself after passing through the eyelet 44 in the tab 36, for example, with hook-and-loop fastening means, which allows fine or micro adjustment of the straps for comfort and fit (e.g., tightness). Therefore, the distance between the rear support hoop 16 and the display unit housing 22 may be adjusted to fit around different head sizes. Such adjustable strap arrangement also allows adjustment while the system is on the user's head, e.g., user can pull straps 42 to posteriorly tighten.

In an example, the thickness and/or width of the rear support hoop 16 and/or the straps 42 may vary along at least a portion of its length. For example, the rear support loop 16 may include wider and thinner sections along its length, e.g., wider sections adjacent the straps 42 to facilitate connection to the temporal arms 26 and to distribute load. Also the straps 42 may be thinner along it free end to facilitate threading through the eyelet 44 in the respective temporal arm 26.

In one form, the width of the rear support hoop 16 may be smaller at superior and inferior ends. The rear support hoop 16 may widen closer to a center. For example, thinner sections of the rear support hoop 16 may overlay the occipital bone and/or the parietal bones. The wider portion may be positioned proximate to, or overlay, a temporal bone.

In one form, the parietal portion 38 may be wider than the occipital portion 40. The connection between the parietal portion 38 and the forehead support strap 48 may contribute to an increased length.

In one form, the wider section of the rear support hoop 16 may narrow along a curved path toward the strap 42. Each strap 42 may be thinner than either the parietal portion 38 and/or the occipital portion 40.

In an example, the rear support hoop 16 is orientated in a generally vertical direction, i.e., arranged in a vertical plane generally parallel to the coronal plane. This arrangement of the rear support hoop 16 appropriately orients the rear support hoop 16 at the crown of the user's head to support the transverse, i.e., horizontal, tension applied by the connection straps 42 and support the weight of the display unit 12, in-use, at the anterior of the user's head.

The rear support hoop 16 and connection straps 42 may be formed from an elastic and/or textile material to assist conforming to the shape of a user's head, e.g. rear support hoop 16 and connection straps 42 provide stretch capacity. Also, such elastic material at the back of the user's head may allow easier lifting of the display unit 12 away from the user's face in use, e.g., move the display unit 12 away from the user's eyes to talk to someone while the positioning and stabilising structure 14 remains on the user's head. For example, the support hoop 16 may be a neoprene material, or other textile-foam composite (e.g., breathable material, e.g., multi-layered construction including at an outer textile layer and an inner foam layer), or spacer fabric. Advantageously, textiles can provide a soft support structure to stabilise the display unit 12 on a user's head and allow the positioning and stabilising structure 14 to cushion against the user's head for optimised comfort.

The forehead support connector 24 of the positioning and stabilising structure 14 comprises a forehead support strap 48 arranged to run generally along or parallel to the sagittal plane of the user's head. The forehead support strap 48 is adapted to connect between the superior edge region 21 of the display unit housing 22 and the parietal portion 38 of the rear support hoop 16. In an example, the strap 48 can be non-adjustably connected, e.g., welded, to the parietal portion 38, and the strap 48 can be adjustably connected to the display unit housing 22 by an adjustment mechanism 50.

The forehead support strap 48 is adjustable to enable dimensional control of the forehead support connector 24. As best shown in FIG. 2C, an end portion or tab portion 54 of the forehead support strap 48, in use, is threaded through a forehead support hole or eyelet 52 in the superior edge region 21 of the display unit 12. The forehead support strap 48 may be secured to itself after passing through the hole 52 in the display unit 12, for example, with hook-and-loop fastening means, which allows fine or micro adjustment of the straps for comfort and fit (e.g., tightness). In an example, the forehead support strap 48 may comprise a similar material to rear support hoop 16 and/or the connection straps 42, e.g., textile-foam composite (e.g., breathable material, e.g., multi-layered construction including at an outer textile layer and an inner foam layer).

The forehead support connector 24 supports the weight of the display unit 12. The length of the forehead support strap 48 between the superior edge region 21 of the display unit 12 and the parietal portion 38 of the rear support hoop 16 may be adjusted by pulling more or less of the strap 48 through the hole 52. Therefore, the forehead support strap 48 is able to be adjusted to raise or lower the position of the display unit 12 relative to the user's nose, e.g., adjust to angle or lift the display unit 12 relative to the user's face. Advantageously, this adjustment can move the display unit housing 22 away from the user's nose to relieve pressure felt on the face, nose, and/or cheeks. The forehead support connector 24 secures the display unit 12 in position so that the display unit does not slide downwards or laterally on the user's head.

In an example, the thickness and/or width of the forehead support strap 48 may vary along at least a portion of its length, e.g., forehead support strap 48 may include wider and thinner sections along its length to facilitate connection and to distribute load.

As illustrated in FIG. 2C, the forehead support strap 48 may be wider proximate to the parietal portion 38, and may narrow toward the display unit 12. For example, the end portion 54 may be the narrowest portion of the forehead support strap 48. In some forms, the forehead support strap 48 may taper from the parietal portion 38 toward the end portion 54.

In some forms, this may assist the end portion 54 in passing through the eyelet 52. Additionally, because the eyelet 52 is a set size, only a predetermined length of the forehead support strap 48 may pass through. This may assist in limiting over-tightening (e.g., by encouraging a user to select a larger size positioning and stabilising structure 14.

In some forms, the varying width of the forehead support strap 48 may provide the end portion 54 a wider target area to attach to. For example, an entire surface of the forehead support strap 48 may include a connection means (e.g., hook or loop material, magnets, etc.) so that the end portion 54 may attach without extending over an edge.

In an example, the adjustment mechanism 50 is positioned, in use, out of contact with a user's frontal bone region.

In an alternative example, the positioning and stabilising structure 14 does not include a forehead support connector 24/forehead support strap 48, e.g., see example of FIGS. 4A to 4C.

FIGS. 3A to 3C show a support for a head-mounted display system or assembly 110 according to a second example of the present technology. In FIGS. 3A to 3C, like reference numerals denote similar or like parts to FIGS. 2A to 2C with the addition of 100 to allow distinguishing between examples, e.g., display unit 112, user interface structure 113, positioning and stabilising structure 114, rear support hoop 116, temporal connector 118, posterior edge region 120, display unit housing 122, forehead support connector 124, temporal arm 126, parietal portion 138, occipital portion 140, connection straps 142, forehead support strap 148, adjustment mechanism 150, forehead support hole 152, end portion 154. Referring to FIG. 3C, the forehead support connector 124 may further comprise a forehead support rigidiser 156. The forehead support rigidiser 156 can provide further stabilisation and support for the display unit 112 above the user's nose and cheeks, i.e., relieve pressure on the user's nose and cheeks. The forehead support rigidiser 156 can be connected to the superior edge region 121 and form at least part of the forehead support hole 152 to receive an end portion or tab portion 154 of the forehead support strap 148 for dimensional adjustment of the positioning and stabilising structure 114. As illustrated the forehead support strap 148 is arranged beneath the forehead support rigidiser 156 for comfort and load distribution.

In some forms, the adjustment mechanism 150 may further comprise an angle adjustment mechanism (not shown) for easy lifting of the visor from an in-use position to a stowed position, i.e., not in-use.

In an example, the system may be structured and arranged to redistribute one or more components from the display unit to the positioning and stabilising structure, e.g., to redistribute weight from the display unit to the positioning and stabilising structure. For example, the forehead support rigidiser 156 and/or forehead support strap 148 may be used to at least partially support one or more components, such as non-location essential electrical components, e.g., batteries, hard drive storage, flow generator, speaker to shift weight from the front of the user's head to a more central location, i.e., to counterbalance weight of the display unit. In alternative examples, one or more components from the display unit may be at least partially supported by the rear support hoop 116 and/or temporal connectors 118 to redistribute weight.

In some forms, a component (e.g., battery cells) may be dispersed throughout the positioning and stabilising structure 110. For example, the component may include various pieces (e.g., different battery cells) connected along the forehead support strap 148, forehead support rigidiser 156, the rear support hoop 116, and/or temporal connectors 118. Dispersing elements of the across the positioning and stabilising structure 110 may assist in weight distribution.

In some forms, the component may be concentrated along the rear support hoop 116, for example along the occipital portion 140. As described below with respect to various other examples (e.g., FIGS. 7, 11, 12, 15D, 16A, etc.), the component may be positioned along the occipital portion in order to overlay the occipital bone and counterbalance the display unit 112.

In some forms, components may be disposed on both temporal connectors 118. This may balance the weight on either side of the user's head. For example, a battery may be connected to both temporal connectors 118, and electrically connected to the display 112.

FIGS. 4A to 4C show a support for a head-mounted display system or assembly 210 according to a third example of the present technology. In FIGS. 4A to 4C, like reference numerals denote similar or like parts to FIGS. 2A to 2C with the addition of 200 to allow distinguishing between examples, e.g., display unit 212, user interface structure 213, positioning and stabilising structure 214, rear support hoop 216, temporal connector 218, posterior edge region 220, display unit housing 222, temporal arm 226, parietal portion 238, occipital portion 240, connection straps 242. In the third example, the support for a head-mounted display assembly 210 does not comprise a forehead support, i.e., the display unit 212 is supported by a positioning and stabilising structure 214 without any forehead support connector or forehead support straps.

FIG. 5 shows a support for a head-mounted display system or assembly 310 according to a fourth example of the present technology. In FIG. 5, like reference numerals denote similar or like parts to FIGS. 2A to 2C with the addition of 300 to allowing distinguishing between examples, e.g., display unit 312, user interface structure 313, positioning and stabilising structure 314, rear support hoop 316, temporal connector 318, display unit housing 322, forehead support connector 324, temporal arm 326, rigidiser 332, parietal portion 338, occipital portion 340, forehead support strap 348. In the fourth example, the support for a head-mounted display system 310 comprises opposing temporal connectors 318 each having a temporal arm 326 with an extended rigidiser 358. Each extended rigidiser 358 may extend from the respective temporal arm 326 to the rear support hoop 316 to enhance support of the display unit 312, in use. Each extended rigidiser 358 may extend along a portion of the rear support hoop 316 and may extend into one or both of the parietal portion 338 and the occipital portion 340. For example, each extended rigidiser 358 may comprise a Y-shaped or T-shaped form as shown in FIG. 5 that extends into both the parietal portion 338 and the occipital portion 340. Alternatively, each extended rigidiser 358 may only extend into one of the parietal portion 338 and the occipital portion 340, e.g., only extend along the occipital portion 340 as shown in FIG. 6A discussed below. In the example of FIG. 5, the parietal and occipital portions of the extended arms of the rigidiser 358 are provided along the parietal portion 338 and occipital portion 340 of the rear support hoop 316 positioned proximal to the parietal and occipital bones of the user's head to support respective portions of the rear support hoop 316.

In some forms, the rigidiser 358 may be similarly shaped as the rear support hoop 316. For example, the rigidiser 358 may be wider as it extends toward and/or along the temporal arm 326. In some forms, the rigidiser 358 may be approximately the same width as the respective temporal arm 326.

In some forms, the rigidiser 358 may narrow as it extends away from the widest portion and may branch in two opposing direction (thus forming the Y-shape or T-shape). One branch may extend along the parietal portion 338 and another may extend along the occipital portion 340.

In one form, these two branches may be substantially symmetrical. For example, they may extend approximately the same distance along the parietal portion 338 and the occipital portion 340 respectively. The two branches may also have approximately the same width.

In one form, the branches may be unequal. For example, the branch along the parietal portion 338 may be longer and/or wider than the branch along the occipital portion 340. Alternatively, this could be reversed and the branch along the occipital portion 340 could be wider and/or longer than the branch along the parietal portion 338.

The extended rigidisers 358 increase the length of the temporal connectors 318 so as to increase the lever-arm moment created about the rear support hoop 316. In use, the larger lever-arm extends the moment of inertia further rearward of the user's head when compared the first and second examples. Advantageously, this can provide more comfort to the user by decreasing the tension applied to the forehead support connector 324 to support the display unit 312.

Additionally, the extended arms of the rigidiser 358 may provide a more even distribution of pressure on the user's head under the weight of the display unit 312 and any clamping force applied by tension induced in the positioning and stabilising structure 314.

The extended arms of the rigidiser 358 can help prevent the rear support hoop 316 of the positioning and stabilising structure 314 from translating vertically upwards on the user's head when tensioning the forehead support connector 324. The extended arms of the rigidiser 358 can more effectively secure the occipital portion 340 of the rear support hoop 316 along the corresponding occipital bone (e.g., along a portion of the occipital bone adjacent a junction where the neck muscles attach to the occipital bone) of the user's head.

FIGS. 6A to 6C show a variation of the fourth example in FIG. 5. In this example, each of the temporal arms 326 comprises a biased extended rigidiser 360. Each biased extended rigidiser 360 may extend from the respective temporal arm 326 to the occipital portion 340 of the rear support hoop 316, i.e., to generally take a J-shaped form, so as to enhance support of the display unit 312, in use.

In some forms, the J-shape may be an elongated member with at least one free end. The elongated member may include an arcuate section. The arcuate section may be off-centered to form the J-shape.

In some forms, the extended rigidiser 360 may be a single component that includes a free end terminating at either temporal arm 326. The J-shape may therefore be visible while viewing the user from the side (e.g., like in FIG. 6A). However, the extended rigidiser 360 as a whole may not include a J-shape.

In some forms, a separate extended rigidiser 360 may be connected to each temporal arm 326. For example, each extended rigidiser 360 may include a J-shape with a free end proximate to the respective temporal arm 326 and a free end proximate to the occipital portion 340 (and to the free end of the other extended rigidiser 360).

The biased extended rigidisers 360 extend along a portion of the occipital bone, e.g., along a portion of the occipital bone adjacent a junction where the neck muscles attach to the occipital bone, to securely anchor the positioning and stabilising structure 314 so as to support the display unit 312 above the user's nose and cheek.

As best shown in FIGS. 6A and 6B, medial and temporal adjustment mechanisms 362, 364 may be provided to the temporal arms 326 and the biased extended rigidisers 360. The medial adjustment mechanism 362 can be mounted about the medial region of the occipital portion between opposed arms of the biased extended rigidisers 360. In an example, the medial adjustment mechanism 362 may be in the form of a strap threaded through opposing holes 363 in respective posterior ends 368 of the opposing arms of the biased extended rigidisers 360 (see FIG. 6B). The distance between the opposing arms of the rigidisers 360 can be controlled by pulling more or less of the strap 362 through the holes 363.

The temporal adjustment mechanism 364 can be disposed on the temporal arm 326, along the temporal region of the user's head. The temporal adjustment mechanism 364 can be adjustable and operate to change the distance between the biased extended rigidisers 360 and the display unit housing 322.

FIG. 7 shows a head-mounted display system 410 according to a fifth example of the present technology and FIG. 8 shows head-mounted display system 410 in an operational position on a user 'U'. In the forms shown in FIGS. 7 to 11, the head-mounted display system of the fifth embodiment take the form of an augmented reality display system. The augmented reality display system 410 comprises an augmented reality display unit 412, and a positioning and stabilising structure 414 (also referred to as a support and stabilising structure) to maintain or hold the display unit 412 in an operational position over a user's face Stabilising structure 414 comprises an air moving device, i.e. a flow generator 406, located at the posterior end of augmented reality display system 410. The flow generator may also be referred to as a 'blower'. The flow generator provides a flow of gas at a pressure greater than ambient. For example, the flow generator 406 creates an air draft 408 to facilitate heat dissipation from the system 410 and/or the user. The draft 408 may be diverted over electronic components 411 (i.e. as part of the componentry of the system 410) to maintain components 411 within a suitable operating temperature and/or to prevent exposure of excessive heat from electronic components 411 to the user. Similarly, the draft 408 may be diverted over the skin of the user to assist in the removal of heat from the user's skin to improve the comfort of the user when using the head-mounted display. For example, the movement of air across the user's skin can assist in the evaporation of sweat that can lower the temperature of the user.

In some forms, the flow generator can direct air flow via the conduit and ducts to specific locations of the user's head. Apart from providing a cooling effect to the user, the airflow may also be used to promote a sensory response in the user, i.e. stimulating the user's senses. This may be enhance the user's augmented (or virtual) reality experience when using the head-mounted display.

Flow generator 406 may be located anywhere on augmented reality system 410. In some forms, the flow generator may be arranged with respect to the user's head in use such that the axis of rotation of the motor is perpendicular to the user's sagittal plane. The flow generator may be spaced from and suspended by the augmented reality system such that vibration generated by the flow generator is isolated from the user's face. Advantageously, this may also dampen sound generated by the flow generator, in-use.

The flow generator may be spaced from and suspended with respect to the augmented reality system 410 by an isolating member. That is, the isolating member can be positioned between the flow generator and the positioning and stabilising structure. The isolating member may be formed of an elastically deformable material (e.g. silicon, foam, etc.) whereby the deformable material dampens vibration from the flow generator. This may help the system 410 absorb motion or vibrations of the flow generator 406 to allow the augmented reality system 410 to remain in place during use. By way of example, without spacing (and/or suspension) by the elastically deformable material, the user's movements might disrupt the position of the augmented reality system on a user's head.

In some forms, the flow generator 406 may be positioned within a portion of the positioning and stabilising structure 414 and may be fully surrounded and/or encased with the isolating member. Thus, the isolating member may be similarly contained within the positioning and stabilising structure 414 (e.g., and not visible while the augmented reality system 410 is in use). The isolating member may cushion and dampen vibrations from the flow generator 406 in order to limit discomfort to the user. Fully suspended the flow generator 406 may maximize vibrational dampening.

In some forms, the flow generator 406 may be partially surrounded by the isolating member, while a portion of the flow generator 410 remains uncovered by the isolating member. For example, a portion of the flow generator 406 proximate to the user's head may be covered and/or suspended using the isolating member in order to limit vibrations on the user's head. The opposite side may remain exposed. This may improve heat transfer away from the flow generator 406 on the side not covered with the isolating member.

In some forms, the flow generator 406 may be connected to the positioning and stabilising structure 414, but remain outside of the strap (e.g., not enclosed by the strap). For example, this may allow the flow generator 406 to be removed and serviced. The flow generator 406 may be connected to the positioning and stabilising structure 414 (e.g., proximate to an occipital portion) using the isolating member in order to minimize vibrational disturbances. The isolating member may completely surround the flow generator 406, or may partially surround the flow generator 406.

Furthermore, spacing the flow generator from the augmented reality system with a material having vibration isolation and/or dampening properties may be advantageous where the flow generator is capable of high rotational speeds and/or where a control system may change the rotational speed frequently during use such that the torque associated with speed changes causes the flow generator to move relative to the user's head. Accordingly, the vibration dampening properties of the material may help to isolate the user's head from what would otherwise be disruptive forces transferred to the user's head.

In some forms, this may assist in limiting irritating vibrations and/or may assist in keeping the user's head steady (e.g., and not moving as a result of the vibrations) in order to improve the experience of the augmented reality system.

Furthermore, electronic components 411, which may be used to control and/or power display unit 412, need not be located adjacent flow generator 406. For example, electronics 411 may be located proximal display unit 412 at the anterior side of system 410 as shown in FIG. 9. In this case, stabilising structure 414 further comprises an air guide arrangement in the form of a conduit 417, coupled to the flow generator, to enable the flow generator to direct air to, or draw air from, one or more selected areas in proximity of the head-mounted display unit 412. For example, the conduit 417 can direct air, i.e. draft 408, to electronics 411. Conduit 417 may further direct a portion of draft 408 to user 'U' or into a space 401 between user 'U' and display unit 412.

The space 401 may refer to the volume of space that exists between the display unit 412 and the user's face. The volume of the space 401 may thus be dependent on where the user wears the system 410 on their nose, the thickness of the display 412, and/or portions of the display that contact the user's forehead and/or cheeks.

In the illustrated example of FIG. 8, the space is shown as existing between the posterior surface of the display 412 (e.g., right-hand side as viewed in FIG. 8) and the user's skin. The space 401 may therefore be larger proximate to a lateral edge of the display 412 where the distance to the user's face is further from the display 412 (e.g., as a result of the facial curvature).

In some forms, the elastically deformable material may be used in other places of the system 410 not specifically associated with the flow generator 406. For example, the elastically deformable material could surround or partially surround the conduit 417 in order to minimize any vibrations caused by the transport of air.

The conduit 417, i.e. the guide arrangement, can direct the draft 408 to e.g. the user 'U' through a port, i.e. an opening in the conduit 417. The conduit 417 can comprise at least one port to allow the flow generator to either draw air into the conduit 417 via the port, and/or direct air from the conduit via the port.

In some forms, the opening of the conduit 417 may face into the space 401. When directing air toward the user, the opening of the conduit 417 exhausts into the space 401. For example, the conduit 417 may direct air generally toward the user's nose (e.g., the center of the display 412). The air in the space 401 may then exhaust out of the space 401. Alternatively, if the flow generator 401 is drawing air out of the space 401, the opening of the conduit 417 may be positioned in order to receive air from a center of the space (e.g., proximate to the user's nose). Additionally, the flow generator 401 could draw air from the environment outside of the space 401, into the space 401, and then into the opening of the conduit 417.

For example, some forms of the system 410 may include a flow generator 406 that directs the draft 408 along the conduit 417 to the port proximate to the user's face. This draft 408 may provide airflow to cool the user 'U' and/or the electronics 411. For example, the draft 408 may blow into the space 401 and across the nose, eyes, and/or cheeks of the user 'U'. The nasal ridge in particular may be in contact with the display unit 412 (see e.g., FIG. 8), and the draft 408 may help to cool the user 'U' and reduce discomfort along the nasal bridge (e.g., from sweat).

In other example, the system 410 may include a flow generator 406 that draws air from the space 401 and toward the flow generator 406. For example, the electronics 411 associated with the display unit 412 may output heat during use. As a result of the proximity of the display unit 412 to the face of the user 'U', the heat may collect in this space, which may provide discomfort for the user 'U'. The flow generator 406 may draw air away from the space 401 in order to limit discomfort for the user 'U'.

In yet another example, the direction of the flow generator 406 may be adjustable by the user 'U'. For example, the system 410 may include a control (e.g., a button, a switch, etc.) that may selectively adjust the rotational direction of the flow generator 406 in order to change the direction of the draft 408. In another example, the rotational direction of the flow generator 406 may be wirelessly controlled (e.g., via an app on a smartphone). In yet another example, the rotational direction of the flow generator 406 may be controlled using a program. For example, a controller in communication with a temperature sensor or thermistor disposed in or proximate to the space 401 may direct the flow generator 406 to rotate in a particular direction based on the temperature measured by the thermistor. In still yet another example, the controller, the mechanical control, and/or the wireless control may control the rotational direction of the flow generator 406.

In some forms, the conduit 417 may include multiple openings that each function as a port. For example, the conduit 417 may include a series of small openings clustered together that each exhaust and/or intake the draft 408.

In one form, multiple openings may disperse the draft 408 over a wider area than a single port. For example, multiple ports may be used to direct the draft 408 across a wider area of the user's face in order to provide cooling to a greater portion of the user's face. Alternatively or additionally, multiple ports may be used to direct the draft 408 toward the user's face and to electronics 411 in order to provide cooling to each using a single conduit.

In one form, the multiple ports in the conduit 417 may be symmetrically spaced on either side of the user's head in order to provide substantially the same flow of the draft 408 to either side of the user's head.

In some forms, the opening to the conduit 417 (or conduits) may be on an inner portion of the rigidised section 415 of the positioning and stabilising structure 414 (see e.g., FIGS. 7 and 8). For example, as viewed in FIG. 9, the openings to the conduits 417 are not visible in the illustrated orientation.

In certain forms, the system 410 may include a light shield or similar structure that extends from the display 412 toward the user's face. The light shield may limit external light from reaching the display and/or limit light from the display from reaching the external environment (e.g., outside of the space 401). This may assist in limiting disturbances to the user and/or to people around the user (e.g., if the display 412 is used in a dark room). The light shield may further distribute the force of system 410 on the user's face.

In FIG. 9, the light shield may be a curved surface connected between the display 412 and the rigidised section 415. The opening to the conduit(s) 417 may be positioned under the light shield. When worn, the light shield may contact or be in close proximity to the user's forehead. The light shield may then held to direct the flow of air exhausted from the conduit 417 into the space 401. For example, this may increase the cooling effect because the ability of the air from the conduit 417 to leave the space 401 is restricted. Because the display 412 may not form a complete seal (e.g., airtight seal) with the user's face so the air is able to escape out of the space 401 as new air is introduced.

Similarly, as air is directed toward the flow generator 406, the light shield may assist in directing the air toward the opening of the conduit 417 so that it can be removed from the space 401.

The flow generator 406 can comprise a housing and the conduit 417 is integrated within the housing. In some forms, the housing may extend at least partially along the positioning and stabilising structure 414, and the at least one port may be at least one opening integrally formed in the housing. In some forms, the housing may only extend around the flow generator 406 so that at least some of the conduit 417 and the at least one port is outside of the housing.

The stabilising structure 414 may comprise at least one wire for connecting between the flow generator 406 and a power supply, e.g. a battery. The wire(s) may provide electrical communication between the flow generator and the power supply such as for power and/or signalling. The wire(s) may be contained within a portion of the positioning and stabilising structure. The wire(s) may comprise a relatively thin cross-section so as to maintain a low-profile and not be uncomfortable for the user. The wire(s) may be configured such that their rigidity is relatively small in comparison to that of the supporting positioning and stabilising structure, so as to not significantly prevent the positioning and stabilising structure from conforming to the user's face. In one example, the wire may be in the form of a flexible printed circuit (FPC).

The wire(s) may provide control signals to the flow generator 406 from a central controller. One or more sensors e.g., a pressure sensor, may be provided with respect to the flow generator for communicating signals to the central controller via the wire(s). It is envisioned that the pressure sensor could alternatively be a sensor configured to sense a different property of the air, e.g. a temperature sensor (e.g., the thermistor described above), flow rate sensor, etc. For example, a temperature sensor may be provided to sense overheating of the electronic components so as to protect the augmented reality system from damage. Alternatively, (and as described later in detail) the temperature sensor may detect the temperature of a user. As such the temperature sensor may be positioned proximal to the electronic components to sense their temperature and/or a temperature sensor may be positioned proximal to the user's face to sense temperature increase of the user. As described above, these measurements may be used to control the speed and/or rotational direction of the flow generator 406.

In certain forms, the flow generator 406 may only be controlled (e.g., by a controller, by a remote device, and/or by a switch) to operate at certain times. In other words, the flow generator 406 may not run constantly while the system 410 is in use. The flow generator 406 may only provide the draft 408 under certain conditions in order to preserve electrical energy. For example, the flow generator 406 may only provide the draft 408 when a temperature of the electrical components exceeds a threshold and/or when the user 'U' indicates that the temperature is uncomfortable. This may also limit noise and/or vibrational disturbances experienced by the user 'U'.

Returning to FIG. 8, flow generator 406 is mounted at the anterior side of augmented reality display system 410 and acts as a counter weight to display unit 412. The gravitational force acting on the mass of flow generator 406 applies a torque to a rigidised section 415 of stabilising structure 414 about the otobasion superior of user 'U'. The torque applies an upward force to display 412 thereby reducing a supporting force on the bridge of user's nose. That is, the rigidised section 415 acts as a lever, applying a lifting force to display 412 to reduce the supporting force that display 412 applies to user's nose. Therefore, the weight of flow generator 406 counterbalances the weight of display 412 to provide greater comfort to user.

Furthermore, the rigidised section 415 may support the weight of the flow generator such that the flow generator is maintained in a desired position and only exceptional outside forces would be able to disrupt, e.g. displace, the augmented reality system from the desired position on the user's head/face.

Augmented reality display system 410' shown in FIG. 9 further comprises a pivot strap 421 connecting to support structure 414 at pivot point 419, located between display unit 412 at the anterior side and flow generator 406 at the posterior side in the parietal region of the user's head. Pivot strap 421 is configured to engage a user's head at a location superior from flow generator 406.

In one example, pivot point 419 is directly above, or posterior to, the otobasion superior of the user when being used by the user. Similar to the counterbalance effect described with reference to FIG. 8, the weight of flow generator 406 creates a torque on rigidised section 415 about pivot point 419 and thereby applies a lifting force to display 412. That is, pivot point 419 forms a fulcrum allowing rigidised section 415 to act as a lever to apply a lifting force to display 412. The lifting force reduces the supporting force on the user's nose, thereby improving the comfort of the user. In addition, pivot point 419 allows for reduced force on the user's ears thereby further increasing the comfort of the user.

In some examples, pivot strap 421 is used as a mounting structure for additional electronics or energy storage devices. For example, as best illustrated in FIG. 9, batteries 423 may be mounted on pivot strap 421.

In certain forms, at least one port or opening in the conduit 417 may by directed along the pivot strap 421 in order to provide cooling to the batteries 423 (or other electrical elements) and/or to the user's head.

Flow generator 406 may be constructed using any suitable cooling fan or motor. For example, flow generator 406 may be piezo flow generator, an axial or centrifugal pump having a volute or any other suitable flow generator. In some forms, the flow generator may be a controllable, brushless DC motor with one or more impellers housed in a volute. In another example, flow generator may include a brushless DC motor with one or more impellers and stator vanes, and housed in a casing. Typical flow rates for air draft 408 are on the order of 1-20 liters per minute (l/min).

In FIG. 7, draft 408 is illustrated as moving in a single direction only. However, in some examples, flow generator 406 is configured to generate draft in more than one direction. For example, FIG. 10 illustrates a flow generator 406' generating a bidirectional draft 408'. In some circumstances, bidirectional draft 408' may be preferred over draft 408 depending on the layout of electronics 411 and cooling requirements in order to provide cooling flow to a larger area of the system 410 and/or the user 'U'.

In some forms, the flow generator 406 may be generally cylindrical shape and comprise a motor having impellers at either end of the motor. In this form, the impellers are arranged in series on a shaft such that impellers are driven simultaneously by the motor. In forms where the flow generator is configured to produce bidirectional draft, the motor may comprise impellers at either end of the motor arranged to generate a flow of air in opposing directions to each other while being driven by the same shaft. For example, the blades of the impellers at either side of the motor can have mirrored blade arrangements.

In alternative forms, whereby the flow generator 406 produces in a single direction only, the impellers may be arranged to generate a flow of air from only one side of the motor. In this form, the blades of the impellers at either side of the motor can have the same blade arrangements. In this way, both sides of the flow generator generate draft in the same direction.

It is envisioned that the flow generator 406 could include two motors in which each motor drives a set of (or a single) impellers. Further, the augmented reality system may comprise more than one flow generator arranged on the stabilising structure 414. For example, in some forms, a flow generator 406 may be arranged on opposing temporal arms (i.e. one flow generator 406 on each arm).

When using more than one flow generator 406, the flow generators 406 can be provided in a smaller format, i.e. size and weight, such that e.g. two flow generators 406 can produce the same flow rate, pressure, etc. as a single flow generator 406 (being larger in size and weight than the smaller format). Advantageously, the smaller flow generators 406 can be spaced on the positioning and stabilising structure 414 to strategically balance the system 410. For example, the smaller flow generator can be placed on each temporal arm, such that the arms are balanced about the user's head, in-use. Another advantage of utilising more than one (i.e. multiple) flow generators 406, is that by distributing the weight of the smaller flow generators 406 around the user's head (i.e. in more than one location), the user may be less aware of the total weight of the (e.g. two) flow generators 406. In other words, the perceived weight of the flow generators 406 can be less if their weight is distributed.

The motor may comprise multiple sets (i.e. stages) of small diameter impellers in parallel flow paths. The parallel stage arrangement may allow the flow generator to generate sufficient pressure to direct draft 408 through conduit 417 and further, facilitate bidirectional draft. This may be particularly advantageous for forms of the augmented reality system where the electronic components to be cooled are disposed in the conduit remote, i.e. spaced at a long distance, from the flow generator 406 and connected via the conduit 417. In such forms, the pressure generated by the flow generator 406 must be sufficiently large to draft air along the length of the conduit 417. By way of example, when the electronic components to be cooled are spaced closer to the flow generator 406, the conduit length would be shorter, and require a relatively lower pressure to be generated by the flow generator 406. The flow generator 406 also comprises one or more inlet(s) and outlet(s) for respectively, drawing air into, and generating air outward from the flow generator 406. As illustrated in FIG. 10, the flow generator 406' may thereby form a flow path, whereby an air draft passes into the flow generator inlet, past the impellers (and other components of the motor e.g. stators), and out of the flow generator outlet (indicated by air flow 408').

FIG. 11 illustrates an alternative embodiment of a head-mounted display 510, which is suitable for use in virtual reality systems. The display unit 512 includes a user interface structure 513 constructed and arranged to be in opposing relation with the user's face. The user interface structure 513 extends about a display contained by the display unit housing 522. The user interface structure 513 may extend about the display and define a viewing opening to the display. The user interface structure 513 extends around the user's eyes, and may engage with the user's face, e.g., along the user's nose, cheeks and/or forehead to define a closed in structure. In use, air trapped in the closed in structure between the user and display unit 512, can heat up as a result of the user's body heat and/or electronics in display unit 512. This heated, trapped air becomes a source of discomfort to the user.

Similar to the arrangement as described above with reference to fifth example of the present technology (e.g., FIGS. 7 to 10), the head mounted display system comprises an air moving device, or flow generator 506 (similar to the flow generator 406). The flow generator 506 provides a flow of gas at a pressure greater than ambient. For example, the flow generator 506 creates an air draft to facilitate heat dissipation from the system 510 and/or the user. The draft may be diverted over electronic components within the display unit 512 to maintain components within a suitable operating temperature and/or to prevent exposure of excessive heat from electronic components to the user.

As described above, flow generator 506 generates an air draft 508. A portion of draft 508 is directed to the closed in space of the display unit 512 through one or more conduits 517. This portion of draft 508 displaces the trapped air in the closed in structure, thereby helping to maintain a comfortable temperature for the user in the closed in space.

In other forms, the flow generator 506 may generate a draft 508 directed toward the flow generator 506 and away from the closed in space of the display unit 512. As described above, the electronics of the display unit 512 may generate heat, which may be drawn away via the draft 508.

In the alternative embodiment of a head-mounted display 510 suitable for virtual reality systems, the flow generator 506 may be spaced from and suspended by the virtual reality system such that vibration generated by the flow generator 506 is isolated from the user's face. Separating the flow generator 506 from the user's face in this way may also dampen sound generated by the flow generator 506, in-use, to improve the comfort of the user.

The flow generator 506 may be spaced from and suspended with respect to the virtual reality system 510 by an elastically deformable material, e.g. silicon. The deformable material may help the system 510 absorb motion or vibrations of the flow generator 506 to stabilise the virtual reality system 510 during use. For example, during operation of the flow generator 506, the motor produces centrifugal forces that may be felt by the user if the flow generator 506 is not at least partially isolated from the user's head. Spacing (or suspension) of the flow generator 506 by the elastically deformable material may allow for dampening of the centrifugal forces created by the motor such that the user is less likely to perceive such forces in-use.

Furthermore, spacing the flow generator 506 from the virtual reality system with a material having vibration isolation and/or dampening properties may be advantageous where the flow generator 506 is capable of high rotational speeds and/or where a control system may change the rotational speed frequently during use such that the torque associated with speed changes causes the flow generator 506 to move relative to the user's head. Accordingly, the vibration dampening properties of the material may help to isolate the user's head from what would otherwise be disruptive forces transferred to the user's head.

In some forms, the flow generator 506 may comprise one or more input devices in the form of buttons or switches to allow a user to interact with the flow generator 506. For example, a button may be provided that enables a user to turn the motor of the flow generator 506 on or off, to change the rotational direction of the flow generator 506, and/or change the rotational speed of the flow generator 506. Advantageously, this may allow the user to conserve battery power in the virtual reality system by manually controlling whether the flow generator 506 is operating. This may also assist in reducing noise and/or vibrational disturbances produced by the flow generator 506 that could disturb the user.

In alternative forms, (and as previously described) the flow generator 506 may be automatically operated via a control system. The control system may automatically adjust, e.g. the rotational speed of the motor as e.g. the temperature of the electronic components increases during use to effect airflow across the electronic components. As described with respect to previous forms, the control system may operate the flow generator 506 so that it does not continuously run, and may only operate the flow generator 506 when a measured temperature exceeds a threshold. This may assist in saving electrical energy, reducing noise, and/or minimizing vibrations.

The control system may comprise a central controller configured to implement one or more algorithms expressed as computer programs stored in a non-transitory computer readable storage medium, such as memory. In some forms the central controller may be integrated within the augmented reality system, and in other forms, the central controller may operate remotely of the virtual reality system.

In some forms, the central controller may be the same controller as the controller that operates the head-mounted display 512 or may be in communication with the controller that operates the head-mounted display 512. The controller(s) may control the flow generator 506 to output the draft 508 based on the output of the head-mounted display 512. In other words, the flow generator 506 may contribute to the immersive experience of the user and may provide the draft 508 in accordance to what is user is viewing on the head-mounted display 512.

The stabilising structure 514 of the head-mounted display system 510 in the form of a virtual reality system may comprise at least one wire for connecting between the flow generator and a power supply, e.g. a battery. This may allow the power supply to be spaced at a distance from the display 512 so as to balance the head-mounted display 512.

The wire(s) may provide electrical communication between the flow generator 506 and the power supply such as for power and/or signaling. The wire(s) may be contained within a portion of the positioning and stabilising structure 514. The wire(s) may comprise a relatively thin cross-section so as to maintain a low-profile and not be uncomfortable for the user. The wire(s) may be configured such that their rigidity is relatively small in comparison to that of the supporting positioning and stabilising structure 514, so as to not significantly prevent the positioning and stabilising structure 514 of the virtual reality system 510 from conforming to the user's face. In one example, the wire may be in the form of a flexible printed circuit (FPC).

The wire(s) may provide control signals to the flow generator 506 from a central controller. The central controller may be positioned within the virtual reality display unit 512, or about the positioning and stabilising structure 514.

One or more sensors e.g., a temperature sensor, may be provided with respect to the flow generator 506 for communicating signals to the central controller via the wire(s). It is envisioned that the temperature sensor may positioned within the display 512 to detect overheating of the air in the space between the display and the user's face/eyes. Advantageously, a sensor in this position can utilised to trigger/activate the flow generator 506 (via the control system) to generate and direct airflow into the display 512 to cool the air in contact with the user's face, in turn, improving the comfort of the user.

As described below, the head-mounted display system 510 according to examples of the present technology is structured and arranged to provide a balanced system, i.e., system that is not overly tight at any singular point along the user's head and/or face. That is, the head-mounted display system 510 according to examples of the present technology provides a more even fit that is structured and arranged to distribute pressure over more of the user's head to lessen hot spots or localised stress points.

Also, the head-mounted display system according to examples of the present technology comprises soft and flexible (e.g., elastic) materials (e.g., breathable material, e.g., textile-foam composite) structured and arranged to allow more conformity to the user's head and cushioning for comfort. In addition, the head-mounted display system 510 according to examples of the present technology comprises simple adjustment mechanisms to facilitate adjustment while on the user's head and allow a wide fit range.

In the illustrated example of FIG. 11, the positioning and stabilising structure 514 comprises a rear support structure 516 (also referred to as a rear support hoop) adapted to contact regions of a user's head (e.g., positionable at a crown of the user's head) and at least one connector structured and arranged to interconnect the rear support structure 516 to the virtual reality display unit 512. In the illustrated example, the at least one connector comprises opposing temporal connectors 518 disposed on respective sides of the user's head that interconnect the rear support hoop 516 to respective posterior edge regions 520 of the display unit housing 522 of the display unit 512, and an optional forehead support connector 524 that extends across the frontal bone of the user to interconnect the rear support hoop 516 with a superior edge region 521 of the display unit housing 522. However, it should be appreciated that more or less connectors may be provided to interconnect the rear support structure 516 to the virtual reality display unit 512.

Each of the opposing temporal connectors 518 comprises a temporal arm 526. Each temporal arm 526 includes an anterior end 528 mounted to the respective posterior edge region 520 of the display unit housing 522 and a posterior end 530 that forms part of a releasable coupling to connect the temporal arm 526 to the rear support hoop 516.

Each temporal arm 526 comprises a rigidiser 532, a textile component 534 and a tab 536 arranged at the posterior end 530 for connecting to the rear support hoop 516. In an example, a portion of each of the temporal arms 526, in-use, is in contact with a region of the user's head proximal to the otobasion superior, i.e., above the user's ear. In an example, the temporal arms 526 are arranged in-use to run generally along or parallel to the Frankfort Horizontal plane of the head and superior to the zygomatic bone, i.e., above the user's cheek bone.

The flow generator 506 is mounted at a lower portion of the rear support hoop, proximal to the occipital portion of the user's head. In this way, the flow generator is mounted at an opposing side of the head to the virtual reality display 512 (e.g., proximate to the user's occipital bone) to act as a counter weight to the display unit 512. The gravitational force acting on the mass of flow generator 506 applies a torque to a rigidised sections 532 of the temporal arms 526 of stabilising structure 514. The torque applies an upward force to display 512 thereby reducing a supporting force on the bridge of user's nose. That is, the rigidized sections 532 act as a lever, applying a lifting force to display 512 to reduce the supporting force that display 512 applies to user's nose. Therefore, the weight of flow generator 506 counterbalances the weight of display 512 to provide greater comfort to user.

Furthermore, the rigidised section 532 may support the weight of the flow generator such that the flow generator is maintained in a desired position and only exceptional outside forces would be able to disrupt, e.g. displace, the virtual reality system from the desired position on the user's head/face.

In some forms, the conduit 517 may be positioned on an outer surface of the rear support structure 516 and/or the temporal connectors 518. For example, the conduit 517 may be exposed and visible while in use. This may allow a user to view the interior of the conduit 517 and determine if cleaning is needed.

In certain forms, the display unit housing 522 may include an opening that allows the conduit 517 to pass through the display unit housing 522. An opening of the conduit 517 may thus be located within the display unit housing 522 in order allow airflow into and/or out of the display unit housing 522.

In one form, the opening of the conduit 517 may be oriented toward a center of the display unit housing 522 (e.g., where the user's nose is located). This may allow the airflow exiting the conduit 517 to be directed into a center of the space within the display unit housing 522 (e.g., and pass over the display 512 and/or the user). Although the virtual reality display system 510 may be positioned closer to the user's skin than the augmented reality display system 410 (described above), there may still be spaces (see e.g., space 501 in FIG. 11-1) between the user and the display unit housing 522 where air is able to escape into an external environment. Similarly, the space may allow air to enter the display unit housing 522 in the event that the flow generator 506 is drawing air into the display unit housing 522 and toward the flow generator 506.

In some forms, the conduit 517 may be positioned within the rear support structure 516 and/or the temporal connectors 518. For example, the rear support structure 516 and/or the temporal connectors 518 may cover and/or enclose the conduit 517 so that it is not exposed. This may provide a more aesthetically pleasing view. The conduit 517 may also be surrounded by a cushioning material (e.g., foam) in order to limit irritation to the user.

In certain forms, the display unit housing 522 may include an opening that allows the conduit 517 to pass from an inner portion of the temporal connector 518 through the display unit housing 522. An opening of the conduit 517 may thus be located within the display unit housing 522 in order allow airflow into and/or out of the display unit housing 522.

Referring to FIGS. 12 to 14 a further embodiment of a positioning and stabilising structure 614 for a head-mounted display system 600 according to a sixth example of the present technology is disclosed. The head-mounted display system 600 primarily differs from the first embodiment shown in FIG. 3 in that the positioning and stabilising structure 614 comprises a crown support hoop 603 that is positionable across both frontal and parietal bones of a user's head. Temporal-crown support connectors 642 interconnect the crown support hoop 603 to opposing temporal connectors 618.

Although the head-mounted display system 600 of the sixth example in FIGS. 12 to 14 takes the form of a virtual reality display system, it can be equally applied to an augmented virtual reality display system. In this form, the crown support hoop 603 may be utilised to support e.g. a flow generator (as set forth above), componentry of the flow generator, or batteries, etc. of the head-mounted display system. Advantageously, the crown support hoop 603 can provide support to the positioning and stabilising structure such that the weight of the abovementioned components can be stably supported on a user's head. For example, the crown support hoop 603 can provide additional 'anchor' type regions on the user's head, such that the additional weight of the abovementioned components are less able to move (e.g. dislocate, skew, etc) the display unit relative to the user's eyes (when in use). Furthermore, the crown support hoop 603 can provide an additional attachment point for the abovementioned components such that they may be located in an optimal position relative to the display unit, e.g. to counter-balance the weight of the display unit.

In some forms, the flow generator may be mounted with respect to the display 512 as previously set forth in the fifth example of the present technology.

A forehead support connector 624 extends across the frontal bone of the user to interconnect the crown support hoop 603 with a superior edge of the display unit housing 622. The forehead support connector 624 can be used in the same way as the forehead support connectors defined in previous embodiments, e.g. as per the forehead support connector 24 shown in FIG. 3a. That is, the forehead support connector may be adjusted in length to allow the positioning and stabilising structure to fit different size heads.

In the further embodiment of the positioning and stabilising structure 614 shown in FIGS. 12 to 14, the crown support hoop 603 may have a ring-like form (e.g., halo shaped) and be arranged to have a three-dimensional contour curve to fit to the shape of a user's head, specifically across the user's frontal and parietal bones, i.e. a top of the user's head. The hoop 603 comprises a parietal portion 638, being in proximity to the parietal bone of the user's head, and a frontal portion 601, being in proximity to the frontal bone.

The three-dimensional shape of the crown support hoop 603 may have a generally round three-dimensional shape adapted to cup the parietal bone and frontal bone of the user's head in use. The term 'three-dimensional' refers to the crown support hoop being shaped to extend from left to right sides of the user's head along the coronal plane, and to extend from front to back of the user's head along the sagittal plane.

The support hoop 603 engages with the frontal and occipital bones in order to maintain the hoop 603 in position and prevent the positioning and stabilising structure 614 from sliding down the user's head, in-use. In particular, the frontal portion 601 engages with the frontal bone in order to maintain the hoop 603 in position and prevent the display unit 612 from sliding down the face of the user's head, in-use. Further, the parietal portion 638 can capture or pass over the upper part of the user's parietal bone, in-use, so as to prevent the positioning and stabilising structure from slipping back down the user's head, in-use.

In some forms, the crown support hoop 603 may be formed with an inverted halo shape. As illustrated in FIGS. 12 and 13, the crown support hoop 603 may be curved between the anterior and posterior regions of the user's head. In the illustrated examples, the crown support hoop 603 sits higher (e.g., more superior) on the user's head at the anterior and posterior regions, and lower in the middle (e.g., thus forming an arcuate shape).

The curvature illustrated in FIGS. 12 and 13 may be in addition to the curvature illustrated in FIG. 14, where the crown support hoop 603 may be formed with a circular or elliptical shape. Together, these two curvatures may form an "inverted halo" shape. These curvatures may form a wider opening so that the crown support hoop 603 may rest lower on the user's head. This, in turn, may assist in providing more stability on the user's head.

This may give the crown support hoop 603 a three-dimensional shape because there are curvatures around two intersecting (e.g., perpendicular) axes. In some forms, the crown support hoop 603 may maintain the three-dimensional shape even when not worn by the user.

The further embodiment of FIGS. 12 to 14 also comprises a rear support hoop 616, having a similar structure to the embodiment of the rear support hoop 16 shown in FIG. 3a. That is, the rear support hoop 616 comprises a ring-like form arranged to have a three-dimensional contour curve to fit to the shape of a user's crown. The rear support hoop 616 of the further embodiment in FIGS. 12 to 14 comprises a parietal portion that is continuous with the parietal portion 638 of the crown support hoop 603. In other words, the crown and rear support hoops share the parietal portion 638.

The rear support hoop 616 may extend toward an inferior portion of the user's head proximate to the user's occipital bone. As illustrated in FIGS. 12 and 13, a portion of the rear support hoop 616 may extend inferior to the user's ear and overlay the user's occipital bone. Tension may pull the rear support hoop 616 into the user's head in order to secure it in place (e.g., to limit slippage in the superior-inferior direction).

In some forms, the rear support hoop 616 may include a three-dimensional shape even when not worn, similar to the crown support hoop 603. The three-dimensional shape provides the curved shape (e.g., which may correspond to the different curvatures of the user's head) and allows the rear support hoop to overlay the parietal and occipital bones to increase stability on the user's head.

The crown support hoop 603 is orientated in a generally horizontal direction, i.e. arranged in a horizontal plane generally parallel to the Frankfort horizontal. This arrangement of the hoop appropriately orients the hoop, in-use, across the frontal and parietal bones of the user's head to support vertical loadings applied by the weight of the display unit 612 (at the anterior of the user's head) and the battery pack 615 (at the posterior of the user's head). The loadings applied by these weights may act through the temporal-crown support connectors 642 and the forehead support connectors 624.

The further embodiment of FIGS. 12 to 14 differs from previously disclosed embodiments (such as FIGS. 3a-3c) in that the three-dimensional crown support hoop 603 may provide greater dynamic stability than the forehead support strap 48. That is, in the embodiment shown in FIG. 3c, the forehead support strap 48 extends primarily along the sagittal plane of the user's head, providing dynamic stability to the head mounted display when the user e.g. moves their head forwards or backwards. The forehead support strap 48 does not extend along the coronal plane in the same way as the crown support hoop 603 of the further embodiment in FIGS. 12 to 14. Thereby, the forehead support strap of FIG. 3c may provide less dynamic support when e.g. the user moves their head from left to right.

Advantageously, the crown support hoop 603 of the further embodiment extends across both sagittal and coronal planes so as to 'cup' around the top of the user's head. In this way, the hoop 603 may stabilise the head mounted display in all directions (i.e. front-to-back and side-to-side) when a user is e.g. moving their head while using the head mounted display.

As best shown in FIG. 14, the hoop 603 can be circular in shape (when viewed from the top of the head) so as to traverse around a portion of the user's head. In some forms, the hoop 603 can be elasticated (e.g. a neoprene material, or other textile-foam composite) so as to be resiliently stretched to conform to the spherical-like shape of the user's head. In this way, the hoop can be provided as a 'one-size-fits-most' component, whereby the hoop is shaped to compliment the shape of the head.

In some forms, the hoop 603 can be provided as a single piece of material, e.g. textile so that the hoop 603 can extend uninterrupted (e.g. without adjustment portions) around the user's head. This can maximise contact between the hoop and the user's head to improve 'grip' of the hoop at the user's head. This may improve the stability of the hoop 603, and in turn, stability head mounted display when in-use.

In some forms, the crown support hoop 603 and straps 642 may be configured with rigidisers (not shown) to provide localised stiffness in the hoop 603 and straps 642. Advantageously, the rigidising elements may prevent some regions of the head mounted display from moving in ways, e.g. directions or magnitudes, that can destabilise the head mounted display when in-use.

In some forms, the crown support hoop 603 may include a continuous rigidiser so that the shape of the crown support hoop 603 is substantially unable to change. For example, the arcuate (e.g., halo) shape may not change as a result of a user wearing the crown support hoop 603 (e.g., stretching and deformation is limited). This may help to consistently position the crown support hoop 603 on the user's head.

In some forms, the crown support hoop 603 may be only partially rigidised. This may allow portions of the crown support hoop 603 to flex and/or stretch, while keeping other portions of the crown support hoop 603 rigid. For example, anterior and posterior portions of the crown support hoop 603 may include rigidisers while the remaining portions may not. As viewed in FIG. 14, this may include rigidisers proximate to the forehead support connector 624 and/or to the battery pack 615, and may not include rigidisers proximate to the connectors 642.

In some forms, other portions of the positioning and stabilising structure 614, like the rear support hoop 616, may include rigidisers. For example, the rear support hoop 616 may contact a rear portion of the user's head (e.g., overlaying the occipital bone). Rigidisers along at least this portion may assist in anchoring the rear support hoop 616 to the user's head (e.g., in order to limit movement during use).

In the form shown in FIGS. 12 to 14, temporal-crown connectors 642 extend generally across the temporal bone of the user to connect the crown support hoop 603 with the temporal connectors 618. In the forms shown in FIGS. 12 to 14, the connectors 642 space the hoop 603 from temporal arms 626. In other words, the hoop 603 and arms 626 are spaced apart and the connectors 642 extend between the space to connect at the hoop and arms.

The temporal-crown connectors 642 are located on both sides of the user's head (as best shown by FIG. 14). Advantageously, the connectors 642 provide lateral support to the crown support hoop 603 by connecting the hoop 603 to the temporal connectors 618. This lateral support may prevent the hoop 603 moving or sliding to either the left or right side of the user's head (i.e. relative to the sagittal plane) during use.

In some forms, as shown in FIG. 12, the connectors 642 can be static and fix the hoop 603 and arms 626 at a predetermined distance from each other. In some other forms, as shown in FIG. 13, the connectors 642 are adjustable and operate to change the distance between the hoop 603 and arms 626 so that the positioning and stabilising structure 614 can fit different head sizes. The adjustability described here could similarly be used in other forms of headgear (e.g., for augmented reality, etc.).

For example, the connectors 642 may be elastic and stretch based on a size of the user's head in order to achieve a proper fit. The connectors 642 may start at a first length prior to use and stretch to a second length (i.e., longer than the first length) when worn by the user based on the size of the user's head. When the user removes the hoop 603, the connectors 642 may return to their original size. This may be repeated with continuous donning and doffing. Additionally, this may allow multiple users with different sized heads to use the same hoop 603. In other examples, the connectors 642 may include hook and loop material so that the user may selectively adjust the length.

In certain forms, one or more of the connectors 642 may be formed with rigidisers. For example, the connectors 642 may be formed from a rigid material, which may be encased in a flexible material. This could involve a rigid plastic piece covered by a textile in order to achieve rigidity and comfort. The connectors 642 may alternatively be formed from a textile with selective stitching to limit elongation and increase rigidity.

In one form, the connectors 642 may be rigidised along a portion of the length so that the length may be partially extended but in limited sections. This may control the total length extension so that the connectors 642 do not overstretch. This may be beneficial when the positioning and stabilising structure 614 comes in different sizes (e.g., small, medium, large, etc.). For example, a user wearing a positioning and stabilising structure 614 that is too small may overstretch the connectors 642 in order to fit their head. In doing so, the connectors 642 may break and/or the remaining components of the positioning and stabilising structure 614 may not fit the user's head. Allowing limited extension may signal to a user that they need a different (e.g., larger) size positioning and stabilising structure 614.

In one form, the arms 626 may be unrigidised or partially rigidised so that they may stretch in order to be length adjustable to different sized heads. The arms 626 may be partially rigidised in order to permit elongation up to a certain point, where the strap then becomes rigid. This may limit over-tightening of the arms 626 and alert a user to use a different sized positioning and stabilising structure 614 if the arms 626 are not tight enough upon reaching the limit.

Referring to the form shown in FIG. 13, the adjustable connectors 642 of the positioning and stabilising structure 614 comprise temporal-crown straps 640 to connect the crown support hoop 603 with the temporal arms 626. The straps 640 can be connected, e.g., by a welded joint, to the crown hoop 603 and can be connected to the arms 626 by an adjustment mechanism 662.

In the form shown in FIG. 13, the adjustment mechanisms 662 comprise eyelet 644 in each of temporal arms 626. The straps 640, in use, are threaded through the eyelets 644 and the length of the connectors 642 between the eyelets 644 and the hoop 603 may be adjusted by pulling more or less of the connector 642 through one or both of the eyelets 644. The connector 642 may be secured to itself after passing through the eyelets in the arms 626, for example, with hook-and-loop fastening means.

The strap 640 is adjustable to enable dimensional control of the temporal-crown connectors 642. The strap therefore is able to be adjusted to change the position of the display unit 612, in-use. For example, the strap 640 can be adjusted to raise or lower the posterior edge regions 620 of the housing 622 such that the display is angled relative to the Frankfort horizontal. In another example, the strap 640 can be adjusted together with forehead support connector 624 to raise or lower the position of the display unit 612 relative to the user's nose.

Advantageously, adjusting the position of the display unit 612 can move the display unit housing 622 away from the user's nose to relieve pressure felt on either of the face, nose, or cheeks. In particular, the forehead support connector 624 can be adjusted to shorten or lengthen the distance between the display unit 612 and the temporal-crown straps 640 adjust the distance between the hoop 603 and the arms 618. The temporal-crown straps 640 and the forehead support connector 624 both secure the display unit 612 in position so that the display unit does not slide downwards or laterally on the user's head.

The adjustable strap 640 (on one or both sides of the positioning and stabilising structure) can be adjusted in length to effectively change the dimensions of the rear support hoop 616. For example, pulling more of the connector 642 through one or both of the eyelets 644 effectively decreases a circumference-like dimension of the rear hoop 616. Such a dimensional change may improve fit of the rear support hoop on a user with a smaller sized head. Conversely, pulling less of the connector 642 through one or both of the eyelets 644 effectively increases the circumference-like dimension of the rear hoop 616. This dimensional change may improve fit of the rear support hoop on a larger sized head.

Adjustment of the strap 640 allows the rear hoop 616 to be adjusted in size (i.e. circumferential length), and also allows the display unit 612 to be moved relative to a user's nose. This dual-type adjustment is a result of the parietal strap 638 being shared by both the rear hoop 616 and the crown support hoop 603. In other words, the parietal portion 638 forms part of both the rear support hoop and the crown support hoop. In some forms, the adjustment of the rear hoop 616 size can be independent of the adjustment made to strap 640 to adjust the position of the display unit 612 relative to a user's nose.

In the further embodiment shown in FIGS. 12 to 14, the forehead support connector 624 of the positioning and stabilising structure 614 comprises a forehead support strap 648 that extends across the frontal bone of the user to interconnect the crown support hoop 603 with a superior edge of the display unit housing 622. The strap 648 can be connected, e.g., by a welded joint, to the frontal portion 601 of the crown hoop 603 and can be connected to the housing 622 by an adjustment mechanism 650.

The strap 648 is adjustable to enable dimensional control of the forehead support connector 624. As represented schematically in FIGS. 12 to 14, the strap 648, in-use, is threaded through a forehead support hole 652 in a forehead tab portion 654 of the superior edge region of the display housing 622. The strap 648 may be secured to itself after passing through the hole in the tab, for example, with hook-and-loop fastening means.

The length of the strap 648 between the tab 654 and the frontal portion 601 of the hoop 603 may be adjusted by pulling more or less of the strap 648 through the tab 654. The strap therefore is able to be adjusted to raise or lower the position of the display unit 612 relative to the user's nose. Advantageously, this adjustment can move the display unit housing 622 away from the user's nose to relieve pressure felt on either of the face, nose, or cheeks. The forehead support connector 624 secures the display unit 612 in position so that the display unit does not slide downwards or laterally on the user's head.

FIGS. 15A-15D and 16A-16H show head-mounted display systems 700 according to a seventh example of the present technology. In these particular examples the head-mounted display systems 700 are configured for use as virtual reality (VR) headsets but, unless the context clearly requires otherwise, the disclosure herein is to be understood as applicable to a head-mounted display system configured for AR or another extended or artificial reality. The head-mounted display system 700 in each of these examples comprises a head-mounted display unit 720. The head-mounted display unit 720 may comprise a display configured for VR, for example as described above.

In some examples, such as those shown in FIGS. 15D and 16A-16H, the head-mounted display system 700 further comprises a battery pack 790. The battery pack 790 is configured for powering the head-mounted display system 700. While various features are described herein in the context of a head-mounted display system 700 comprising a battery pack 790 separate from a head-mounted display unit 720, it is to be understood that, unless the context requires otherwise, each feature may also be applied in head-mounted display system 700 which does not comprise a battery pack 790 separate from a head-mounted display unit or which includes a battery pack 790 located elsewhere than posterior to the user's head. In some examples the head-mounted display system 700 is powered by a power cable connected to a non-head-mounted power supply and, in other examples, is powered by one or more batteries within the head-mounted display unit 720.

Each head-mounted display system 700 comprises a positioning and stabilising structure 750 configured to hold the head-mounted display unit 720 anterior to a user's eyes such that the display is viewable by the user in use. The head-mounted display unit 720 may also be configured to hold the battery posterior to the user's head in use.

In some forms of the seventh example, the head-mounted display unit 720 may also be configured to support a flow generator (e.g. a blower) and related componentry with respect to the display unit 720. The flow generator may be used as a counterweight to help balance the display unit 720. For example, the positioning and stabilising structure 750 may be configured to hold the flow generator in a location overlying the occipital bone of the user's head in use. The flow generator may be arranged with respect to the positioning and stabilising structure as otherwise described in relation to the fifth example of the present technology. In other forms, the flow generator may be mounted with respect to the display unit 720 as previously set forth in the fifth example of the present technology.

The positioning and stabilising structure 750 in the examples shown in FIGS. 15A-15D and 16A-16H also comprises a posterior support portion 752 configured to engage a posterior portion of a user's head. The posterior support portion 752 may anchor against the posterior surfaces of the user's head and may be connected to the head-mounted display unit 7207 via one or more strap portions configured to provide a force to hold the head-mounted display unit 720 against the user's face in use. The head-mounted display systems 700 shown in FIGS. 15A-15D and 16A-16H may each comprise an anterior support portion 754 connected between the posterior support portion 752 and the head-mounted display unit 720. The anterior support portion 754 may comprise one or more strap portions under tension in use to pull the head-mounted display system in a posterior direction to hold it against the user's face.

The posterior support portion 752 and anterior support portion 754 may be formed from one or more strap portions. The strap portions may be in forms described elsewhere herein. For example, the strap portions may be formed from a foam inner layer and textile outer layer(s). Strap portions may be substantially inextensible or may be elastically extendable. Some particular strap portions described herein may be one of inextensible or extendable, depending on the particular positioning and stabilising structure 750 being described.

In examples in which the head-mounted display system 700 comprises a battery pack 790 (or other counterweight), the positioning and stabilising structure 750 may be configured to hold the battery pack 790 (or other counterweight) in a low position on the user's head. In some examples, the positioning and stabilising structure 750 is configured to hold the battery pack 790 in a location overlying the occipital bone of the user's head in use. The battery pack 790 may be connected to the positioning and stabilising structure 750 by a hook-and-loop connection, press studs or the like or comprise an interlocking connection to one of the strap portions of the positioning and stabilising structure 750, such as to a sagittal strap portion 756 or top strap portion 758.

In some examples the head-mounted display unit 720 may comprise arms to which the positioning and stabilising structure 750 is able to connect. In some examples the head-mounted display unit 720 comprises a housing and a pair of arms extending from the housing, for example in a posterior direction. The anterior support portion 754 of the positioning and stabilising structure 750 may connect to the arms. For example, lateral strap portions 760 of the positioning and stabilising structure 750 may connect to the arms.

With reference to the head-mounted display system 700 shown in FIGS. 15A-15C, the head-mounted display system 700 comprises a head-mounted display unit 720 comprising a display, and a positioning and stabilising structure 750 configured to hold the head-mounted display unit 720 in an operable position on the user's head in use. In the example illustrated in FIGS. 15A-15C the head-mounted display unit 720 is configured for VR display but in other examples it may be configured for AR display. Features of the positioning and stabilising structure 750 described with reference to FIGS. 15A-15C are suitable for both VR and AR headsets, as described above.

As shown in FIGS. 15A-15C, the positioning and stabilising structure 750 also comprises a pair of superior support pads 762. Each of the superior support pads 762 is located on a respective lateral side of the user's head and is configured to lie against an at least partially superior-facing portion of the user's head in use to support at least some weight of the head-mounted display system 700. The superior support pads 762 may each lie against partially superior and partially lateral facing surfaces of the user's head. The superior support pads 762 may have stiffnesses sufficient to resist sliding down the side of the user's head.

In some forms, each superior support pad 762 contacts the user's head above the user's respective ear, generally parallel to or in the coronal plane and/or extending substantially between or along the posterior and anterior auricle lines. For example, each superior support pad 762 may overlay the respective temporal bone and/or the parietal bone. In some forms, the superior support pads 762 may at least partially intersect the user's coronal plane. Pads may have a curved shape (curved inwardly from inferior to superior end) to help cup the user's head.

The posterior support portion 752 in the example illustrated in FIGS. 15A-15C comprises an occipital strap portion 764. The occipital strap portion 764 is configured to overlie or lie below an occipital bone of the user's head. The occipital strap portion 764 may be substantially inextensible.

The anterior support portion 754 in this example comprises a frontal support portion 766 configured to engage the user's head at a region overlying a frontal bone of the user's head. The frontal support portion 766 may alternatively be known as a forehead support. The frontal support portion 766 in this example lies against a surface of the user's forehead that faces anteriorly more than superiorly, although in other examples it may lie against a surface overlying the frontal bone which faces more superiorly than anteriorly. The frontal support portion 766 may be substantially inextensible. The positioning and stabilising structure 750 also comprises a band portion 768 configured to fit around the user's head. The band portion 768 comprises the occipital strap portion 764 and the frontal support portion 766 (e.g. the occipital strap portion 764 is the posterior portion of the band portion 768 and the frontal support portion 766 is the anterior portion of the band portion 768), although in other examples the band portion 768 may be a separate portion. The band portion 768 may be integrally formed in some examples.

In this example of the present technology, each of the superior support pads 762 extends superiorly and medially from the band portion 768 on a respective side of the user's head. The superior support pads 762 may extend from the band portion 768 superiorly and medially to match superiorly and laterally facing surfaces of the user's head. For example, the superior support pads 762 may be integrally formed with the band portion 768. Or, the superior support pads 762 may be removably attached to the band portion 768. In this example the superior support pads 762 each curve medially. This may allow the superior support pads 762 to fit against correspondingly curved surfaces of the user's head. The superior support pads 762 may be partially compliant or may comprise a compliant portion configured to fit to a range of curvatures, which may enable the superior support pads 762 to fit securely against a variety of user head shapes and sizes. The compliant portion may be a foam layer, silicone layer or the like.

In some forms, each superior support pad 762 may be bendable or flexible (e.g., made from a plastically deformable material) in order to allow the user to make individualized adjustments. For example, the user may be able to apply a desired curve to each support pad 762 in order to match the curvature of the user's head.

In certain forms, the superior support pads 762 may remain stiff despite being bendable. In other words, the superior support pads 762 may retain their portion after being bent (e.g., elastically deformable). Additionally, contact with the user's head may not substantially change the desired curvature of the superior support pads 762.

In some forms, each superior support pad 762 may be pre-curved, and the user may not be limited from further curving the superior support pads 762. In this case, the superior support pads 762 may come in different sizes that a user can select based on their specific head side.

In some forms, the superior support pads 762 are constructed from a different material than the band portion 768. For example, the superior support pads 762 may be stiffer than the band portion. This may help the superior support pads 762 maintain a desired curvature and/or assist in supporting the weight of the display unit 720.

As illustrated, each of the superior support pads 762 is located in (e.g. intersects) a mid-coronal plane of the user's head in use. In this example, the superior support pads 762 are not connected to each other across a superior surface of the user's head. The superior support pads 762 may not intersect the sagittal plane of the user's head in use. In other examples the superior support pads 762 may be connected or connectable by a strap portion, for example. In still other examples, a single superior support pad 762 may extend across the user's head in use. An advantage of the superior support pads 762 not extending across the top of the user's head, and an advantage of the lack of a top strap portion, is that much of the user's hair is left untouched. This may allow the user to use the head-mounted display system 700 without worry that the positioning and stabilising structure 750 will flatten or mess up the user's hair.

The superior support pads 762 may advantageously transmit some of the weight of the head-mounted display system 700 to partially superior-facing surfaces of the user's head. Supporting some of the weight of the system 700 at these points may advantageously reduce a force with which other parts of the head-mounted display system 700 are required to engage the user's head (in particular, a clamping/constricting force created by tension in the band portion 768 may not need to be as large if some of the weight is supported by the superior support pads 762).

The superior support pads 762 may resist weight of the head-mounted display system 700 with a combination of contact pressure and friction. The lateral spacing between the superior ends of the superior support pads 762 may be less than a width of the user's head, meaning the superior support pads 762 will support weight of the head-mounted display system 700, provided they are sufficiently stiff that they are able to resist being spread apart by the user's head. The superior support pads 762 may each have lateral stiffness (e.g. stiffness to resist forces acting in the lateral directions), to push back on the surface of the user's head in use to support weight of the head-mounted display system 700. In some examples, each superior support pad 762 may be biased medially to engage the user's head in use.

The superior support pads 762 may provide for a large surface area of contact (at least in comparison to the band portion 768 alone) between the head-mounted display system 700 and the user's head, which keeps contact pressure low for a given force (e.g. given weight of the system that needs to be supported). This may also provide for good stability. A head-mounted display system 700 stationary on the head with the user upright and straight will bear load differently on the head to when the user looks all the way down or all the way up, tilts head to the side or shakes their head (e.g. during gameplay). When the user moves their head, the portion of the head-mounted display system 700 that supports the majority of the weight will change. The superior support pads 762 provide two contact zones additional to the front and back portions of the positioning and stabilising structure 750, creating four contact zones, e.g. in anterior, posterior, left and right positions. This may advantageously result in a head-mounted display system 700 that is stable during dynamic use (e.g. movement) as there are pairs of opposing contact zones in both the anterior-posterior axis and the left-right axis, which may provide good support when the user's head is in any of many possible orientations.

As shown in FIGS. 15A and 15B, the positioning and stabilising structure 750 in this particular example comprises a frontal connector 770 connected between the frontal support portion 766 and the head-mounted display unit 720. The frontal connector 770 is located substantially in the sagittal plane of the user's head in this example. In other examples there may be multiple frontal connectors 770, some or all of which are spaced from the sagittal plane, for example symmetrically across the sagittal plane. The frontal connector 770 may restrict (e.g. limit or prevent) downwards movement of the head-mounted display unit 720 in use, especially when the user moves their head. The frontal connector 770 may be configured to pivot with respect to the frontal support portion 766. Additionally, or alternatively, the head-mounted display unit 720 may be able to pivot with respect to the frontal connector 770. The ability for the frontal connector 770 and/or head-mounted display unit 720 to pivot with respect to the user's head may enable the user to achieve a more comfortable fit and/or position the head-mounted display unit 720 in a more optimal position in use. The frontal connector 770 may in some examples be formed from a substantially rigid material, such as a thermoplastic material.

In some examples, the occipital strap portion 764 is adjustable in length. This may enable positioning and stabilising structure 750 to fit a range of head sizes and/or may enable the user to achieve a more comfortable or stable fit. In some examples, the occipital strap portion 764 may be elastically extendable. For example, it may comprise an elastic portion, such as a strap portion formed from an elastically extendable material.

As shown in FIG. 15C in particular, the positioning and stabilising structure 750 may comprise a pair of lateral occipital strap portions 772, each located on a respective side of the user's head, and a medial occipital strap portion 774 connecting medial ends of the lateral occipital strap portions 772. In some examples, the medial occipital strap portion 774 is elastically extendable to provide for length adjustment of the occipital strap portion 764. In some examples the lateral occipital strap portions 772 are adjustable in length. For example, the lateral occipital strap portions 772 may be configured to be releasably connected to the medial strap portion 774. The lateral occipital strap portions 772 may comprise magnetic clips, for example, configured to magnetically connect to corresponding connection points on the medial occipital strap portion 772.

As shown in FIG. 15D, in some examples a head-mounted display system 700 comprising the positioning and stabilising structure 750 shown in FIGS. 15A-15C may comprise a battery pack 790 for powering the head-mounted display system 700. The battery pack 790 may be connected to the occipital strap portion 764, as illustrated in FIG. 15D. The battery pack 790 is configured to be located in the sagittal plane of the user's head in use. Providing a battery pack 790 at the rear of the user's head may provide similar advantages to those discussed elsewhere herein in relation to examples in which a battery pack 790 is provided at the rear of the user's head. For example, the combined weight of the head-mounted display unit 720 and the battery pack 790 is distributed across the front and rear of the user's head, instead of all of the combined weight being located at the front of the user's head. This distributed weight may provide a comfortable fit as the overall centre of mass is located at or proximate the centre of the user's head (e.g. at or proximate an intersection of sagittal and mid-coronal planes), which may reduce neck strain. The distributed weight may also provide for better stability than if batteries were provided interior to the head-mounted display unit 720, since the head-mounted display unit 7207 may then be larger and have a centre of mass spaced further away from the axis of rotation of the user's head than if the batteries are provided separately and behind the user's head. Distributing hardware around the user's head may keep the moment of inertia in any one component low, since each component may be able to be made to be low-profile.

Referring now to FIG. 15E, the positioning and stabilising structure 750 is shown in a form whereby the superior support pads 762, the frontal support portion 766 and the occipital strap portion 764 each comprise hardware components H. Each of the hardware components H is positioned such that its weight is applied at contact zones C (illustrated by dotted lines).

In some forms, the positioning and stabilising structure 750 may be thickened in locations that include the hardware component H. This may provide protection to the hardware and/or comfort to the user along the contact zone C.

FIGS. 16A-16H show a head-mounted display system 700 according to another example of the present technology. Like the examples shown in FIGS. 15A-15D, the head-mounted display system 700 comprises a head-mounted display unit 720 comprising a display, and a positioning and stabilising structure 750 configured to hold the head-mounted display unit 720 in an operable position on the user's head in use.

The head-mounted display unit 720 and display are configured for VR in the illustrated example but in other examples they may be configured for AR or another extended/artificial reality technology. In particular, the positioning and stabilising structure 750 and any or all of its features described herein may be applied in a head-mounted display system 700 configured for VR, AR or any related technology.

As shown in FIGS. 16A-16H and as described above, the positioning and stabilising structure 750 comprises a posterior support portion 752 configured to engage a posterior portion of a user's head and an anterior support portion 754 configured to connect the posterior support portion 752 and the head-mounted display unit 720 in use. The posterior support portion 752 and the anterior support portion 754 are together formed by a plurality of strap portions in these examples. The strap portions may be configured to be in tension in use to hold the positioning and stabilising structure 750 against the user's face in use.

The positioning and stabilising structure 750 in the examples shown in FIGS. 16A-16H further comprises a dial adjustment mechanism 776. The dial adjustment mechanism 776 may comprise a rotatable dial 778. The dial adjustment mechanism may be configured to cause a change in length of at least one of the strap portions of the posterior support portion 752 and anterior support portion 754 when the dial 778 is rotated.

The posterior support portion 752 may comprise an occipital strap portion 764 configured to overlie or lie inferior to the occipital bone of the user's head. In some examples, such as the examples shown in FIGS. 16A-16F, the dial adjustment mechanism 776 is configured to cause a change in length of the occipital strap portion 764 when the dial 778 is rotated.

The posterior support portion 752 may comprise a parietal strap portion 780 configured to overlie the parietal bones of the user's head. In some examples, such as the example shown in FIGS. 16C-16F, the dial adjustment mechanism 776 is configured to cause a change in length of the parietal strap portion 780 when the dial 778 is rotated.

The anterior support portion 754 may comprise a pair of lateral strap portions 760 configured to connect between the posterior support portion 752 and the head-mounted display unit 720, each configured to be located on a respective lateral side of the user's head in use.

In some examples the head-mounted display unit 720 may comprise arms 730 to which the lateral strap portions 760 connect. The arms 730 may extend from a display unit housing of the head-mounted display unit 720. The lateral strap portions 760 may each connect to a respective one of the arms 730. In particular, each lateral strap portion 760 may connect to a posterior end of a respective one of the pair of arms 730. Each lateral strap portion 760 may pass through an eyelet at the posterior end of the respective arm and may be fastened back onto itself (for example with a hook-and-loop connection, press stud or the like). Each arm may be able to pivot with respect to the display unit housing 735.

In some examples, such as the example shown in FIGS. 16G and 16H, the dial adjustment mechanism 776 is configured to cause a change in length of the lateral strap portions 760.

As shown schematically in each of FIGS. 16A-16H, the dial adjustment mechanism 776 may comprise a pair of extending portions 782 (represented by dotted lines in FIG. 16H). The extending portions 782 may connect to and extend away from the dial 778. Each extending portion 782 may be fixedly connected to a portion of the positioning and stabilising structure 750 or to the head-mounted display unit 720. Rotation of the dial 778 causes a change in an amount of extension away from the dial 778 of each extending portion 782. In particular, the user may rotate the dial 778 to cause the extending portions 782 to extend from the dial 778 to a lesser extent than prior to rotation of the dial 778 (e.g. extend away to a greater extent than already extending). The user may rotate the dial 778 to draw the extending portions 782 towards the dial 778. The user may rotate the dial 778 in a first direction to reduce an extension of the extending portions 782 away from the dial 778. The user may rotate the dial 778 in a second direction opposite to the first direction to increase an extension of the extending portions 782 from the dial 778. In some examples the dial 778 may, upon rotation, transfer a force to the extending portions 782 to pull or push them.

Each extending portion 782 may be located within a hollow interior of the strap portion that it is provided to. The strap portion in one form is formed from knitting, e.g. a knitted tubular sleeve. In some examples the extending portions 782 may be located within sleeves connected to (e.g. on an exterior surface) of the strap portion to which the extending portions 782 are provided.

In some forms, the extending portions 782 may therefore not be visible while in use. The strap could be formed so that the extending portion 782 is permanently covered. In other examples, the hollow interior of the strap may be formed by wrapping the strap around the extending portion 782 and securing it with a connector (e.g., hook and loop material) so that the user may selectively expose the extending portion 782.

One or more strap portions to which the extending portions 782 are provided may be in tension in use, and may be elastically extendable. In some examples, the strap portion may be in tension throughout the entire adjustment range of the dial adjustment mechanism 776 when the head-mounted display system 700 is worn by a user. One advantage of this configuration is that even the smallest head accommodated by the positioning and stabilising structure 750 is able to experience the feeling of the headgear stretching over their head and then snugly fitting to their head. Another advantage is that throughout the entire adjustment range the strap does not bunch up since at its smallest length it is under tension and therefore held taut. This may advantageously provide a pleasing appearance and may avoid skin marks which may otherwise be caused by creases in the material forming the strap portion.

In some forms, the extending portions 782 are also in tension even while not in use (e.g., the head-mounted display system 700 is not worn by a user), because as described above, each adjustable position of the strap may be in tension. Thus, the tension may be the result of the dial adjustment mechanism 776 and not the user's head.

In some examples, each extending portion 782 may comprise a non-elastic portion. In some examples each extending portion 782 may be partially or completely formed from a non-elastic material. The non-elastic material may be substantially inextensible, such as a cord (which may be formed from a plastic material) or may be a wire (e.g. steel wire), for example. The non-elastic material may have a sufficient stiffness that it is able to hold a shape. A non-elastic material may have the benefit of reliably maintaining its length.

In some examples, each extending portion 782 comprises an elastic portion. The extending portions 782 may comprise an elastic portion in series with a non-elastic portion 782. The elastic portion may comprise an extension stiffness sufficiently high that yielding in the elastic portion caused by overtightening is unlikely. In some examples, the dial adjustment mechanism 776 may comprise one or more extension limiters configured to limit extension of an elastic portion of the extending portion 782 to an extension less than an extension at which yielding may begin. For example, each elastic portion may comprise a non-elastic portion (e.g. an inelastic cord) in parallel with the elastic portion which has a length equal to a limit on an extension of the elastic portion. If the elastic portion reaches this limit on extension the non-elastic portion becomes taut and resists further extension (due to its inextensibility).

In some examples, each extendable portion 782 has a stiffness sufficient to hold its shape. The stiffness may be sufficient to hold the strap portion to which it is provided in a curved shape while under tension, resisting straightening. In some examples each extendable portion 782 may be flexible to conform to the shape of the user's head. In some examples each extendable portion 782 may be elastic to stretch during fitting and/or to provide temporary small changes in length caused by dynamic movements during active use while maintaining tension to remain snug while accommodating dynamically changing forces.

In examples in which the extending portion 782 is formed from a plastic material, it may be connected to a strap portion of the positioning and stabilising structure 750 by sewing or heat-staking, or another suitable method. In examples in which the extending portion 782 is formed from a textile material, such as an elastic band, it may be connected to a strap portion by sewing, RF welding, gluing, or another suitable method.

In other examples, the dial adjustment mechanism 776 may comprise a rack and pinion assembly. The occipital strap portion 764 may be formed in two portions (e.g. halves) connected at or by the dial adjustment mechanism 776. The dial adjustment mechanism 776 may cause two portions of the occipital strap portion 764, or two extending portions 782 connected to the occipital strap portion 764, to move telescopically. The dial adjustment mechanism 776 may comprise one or more rack portions forming extending portions 782 and provided to the occipital strap portion 764, for example two rack portions each provided to a respective one of two halves of the occipital strap portion 764. The rack portions may be configured to engage a pinion or cog connected to a dial 778 rotatable by the user. Each of the rack portions and pinion may comprise teeth, ribs or the like configured to engage with one another. Rotating the dial 778 in a first direction (e.g. clockwise) may pull the rack portions provided to the occipital strap portion 764 together and increase an overlap between the two rack portions, thereby reducing an effective length of the occipital strap portion 764. Rotating the dial 778 in a second direction (e.g. anti-clockwise) may push the rack portions apart, reduce an overlap between the rack portions and increase an effective length of the occipital strap portion 764. In some examples the dial adjustment mechanism 776 may have static torque resistance, for example provided by static friction or corresponding features such as indentations, to provide for a minimum force required to lengthen the occipital strap portion 764 or other strap portion to which the dial adjustment mechanism 776 is connected, to avoid unintentional lengthening of the occipital strap portion 764 or other strap portion. The rack portions may be rigid portions over-moulded to flexible portions of the occipital strap portions 764 or may be provided within or to an exterior of the occipital strap portion 764.

The dial adjustment mechanism 776 may provide for intuitive and easy adjustment of a strap portion, allowing the user to achieve a good fit. It is to be understood that the dial 778 may be applied to any strap portion of a head-mounted display system 700. The dial 778 may facilitate the positioning and stabilising structure 750 fitting a range of user head sizes. A head-mounted display system 700 may comprise a dial adjustment mechanism 776 on any one or more of the occipital strap portion 764, parietal strap portion 780 and one or both of the lateral strap portions 758. In positioning and stabilising structures 750 comprising a top strap portion, a dial adjustment mechanism 776 may be provided to adjust a length of the top strap portion. More generally, a head-mounted display system 700 may comprise an adjustment mechanism on any one or more of the occipital strap portion 764, parietal strap portion 780, top strap portion 758 and one or both of the lateral strap portions 758, or on any other strap portion. The adjustment mechanism may be a dial adjustment mechanism 776 having any one or more of the features described above or may be another mechanism for adjusting a length or lengths of one or more strap portions.

FIGS. 16A-16H show several examples of head-mounted display systems 700 of the present technology comprising positioning and stabilising structures 750 having strap portions adjustable in length by a dial adjustment mechanism 776. The positioning and stabilising structures 750 in these particular examples have posterior support portions 752 and anterior support portions 754 being formed from a plurality of strap portions. The strap portions may include an occipital strap portion 764, parietal strap portion 780 and a pair of lateral strap portions, for example as described above.

FIGS. 16A and 16B show an example of a head-mounted display system 700 comprising a positioning and stabilising structure 750 comprising a dial 778 provided to the occipital strap portion 764. In this example, each extending portion 782 of the dial adjustment mechanism 776 is fixedly connected to the occipital strap portion 764 at a respective location spaced from the dial. Rotation of the dial 778 of the dial adjustment mechanism 776 causes a change in length of the occipital strap portion 764 in this particular example. The occipital strap portion 764 may be elastically extendable, for example formed from an elastic material, for example a textile material knitted with a structure that allows for elastic extension. As illustrated in FIG. 16A, each extending portion 782 is fixedly connected to a respective end of the occipital strap portion 764. The extending portions 782 may be located with a hollow interior of the occipital strap portion 764. For example, the occipital strap portion 764 may be formed from a knitted tubular sleeve within which each extending portion 782 is located. Rotation of the dial 778 in this example causes tightening or loosening of the occipital strap portion 764, allowing the user to tighten the occipital strap portion 764 against posteroinferior surfaces of their head to provide a secure fit and/or loosen the occipital strap portion 764 to alleviate an overly tight fit.

As illustrated in FIGS. 16A and 16B, the posterior support portion 752 further comprises a parietal strap portion 780 configured to overlie the parietal bones of the user's head, and the anterior support portion 754 comprises a pair of lateral strap portions 760 configured to connect between the posterior support portion 752 and the head-mounted display unit 720, each lateral strap portion 760 configured to be located on a respective lateral side of the user's head in use. The extending portions 782 of the dial adjustment mechanism 776 are in this example each fixedly connected to a junction between the parietal strap portion 780, occipital strap portion 764 and a respective one of the lateral strap portions 760. The parietal strap portion 780 and/or the lateral strap portions 760 may be substantially inextensible although in some examples they may be elastically extensible.

In some forms, the parietal strap portion 780 and/or the lateral strap portions 760 may not be under tension prior to use. In examples where at least one strap is inextensible, the strap portions 760, 780 may still be loose prior to being worn by the user. After the user dons the positioning and stabilising structure 750, the strap portions 760, 780 may extend to their full length but may be incapable of stretching. Tightening or loosening the dial adjustment mechanism 776 may assist in ensuring that the positioning and stabilising structure 750 fits appropriately (e.g., snuggly) on the user's head.

In some forms where the parietal strap portion 780 and/or the lateral strap portions 760 are extensible (e.g., constructed from an elastic material), the strap portions 760, 780 may extend to their full length when the user dons the positioning and stabilising structure 750. The strap portions 760, 780 may be able to further adjust as a result of the extensibility to make additional adjustments on top of the adjustments of the extending portion 782.

FIGS. 16C-16F also show positioning and stabilising structures 750 comprising occipital strap portions 764 which are adjustable in length by a dial adjustment mechanism 776, to be described below.

In each of the examples shown in FIGS. 16A-16H, the positioning and stabilising structure 750 further comprises a sagittal strap portion 756 connecting between the parietal strap portion 780 and the occipital strap portion 764 and configured to lie against the user's head along a path in the sagittal plane of the user's head in use. The sagittal strap portion 756 may maintain a spacing between the parietal strap portion 780 and the occipital strap portion 764 and may provide further anchoring against the posterior surfaces of the user's head. A battery pack 790 may be attached to the sagittal strap portion 756. In some examples the sagittal strap portion 756 connects to the head-mounted display unit 720. The sagittal strap portion 756 may form a top strap portion 758 of the positioning and stabilising structure 750 in some examples. The sagittal strap portion 756 may be substantially inextensible but may be flexible to conform to the shape of the posterior surface of the user's head.

In some examples the parietal strap portion 780 may be immovable with respect to the sagittal strap portion 756. In some examples the occipital strap portion 764 may be immovable with respect to the sagittal strap portion 756. The parietal strap portion 780 and/or the occipital strap portion 764 may be fixedly connected to the sagittal strap portion 756.

In some examples in which the sagittal strap portion 756 forms a top strap portion 758, the top strap portion 758 may be adjustable in length. The top strap portion 758 may connect to the head-mounted display unit 720 at an eyelet provided to the head-mounted display unit 720. For example, the top strap portion 758 may be configured to be passed through the eyelet and then secured back onto itself, for example by a hook and loop fastening, press stud or the like.

In the examples shown in FIGS. 16C-16F, the posterior support portion 752 comprises a parietal strap portion 780 configured to overlie the parietal bones of the user's head. The dial 778 in these examples is provided to the occipital strap portion 764 and each extending portion 782 of the dial adjustment mechanism 776 causes a change in length of both the occipital strap portion 764 and the parietal strap portion 780.

For example, movement (e.g., rotation) of the dial adjustment mechanism 776 may cause simultaneous adjustment of the occipital strap portion 764 and the parietal strap portion 780. This may enable the user to adjust multiple straps using only a single motion. In some forms, the simultaneous adjustment may assist in providing even (e.g., symmetrical) adjustment of the different strap portions 764, 780, which may assist in providing a snug fit.

In some forms, both the occipital strap portion 764 and the parietal strap portion 780 may be under tension at any adjusted position regardless of whether the positioning and stabilising structure 750 is worn by the user. The remaining straps of the positioning and stabilising structure 750 may be loose until donned by the user and the dial adjustment mechanism 776 is tightened.

As shown in FIGS. 16C-16F, each extending portion 782 is connected to the parietal strap portion 780 at or proximate the sagittal plane of the user's head in use. In these particular examples the positioning and stabilising structure 750 comprises a sagittal strap portion 756, for example as described above. Each extending portion 782 may be connected to the parietal strap portion 780 at or proximate the sagittal strap portion 756. In some examples the extending portions 782 may connect to the sagittal strap portion 756. In further examples the extending portions 782 may connect to each other, for example at a location at or proximate the sagittal plane.

In the examples shown in FIGS. 16C-16F, the occipital strap portion 764 is elastically extendable. In these particular examples the parietal strap portion 780 is also elastically extendable. The parietal strap portion 780 may be elastically extendable in the same way as the occipital strap portion 764 has been described as being elastically extendable above, e.g. it may be formed from a knitted tube and/or may be configured to be in tension throughout a full adjustment range of the dial adjustment mechanism 776.

In the FIG. 16C-16F examples, the change in length of the occipital strap portion 764 upon rotation of the dial 778 is substantially equal to the change in length of the parietal strap portion 780. In these examples the anterior support portion 754 comprises a pair of lateral strap portions 760 configured to connect between the posterior support portion 752 and the head-mounted display unit 720, each lateral strap portion 760 being configured to be located on a respective lateral side of the user's head in use. Each lateral strap portion 760 connects a junction between the occipital strap portion 764 and parietal strap portion 780 to the head-mounted display unit 720. Advantageously, an equal change in length in both the occipital strap portion 764 and parietal strap portion 780 may result in the lateral strap portions 760 being pulled in a substantially posterior direction. If the lateral strap portions 760 are pulled in too much of a superior direction or inferior direction, the tension transmitted to the head-mounted display unit 720 may not be applied in an optimal direction and/or the lateral strap portions 760 may be pulled into the tops of the user's ears.

Each extending portion 782 may be located within a hollow interior of the occipital strap portion 764 and/or may be located within a hollow interior of the parietal strap portion 780.

In the examples shown in FIGS. 16C-16F, the positioning and stabilising structure 750 comprises a pair of guides 784. Each guide 784 is configured to guide a respective extending portion 782 of the dial adjustment mechanism 776 to change direction. One guide 784 is provided on each lateral side of the positioning and stabilising structure 750 corresponding to a respective lateral side of the user's head. In these examples each guide 784 redirects a respective extending portion 782 from the occipital strap portion 764 into the parietal strap portion 780.

Each guide 784 may function like a pulley to redirect an extending portion 782. As illustrated in FIGS. 16C and 16E each guide 784 may comprise a curved portion configured to allow a respective extending portion 782 to travel over the curved portion. In these examples each curved portion may face anteriorly such that the extending portion 782 travels over an anterior side of the guide 784 in use, e.g. during adjustment of the dial adjustment mechanism 776. In some examples, each guide 784 comprises a semicylindrical structure comprising the curved portion. The curved portion may define a circumferential surface over which a respective extending portion 782 is able to slide. In some examples the guides 784 may comprise cylindrical structures. In further examples the guides 784 may each comprise a cylindrical structure having a rotatable outer surface, for example provided by a bearing, defining a curved portion over which the extending portions 782 are able to travel, aided by rotation of the outer surface.

FIGS. 17A-17C show alternative forms that the guides 784 may take. In these examples the guides 784 each comprise a sheath portion through which the respective extending portion 782 passes. The sheath portion comprises a curved portion, for example within its interior passage, as shown in FIG. 17A. The sheath portion may be fully enclosed, as shown by the cross section view in FIG. 17B, or may be partially enclosed, as shown in FIG. 17C. The sheath portion may extend into the occipital strap portion 764 and/or parietal strap portion 780.

The occipital strap portion 764 and parietal strap portion 780 may each comprise a pair of ends. Each end of the occipital strap portion 764 may be connected to a respective end of the parietal strap portion 780. Each guide 784 may be fixedly located at a respective junction between the occipital strap portion 764 and the parietal strap portion 780, as shown in FIGS. 16C and 16E for example. In some examples each guide 784 is internal to the parietal strap portion 780 and/or occipital strap portion 764. In other examples each guide 784 may be external to the parietal strap portion 780 and/or occipital strap portion 764.

In some examples the anterior support portion 754 comprises a pair of substantially inextensible lateral strap portions 760.

In each of the examples shown in FIGS. 16A-16F, the anterior support portion 754 comprises a pair of elastically extendable connector strap portions 786. Each elastically extendable connector strap portion 786 is configured to be located a respective lateral side of the user's head in use and each is configured to connect between the posterior support portion 752 and the head-mounted display unit 720 to allow a predetermined amount of separation of the posterior support portion 752 from the head-mounted display unit 720. Additionally, the anterior support portion 754 comprises a pair of lateral strap portions 760 which are substantially inextensible and are each configured to releasably attach the posterior support portion 752 to the head-mounted display unit 720 to prevent separation of the posterior support portion 752 from the head-mounted display unit 720. In these examples, the lateral strap portions 760 and elastically extendable connector strap portions 786 are provided in parallel on either lateral side of the user's head. The combination of releasably attachable lateral strap portion 760 and elastically extendable connector strap portion 786 may be identified as a lockable extendable connection portion. Further details of lockable extendable connection portions were described in International (PCT) Patent Application No. PCT/AU2021/050277, which is hereby incorporated by reference herein in its entirety.

Each elastically extendable connector strap portion 786 and each lateral strap portion 760 connects a junction of the parietal strap portion 780 and occipital strap portion 764 to the head-mounted display unit 720. Each lateral strap portion 760 comprises a magnetic clip 788 configured to magnetically attach to a connection point to releasably attach the posterior support portion 752 to the head-mounted display unit 720. In the example shown in FIGS. 16E and 16F, each connection point is located at or proximate a respect one of the junctions of the parietal strap portion 780 and occipital strap portion 764. In the examples shown in FIGS. 16A-16B, 16E-16F and 16G-16H, each connection point is located at or proximate the head-mounted display unit 720. In some examples the connection point may be provided to an arm extending posteriorly from the head-mounted display unit 720.

The elastically extendable connector strap portion 786 may be configured to allow a predetermined amount of separation between the posterior support portion 752 and the head-mounted display unit 720, when the lateral strap portion 760 is disconnected from its connection point. That is, the elastically extendable connector strap portion 786 may elastically extend to a predetermined extent to allow the separation (this may assist a user in donning and doffing the head-mounted display system 700). The lateral strap portion 760 may be configured to releasably attach the posterior support portion 752 to the head-mounted display unit 720 to prevent separation thereof (or at least reduce the degree of possible separation). This secures the head-mounted display system 700 on the user's head in use. The elastically extendable connector strap portion 786 may advantageously hold the head-mounted display system 700 on the user's head with sufficient stability to enable the user to make adjustments to the fit prior to connection of the lateral strap portions 760 to the connection point.

FIGS. 16G and 16H show an example of a head-mounted display system 700 comprising a positioning and stabilising structure 750 according to another example of the present technology. In this example the positioning and stabilising structure 750 comprises posterior support portion 752 comprising a parietal strap portion 780 and occipital strap portion 764, which may be as described elsewhere herein. The parietal strap portion 780 and occipital strap portion 764 may be substantially inextensible in this example. Additionally, the positioning and stabilising structure 750 comprises an anterior support portion 754 comprises a pair of lateral strap portions 760 configured to connect between the posterior support portion 752 and the head-mounted display unit 720. Each lateral strap portion 760 is configured to be located on a respective lateral side of the user's head in use.

The positioning and stabilising structure 750 in the example shown in FIGS. 16G and 16H comprises a dial adjustment mechanism 776 in which the dial 778 is provided to the occipital strap portion 764 and each extending portion 782 of the dial adjustment mechanism 776 is fixedly connected to a respective one of the lateral strap portions 760 or to a respective side of the head-mounted display unit 740. In this example, rotation of the dial 778 of the dial adjustment mechanism 776 causes a change in length of the lateral strap portions 760.

In this example, each extending portion 782 is located within a hollow interior of the occipital strap portion 764. Each extending portion 782 may be located exterior to a respective one of the lateral strap portions 760. In this example, each lateral strap portion 760 is elastically extendable and may be elastically extended under tension throughout the entire adjustment range of the dial adjustment mechanism 776, in the same way that the occipital strap portion 780 has been described above as being configured to be in tension throughout the entire adjustment range. The occipital strap portion 764 in this example is substantially inextensible. The parietal strap portion 780 is also substantially inextensible. Accordingly, when the dial 778 is rotated, the dial adjustment mechanism 776 may cause a change in length of the lateral strap portions 760 but not of the occipital strap portion 764 or parietal strap portion 780.

In some forms, the lateral strap portions 760 may be under tension at all times regardless of whether the positioning and stabilising structure 750 is worn by the user. The other straps (e.g., the occipital strap portion 764 and/or the parietal strap portion 780) may be inextensible (or extensible) but may not be under tension prior to being donned by the user and the dial 778 being rotated.

In other examples, rotation of the dial 778 may cause adjustment of the lateral strap portions 760 and the occipital strap portion 764. For example, this adjustment may be simultaneous as described with previous examples.

As shown in FIG. 16G, in this example the positioning and stabilising structure 750 comprises a pair of guides 784, each guide 784 being configured to guide a respective extending portion 782 of the dial adjustment mechanism to change direction. The guides 784 may have the same form as any of the examples of guides 784 described with reference to FIGS. 16C-16F. However, in this example the guides 784 may each comprise a curved portion that faces superiorly and/or posteriorly such that each extending portion 782 travels over a superior and/or posterior side of the guide in use. This arrangement redirects each extending portion 782 from extending in an anterior and superior direction in the occipital strap portion 764 to a substantially anterior or anterior and inferior direction in the lateral strap portion 760, to redirect tension in each extending portion 782 to apply a force in a posterior direction to the respective lateral strap portion 760 at the connection between each extending portion 782 and the respective lateral strap portion 760.

As illustrated in FIG. 16G, each guide 784 may be fixedly located at a respective junction between the occipital strap portion 764 and respective one of the lateral strap portions 760. The guides 784 may be internal to the occipital strap portion 764 and respective lateral strap portion 760 or may be external to the occipital strap portion 764 and respective lateral strap portion 760.

In the example shown in FIGS. 16G and 16H, the anterior support portion 754 of the positioning and stabilising structure 750 comprises a single strap portion on each lateral side of the user's head. The single strap portion in this example is an elastically extendable lateral strap portion 760. In other examples the anterior support portion 754 may comprise two strap portions in parallel on each lateral side of the user's head, one of which being elastically extendable and the other of which being substantially inextensible. In some examples the elastically extendable lateral strap portion 750 shown in FIG. 16G may be replaced by a lockable extendable connection portion as described above, e.g. the substantially inextensible lateral strap portion 750 and elastically extendable connector strap portion 786 as included in the examples shown in FIGS. 16A-16F.

In some forms, the head-mounted display system 700 or at least a portion thereof, is designed to be used by a single user, and cleaned in a home of the user, e.g., washed in soapy water, without requiring specialised equipment for disinfection and sterilisation. Specifically, the positioning and stabilising structure 750 and the interfacing structure 713 are designed to be cleaned, as they are both in direct contact with the user's head.

In some other forms, the components of the positioning and stabilising structure 750 and interfacing structure 713 are used in labs, clinics and hospitals wherein a single head-mounted display may be reused on multiple persons or used during medical procedures. In each of the labs, clinics and hospitals the head-mounted displays, or relevant components thereof, can be reprocessed and be exposed to, for example, processes of thermal disinfection, chemical disinfection and sterilisation. As such, the design of the positioning and stabilising structure and interfacing structure may need to be validated for disinfection and sterilisation of the mask in accordance with ISO17664.

Materials may be chosen to withstand reprocessing. For example, robust materials may be used in the positioning and stabilising structure 750 to withstand exposure to high level disinfection solutions and agitation with a brush. Further, some components of the positioning and stabilising structure are separable, and in-use may be disconnected to improve the reprocessing efficacy.

In some examples, the interfacing structure 713 may, in use, be in contact with the user's head and therefor may become dirty (e.g., from sweat). The interfacing structure 713 may be designed to be removed from the display unit housing 735, to provide the ability to remove it for cleaning and/or replacement. It may be desirable to wash the interfacing structure 713 while not getting the positioning and stabilising structure 750 wet. Alternatively or in addition, the positioning and stabilising structure 750 may be dirty from contact with the user's head, and may be removed for cleaning and/or replacement independently of the interfacing structure 713. In either case, this may be facilitated by allowing these components to disconnect for such a purpose.

In some examples, a cover (e.g., constructed from a textile, silicone, etc.) may be removably positioned over the interfacing structure and can be removed to be cleaned and/or replaced after each use. The cover may allow the interface structure 3400 to remain fixed to the display unit housing 735, and still provide a surface that can be easily cleaned after being used.

In some forms, the head-mounted display system 700 (e.g., VR, AR, and/or MR) may be used in conjunction with a separate device, like a computer or video game console. For example, the display interface may be electrically connected to the separate device.

In some forms, at least some processing for the head-mounted display system 700 may be performed by the separate device. The separate device may include a larger and/or more powerful processor than could be comfortably supported by the user (e.g., the processor of the separate device may be too heavy for the user to comfortably support on their head).

FIGS. 18A and 18B show a support for an augmented reality display system or assembly 810 according to an eighth example of the present technology. The head-mounted display system 810 is in the form of an augmented reality system, but could also take the form of a virtual reality system, e.g. as described with respect to FIGS. 2A-2C. The head-mounted display system 810 comprises a display unit 812, user interface structure 813, positioning and stabilising structure 814, rear support hoop 816, temporal connector 818, display unit housing 822, forehead support connector 824, temporal arm 826, rigidiser 832, parietal portion 838, occipital portion 840, forehead support strap 848, and forehead support rigidiser 856.

In the eighth example, the support for an augmented reality display system 810 comprises opposing temporal connectors 818 each having a temporal arm 826 with a rigidiser that extends rearward from the display unit housing 822. The user interface structure 813 is constructed and arranged to be in opposing relation with the user's face, and to extend around at least a portion of the outer perimeter of the display 812 contained by the display unit housing 822. In general, the user interface structure 813 of the eighth example extends around an in-use upper region of the user's eyes, and may engage with the user's face in this region, e.g. along the user's forehead 813*a*, nose 813*b* and in some forms the user's temples 813*c*. The in-use lower portion of the housing 822, with the exception of the user interface structure 813 in the region proximal the user's nose 813*b*, can be spaced away from the user's face, i.e. without a user interface structure 813 engaged therebetween such that the in-use lower portion of the display 812 and/or housing 822 does not rest against, or interact with, the user's face (e.g. across the cheeks). The open gap between the in-use lower portion of the housing 822 and the user's face may allow light and airflow to ingress therethrough which may improve the user's comfort during an augmented interactive experience with the surrounding real-world environment. In some forms, the display 812 can also be at least partially translucent so as to allow the ingress of light therethrough in addition to the real-time view of the surrounding environment.

A forehead support strap 848 is arranged to extend from the in-use central upper portion of the display unit housing 822. The forehead support strap 848 connects to the rear support hoop 816 so as to assist the positioning and stabilising structure 814 in improving the distribution of the load of the display 812 across the top of the user's head. The forehead support strap 848 can comprise a forehead support rigidiser 856 that provides further stabilisation and support for the display unit 812 from above, thereby relieving pressure on the user's nose.

In a manner similar to the first example described above, a rigidiser 832 (or the temporal connector 818 or the temporal arm 826) can be rigid along at least a portion of its length. The rigid nature, i.e., inextensibility, of the rigidiser 832 of each temporal arm 826 can act to limits the magnitude of elongation or deformation of the temporal arm 826 while in-use. This configuration can enable a more effective, i.e., direct, translation of tension through the temporal arm 826. The rear support hoop 816 further comprises opposing connection straps or tabs 842 that are adjustable and operate to change the distance between the rear support hoop 816 and the display unit housing 822 of the display unit 812. Each of the straps 842, in use, can be threaded through an eyelet in the tab of a respective temporal arm. In this manner, the length of each strap 842 can be adjusted by pulling more or less of the strap 842 through a respective eyelet. The strap 842 is securable to itself after passing through the eyelet, for example, with hook-and-loop fastening means, which allows fine or micro adjustment of the straps for comfort and fit (e.g., tightness). The adjustment mechanism enables the distance between the rear support hoop 816 and the display unit housing 822 to be adjusted to fit around different head sizes, and can in some forms be permit adjustment while the system is on the user's head. The adjustment mechanism allows the user to tailor the tightness to suit their particular head size and desired comfort level, and may thus improve the comfort and experience for the user.

Two power units 860, e.g. batteries, are provided along the occipital portion 840 of the rear support hoop 816. The power units 860 are configured, when in use, to provide electrical power to the display unit 812. The wiring that connects the power units 860 to the display unit 812 can, in some forms, be mounted within one or both of the temporal arms 826. By providing two power units 860, and in some forms more than two power sources, each of the individual power units 860 can be smaller and lighter. The individual power units 860 can be located on either side of the user's head on the occipital portion 840 of the rear support hoop 816 so as to improve the distribution of the weight load across the user's head. The reduced weight can also help to reduce the momentum effects of the augmented reality display system 810 during dynamic movements. The overall comfort and stability of the augmented reality display system 810 can also thus be improved.

FIGS. 19A to 19C show a support for an augmented reality display system or assembly 910 according to a ninth example of the present technology. In FIG. 19, like reference numerals denote similar or like parts to FIGS. 18A and 18B with the addition of 100 to allowing distinguishing between examples, e.g., display unit 912, user interface structure 913 (which may be for contacting areas along the user's forehead 913*a* and/or nose 913*b*), positioning and stabilising structure 914, rear support hoop 916, temporal connector 918, display unit housing 922, forehead support connector 924, temporal arm 926, rigidiser 932, parietal portion 938, occipital portion 940, forehead support strap 948, and forehead support rigidiser 956.

In the ninth example, which is similar to the eighth example described above, the augmented reality display system 910 additionally comprises a sensor system 980 that is mounted to the forehead support strap 948 that connects from the display unit 912 to the rear support hoop 916. The sensor system 980 can be powered by the plurality of power units 960 by wiring that is mounted to, or within, the straps of the positioning and stabilising structure 914. The sensor system 980 can comprise one or more sensors that can be used to enhance the augmented reality experience such as, but not limited to motion sensors, temperature sensors, light sensors, tactile sensors, altitude sensors etc. The information detected and processed by the sensors can in some forms be provided in real-time to the user as sensory feedback that may cross multiple modalities, including visual, auditory, haptic, somatosensory and olfactory.

In some forms, the user interface structure 913 at the user's forehead 913*a* can be configured to comprise one or more sensors that can be integrated with, or can be used in place of the sensor system 980 on the forehead support strap 948.

Referring to each of the eighth and ninth examples of the present technology, a flow generator may also be provided in each of the respective systems as set forth in the fifth example of the present technology (and shown in FIGS. 7 to 11). That is, in some forms of the eighth and ninth examples, the augmented reality display system or assembly 810, 910 may also be configured to support a flow generator (e.g. a blower) and related componentry with respect to the display unit 812, 912. In these forms, the flow generator may be used as a counter weight to help balance the display unit.

For example, the positioning and stabilising structure 814, 914 may be configured to hold the flow generator in a location overlying the parietal portion 938, in use. The flow generator may be arranged with respect to the positioning and stabilising structure as otherwise described in relation to the fifth example of the present technology. Further, the flow generator may be mounted with respect to the display unit 812, 912, as previously set forth in the fifth example of the present technology.

FIGS. 20 to 22 show a head-mounted display system or assembly 1000 according to a tenth example of the present technology.

The head-mounted display system 1000 is in the form of an augmented reality system and comprises an augmented reality display unit 1012, and a positioning and stabilising structure 1014 to maintain or hold the display unit 1012 in an operational position over a user's face, in use.

In the tenth example, the positioning and stabilising structure 1014 is configured to support the augmented reality display unit 1012 away from a user's nose, e.g. nose bridge. In some forms, the structure 1014 can support the display unit 1012 against a user's frontal bone, i.e. brow.

The positioning and stabilising structure 1014 comprises arms 1015 extending from the display 1012 and an over-extension portion 1016 that is configured to support a battery pack 1018 and electronic components 1011, e.g. signal processors on the user's head in-use.

The over-extension portion 1016 can be generally shaped to compliment the shape of the user's head, so as to hold against the user's head, in-use. This provides an advantage of stabilising the system when in-use, by increasing the surface contact area on the user's head.

As shown in FIG. 20, the positioning and stabilising structure 1014 is generally S-shaped in profile. Configuration in this shape can assist the over-extension portion in absorbing movement in the system 1000.

The over-extension portion can be configured to deflect so as to absorb movement in the system. Such movement may arise from the weight of the battery pack acting to pull the system downward from a user's head. The over-extension portion therefore acts as a biasing mechanism, i.e. a spring, and can stabilise the movement of the system, in-use.

In the embodiment shown in FIG. 20, the over-extension portion 1016 can support the electronic components 1011 above a user's ear, such that the positioning and stabilising structure 1014 does not bear the weight of the electronic components 1011 on the ear of the user.

In the form shown in FIG. 20, the electronic components are supported in a lower arm 1022 of the over-extension portion 1016. The lower arm of the over extension portion is shaped similar to a traditional optical glasses arm, however, is not configured to contact the ear. The arm 1022 is spaced from the ear such that no weight is transferred from the electrical components 1011 onto the user's ear, when the user is in a resting position, e.g. standing still. When the user is in a non-resting position, e.g. moving, head-turning, the over-extension portion can be configured to deflect to absorb the movements of the user. When the over-extension portion deflects to an extreme position, the arm 1022 can move into contact with the user's ear. By contacting the user's ear, the arms 1022, and in-turn the positioning and stabilising structure can be prevented from falling off the user's head.

The over-extension portion further comprises an upper arm 1024 configured to offset the center of balance of the augmented reality display system 1000 towards the frontal bone of the user's head. As shown in FIG. 20, the upper arm is configured to extend forward of the coronal plane C such that it acts as a lever arm to support the weight of the battery pack from its extension into the coronal plane.

The stiffness of the over-extension portion can be affected, i.e. adjusted by the material used, the dimensions, and the cross-sectional shape of the over-extension portion 1016.

The stabilising structure 1014 is configured such that system is balanced when in-use on a user's head. That is, the weight of the display 1012 biasing the system towards the frontal bone of the user is balanced with the weight of the battery pack 1018 biasing the system towards the occipital bone of the user.

In some forms, the battery pack can be moveable about the sagittal plane of the user's head and can be secured in multiple locations on and between the parietal bone and occipital bone of the user.

When referring to FIG. 21, the stabilising structure 1012, i.e. the over-extension portion 1016 takes a W-shape. The W-shape is configured to absorb lateral movement of the system. For example, the weight of the battery pack can induce movement of stabilising structure when in-use. The W-shape is configured absorb the movement of the battery pack about a central spine 1026 such that the remainder of the stabilising structure experiences minimal movement.

Referring now to FIGS. 23A and 23B, an augmented reality display system or assembly 2000 according to an eleventh example of the present technology is shown.

The augmented reality display system 2000 comprises an augmented reality display unit 2012, and a positioning and stabilising structure 2014 to maintain or hold the display unit 2012 in an operational position over a user's face, in use.

The augmented reality display system 2000 primarily differs from the augmented reality display system 5800 in that it is provided with a positioning and stabilising structure 2014 configured to extend directly from the display 2012 to a rear of a user's head, i.e. proximal to a user's occipital bone.

The structure 2014 is shaped with a rear hook portion 2028 configured to nest below a user's occipital bone. As shown in FIG. 23B, the rear hook can be shaped with lateral wings 2028A to further support the structure 2014 on the user's head. The hook can act to resist movement of the system 2000 in a forward direction, i.e. toward contact with a user's nose.

In the form shown in FIG. 23B, a battery pack can be located in the hook portion of the structure 2014, and the weight therein can act to resist movement of the structure in a forward direction.

The structure 2014 can further comprise adjustable portions 2030 for increasing or decreasing the distance between the display 2012 and the hook 2028, i.e. the structure's length. When in-use, the adjustable arms 2030 act to move the display towards or away from contact with a user's nose. This movement can, e.g. allow a user to adjust the position of the display to align with their eyes.

Referring to each of the tenth and eleventh examples of the present technology, a flow generator may also be provided in each of the respective systems as set forth in the fifth example of the present technology (and shown in FIGS. 7 to 11). That is, in some forms of the tenth and eleventh examples, the augmented reality display system or assembly 1000, 2000 may also be configured to support a flow generator (e.g. a blower) and related componentry with respect to the display unit 1012, 2012. In these forms, the flow generator may be used as a counter weight to help balance the display unit.

For example, the positioning and stabilising structure 1014, 2014 may be configured to hold the flow generator in a location overlying the parietal portion, in use. When referring to the tenth example, the flow generator may be arranged on the central spine 1026 with respect to the battery pack 1018. When referring to the eleventh example, the flow generator may be arranged on the structure 2014 with respect to the rear hook portion 2028.

Alternatively, the flow generator may be arranged with respect to the positioning and stabilising structure as otherwise described in relation to the fifth example of the present technology. In other forms, the flow generator may be mounted with respect to the display unit 1012, 2012, as previously set forth in the fifth example of the present technology.

Referring now to FIGS. 24 to 26, a head-mounted display system or assembly 3000 is shown according to a twelfth example of the present technology. The head-mounted display system 3000 is in the form of an augmented reality system and comprises an augmented reality display unit 3012, and a positioning and stabilising structure 3014 to maintain or hold the display unit 3012 in an operational position on a user's face. It should be understood that although the twelfth example of the present technology is illustrated in the form of an augmented reality system, the twelfth example of the present technology can also be utilised with a virtual reality system as set forth below.

The positioning and stabilising structure 3014 may be removably connectable to a portion of the display unit 3012 via a headgear connector 3150.

In some forms, the positioning and stabilising structure 3014 may include at least one electrical component (e.g., similar to what is illustrated in FIGS. 7 to 11) that is electrically connectable to the display unit 3012. For example, the electrical component of the positioning and stabilising structure 3014 may be electrically connected to the display unit 3012 when the positioning and stabilising structure 3014 is connected to the headgear connector 3150.

In some forms, the positioning and stabilising structure 3014 may be permanently connected to a portion of the display unit 3012 via the headgear connector 3150.

The positioning and stabilising structure 3014 may comprise at least one strap 3101 (shown separate from the display unit 3012 in FIG. 24C) and at least one rigidiser arm 3102 (shown separate from the strap 3101 in FIG. 24B). The strap 3101 may be made of an elastic material and may have elastic properties. In other words, the strap 3101 may be elastically stretched, e.g., by a stretching force applied by the user (as illustrated in FIG. 25B) and, upon release of the stretching force, returns or contracts toward its original length in a neutral state. For example, the in use position of the strap 3101 (see e.g., FIG. 25A) is contracted from the stretched length during the donning process (see e.g., FIG. 25B), but is still more stretched than the neutral position. The strap 3101 may be made of or comprise any elastomeric material such as elastane, TPE, silicone etc.

The strap 3101 may be a single layer or multilayer strap. The strap 3101, particularly side strap portions 3115, 3116 (best shown in FIGS. 24A, 25A and 25B) in contact with the user 3300 during use, may be woven, knitted, braided, molded, extruded or otherwise formed. The strap 3101 may comprise or may be made of a textile material such as a woven material. Such material may comprise artificial or natural fibers for, on the one hand, providing desired and beneficial surface properties such as tactile properties and skin comfort. On the other hand, the material of the strap 3101 may include elastomeric material for providing the desired elastomeric properties. The entire strap 3101, including the side strap portions 3115, 3116 and back strap portion 3117, may all be stretchable. This enables the entire length of the strap 3101 to be stretched which leads to a comfortable force displacement profile. In order for the strap 3101 to be stretched in use, the length of the strap 3101 may be less than the average small head circumference of users. For example, the length of the strap 3101 may be less than 590 mm in one example and less than 500 mm in another example. However, straps 3101 of different lengths may be provided to users depending on their head circumference, which may be gender specific. For example, a small sized strap may be 490 mm in length and a large sized strap may be 540 mm. In some circumstances this means that the length of the strap 3101 need not be stretched by a large distance (i.e. small sized strap for a large head circumference) which would have unnecessarily high headgear tension for such user and also a less smooth force displacement profile as the small sized strap 3101 is being stretched to longer lengths.

The strap 3101 may be rigidised at certain sections, for example, from display unit housing 3222 of the display unit 3012 up to a position proximal to the user's cheekbone by inserting rigidiser arms 3102. The strap 3101 may take the form of a hollow ribbon. The strap 3101 may be considered to be threaded over the rigidiser arm 3102 when it is slipped onto the rigidiser arm 3102 and secured at one end of the rigidiser arm 3102 proximal to the frame 3222.

In some forms, the strap 3101 may be rigidised at certain sections prior to the insertion of the rigidiser arms 3102. For example, a portion of the strap 3101 (e.g., structured to overlay the temporal bone) may be formed with a rigid material in order to limit flexion of at least a portion of the strap 3101. In some forms, a textile and/or elastic material of the strap 3101 may be formed around a rigid material (e.g., rigid plastic). In some forms, the strap 3101 may be rigidised using a stitching process. The rigidiser portion of the strap 3101 may still receive the rigidiser arm 3102 to provide further rigidity.

In one example, the strap 3101 including the side strap portions 3115, 3116 and back strap portion 3117 are made by warp knitting a textile material. The strap 3101 is a 3D knitted fabric that is knit by computer control as a single unitary piece. Variation in the thread and stitching may occur at various positions along the strap 3101 to adjust the elasticity and strength and durability of the strap 3101 at certain locations. For example, at the locations of openings 3104 in the strap (shown in FIG. 24C), e.g. for connecting the strap to the headgear connector 3150, and a bifurcation point 3124 for the back strap portions 3117a, 3117b, an additional thread may be knitted to provide reinforcement of the strap 3101 to prevent failure/breakage of the strap 3101 at these locations that subject to high stress when the strap 3101 is stretched during repeated and prolonged use. Both the knitting method (i.e. warp knitting) and the elastic textile material (e.g. elastane) of the strap 3101 contribute to the elastic recovery of the strap 3101 after washing the strap 3101 in water and dried. In other words, the elasticity of the strap 3101 can be maintained after prolonged use by periodically washing the strap 3101 and therefore its operational life is extended.

Referring to FIG. 24C, the strap 3101 is shown as a single continuous strap with two pocketed ends 3111 for being attached, directly (e.g. by adhesion) or via headgear connector 3150, to the arms 3102. However, it may be appreciated that the strap 3101 may comprise multiple individual straps which are or may be directly connected to one another, for example, stitching or ultrasonic welding.

In FIGS. 24A to 24C, the strap 3101 of the positioning and stabilising structure 3014 is shown without any adjustment or variation means. Such adjustment may be provided, however, by varying where the strap 3101 is secured to the arms 3102 or other connection elements more rigid than the strap 3101. Additionally or alternatively, adjustment could be allowed by adding a mechanism, such as slide over ladder lock clips (not shown) on the arms 3102.

The strap 3101 may have a tube- or sleeve-like configuration (not shown). However, it will be appreciated that the strap 3101 may take any other shape such as flat or sheet-like shape, single, multi-layer or laminate construction. The strap 3101 has a longitudinal axis Z-Z which may be understood to be the axis substantially parallel to the paper plane, along which the strap 3101 extends.

In the form shown in FIG. 24A to 24C, the strap 3101 is hollow in order to receive the insertion of the rigidiser arm 3102 which is slid into the strap 3101 via openings 3104. In other forms, the rigidiser arms 3102 may be permanently connected to the strap 3101 at least in one location, for example, at an anchor point it is overmolded or glued to form an integral chemical bond (molecular adhesion) between the rigidiser arm 3102 and the strap 3101.

For example, at least one pocketed end 3111 of the strap 3101 may be permanently connected to the rigidiser arm 3102 in order to maintain an electrical connection between the an electrical component in the strap 3101 and the display unit 3012. This may help to ensure proper electrical connection is maintained.

The strap 3101 have may reinforced stitching to improve durability and minimise or prevent failure points. For example, the areas of the strap 3101 at the openings 3104 and also at the location where it bifurcates into two back strap portions 3117a, 3117b, at bifurcation points 3124, are subject to high stress when stretched. The tendency of the material is to split away from each other at a split region 3126 and therefore reinforced stitching at these areas is one way to address this concern. In an example, a central seam runs along the center longitudinal axis Z-Z of the strap 3101 and functions as reinforced stitching. Also, the distal edges (i.e. ends of pockets 3111) of the strap 3101 and the openings 3104 may be ultrasonically welded to fuse any stray fibers and strengthen the strap 3101 in these regions. Advantageously, this also prevents fraying of the fibers of the strap 3101 after extended use and repeated washing. Other techniques are envisaged for reinforcing and strengthening the pocketed end 3111 and openings 3104, which may include additional material such as (adhesive) tape.

The bifurcation points 3124 that exists where the upper back strap portion 3117a and the lower back strap portion 3117b split off from a side strap portion 3115, 3116 may be further reinforced by e.g. additional stitching or welding at or proximal to the bifurcation point 3124. The reinforcing may aid in preventing the side strap portions 3115, 3116 from splitting and/or tearing due to stress from the repeated separation of the upper back strap portion 3117a and the lower back strap portion 3117b. In other words, the reinforced portion 3125 may provide additional strength at a location of stress concentration near the bifurcation point 3124.

The upper back strap portion 3117a and the lower back strap portion 3117b are shown at various angles of separation θ in FIGS. 25A and 25B. When the upper back strap portion 3117a and the lower back strap portion 3117b are spread from one another at large angles θ, the reinforced bifurcation point 3124 provides additional strength at the split.

Referring in particular to FIG. 24C, in one form of the present example, the ends 3111 of the strap 3101 may be reinforced with a material folded over the end of the strap 3101. This provides further reinforcement in this area in addition to the welded ends previously described. The material of the reinforcement applied to the ends 3111 may be a different material to the strap 3101. The reinforced ends may avoid or mitigate the likelihood of a user 3300 tearing or ripping the strap 3101 along its longitudinal axis beginning from this area. Further, the reinforced end may help provide a visual and tactile indication to the user 3300 on how to slip on or remove the strap 3101 from the rigidiser arm 3102 because it may assist in identifying the location of the openings 3104.

An example of the rigidiser arm 3102 is shown in FIG. 24B. The rigidiser arm 3102 may be shaped to fit within strap 3102. The rigidiser arm 3102 may have a generally elongate and flat configuration. In other words, the rigidiser arm 3102 is far longer and wider (direction from top to bottom in the paper plane) than thick (direction into the paper plane).

The rigidiser arm 3102 has a three-dimensional shape which has curvature in all three axes (X, Y and Z). Although the thickness of the rigidiser arm 3102 may be substantially uniform, its height may vary throughout its length. The purpose of the shape and dimension of the rigidiser arm 3102 is to conform closely to the facial structure of the user in order to frame the user's face to assist stabilising the head-mounted display when in-use. The ends 3119 of rigidiser arm 3102 may be rounded and/or slightly angled relative to the remainder of the rigidiser arm 3102.

The rigidiser arm 3102 may also have a desired spatial configuration in the direction into the paper plane of FIG. 24B in order to allow improved alignment with the shape of a user's face, such as the shape of a user's cheek, ear or head side region. The rigidiser arm 3102 may have a longitudinal axis Y-Y which may be understood to be the axis substantially parallel to the paper plane, along which the rigidiser arm 3102 extends (see dashed line in FIG. 24B).

The rigidiser arm 3102 is more rigid than the strap 3101 and less rigid than the display unit housing 3222. In particular, the rigidiser arm 3102 and/or the strap 3101 are such that in combination the rigidiser arm 3102 imparts a shape, and an increased degree of rigidity in at least one direction or, in or around, at least one axis to the strap 3101. Also, the rigidiser arm 3102 guides or defines the direction or path of stretch for the strap 3101. In other words, the user stretches the strap 3101 in a direction substantially parallel to the longitudinal axis of the rigidiser arm 3102. Stretching of the strap 3101 in other directions leads to rotation of the rigidiser arm 3102 relative to the head-mounted display unit 3012, which is undesirable.

The rigidity of the rigidiser arm 3102 biases the rigidiser arm 3102 towards its natural, unrotated, untwisted and undeformed state. To some degree, this enables the positioning and stabilising structure 3014 to be self-adjusting headgear. The self-adjusting function avoids manually shortening or lengthening the material length of headgear straps 3101 and then remembering the adjusted length. Advantageously, this avoids the user adjusting the length of the headgear straps on both sides of the face, e.g. to be shortened or lengthened, one at a time. Furthermore, this may remove the ability for users to over-tighten the headgear when such high levels of headgear tension are not required to support the head-mounted display on the user's face.

In some forms, the rigidiser arm 3102 may bend or flex as a result of the user donning the positioning and stabilising structure 3014. For example, the rigidiser arms 3102 may move away from one another in order to accommodate the width of the user's head. The rigidiser arms 3102 may return to an original position after the user removes the positioning and stabilising structure 3014.

In some forms, the rigidiser arm 3102 may be more flexible or bendable in one direction as compared to another. For example, the rigidiser arm 3102 may be more bendable along a length than along a width. In other words, the rigidiser arm 3102 may be more bendable or flexible into and out of the page of FIG. 24B than in the superior-inferior direction of FIG. 24B.

Referring now to FIGS. 25A, 25B and FIGS. 26A to 26D, side strap portions 3115, 3116 are adapted to extend along the sides of a user's head when being worn. The back strap portion 3117 is adapted to extend along the back of a user's head. Back strap portion 3117 may be comprised of two, three or more straps arranged in parallel, particularly for providing stability. Although the smaller back strap portions 3117a, 3117b have been illustrated as equal in length, it is envisaged that one back strap portion is longer than the other back strap portion. The greater the number of smaller back strap portions 3117a, 3117b for the back strap portion 3117, the greater the spring effect provided. In other words, as the number of same sized smaller back strap portions 3117a, 3117b increases when the strap 3101 is manufactured, the more tension is exerted on the side strap portions 3115, 3116 to be pulled closer to each other by the back strap portions 3117a, 3117b.

In the form shown in 25A, 25B and FIGS. 26A to 26D, side strap portions 3115, 3116 of strap 3101 bifurcate into two back strap portions 3117a, 3117b. In some forms, each back strap portion 3117a, 3117b has half the amount of elastane material compared to each side strap portion 3115, 3116 of the strap 3101. In some forms, each back strap 3117a, 3117b may have a different level of elasticity (e.g., one strap may be capable of stretching further than the other).

The strap 3101 is connected to the arms 3102 via the headgear connections 3150. The strap 3101 is configured to be removably connected to the rigidiser arm 3102 via openings 3104.

The rigidiser arms 3102 can be integrally formed (i.e. permanently connected) with the display housing 3222. In some variations, the arms 3102 may be a separately moulded component that is connected, e.g. by adhesive, to the housing 3222. In other forms, the arms 3102 may be separately formed, before being connected to the housing 3222 by and over-moulding process so as to form a flexible joint e.g. made from TPE, between the arms 3102 and the display unit housing 3222.

In alternative forms, the arms 3102 may be hingedly connected to the display unit housing 3222 according to a traditional e.g. sunglasses or spectacles configuration.

The engagement of the strap 3101 to the rigidiser arm 3102 may occur in one location proximal to the display housing 3222, e.g. at the headgear connector 3150. This type of engagement allows for a maximum range of motion i.e. stretching of the strap 3101. This engagement is configured to be removable so as to enable the strap 3101 to be fully detachable from the rigidiser arm 3102 and in turn, the display unit 3012 to facilitate washing of the strap 3101. The headgear connector 3150 functions as an anchor point for the strap 3101 such that when the strap 3101 is stretched, the stretching force is directed outwardly away from the anchor point. When the strap 3101 is mounted to arms 3102, the end 3111 of the strap 3101 at the anchor point is retained by at least an edge of the headgear connector 3150.

It will be appreciated by the skilled person that the rigidiser arm 3102 as referred to herein may be more rigid than the strap 3101 and allows the rigidiser arm to impart a shape to the strap 3101. The rigidiser arm 3102 may be more rigid in or around at least one axis and is inextensible in contrast to the strap 3101 which can be stretched along at least one axis. In some forms, the rigidiser arm 3102 may be extensible/stretchable in a direction substantially parallel to its longitudinal axis Y-Y. Although elastomers typically can stretch, some thermoplastic polyester elastomers do not stretch, but are flexible, for example, Hytrel® 5556 manufactured by DuPont®. For example, the rigidiser arm 3102 may have a scissor linkage structure or telescopic structure which enables the rigidiser arm 3102 to move between a compressed position to a fully elongated position. An extensible rigidiser arm 3102 may allow a better fit for users 3300 who have longer faces so that the length of the rigidiser arm 3102 can be adjusted appropriately. Alternatively, the rigidiser arm 3102 may be referred to as a yoke and/or a stiffener. A yoke may be understood to be a rigid element adapted to support the straps 3101 of the positioning and stabilising structure 3014. A rigidiser arm 3102 may be understood to be a rigid element shaping the straps 3102 of the positioning and stabilising structure 3014 when worn on the face.

The side strap portions 3115, 3116 of strap 3101 shown in FIGS. 24A and 24C each include openings 3104. In the form shown in FIG. 24C, the openings are located at the inner surface of strap 3101, i.e., the surface facing towards the user 3300 when being worn, and are adapted to receive rigidiser arm 3102 in order to insert the rigidiser arm 3102 into the interior of the tube- or sleeve-like strap 3101 or to remove it therefrom. Alternatively, the openings 3104 may be located at an outer surface of the strap 3101, i.e. the surface facing away from the user 3300 when being worn. In still other forms, the openings 3104 may be positioned in the pocketed end 3111.

The openings 3104 may be oriented and/or shaped such that the rigidiser arm 3102 may be inserted and/or removed through such opening in order to assemble the positioning and stabilising structure 3014 while still preventing accidental removal or separation of the rigidiser arm 3102 from the strap 3101 during use. As shown in FIG. 24C, this may be achieved by providing openings 3104 with oval-like configurations. Alternatively, the openings 3104 may be provided with slit-like configurations, e.g., similar to buttonholes, which may be oriented alongside, or transversely to, the strap 3101. Alternatively, the openings 3104 may be oriented across the strap 3101 if required. In other words, the elongate extension of the openings 3104 may extend substantially coaxial to the longitudinal axis Z-Z of both the strap 3101 and the longitudinal axis Y-Y of the rigidiser arm 3102. This allows, particularly due to the elasticity of strap 3101, an easy insertion of the rigidiser arm 3102 into the tube- or sleeve-like strap 3101 while, at the same time, preventing its accidental removal.

The end portion of the strap between the distal tip of the strap 3101 and the opening 3104 wraps over the edge 3160 of the rigidiser arm 3102 and functions as an anchor point. This edge 3160, or anchor point, of the rigidiser arm 3102 may be a catching member. This end portion of the strap 3101 is also referred to as the pocketed end 3111. This prevents the strap 3101 from slipping off the inserted rigidiser arm 3102 when the strap 3101 is stretched and adjusted while donning or doffing the user interface 3300.

The rigidiser arm 3102 may be inserted into a first opening 3104 of the strap 3101. Said another way, the strap 3101 may be slipped over the rigidiser arm 3102 via the opening 3104. The distal free end 3119 of the rigidiser arm 3102 is first inserted into the strap 3101 via the opening 3104. The rigidiser arm 3102 is pushed further inside the strap 3101 until most of the rigidiser arm 3102 is inserted into the strap 3101 such that the end portion of the strap 3101 can securely anchor to the edge 3160 of the rigidiser arm 3102. Some material of the strap 3101 near the opening 3104 is adjusted to sit beneath (or behind) the outer side 3118 of the headgear connector 3150. In this way, the opening 3104 is configured to fit, or mount, around a spacing element 3107 connecting between the housing 3222 and the rigidiser arm 3102. The spacing element 3107 is best shown in FIG. 24D.

Once inserted in the strap 3101, the rigidiser arm 3102 may be left floating generally unrestricted inside the strap 3101. The opening 3104 should locate within a space between the rigidiser arm 3102 and the display unit housing 3222, whereby the end portion of the strap 3101 is caught against the edge 3160 of the rigidiser arm 3102 to secure the strap 3101 to the rigidiser arm 3102. When the strap 3101 is stretched, the end portion of the strap catches the edge 3160 so as to pull against the edge 3160.

The type of attachment between the rigidiser arm 3102 and strap 3101, e.g. via openings 3104, facilitates easy removal of the strap 3101 from the rigidiser arm 3102. Easy removal of the strap is advantageous e.g. to enable separate washing of the strap 3101. To remove the strap 3101 for cleaning, the user 3300 slightly stretches the strap 3101 around the opening 3104 to unfasten the strap 3101 from the edge 3160 of the rigidiser arm 3102. After the distal end of the strap 3101 is unfastened, the strap 3101 may be pulled off completely from the rigidiser arm 3102 via the opening 3104.

In addition or alternatively, the rigidiser arm 3102 may be affixed to the strap 3101. The fixation may be localised, e.g. in the area adjacent to the opening 3104. The affixing may be performed by way of sewing, welding, gluing, heat staking, clamping, buttoning, snapping a cover over the end or snapping on an external part by pushing the rigidiser arm 3102 inside the strap 3101 and fixing both the strap and the rigidiser arm 3102 to an external component, such as an external clip that holds both the strap and the respective end of the rigidiser arm 3102. The strap 3101 may alternatively be chemically bonded to the rigidiser arms 3102. The clip may also be used to attach the end of the strap 3101 to a respective side of the display unit housing 3222. As such, the clip may be a part of the housing 3222 itself.

In the present example, while the strap 3101 is arranged to take the shape of the rigidiser arm 3102, it is still able to stretch substantially along its entire length. Thus, the rigidiser arm 3102 imparts the required shape which directs the pressure of the positioning and stabilising structure 3014 to the required portions of the face, while the elastic positioning and stabilising structure 3014 maintains its entire operational length and is able to freely stretch over the rigidiser arm 3102.

Although being shown and discussed with regard to the specific examples shown in FIGS. 24 to 26, it will be appreciated that strap 3101, or each of the strap side strap portions 3115, 3116 may be provided with one opening 3104 only. However, two or more openings may be provided. Alternatively or in addition, the strap 3101 may not be tube-like or sleeve-like but may have a flat single or laminate layer configuration. Here, the rigidiser arm 3102 may be positioned relative to the strap 3101 by the provision of retaining means including one or more loops, sleeve-like portions or pockets provided at the outer surface (e.g., the surface facing away from the user in use) of strap 3101.

In addition or alternatively, combinations of the different connection mechanisms described herein may be provided. For example, rigidiser arm 3102 may be fixed to the strap 3101 at a single point or localised area, as discussed above, adjacent, e.g. pocketed ends 3111 of strap 3101 while being held next to strap 3101 by provision of a loop or sleeve-like element provided at the outer surface of strap 3101. In other words, the rigidiser arm 3102 may be connected to the strap 3101 by fixing it at one localised point or area only, while functioning as an additional guiding element to strap 3101. Such guiding element functionality may be provided by a loop- or sheath-like portion or passage or a pocket of the strap 3101 into which or through which rigidiser arm 3102 extends based on the shape of the strap 3101 shown in FIG. 24C.

The strap 3101 may be tubular, but not necessarily cylindrical. This allows the longest stretch path possible for the strap 3101. Alternatively, the rigidiser arm 3102 may be disposed unattached into one or more pockets (e.g., a single open-ended pocket of sheath of appreciable length supporting the rigidiser arm somewhere in the middle, or a pair of pockets, each supporting a respective end of the rigidiser arm), or a plurality of loops distributed along the length of the strap 3101. Such guiding element functionality, whether attached at one end or not, allows substantially free movement or floating of the rigidiser arm 3102 relative to the strap 3101. Such configuration would allow the same advantages and benefits as the configuration discussed above. Additionally, the rigidiser arms 3102 do not stretch or flex in the same direction as the strap 3101. Rather, the rigidiser arm 3102 may stretch or flex in a plane substantially perpendicular to its longitudinal axis.

The attachment of the strap 3101 to the rigidiser arm 3102 described in the preceding section may also affect the size of head that the positioning and stabilising structure 3014 may accommodate. In other words, by providing a greater length of strap 3101 along the rigidiser arm 3102 it may be possible to increase the total stretchable length of the positioning and stabilising structure 3014 such that even larger circumference heads may be accommodated without needing to increase the stretchability of the strap 3101. Furthermore, it may be possible to vary, along the length of the rigidiser arm 3102, where the strap 3101 is connected. This would allow for an even greater range of head sizes and circumferences to be accommodated without the need to alter the stretchability of the strap 3101.

Referring now to FIG. 26A to 26D. The strap 3101 may provide a comfortable level of headgear tension for most head sizes. There may be two lengths or sizes of straps which are gender specific, the one for the male population being longer than the female version. In some forms, there may be two sizes/lengths of the strap 3101 for each gender.

The strap 3101 applies a comfortable level of headgear tension to retain the display unit 3012 on a user's face. As indicated by dotted-lines 'C' in FIGS. 26A to 26D, the tension applied by the strap 3101 pulls the head-mounted display unit 3012 into contact with the user's head. Typically, the head-mounted display unit 3012 will contact at the user's forehead and/or nasal bridge when the strap 3101 is tensioned about the rear of the user's head. Supporting the head-mounted display system at these locations, e.g. the nose-bridge, can assist with stabilisation of the head-mounted display system during use. Contact with the nasal bridge, in particular, is described in further detail later.

The split regions 3126 of the strap 3101 are configured to 'cup' the back of the user's head. In other words, the length of the split region 3126 must be sized such that the two back strap portions 3117a, 3117b are able to 'cup' the back of the user's head. This allows the straps to maintain their position during use, and in turn, maintain the headgear tension during use. If the length of the split region 3126 is too long, the two back strap portions 3117a, 3117b will separate in front of the user's ears and therefore be uncomfortable as they pass over the ears rather than above/around them. As such, the maximum angle range for the two back strap portions 3117a, 3117b will be reduced with respect to each other.

In the neutral and unstretched condition of the strap 3101, the two back strap portions 3117a, 3117b have an angle $\theta$ from each other at about 0° to about 10°. After donning the head-mounted display system 3000, the two back strap portions 3117a, 3117b may be split from each other such that the angle $\theta$ may be up to about 180°. This allows a maximum angular range of 180° which in turn gives a large range for the reduction of headgear tension through incrementally spreading apart the two back strap portions 3117a, 3117b. Conversely, the angular range may be narrowed to increase the tension applied by the headgear.

The user may use one or both hands to move the two back strap portion 3117a, 3117b under tension on the back of their head, apart or together. By moving the two back strap portion 3117a, 3117b further apart from each other, the split region 3126 enlarges, leading to a reduction in headgear tension from the unsplit headgear tension.

As will be appreciated, the head-mounted display system 3000 may comprise one or more rigidiser arms 3102. While the above discussion concentrates on the relationship of a rigidiser arm 3102 with a strap 3101, it is to be noted that the form shown in FIGS. 24 to 26, the head-mounted display system 3000 comprises two rigidiser arms 3102, one being provided in each respective side strap portion 3115, 3116 of strap 3101. The above comments, although eventually referring to one rigidiser arm 3102, thus equally apply to two or more rigidiser arms 3102 connected to a head-mounted display 3012.

The provision of two elastic straps or back strap portions 3117a, 3117b at the back allows the head to be cupped and the tension vector(s) to be adjusted by suitably positioning them, e.g. by spreading. The provision of two back strap portions 3117a, 3117b also allows better support and stability, as well as increased flexibility in avoiding specifically sensitive regions of the back of the head. The back strap portions 3117a, 3117b are intended to cup the head at the calvaria to maintain position and engagement. In one example, depending on the particular head shape of a user and the amount of splitting of the back strap portions 3117a, 3117b, the upper back strap portion 3117a is to be located proximal to the parietal bone and the lower back strap portion 3117b is to be located proximal to the occipital bone or superior fibers of the trapezius muscle (i.e. near the nape of the neck or nuchal). The lower back strap portion 3117b may be configured to engage the head of the user at a position on or lower than the external occipital protuberance.

Referring now to FIGS. 26B to 26D, the two back strap portions 3117a, 3117b also allow a user to control the orientation of the head-mounted display on their face. By 'cupping' the back of the user's head, the two back strap portions 3117a, 3117b can hold the rigidiser arms 3102 in a relatively fixed position. Further, the upper back strap portion 3117a can support the rigidiser arm in spaced relation, i.e. away, from contact with the user's ear in use. As shown for comparative purposes in FIGS. 26B and 26C, providing the strap 3101 with a single lower backstrap portion 3117b tends to pull the rigidiser arms 3102 downwards, into contact with the user's ear. The natural 'slope' at the rear of the user's head (towards the cervical region of the spine) acts to direct the strap portion 3117b away from a tensioned position, i.e. towards the narrower dimension near the nape of the user's neck or nuchal. The upper backstrap portion 3117a counteracts the downward slide (i.e. downward force vector) of the lower backstrap portion 3117b, acting to hold the rigidiser arm in a generally horizontal orientation.

In contrast to head-mounted display systems of existing virtual and augmented reality devices (i.e. as sold commercially) which require material length adjustment (shortening or lengthening), the tension provided by the strap 3101 is adjustable simply by opening or closing the relative angle between the two back strap portions 3117a, 3117b. To reduce headgear tension, the two back strap portions 3117a, 3117b are separated further apart on the back of the head when the head-mounted display system is worn. To increase headgear tension, the two back strap portions 3117a, 3117b are brought closer together.

This manner of adjustment is advantageous over notched straps which only permit preset incremental adjustment of headgear tension. It is also advantageous over Velcro™ (unbroken loop fabric) straps which require several attempts at fastening and unfastening until the desired headgear tension is obtained, or looping a strap through a buckle that is easier to increase headgear tension, rather than decrease headgear tension, because of the motion of pulling the strap through the buckle for tightening.

The two smaller straps or back strap portions 3117a, 3117b at the back of the head may be equal in length and not adjustable except through the elasticity of the material or through increasing both in tightness equally by shortening the total length at the side strap portions 3115, 3116 of the strap 3101. In some forms, a sliding mechanism (not shown) may be provided that allows the straps 3101 to be overlapped to a different extent, thus changing the overall length of the positioning and stabilising structure 3014. Non-independently adjustable strap lengths allow the two back strap portions 3117a, 3117b to naturally center themselves on the crown of the head. The two back strap portions 3117a, 3117b may be symmetrical or asymmetrical. In other words, the upper back strap portion 3117a may naturally settle at the top of the head, while the lower back strap portion 3117b may naturally settle at the back of the head near or below the occipital lobe. This may reduce the possibility of manually over tightening one strap to compensate for the other being too loose resulting in a misfit of the positioning and stabilising structure 3014. This, again, might lead to discomfort.

The aggregated width of both back strap portions 3117a, 3117b may be substantially equal to the width of a side strap portion 3115. This is aesthetically pleasing as well as providing a visual indicator to the user to adjust the back strap portions 3117a, 3117b when donning the head-mounted display system 3000. Although two back strap portions 3117a, 3117b have been described, more are possible which may provide differing degrees of adjustment of headgear tension. When the strap 3101 is in the neutral state and unstretched, the two back strap portions 3117a, 3117b are partially separated such that a gap exists between them for inviting or indicating to the user to adjust the back strap portions 3117a, 3117b when donning the head-mounted display system 3000. This improves the intuitiveness for adjusting headgear tension, and visually indicates how the headgear tension may be adjusted.

As indicated above, two or more joints could be provided creating the positioning and stabilising structure 3014 from three, four or more separate straps rather than the strap 3101 being one continuous piece. This might complicate the assembly, but may simplify the manufacturing process. Joints may be placed at the bifurcation point 3124 between the side strap portions 3115, 3116 and two back strap portions 3117a, 3117b or centered at the back. The joints may be sewn, welded, glued, or over molded and could incorporate a high friction material to help reduce movement on the head. High friction materials may include pad printing, silicone printing to increase relative surface friction between the straps 3101, 3117a, 3117b and the user's skin or hair in order to maintain position of the straps 3101, 3117a, 3117b on the user's head. The high friction materials may be present only on the user contacting surface of the back strap portions 3117a, 3117b since the rigidiser arms 3102 may perform some or most of the function of maintaining position of the side strap portions 3115, 3116 relative to the user's face.

High friction materials may also be added to the inside surface of the back and side strap portions 3115, 3116, 3117a, 3117b, to reduce the straps from slipping against the user's face or hair. For the arms or side strap portions 3115, 3116 this would help the positioning and stabilising structure 3014 stay on the cheeks and at the back strap portion 3117 it could stop the positioning and stabilising structure 3014 from sliding across the back of the head. Such material may be printed, cast or molded onto the surface or incorporated into joints, sewing or welding processes as mentioned above. Another way to reduce strap slippage is to have elastic yarns protruding from the textile material.

Instead of being inserted from the openings 3104 located close to the head-mounted display 3012, as shown in FIG. 24C, the rigidiser arm 3102 could optionally be inserted from an opening located proximal to the bifurcation point 3124 where the positioning and stabilising structure 3014 bifurcates. Once the rigidiser arm 3102 is inserted, the elasticity of the material could be used to hook back the rigidiser arm 3102 inside the opening of one of the small back strap portions 3117a, 3117b (upper or lower). This may prevent the rigidiser arm 3102 from moving, thus securing it in place. Otherwise the openings 3104 could be sewn, molded or otherwise closed permanently in order to trap the rigidiser arm 3102 inside the strap 3101.

The split region 3126 at the back may include two, three or more straps for stability. A positioning and stabilising structure 3014 of this form may be used with a virtual reality display system in order to provide greater stability (and tension) to the display units, which are often heavier in weight compared to augmented reality display systems. In some forms, such back straps may also be provided with a default angle of e.g. 45° for the split between two back straps in order to immediately cup and engage the user's head during donning. The back straps may be pivoted relative to each other after donning to fix the user interface into a position to provide tension to the head-mounted display 3012 against the user's face. The two back straps are biased to return to the e.g. 45° angle once the display system has been doffed.

The strap 3101 of the positioning and stabilising structure 3014 is configured to fit a large range of head sizes. This may effectively be a "one size fits most" positioning and stabilising structure 3014, which means that the 'out of the box' head-mounted display system is more likely to fit a user even if the user has not previously tried or used the positioning and stabilising structure 3014.

The textile of the strap 3101 may allow the skin to breathe and sweat naturally without silicone, foam or plastics creating and retaining surface heat and condensate from perspiration.

In some forms, any of the examples illustrated in FIGS. 24A to 26D could be incorporated into the examples illustrated in FIGS. 7 to 11. For example, the strap 3101 could house electrical components (e.g., similar to component 411) and/or a flow generator (e.g., similar to flow generator 406).

In some forms, the rigidised arm 3102 may be similar to the rigidised section 415. In this example, the strap 3101 may be large enough and/or flexible enough to accommodate the rigidised arm 3102 and a conduit (e.g., similar to conduit 417). The rigidised arm 3102 and the strap 3101 may be permanently connected in order to maintain proper connection of the conduit. However, other examples may include a removable strap so that the conduit can be cleaned or replaced by a user.

In some forms, the strap 3101 may include one or more batteries (e.g., similar to batteries 423). The strap 3101 may provide electrical connection between the batteries and the display unit 3012.

In certain forms, the strap 3101 may include a charging port (not shown) that may allow a power cable to connect to the strap 3101 and recharge the batteries. This may allow the strap 3101 to remain fixed to the rigidised arm 3102 in order to limit disturbances to the electrical connection.

In other forms, the strap 3101 may be removable from the rigidised arms 3102 (e.g., as described above) and/or the batteries may be removable from the strap 3101. This may allow replacement batteries and/or a replacement strap 3101 to be used when the charge in the batteries can no longer power the display unit 3012. This may allow a user to continue to use the display unit 3012 even when one set of batteries need to be recharged and/or replaced.

In certain forms, the headgear connector 3150 may assist in forming an electrical connection when the strap 3101 is connected to the rigidised arm 3102. For example, the strap 3101 may include an electrical connector proximate to the opening 3104 that may engage with a complementary electrical connector in order to establish an electrical connection between the strap 3101 and the display unit 3012.

In some forms, the rigidised arm 3102 may assist in maintaining the shape of the strap 3101. As described above, the strap 3101 may be positioned around the arm 3102 so that the strap 3101 takes on a similar shape to the arm 3102. For example, the portion of the strap 3101 along the rigidised arm 3102 may appear rigidised, even if the strap 3101 itself is flexible or floppy. This may assist in protecting wires that form electrical connections because the wires may not be able to bend or crease, which could otherwise disturb the electrical connection.

Referring now to FIGS. 27A to 27D and FIGS. 28A-1 to 28C-2, a head-mounted display system 4000 according to a thirteenth example of the present technology is shown. The head-mounted display system 4000 differs from the previous examples shown in FIGS. 2 to 26D in that the head-mounted display system 4000 further comprises a central support structure 4162, e.g., a hub component, arranged to locate around a user's ear. Although the head-mounted display system 4000 of the thirteenth example in FIGS. 27A to 27D and FIGS. 28A-1 to 28C-2 takes the form of an augmented reality display system, it can be equally applied to a virtual reality display system.

In the illustrated example of FIG. 27A, the central support structure 4162 comprises a central part, or hub, of the positioning and stabilising structure 4114 that connects to rigidiser arms 4002.

The hub component 4162 may be rotatably connected to the rigidiser arms 4002 whereby the arms 4002 may articulate about the hub 4162 to enable the head-mounted display 4212 to, for example, rotate forward or rearward relative to the coronal plane. Referring to FIG. 27B, the head-mounted display 4212 is configured in an in-use position in front of a user's eyes. The display unit may articulate about the hub 4162 to enable the display unit to rotate i.e., move relative to the Frankfort horizontal. For example, the display unit can be raised or lowered relative to the eyes of the user. That is, the support structure 4162 may allow for upward, e.g., superior, pivoting movement (or pivotal movement) of the display unit to allow for movement of the display unit to a non-operational position without removal of the positioning and stabilising structure (e.g. a 'flip-up' function).

In some forms, the pivoting movement (or pivotal movement) of the display unit involves a pivoting arrangement (or pivotal movement) which includes the support structure. In some forms, this pivoting arrangement may provide a release mechanism at the hub 4162 (e.g. a release mechanism to releasably lock the display unit in operational (i.e. lowered) and non-operational (i.e. raised) positions).

Referring to FIG. 27C, the hub 4162 can, in-use, direct the force applied by the head-mounted display 4212 around the user's ear. For example, as the head-mounted display 4212 is articulated (via arms 4002) about the hub 4162 e.g. into an in-use position in front of a user's eyes, the load applied by the weight of the head-mounted display can translate to, and around, the perimeter of the hub 4162. In this way, the hub component 4162 may accommodate some of the weight of the display unit 4212, thereby creating a pivot axis for the head mounted display system 4000 about the user's ears and in the region of the mid coronal plane. This can relieve loading on the nasal bridge and assist in angular adjustment of the display unit 4212 about the hub 4162.

The arms 4002 can be configured to bias into, i.e. towards, contact with the each of the user's ears such that the hubs 4162 hold (by application of a weak pressure) against the user's head. In this way, the hubs 4162 on the user's ears can support at least part of the weight of the head-mounted display.

Examples of two possible configurations of the display unit 4212 are illustrated in FIG. 27D. In a first example, the display unit 4212 is configured in front of the user's eyes, i.e. generally parallel with the Frankfort horizontal. In a second example, the display unit is shown in a raised position above the user's eye, i.e. angled relative to the Frankfort horizontal. Advantageously, moving the display unit 4212 between these two positions enables the user to move the display unit 4212 away from their eyes during use (e.g., game play), or before donning and doffing the head-mounted display system 4000.

Referring to FIGS. 28A-1 to 28C-2, disclosed is a further embodiment of the head-mounted display system according to another version of the thirteenth example of the present technology. The head-mounted display system 4300 differs from the embodiment shown in FIGS. 27A to 27D in that the head-mounted display system 4300 further comprises coronal portion 4138 and/or an occipital portion 4140 connected to the central support structure, i.e. hub 4162.

The hub component 4162 is rotatably connected to each of the coronal portion 4138 and/or the occipital portion 4140 (also referred to as a posterior portion). The coronal portion and occipital portion may articulate about the hub 4162 to enable the coronal portion 4138 to, for example, rotate forward or rearward relative to the coronal plane, and the occipital portion 4140 to raise or lower relative to the Frankfort horizontal.

Referring to FIGS. 28A-1 to 28B-2, examples of two possible configurations of the coronal portion 4138 and occipital portions 4140 relative to the hub 4162 are illustrated. In a first example (shown in FIGS. 28A-1 and 28A-2), the head-mounted display system 4300 comprises only a coronal portion 4138 configured in a position proximal to (and in alignment with) the coronal suture, i.e. at the juncture between the parietal and frontal bones. In a second example (shown in FIG. 28B-2), the head-mounted display system 4300 comprises both a coronal portion 4138 and an occipital portion 4140. In this second example, the occipital portion 4140 is configured in a position proximal to (and in alignment with) the lambdoid suture, i.e. at the juncture between the parietal and occipital bones.

In some forms, the coronal portion 4138 can be independently angled (or moved) relative to the occipital portion 4140. The coronal portion can be adjusted to move towards the centre of gravity of the display system. In some forms, the occipital portion can move upwards or downwards to support the positioning and stabilising structure 4114 (via the occipital portion) against the occipital bone of the user's head. In some other forms the occipital portion 4140 can comprise a type of counter-weight to balance the display unit 4212.

Referring in particular to FIGS. 28A-1 and 28A-2, the hub 4162 and coronal portion 4138 can, in-use, direct the force applied by the head-mounted display 4212 around the user's ear and about the coronal suture of the user's head, as indicated by dotted-lines. Similarly, in the alternative embodiment shown in FIG. 28B-2, the occipital portion can additionally direct the force applied by the head-mounted display 4212 into (e.g. at, or about) the lambdoid suture of the user's head. It should be appreciated that although the contact point for the coronal and occipital portions are defined by the respective coronal and lambdoid sutures, the contact point for the coronal and occipital portions can be on the user's head either side of said sutures.

Similar to the coronal portion 4138, the occipital portion 4140 can be articulated about the hub 4162 into a position angled with respect to the rigidiser arms 4002. In this way coronal and occipital portions of the positioning and stabilising structure can be moved (i.e. angled) relative to the rigidiser arm to support the weight of the head-mounted display 4212. Further, the forces applied to the occipital portion 4140 can translate around the perimeter of the hub 4162 and through the coronal portion 4138.

Examples of two possible configurations of the display unit 4212 are illustrated in FIG. 28D. In a first example, the display unit 4212 is configured in front of the user's eyes, i.e. generally parallel with the Frankfort horizontal. In a second example, the display unit is shown in a raised position above the user's eye, i.e. angled relative to the Frankfort horizontal. In the form shown in FIG. 28B-1, when in the raised position, the display unit is configured to locate above the coronal portion, and in some forms may be configured to connect with the coronal portion to securely, and releasably, attach the display unit 4212 thereat. Alternatively, and as previously described, each of the display unit 4212, coronal portion 4138 and occipital portion 4140 can be fixed in position relative to the hub via a release mechanism in the hub 4162. In this case, the release mechanism can releasably lock the display unit, coronal portion and occipital portion at various angles relative to each other. For example, the display unit can be positioned in either operational (i.e. lowered) and non-operational (i.e. raised) positions, and the coronal and occipital portions angled to mount (i.e. contact with) respective positions on the user's head.

Referring to FIGS. 28C-1 and 28C-2, in some forms, the coronal portion can be detachable from the head-mounted display unit 4212. As shown in FIGS. 28C-1 and 28C-2, the coronal support 4138 is configured to mount about the hub 4162 and extend across the user's head, similar to a traditional 'headphone'-type' device.

In certain forms, the coronal support 4138 and the hub 4162 may be used independently from the head-mounted display unit 4212 as headphones.

In either of the embodiments set forth above, the head-mounted display system 4300 of the thirteenth example may exhibit a high degree of adjustment in a manner that provides intuitive fit and adjustment. The hub 4162, coronal portion 4138 and/or occipital portion provides responsive stability that can cater for dynamic movements of the user.

A further feature of the design is that reactive forces induced by the display unit 4212 can be supported by the coronal and occipital portions 4138, 4140 whilst still allowing for fine independent adjustment of the display unit 4212. In particular, adjustment of the display unit in an anterior and posterior direction controls the contacting pressure of the interfacing structure on the face. For example, adjustment of the display unit until e.g. a nose or forehead pad provided to display unit housing 4122, lightly touches the face.

Adjustment of the coronal portion 4138 assists in accommodating different head sizes and location of the display unit 4212. In some forms, the coronal portion can be adjusted in size, e.g. via a headphone-style adjustment, so as to adjust the superior-inferior position of the head-mounted display 4212 with respect to the user's eyes.

Adjustment of the occipital portion 4140 assists in fit, location of contacting points, and the amount of counter-moment generated, so as to aid comfort and load distribution in the positioning and stabilising structure 4114. The occipital portion 4140 can provide a combination of properties (including, but not limited to); rigidity to control the direction of pull (from the display unit 4212 weight), conformability to the head shape for comfort and grip, elasticity to automatically hold the system snug to a user's head: all coupled with selectable adjustment.

In some forms, an audio device 'A', i.e. headphones (e.g. noise cancelling), can be located on the hub 4162. The audio device 'A' can be configured to releasably engage with the hub 4162, e.g. about a snap-lock type feature. In some forms, an audio device 'A' can be placed on the hub 4162 to encapsulate a user's ear, in-use.

In certain forms, the audio device 'A' may contribute to the virtual or augmented reality experience by providing sound output to the user consistent with the images shown on the display unit 4212. For example, sounds from the game being played on the display unit 4212 may be output to the user using the audio device 'A' in the hub 4162.

In certain forms, the audio device 'A' may include wireless connectivity (e.g., Bluetooth) in order to connect to an external device. For example, the display unit 4212 may provide a visual augmented reality to the user, but may not output sound. A user may listen to audio (e.g., music, podcast, audiobook, white noise, etc.) from a separate device (e.g., a smartphone) while using the display unit 4212.

As shown in FIGS. 28C-1 and 28C-2, one form of the hub 4162 may be separable from the display unit 4212. In some forms, this may assist the user in storage. In some forms, the hub 4162 may be usable as headgear (e.g., wireless headphones) separately from the display unit 4212. Further details of headgear portions covering a user's ear were described in International (PCT) Patent Application No. PCT/SG2021/050590, which is hereby incorporated by reference herein in its entirety.

Referring to each of the twelfth and thirteenth examples of the present technology, a flow generator may also be provided in each of the respective systems as set forth in the fifth example of the present technology (and shown in FIGS. 7 to 11). That is, in some forms of the twelfth and thirteenth examples, the augmented reality display system or assembly 3000, 4300 may also be configured to support a flow generator (e.g. a blower) and related componentry with respect to the display unit 3012, 4212. In these forms, the flow generator may be used as a counter weight to help balance the display unit.

For example, the positioning and stabilising structure 3014, 4114 may be configured to hold the flow generator in a location towards the posterior of the user's head, e.g. towards back strap portions 3117a and 3117b. When referring to the twelfth example, flow generator may be mounted to a rigidiser arm. Alternatively, the flow generator may be mounted with respect to the display housing 3222.

When referring to the thirteenth example, the flow generator may be arranged on, or within (i.e. to be concealed by), the central hub 4162. Alternatively, the flow generator may be mounted with respect to the occipital portion 4138. Alternatively, the flow generator may be arranged with respect to the display 4212 as otherwise described in relation to the fifth example of the present technology.

FIGS. 29 to 32 show a head-mounted display system or assembly 5000 according to a fourteenth example of the present technology. The head-mounted display system 5000 comprises a head-mounted display unit 5012, and a positioning and stabilising structure 5014 to maintain or hold the display unit 5012 in an operational position over a user's face, in use.

The display unit 5012 includes a user interface structure 5013 constructed and arranged to be in opposing relation with the user's face. The user interface structure 5013 extends about a display contained by the display unit housing 5022. The user interface structure 5013 extends around the user's eyes, and engages with the user's face, e.g., along the user's cheeks and/or forehead.

In the form shown in FIG. 29, an in-use lower portion of the interface structure 5013 can be configured so as to avoid contact the user's nose, i.e. the user interface structure 5013 terminates at the region proximal the user's nose. In this way, the in-use lower portion of the housing 5022 and/or display 5012 does not rest against, or interact with, the user's nose (e.g. across the user's nose).

The user interface structure 5013 is structured and arranged to provide a balanced system, i.e., system that is not overly tight (or pressured) at any singular point along the user's face. That is, user interface structure 5013 according to the fourteenth example of the present technology provides a more even fit that is structured and arranged to distribute pressure over more of the user's face to lessen hot spots or localised stress points.

Also, the user interface structure 5013 can comprise soft and flexible (e.g., elastic) materials structured and arranged to allow more conformity to the user's face and cushioning for comfort. Examples of materials include breathable material, for instance, textile-foam composite.

The head-mounted display system 5000 according to the fourteenth example further comprises a temporal connector 5018 structured and arranged to interconnect a rear support structure 5016 to the head-mounted display unit 5012. The temporal connector 5018 and rear support structure 5016 each form part of the positioning and stabilising structure 5014. The rear support structure 5016 is adapted to contact regions of a user's head (e.g., positionable at a crown of the user's head). The temporal connectors 5018 are disposed on respective sides of the user's head, i.e. are opposing, and interconnect the rear support structure 5016 to respective posterior edge regions 5020 of the housing 5022.

Each of the opposing temporal connectors 5018 comprises a temporal arm 5026. Each temporal arm 5026 includes an anterior end 5028 mounted to the respective posterior edge region 5020 of the display unit housing 5022 and a posterior end 5030 that forms part of a releasable coupling 5031 to connect the temporal arm 5026 to the rear support hoop 5016.

Although the illustrated embodiments of FIGS. 29-32, show the temporal arms 5026 connected to the display unit housing 5022, in some forms not shown, the rear support structure can be adapted to connect to the interface structure 5013.

Each temporal arm 5026 can comprise a rigidiser and a textile component. In some forms, the temporal arms 5026 only comprises a rigidiser, i.e. without a textile component.

Referring now to FIG. 31, a portion of each of the temporal arms 5026, in-use, is in contact with a region of the user's head proximal to the otobasion superior, i.e., above the user's ear. The temporal arms 5026 are arranged in-use to run generally along or parallel to the Frankfort Horizontal plane of the head and superior to the zygomatic bone, i.e., above the user's cheek bone.

In other forms not shown, a forehead support connector can extend across the frontal bone of the user to interconnect the rear support structure 5016 with a superior edge region 5021 of the display unit housing 5022 (or in some alternative forms, a superior edge region of the user interface structure 5013). However, it should be appreciated that more or less connectors may be provided to interconnect the rear support structure 5016 to the head mounted display unit 5012.

The user interface structure 5013 is constructed and arranged to be in opposing relation with the user's face, and to extend around at least a portion of the outer perimeter of the display 5012. In some forms the user interface structure 5013 is arranged to be spaced from the display housing 5022 along at least portions of its perimeter to provide a gap therebetween.

As best shown in FIG. 29, the user interface structure 5013 of the fourteenth example takes the form of a stabilising flange 5015 positioned in-use to engage with the user's face generally around a periphery of a user's eyes. The flange 5015, in-use, overlays one or more of a portion of the frontal bone region and each of the left and right infraorbital margin regions of the face. In some forms (not shown) the stabilising flange can overlay a portion of the nasal ridge region.

The flange 5015 can be generally curved laterally across the user's face. As best shown in FIGS. 29 and 32, the flange can be configured to space apart the display housing 5022 and the user's face (a distance, d) and in turn, to provide one or more spaces between the flange and the display housing 5022. The curvature of the stabilising flange can change laterally across its length to space the housing 5022 at varying distances from the user's face. In other words, the flange can space the housing at a greater distance from the face in the regions proximal the sides of the user's face, in comparison to the smaller distance formed in the region proximal the central forehead of the user's face. In some forms where the flange is of relative constant thickness, this can provide one or more gaps between the flange and the display housing 5022 that are similarly at varying sizes around user's eyes.

Spacing the flange 5015 from the housing 5022 at a distance d provides an open gap between the in-use housing and the flange that allows light and airflow to ingress therethrough. This open gap can improve the user's comfort during an augmented interactive experience with the surrounding real-world environment.

In some forms, the flange 5015 can provide a cushioning function so as to improve the overall comfort for a user. For example, the flange can comprise a textile component to provide a soft support structure to stabilise the display unit 5012 on a user's head. The flange can also be flexible to deflect when compressed against a user's face. The cushioning function of the flange 5015 will be discussed in more detail later.

The stabilising flange 5015 can be attached to at least a portion of the display unit housing 5022 whereby the display 5012 contained by the display unit housing 5022 is held in an operable position on a user's face.

In some forms of the fourteenth example, a system is provided whereby the interfacing structure 5013, i.e. the stabilising flange 5015, is integrally formed with the display unit housing 5022. In some other forms, a system is provided whereby the interfacing structure is formed as a separate removable component. In this form, the flange is configured to integrate with, and be retained by, the display unit housing so as to engage with, and be in opposing relation to, the user's face, in-use. A removable flange can allow for applications such as medical use, whereby the flange 5015 may be disposable or may allow separate cleaning to comply with surgical procedures.

When the flange is formed as a removable component it can comprise one or more engagement elements at its periphery configured to detachably mate with a corresponding element configured on the display unit housing 5022. Suitable engagement elements may include one or more of a clip, fastener, magnet, or Velcro. The engagement elements relatively fix the flange 5015 and display unit housing 5022 to one another, i.e. provide a connection without allowing significant slippage to occur therebetween.

In some forms, the removable flange can be provided in more than one size to correspond to a different size and/or shape range of a user's head. For example, the head-mounted display system 5000 may comprise one form of a stabilising flange 5015 suitable for a large sized head. The large size would be configured suitable for users with large sized heads and may not be suitable for users with smaller sized heads. In this way, each size can provide optimised comfort and performance for respective user's head size. A removable stabilising flange may be advantageous to enable a user to customise the head-mounted display system 5000 and to select the stabilising flange that best fits their individual facial anthropomorphic features.

In some further embodiments, a user can have their facial anthropomorphic features measured in order to custom design and form a suitable stabilising flange.

In one form of the fourteenth example, the flange 5015 may be encapsulated within the textile component (not shown). In other forms, the stabilising flange can act as a base for locating the textile component thereon. In this arrangement, the flange can provide rigidity and necessary structure while the textile component can provide the cushioning function.

The stabilising flange 5015 can be formed of rigid, or semi-rigid, material. For example, some embodiments of the flange can be formed of a plastic material.

The textile component includes a face contacting side (i.e. surface) (indicated in FIGS. 29 and 32 by reference 5017) arranged on one side of the flange that can provide a soft, face contacting surface adapted to contact the user's face, in use. The textile can be attached to the flange with adhesive, or otherwise attached, e.g. overmolded.

In an example, the textile component may comprise a textile material or a textile-foam composite, e.g., breathable material, multi-layered construction including an outer textile layer and an inner foam layer, to provide a soft support for the flange to cushion against the user's head for optimised comfort.

In some forms, a soft plastic, e.g. silicon can be over-moulded onto the flange 5015 to provide the cushioning function. In this form, the flange can comprise one or more regions of silicon (or if textile is used instead of silicon, one or more layers of a textile material or foam). In variations of this form, a combination of two or more materials types, e.g. silicon and textile can be used. In this way, different materials can be used to contact different regions of the user's face and can allow each material to respond independently to the compression pressure applied when interacting with a user's face in-use. This may improve retention of the display system 5012 on the user's face whilst also improving user comfort.

The one or more regions of e.g. silicon can be formed to have varying thicknesses, densities and/or varying surface finishes, whereby the resultant face engaging surface can have a variable compliance therealong when compressed against a user's face in-use.

In some other forms, the flange can be formed entirely of textile, whereby the textile component can be made of materials that can be selectively rigidised by heat treatment (e.g., heat treatment).

In the form shown in FIGS. 29-32, the flange is formed as a single component. In this form, the flange can comprise varying thicknesses and finishes thereacross so as to provide the desired level of rigidity or desired level of cushioning effect at the face engaging surfaces.

The flange, in some forms, can be formed entirely of silicon. In this form, the flange can have a thickness selected to provide a compliant, yet resilient, spring-like support to that engages and conforms to the contours of the user's face. Further, the flange can have a varying thickness such that some portions can respond independently to the compression pressure applied when interacting with a user's face in-use.

In a variation (not shown), the flange can be formed of two or more chassis elements that can be adhesively, mechanically or over-moulded together to form a composite flange body. Such a composite body can comprise both flexible (facilitated by e.g. the over-moulded soft material) and rigid portions (facilitated by the plastic materials, i.e. chassis elements) to provide the desired level of flexibility and/or rigidity in the flange. In this way, the two or more chassis elements can respond independently to the compression pressure applied when interacting with a user's face in-use. Further, the composite body can provide soft, face contacting surfaces to provide the desired level of cushioning effect.

It can be advantageous for the stabilising flange 5015 to balance compliance against resilience and rigidity, so as to spread the resistance force applied by the flange when compressed against a user's face, in-use. In the form shown in FIGS. 29-32, the stabilising flange is spaced from the display housing such that when compression pressure is applied to the flange by the user's face, the position of the flange translates to absorb the compression. In other words, the flange moves towards the display housing. This translation can take place when compressive forces are applied by a user fitting the head-mounted display 5000 to their head or when the head-mounted display moves, when in-use, as a result of movement of the user, i.e. head turns, body movements, etc. That is, the flange 5015 can adaptably mould to the user's face.

In this form, the flange behaves in a similar manner to a spring. That is, the stiffness of the flange can influence the stability of the system 5000 on a user's face, in-use. For example, a stiff flange will deflect by a smaller magnitude when compressed, compared to a relatively less stiff flange. The stiff flange will provide more stability to the system, whereas the relatively less stiff flange can absorb greater compression, e.g. movement, of the system 5000 when in-use.

It is an advantage that this adaptive moulding can maintain constant contact between the flange and the user's face. This can assist with spreading the pressure evenly across the user's face for improved comfort.

In some forms, the face contacting surfaces of the flange can be provided with a surface finish which, when in contact with the user's face, can resist movement, e.g. resist sliding or slippage along the user's face as a result of movement of system 5000, e.g. movement due to the user's head-movement, or due to the weight of the system 5000. Some or all of the face contacting (i.e. engaging) surfaces may be regions of relatively high friction. For example, where silicone is used, this may be achieved by providing a (so-called) polished surface finish. With a polished face contacting surface, the flange may adhere to the user's face more than with a region of low friction. Likewise, a textile or foam material having relatively high friction surface finishes can provide similar resistance to movement on a user's face.

While the fourteenth example of the present technology is disclosed in FIGS. 29 to 32 as having a temporal connectors interconnected by a single rear connector, it is anticipated that the stabilising flange 5015 of the fourteenth example can be combined with any of positioning and stabilising structures of the examples set forth previously.

For example, the stabilising flange 5015 of the fourteenth example can be combined with the rear support hoop of the first example.

In other forms of the fourteenth example, the stabilising flange can be combined with the crown support hoop of the sixth example.

In other forms of the fourteenth example, the stabilising flange can be combined with the support portions of the positioning and stabilising structure as defined in seventh example.

In other forms of the fourteenth example, the stabilising flange can be combined with the augmented reality display system of the eighth and ninth example.

In other forms of the fourteenth example, the stabilising flange can be combined with the over-extension portion of the tenth example.

In other forms of the fourteenth example, the stabilising flange can be combined with the rear hook portion of the eleventh example.

In other forms of the fourteenth example, the stabilising flange can be combined with the strap and rigidiser arms of the twelfth example.

In further forms of the fourteenth example, the stabilising flange can be combined with the central support structure of the thirteenth example.

Furthermore, it is anticipated that any of the abovementioned examples can be used with the stabilising flange 5015 in combination the flow generator as defined in the fifth example of the present technology.

The above-described head-mounted display systems (including e.g. augmented reality systems and virtual reality systems) provide alternative examples of the present technology structured and arranged to enhance comfort, fit range, usability, system architecture, use in a medical environment, and manufacturability.

The head-mounted display systems according to examples of the present technology provide enhanced comfort with minimised facial markings and pain from prolonged use. For example, comfort may be achieved by providing universal load distribution in which load is optimised on all contact surfaces by avoiding or minimising load on areas prone to discomfort and redistributing this load to areas able to comfortably bare the load, e.g., avoid or minimise load on the nasal bridge and sides of the nose and apply or redistribute this load to the top and/or rear of the head. Also, comfort may be achieved by providing regional load distribution in which load is evenly distributed by design and material selection in regions of the face where contact is unavoidable, e.g., contact points around the eyes may comprise compliant materials that evenly distribute load and avoid pain points/facial marking. In addition, comfort may be achieved by minimising weight as less weight in the overall system leads to less tension to position and maintain the system in the right configuration. In this regard, the head-mounted display systems according to examples of the present technology provide a minimalist design (e.g., low profile) to achieve fit range, comfort, and correct configuration, e.g., componentry optimised to minimise size and number of components to achieve function and use of robust and lightweight materials.

The head-mounted display systems according to examples of the present technology provide enhanced fit range or universal fit without trading off comfort, usability and cost. For example, fit range may be achieved by providing adjustability with geometry and material selection and adjustment mechanism. The components of the positioning and stabilising structure are designed and materials may be selected to provide desired force versus displacement, e.g., straps may stretch to a desired length under a predetermined force. The adjustment mechanism provides simplicity as sizing of the positioning and stabilising structure and associated straps may be manually adjusted and set, and componentry can be minimised while maximising ease of use, e.g., single handed adjustment of straps and alternative use of magnetic clips for connection. Also, the adjustment mechanism provides minimal size and weight which reduces the bulk of adjustment mechanisms with optimal materials and minimal components. Further, enhanced fit range may be achieved by anthropometrics in which adjustment range may be designed to fit the optimal anthropometric range of the desired market.

The head-mounted display systems according to examples of the present technology provide enhanced usability with low-touch simple set up solutions and low dexterity threshold solutions. For example, low-touch set up may be achieved with self-adjusting solutions including stretchable materials or simple mechanical actuation where only a few minor adjustments may be necessary for correct fit. Also, the system may include adjust and lock solutions to facilitate usability (i.e., set and forget), e.g., mechanisms to guide adjustment (e.g., magnets) and locking mechanisms to set adjustment (e.g., clips). Further, the system provides ease of use so that it is capable of adjustment when worn by a user with low-dexterity and/or minimal vision.

The head-mounted display systems according to examples of the present technology provide enhanced system architecture which optimises componentry location such that it minimises cost while maximising comfort, fit range and usability. For example, the system may provide enhanced weight distribution in which electrical and/or mechanical components are positioned in ideal locations from a comfort perspective. Also, the system may comprise modularity such that components may be selected or upgraded based on user preference, e.g., electrical component, face contacting cushions, straps, and/or ear buds may be selected based on preference.

The head-mounted display systems according to examples of the present technology enhance use in a medical environment. For example, the system may be biocompatible and/or cleanable with materials selected that are cleanable for re-use in a medical environment and/or pass biocompatibility requirements.

The head-mounted display systems according to examples of the present technology enhance manufacturability by providing mass producible solutions at low cost while maintaining high quality and functionality.

In the claims which follow and in the preceding description of examples of the present technology, except where the context requires otherwise due to express language or necessary implication, the word "comprise" or variations such as "comprises" or "comprising" is used in an inclusive sense, i.e., to specify the presence of the stated features but not to preclude the presence or addition of further features in various examples of the present technology.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements or examples. Furthermore, although process steps in the methodologies may be described or illustrated in an order, such an ordering is not required. Those skilled in the art will recognise that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| REFERENCE SIGNS LIST | |
|---|---|
| Feature Item | Number |
| head-mounted display system | 10 |
| display unit | 12 |
| user interface structure | 13 |
| positioning and stabilising structure | 14 |
| rear support hoop | 16 |
| temporal connectors | 18 |
| posterior edge region | 20 |
| superior edge region | 21 |
| display unit housing | 22 |
| forehead support connector | 24 |
| temporal arm | 26 |
| anterior end | 28 |
| posterior end | 30 |
| rigidiser | 32 |
| textile component | 34 |
| face contacting surface | 35 |
| tab | 36 |
| parietal portion | 38 |
| occipital portion | 40 |
| connection straps | 42 |
| eyelet | 44 |
| forehead support strap | 48 |
| adjustment mechanism | 50 |
| forehead support hole | 52 |
| tab portion | 54 |
| head-mounted display system | 110 |
| display unit | 112 |
| user interface structure | 113 |
| positioning and stabilising structure | 114 |
| rear support hoop | 116 |
| temporal connector | 118 |
| posterior edge region | 120 |
| superior edge region | 121 |
| display unit housing | 122 |
| forehead support connector | 124 |
| temporal arm | 126 |
| parietal portion | 138 |
| occipital portion | 140 |
| connection straps | 142 |
| forehead support strap | 148 |
| adjustment mechanism | 150 |
| forehead support hole | 152 |
| tab portion | 154 |
| forehead support rigidiser | 156 |
| head-mounted display system | 210 |
| display unit | 212 |
| user interface structure | 213 |
| positioning and stabilising structure | 214 |
| rear support hoop | 216 |
| temporal connector | 218 |
| posterior edge region | 220 |
| display unit housing | 222 |
| temporal arm | 226 |
| parietal portion | 238 |
| occipital portion | 240 |
| connection straps | 242 |
| head-mounted display system | 310 |
| display unit | 312 |
| user interface structure | 313 |
| positioning and stabilising structure | 314 |
| rear support hoop | 316 |
| temporal connectors | 318 |
| temporal connector | 318 |
| display unit housing | 322 |
| forehead support connector | 324 |
| temporal arm | 326 |
| rigidiser | 332 |
| parietal portion | 338 |
| occipital portion | 340 |
| forehead support strap | 348 |
| extended rigidiser | 358 |
| biased extended rigidiser | 360 |
| medial adjustment mechanism | 362 |
| holes | 363 |
| temporal adjustment mechanism | 364 |
| posterior ends | 368 |
| flow generator | 406 |

REFERENCE SIGNS LIST

| Feature Item | Number |
|---|---|
| flow generator | 406' |
| air draft | 408 |
| air draft | 408' |
| head-mounted display system (augmented reality display system) | 410 |
| electronic components | 411 |
| augmented reality display unit | 412 |
| positioning and stabilising structure | 414 |
| rigidised section | 415 |
| conduit | 417 |
| pivot point | 419 |
| pivot strap | 421 |
| batteries | 423 |
| flow generator | 506 |
| air draft | 508 |
| head-mounted display system (virtual reality display system) | 510 |
| virtual reality display unit | 512 |
| interface structure | 513 |
| positioning and stabilising structure | 514 |
| rear support structure | 516 |
| conduit | 517 |
| temporal connectors | 518 |
| posterior edge regions | 520 |
| superior edge region | 521 |
| display unit housing | 522 |
| forehead support connector | 524 |
| temporal arm | 526 |
| anterior end of temporal arm | 528 |
| posterior end | 530 |
| rigidiser | 532 |
| textile component | 534 |
| tab | 536 |
| head-mounted display system | 600 |
| hoop frontal portion | 601 |
| crown support hoop | 603 |
| interface structure | 613 |
| positioning and stabilising structure | 614 |
| battery pack | 615 |
| rear support hoop | 616 |
| opposing temporal connectors | 618 |
| posterior edge regions | 620 |
| display unit housing | 622 |
| forehead support connector | 624 |
| temporal arms | 626 |
| hoop parietal strap | 638 |
| temporal-crown straps | 640 |
| temporal-crown support connectors | 642 |
| adjustment mechanisms eyelet | 644 |
| forehead support strap | 648 |
| adjustment mechanism | 650 |
| forehead support hole | 652 |
| forehead tab portion | 654 |
| adjustment mechanism | 662 |
| head-mounted display systems | 700 |
| interfacing structure | 713 |
| head-mounted display unit | 720 |
| arms | 730 |
| positioning and stabilising structure | 750 |
| posterior support portions | 752 |
| anterior support portion | 754 |
| sagittal strap portion | 756 |
| top strap portion | 758 |
| lateral strap portion | 760 |
| superior support pads | 762 |
| occipital strap portion | 764 |
| frontal support portion | 766 |
| band portion | 768 |
| frontal connector | 770 |
| lateral occipital strap portion | 772 |
| medial occipital strap portion | 774 |
| dial adjustment mechanism | 776 |
| rotatable dial | 778 |
| parietal strap portion | 780 |
| extending portions | 782 |
| guide | 784 |
| elastically extendable connector strap portion | 786 |
| magnetic clip | 788 |
| battery pack | 790 |
| contact zone | C |
| hardware components | H |
| display unit | 812 |
| user interface structure adjacent to a user's forehead | 813a |
| user interface structure adjacent to a user's nose | 813b |
| user interface structure adjacent to a user's temples | 813c |
| positioning and stabilising structure | 814 |
| rear support hoop | 816 |
| temporal connector | 818 |
| display unit housing | 822 |
| forehead support connector | 824 |
| temporal arm | 826 |
| rigidiser | 832 |
| parietal portion | 838 |
| occipital portion | 840 |
| connection straps | 842 |
| forehead support strap | 848 |
| rigidiser | 856 |
| power unit | 860 |
| head-mounted display system | 910 |
| display unit | 912 |
| user interface structure engaging with a user's forehead | 913a |
| user interface structure adjacent to a user's nose | 913b |
| positioning and stabilising structure | 914 |
| rear support hoop | 916 |
| temporal connector | 918 |
| display unit housing | 922 |
| forehead support connector | 924 |
| temporal arm | 926 |
| rigidiser | 932 |
| parietal portion | 938 |
| occipital portion | 940 |
| connection straps | 942 |
| forehead support strap | 948 |
| power unit | 960 |
| sensor | 980 |
| head-mounted display system (augmented reality display system) | 1000 |
| electronic components | 1011 |
| augmented reality display unit | 1012 |
| positioning and stabilising structure | 1014 |
| arms | 1015 |
| over-extension portion | 1016 |
| battery pack | 1018 |
| lower arm | 1022 |
| upper arm | 1024 |
| central spine | 1026 |
| head-mounted display system (augmented reality display system) | 2000 |
| augmented reality display unit | 2012 |
| positioning and stabilising structure | 2014 |
| rear hook portion | 2028 |
| lateral wings | 2028A |
| adjustable arms | 2030 |
| User | U |
| coronal plane | C |
| head-mounted display system or assembly | 3000 |
| augmented reality display unit | 3012 |
| positioning and stabilising structure | 3014 |
| strap | 3101 |
| rigidiser arm | 3102 |
| opening | 3104 |
| spacing element | 3107 |
| pocketed end | 3111 |
| side strap portion | 3115 |
| side strap portion | 3116 |
| back strap portion | 3117 |
| back strap portion | 3117a |
| back strap portion | 3117b |
| outer side of headgear connector | 3118 |
| distal free end | 3119 |
| bifurcation point | 3124 |
| split region | 3126 |
| headgear connector | 3150 |
| edge of rigidiser arm | 3160 |

-continued

REFERENCE SIGNS LIST

| Feature Item | Number |
|---|---|
| display unit housing | 3222 |
| user | 3300 |
| contact region | C |
| head-mounted display system | 4000 |
| rigidiser arms | 4002 |
| positioning and stabilising structure | 4114 |
| display unit housing | 4122 |
| coronal portion | 4138 |
| occipital portion | 4140 |
| central support structure | 4162 |
| head-mounted display | 4212 |
| head-mounted display system | 4300 |
| audio device | A |
| head-mounted display system or assembly | 5000 |
| head mounted display unit | 5012 |
| user interface structure | 5013 |
| positioning and stabilising structure | 5014 |
| stabilising flange | 5015 |
| rear support structure | 5016 |
| face contacting surface of textile component | 5017 |
| temporal connector | 5018 |
| posterior edge region | 5020 |
| display unit housing | 5022 |
| superior edge region | 5021 |
| temporal arm | 5026 |
| anterior end of temporal arm | 5028 |
| posterior end of temporal arm | 5030 |
| distance of open gap | D |

The invention claimed is:

1. An augmented reality display system, comprising:
an augmented reality display unit having a display; and
a positioning and stabilising structure to hold the augmented reality display unit in an operational position over a user's face in use, the positioning and stabilising structure comprising:
at least one strap housing at least one electrical component in electrical communication with the augmented reality display unit; and
at least one rigidiser arm, wherein the positioning and stabilising structure positions the at least one strap and the at least one rigidiser arm with regard to one another such that the at least one rigidiser arm imparts a predetermined shape to the at least one strap at a rigidised portion of the at least one strap,
wherein the at least one strap comprises a hollow sleeve configured to receive the at least one rigidiser arm and at least one opening configured to receive the at least one rigidiser arm into the sleeve.

2. The augmented reality display system according to claim 1, wherein the positioning and stabilising structure positions the at least one strap and the at least one rigidiser arm with regard to one another to allow at least the rigidised portion of the at least one strap to move relative to the at least one rigidiser arm, and wherein the at least one rigidiser arm is affixed to the at least one strap at one localised point or area only.

3. The augmented reality display system according to claim 2, wherein the at least one rigidiser arm is affixed to the at least one strap in a limited area of the at least one strap the limited area is adjacent a pocket or a sleeve opening of the at least one strap.

4. The augmented reality display system according to claim 1, wherein the at least one rigidiser arm is multi-axially deformable to conform to a user's facial profile.

5. The augmented reality display system according to claim 1, wherein the at least one strap is made of an elastic textile material and the positioning and stabilising structure is arranged such that the at least one strap is substantially free to move by elastically expanding and/or contracting relative to the at least one rigidiser arm and along a longitudinal axis of the at least one strap and/or rigidiser arm.

6. The augmented reality display system according to claim 5, wherein the elastic textile material is any one from the group consisting of: elastane, TPE, nylon and silicone.

7. The augmented reality display system according to claim 5, wherein the positioning and stabilising structure is able to stretch along its substantially entire length.

8. The augmented reality display system according to claim 5, wherein the at least one strap has a stretchable length that remains substantially unaltered relative to the at least one strap without the at least one rigidiser arm.

9. The augmented reality display system according to claim 1, wherein the sleeve and the at least one rigidiser arm are configured to allow the at least one rigidiser arm to move substantially axially inside the sleeve.

10. The augmented reality display system according to claim 1, wherein an end portion of the at least one rigidiser arm is affixed to the at least one strap by sewing, welding, gluing, heat staking, clamping, buttoning, snapping a cover over an end, and/or snapping on an external part.

11. The augmented reality display system according to claim 1, wherein the imparted predetermined shape directs pressure of the positioning and stabilising structure to predetermined portions of the user's face.

12. The augmented reality display system according to claim 1, further comprising two or more rigidiser arms forming opposing temporal connectors adapted configured to be disposed on opposing sides of the user's head and extend along temporal regions of the user's head.

13. The augmented reality display system according to claim 1, wherein the at least one rigidiser arm is completely removable from the at least one strap.

14. The augmented reality display system according to claim 1, wherein the positioning and stabilising structure maintains its entire operational length and is able to freely stretch along the at least one rigidiser arm.

15. The augmented reality display system according to claim 1, wherein the at least one strap includes two side strap portions configured to extend from a user interface along the sides of a user's head and two back strap portions configured to extend along the back of the user's head, the two back strap portions are not adjustable except through an elasticity of the back strap portions or through increasing the back strap portions in tightness equally by shortening the total length of the positioning and stabilising structure.

16. The augmented reality display system according to claim 1, wherein the at least one strap comprises a back portion that is split into at least two back straps.

17. The augmented reality display system according to claim 16, wherein the at least two back straps comprise a first back strap configured to engage a user proximal to the crown of the head and a second back strap configured to engage the user proximal to the rear of the head.

18. The augmented reality display system according to claim 16, wherein each of the at least two back straps are configured to retain the augmented reality display unit on the nose of a user with substantially equal tension forces on each of the at least two back straps.

19. The augmented reality display system according to claim 16, wherein each of the at least two back straps are non-independently adjustable such that the at least two back straps naturally center on respective sides of the crown of the head of a user.

20. The augmented reality display system according to claim 19, wherein the at least two back straps are symmetrical.

21. The augmented reality display system according to claim 1, wherein the at least one electrical component is a battery configured to provide electrical charge to the augmented reality display unit.

22. The augmented reality display system according to claim 1, wherein the at least one rigidiser arm includes a headgear connector having an electrical connector and configured to engage a complementary connector of the at least one strap.

23. An augmented reality display system, comprising:
an augmented reality display unit having a display; and
a positioning and stabilising structure to hold the augmented reality display unit in an operational position over a user's face in use, the positioning and stabilising structure comprising:
at least one strap housing at least one electrical component in electrical communication with the augmented reality display unit; and
at least one rigidiser arm, wherein the positioning and stabilising structure positions the at least one strap and the at least one rigidiser arm with regard to one another such that the at least one rigidiser arm imparts a predetermined shape to the at least one strap at a rigidised portion of the at least one strap,
wherein the at least one strap is made of an elastic textile material and the positioning and stabilising structure is arranged such that the at least one strap is substantially free to move by elastically expanding and/or contracting relative to the at least one rigidiser arm and along a longitudinal axis of the at least one strap and/or rigidiser arm,
wherein the at least one strap has a stretchable length that remains substantially unaltered relative to the at least one strap without the at least one rigidiser arm, and
wherein the at least one strap is stretchable and is in the form of a sleeve arranged to slip over the at least one rigidiser arm, the arrangement being such that the at least one strap maintains its substantially entire stretchable length and is able to substantially freely stretch over the at least one rigidiser arm.

24. An augmented reality display system, comprising:
an augmented reality display unit having a display; and
a positioning and stabilising structure to hold the augmented reality display unit in an operational position over a user's face in use, the positioning and stabilising structure comprising:
at least one strap housing at least one electrical component in electrical communication with the augmented reality display unit;
at least one rigidiser arm, wherein the positioning and stabilising structure positions the at least one strap and the at least one rigidiser arm with regard to one another such that the at least one rigidiser arm imparts a predetermined shape to the at least one strap at a rigidised portion of the at least one strap; and
three, four or more separate straps connected by two or more joints.

25. An augmented reality display system, comprising:
an augmented reality display unit having a display; and
a positioning and stabilising structure to hold the augmented reality display unit in an operational position over a user's face in use, the positioning and stabilising structure comprising:
at least one strap housing at least one electrical component in electrical communication with the augmented reality display unit; and
at least one rigidiser arm, wherein the positioning and stabilising structure positions the at least one strap and the at least one rigidiser arm with regard to one another such that the at least one rigidiser arm imparts a predetermined shape to the at least one strap at a rigidised portion of the at least one strap,
wherein the at least one strap comprises two pockets, each pocket receiving a rigidiser arm to releasably secure the at least one strap to the rigidiser arms.

26. An augmented reality display system, comprising:
an augmented reality display unit having a display; and
a positioning and stabilising structure to hold the augmented reality display unit in an operational position over a user's face in use, the positioning and stabilising structure comprising:
at least one strap housing at least one electrical component in electrical communication with the augmented reality display unit; and
at least one rigidiser arm, wherein the positioning and stabilising structure positions the at least one strap and the at least one rigidiser arm with regard to one another such that the at least one rigidiser arm imparts a predetermined shape to the at least one strap at a rigidised portion of the at least one strap,
wherein the at least one electrical component is a flow generator in the form of a bidirectional blower, configured to provide airflow to a space proximate to the augmented reality display unit and/or to draw air from the space proximate to the augmented reality display unit, and wherein the bidirectional blower is further configured to simultaneously generate a bidirectional draft in opposing directions.

27. The augmented reality display system according to claim 26, wherein the at least one strap includes a conduit configured to convey airflow to or from the flow generator.

28. An augmented reality display system, comprising:
an augmented reality display unit having a display; and
a positioning and stabilising structure to hold the augmented reality display unit in an operational position over a user's face in use, the positioning and stabilising structure comprising:
at least one strap housing at least one electrical component in electrical communication with the augmented reality display unit;
at least one rigidiser arm, wherein the positioning and stabilising structure positions the at least one strap and the at least one rigidiser arm with regard to one another such that the at least one rigidiser arm imparts a predetermined shape to the at least one strap at a rigidised portion of the at least one strap; and
a spacing element configured to space the at least one rigidiser arm away from the augmented reality display unit, and wherein the at least one strap engages the spacing element.

* * * * *